US012559454B2

(12) United States Patent
Gunning et al.

(10) Patent No.: US 12,559,454 B2
(45) **Date of Patent: *Feb. 24, 2026**

(54) BENZENESULFONAMIDE DERIVATIVES AND USES THEREOF

(71) Applicants: 2692372 Ontario, Inc., Mississauga (CA); Dunad Therapeutics LTD., Great Cambourne (GB)

(72) Inventors: Patrick T. Gunning, Mississauga (CA); Ji Sung Park, Milton (CA); Siawash Ahmar, Toronto (CA); Aaron D. Cabral, Mississauga (CA); Gary K.C. Tin, Richmond Hill (CA); Sana Rasheed, Mississauga (CA); Ayah Abdeldayem, Mississauga (CA); David Armstrong, Mississauga (CA); Geordon A. Frere, Drayton (CA); Erica J. Quilates, Brampton (CA); David Alexander Rosa, Toronto (CA); Olga Gozhina, Ontario (CA); Jeffrey Alan Omeara, Halton Hills (CA); Graham Simpson, Great Wymondley (GB); Vittoria Zoppi, Ontario (CA)

(73) Assignees: 2692372 Ontario, Inc., Mississauga (CA); Dunad Therapeutics LTD., Cambridge (GB)

( * ) Notice: Subject to any disclaimer, the term of this patent is extended or adjusted under 35 U.S.C. 154(b) by 897 days.

This patent is subject to a terminal disclaimer.

(21) Appl. No.: 17/627,307

(22) PCT Filed: Jul. 17, 2020

(86) PCT No.: PCT/IB2020/000670

§ 371 (c)(1),
(2) Date: Jan. 14, 2022

(87) PCT Pub. No.: WO2021/009568

PCT Pub. Date: Jan. 21, 2021

(65) Prior Publication Data

US 2022/0281812 A1 Sep. 8, 2022

Related U.S. Application Data

(60) Provisional application No. 62/875,456, filed on Jul. 17, 2019, provisional application No. 62/875,457, filed on Jul. 17, 2019.

(51) Int. Cl.

| | |
|---|---|
| ***C07C 311/29*** | (2006.01) |
| ***A61K 9/00*** | (2006.01) |
| ***A61K 9/08*** | (2006.01) |
| ***A61K 9/48*** | (2006.01) |
| ***C07C 311/39*** | (2006.01) |
| ***C07D 205/04*** | (2006.01) |
| ***C07D 213/30*** | (2006.01) |
| ***C07D 213/74*** | (2006.01) |
| ***C07D 239/48*** | (2006.01) |

(Continued)

(52) U.S. Cl.

CPC .......... *C07C 311/29* (2013.01); *A61K 9/0019* (2013.01); *A61K 9/08* (2013.01); *A61K 9/4825* (2013.01); *C07C 311/39* (2013.01); *C07D 205/04* (2013.01); *C07D 213/30* (2013.01); *C07D 213/74* (2013.01); *C07D 239/48* (2013.01); *C07D 295/096* (2013.01); *C07D 305/06* (2013.01); *C07D 487/04* (2013.01); *C07K 1/1077* (2013.01)

(58) Field of Classification Search

CPC .................................................... C07C 311/29

See application file for complete search history.

(56) References Cited

U.S. PATENT DOCUMENTS

| | | | |
|---|---|---|---|
| 4,883,914 | A | 11/1989 | Alvarado et al. |
| 5,846,514 | A | 12/1998 | Foster et al. |

(Continued)

FOREIGN PATENT DOCUMENTS

| | | | |
|---|---|---|---|
| CA | 2238488 | A1 | 6/1997 |
| CN | 1225009 | A | 8/1999 |

(Continued)

OTHER PUBLICATIONS

STN 1877649-61-0 benzenesulfonamides. stn files (pp. 1-3) Retrieved from the Internet: URL:ww.stn.org [retrieved on Jun. 14, 2023] (Mar. 2, 2016).

(Continued)

*Primary Examiner* — Golam M Shameem

(74) *Attorney, Agent, or Firm* — Elmore Patent Law Group, PC Joseph C. Zucchero Carolyn S. Elmore

(57) ABSTRACT

Provided herein are benzenesulfonamide derivatives having Formula (III), pharmaceutical compositions comprising said compounds, and method for using said compounds for disrupting proteins/polypeptides, protein/polypeptide function, and for the treatment of diseases through the disruption of proteins or polypeptides involved in the etiology of the disease. Said compounds comprise fluorinated benzene sulfonamide structures.

Formula (III)

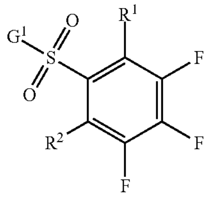

18 Claims, 18 Drawing Sheets

(51) Int. Cl.

| | |
|---|---|
| ***C07D 295/096*** | (2006.01) |
| ***C07D 305/06*** | (2006.01) |
| ***C07D 487/04*** | (2006.01) |
| ***C07K 1/107*** | (2006.01) |

(56) References Cited

U.S. PATENT DOCUMENTS

| | | | |
|---|---|---|---|
| 5,880,151 | A | 3/1999 | Medina et al. |
| 6,334,997 | B1 | 1/2002 | Foster et al. |
| 6,482,860 | B1 | 11/2002 | Flygare et al. |
| 2003/0162817 | A1 | 8/2003 | Flygare et al. |
| 2010/0081654 | A1 | 4/2010 | Stockwell et al. |
| 2015/0148358 | A1 | 5/2015 | Naik et al. |
| 2016/0015658 | A1 | 1/2016 | Kelner |
| 2016/0347717 | A1 | 12/2016 | Bock et al. |
| 2018/0334454 | A1 | 11/2018 | Lanman et al. |
| 2022/0281812 | A1 | 9/2022 | Gunning et al. |
| 2023/0055961 | A1 | 2/2023 | Kraskouskaya et al. |
| 2024/0018153 | A1 | 1/2024 | Gunning et al. |
| 2024/0092756 | A1 | 3/2024 | Gunning et al. |

FOREIGN PATENT DOCUMENTS

| | | | |
|---|---|---|---|
| CN | 106336413 | A | 1/2017 |
| CN | 110317137 | A | 10/2019 |
| EP | 0115405 | A2 | 8/1984 |
| JP | 2000204075 | A | 7/2000 |
| JP | 2001514167 | A | 9/2001 |
| WO | WO-9719942 | A1 | 6/1997 |
| WO | WO-9730677 | A2 | 8/1997 |
| WO | WO-9805315 | A1 | 2/1998 |
| WO | WO-9823613 | A1 | 6/1998 |
| WO | 9906397 | A2 | 2/1999 |
| WO | 9910320 | A1 | 3/1999 |
| WO | WO-9967258 | A1 | 12/1999 |
| WO | WO-0035865 | A2 | 6/2000 |
| WO | WO-0042002 | A1 | 7/2000 |
| WO | WO-0073302 | A1 | 12/2000 |
| WO | WO-0113122 | A2 | 2/2001 |
| WO | WO-0170677 | A1 | 9/2001 |
| WO | 0200661 | A1 | 1/2002 |
| WO | WO-0220474 | A2 | 3/2002 |
| WO | WO-03086394 | A1 | 10/2003 |
| WO | WO-2005097764 | A1 | 10/2005 |
| WO | WO-2006051662 | A1 | 5/2006 |
| WO | WO-2006081332 | A1 | 8/2006 |
| WO | 2009055674 | A1 | 4/2009 |
| WO | WO-2010151710 | A2 | 12/2010 |
| WO | 2012058645 | A1 | 5/2012 |
| WO | WO-2012101239 | A1 | 8/2012 |
| WO | 2014039714 | A2 | 3/2014 |
| WO | WO-2015083028 | A1 | 6/2015 |
| WO | WO-2015101609 | A1 | 7/2015 |
| WO | WO-2016179558 | A1 | 11/2016 |
| WO | WO-2017058370 | A1 | 4/2017 |
| WO | WO-2018071794 | A1 | 4/2018 |
| WO | WO-2018136935 | A1 | 7/2018 |
| WO | WO-2018234483 | A1 | 12/2018 |
| WO | WO-2019056120 | A1 | 3/2019 |
| WO | WO-2019075386 | A1 | 4/2019 |
| WO | WO-2019141694 | A1 | 7/2019 |
| WO | WO-2021009568 | A1 | 1/2021 |
| WO | WO-2021084765 | A1 | 5/2021 |
| WO | WO-2021085653 | A1 | 5/2021 |
| WO | WO-2021099842 | A1 | 5/2021 |
| WO | WO-2022106897 | A2 | 5/2022 |
| WO | WO-2022106902 | A2 | 5/2022 |

OTHER PUBLICATIONS

Zubriene et al. Intrinsic Thermodynamics and Structures of 2,4- and 3,4-Substituted Fluorinated Benzenesulfonamides Binding to Carbonic Anhydrases. ChemMedChem 12(2):161-176 (2017).

STN 1461713-74-5 Benzenesulfonamide, 2-(Chloromethyl)-3,4,5-trifluorobenzenesulfonamide. STN files. Retrieved from the Internet: URL: www.stn.org [retrieved on Jun. 14, 2023] (Oct. 21, 2013).

STN 1806587-81-4 Benzenesulfonamide, 3,4,5-Trifluoro-2-methoxybenzenesulfonamide. STN files. Retrieved from the Internet: URL: www.stn.org [retrieved on Jun. 14, 2023] (Sep. 13, 2015).

STN 1856780-48-7 Benzoic acid, 6-(Aminosulfonyl)-2,3,4-trifluorobenzoic acid. STN files. Retrieved from the Internet: URL: www.stn.org [retrieved on Jun. 14, 2023] (Feb. 1, 2016).

STN 1876267-28-5 Benzenesulfonamide, 3,4,5-Trifluoro-2-formylbenzenesulfonamide. STN files. Retrieved from the Internet: URL: www.stn.org [retrieved on Jun. 14, 2023] (Feb. 29, 2016).

STN, CAS Registry No. 2238808-11-0 Benzenesulfonamide, 2,3,4,5-tetrafluoro-6-(1-pipridinyl)-N-[(trifluoromethyl)sulfonyl]. STN files. Retrieved from the Internet: URL: www.stn.org [retrieved on Apr. 15, 2024] (Aug. 13, 2018).

STN, CAS Registry No. 2265915-46-4 Absolute stereochemistry. STN files. Retrieved from the Internet: URL: www.stn.org [retrieved on Apr. 15, 2024] (Feb. 4, 2019).

International Preliminary Report on Patentability dated May 17, 2022 for International Application No. PCT/IB2020/000981.

Berge et al. Pharmaceutical Salts. Journal of Pharmaceutical Sciences 66(1):1-19 (Jan. 1977).

Caddick et al., A generic approach for the catalytic reduction of nitriles. Tetrahedro, , 59:5417-5423 (2003).

Casini et al., Carbonic anhydrase inhibitors with strong topical antiglaucoma properties incorporating a 4-(2-aminopyrimidin-4-yl-amino)-benzenesulfonamide scaffold. J Enzyme Inhib Med Chem 17(1):9-18 (2002).

Casini et al., Cysteine-Modifying Agents: A Possible Approach for Effective Anticancer and Antiviral Drugs. Environ Health Perspect 110(Supp 5):801-806 (2002).

Dajek et al., trans-1,2-Diaminocyclohexane-based sulfonamides as effective hydrogen-bonding organocatalysts for asymmetric Michael-hemiacetalization reaction. Catalysis Science and Technology 8(17):4358-4363 (2018).

Davies et al., One-Pot, Three-Component Sulfonimidamide Synthesis Exploiting the Sulfinylamine Reagent N-Sulfinyltritylamine, TrNSO. Angew Chem Int Ed., 56:14937-14941 (2017).

Fell et al., Identification of the Clinical Development Candidate MRTX849, a Covalent KRASG12C Inhibitor for the Treatment of Cancer. J Med Chem 63:6679-6693 (2020).

Goedken et al., Tricyclic Covalent Inhibitors Selectively Target Jak3 through an Active Site Thiol. J Biol Chem 290:4573-4589 (2015).

Gu et al., The Wittig-Horner reaction for the synthesis of neratinib. Res Chem Intermed 39:3105-3110 (2013).

Kabalka et al. The Synthesis of Radiolabeled Compounds via Organometallic Intermediates. Tetrahedron 45(21):6601-6621 (1989).

Kim et al., Imidazo[1,5-a]quinoxalines as irreversible BTK inhibitors for the treatment of rheumatoid arthritis. Bioorg Med. Chem Lett 21:6258-6263 (2011).

Lam et al., Benzannulation via the Reaction of Ynamides and Vinylketenese. Application to the Synthesis of Highly Substituted Indoles. J. Org Chem 78(18):9396-414 (2013).

Lanman et al., Discovery of a Covalent Inhibitor of KRASG12C (AMG 510) for the Treatment of Solid Tumors. J Med Chem 63:52-65 (2020).

Laudadio et al., Sulfonamide Synthesis through Electrochemical Oxidative Coupling of Amines and Thiols. J Am Chem Soc 141(14):5664-5668 (2019).

Lee et al., Palladium-Catalyzed Synthesis of Arylamines from Aryl Halides and Lithium Bis(trimethylsilyl)amide as an Ammonia Equivalent. Org Lett 3(17):2729-2732 (2001).

Lelais et al., Discovery of (R,E)-N-(7-Chloro-1-(1-[4-(dimethylamino)but-2-enoyl]azepan-3-yl)-1H-benzo[d]imidazol-2-yl)-2-methylisonicotinamide (EGF816), a Novel, Potent, and WT Sparing Covalent Inhibitor of Oncogenic (L858R, ex19del) and Resistant (T790M) EGFR Mutants for the Treatment of EGFR Mutant Non-Small-Cell Lung Cancers. J Med Chem 59:6671-6689 (2016).

Linkuviene et al., Introduction of the Intrinsic Kinetics of Protein-Ligan Interactions and Their Implications for Drug Design. J Med Chem 61(6):2292-2302 (2018).

(56) References Cited

OTHER PUBLICATIONS

Lohier et al., Mechanistic investigation of the NH-sulfoximination of sulfide. Evidence for λ6-sulfanenitrile intermediates. Chem Commun (Camb) 53(12):2064-2067 (2017).
Lopez-Tapia et al., Linker Variation and Structure-Activity Relationship Analyses of Carboxylic Acid-based Small Molecule STAT3 Inhibitors. ACS Med. Chem. Lett. 9(3): 250-255 (2018).
Mao et al., A New and Improved Process for N-(4-Chloro-3-cyano-7-ethoxyquinolin-6-yl)acetamide, Org. Process Res. Dev., 16(12):1970-1973 (2012).
Marriott et al., Synthesis of the farnesyl ether 2,3,5-trifluoro-6-hydroxy-4-[(E,E )-3,7,11-trimethyldodeca-2,6,10-trien-1-yloxy]nitrobenzene, and related compounds containing a substituted hydroxytrifluorophenyl residue: novel inhibitors of protein farnesyltransferase, geranylgeranyltransferase I and squalene synthase. Journal of the Chemical Society, Perkin Transactions 1:4265-4278 (2000).
Medina et al., Novel Halogenated Sulfonamides Inhibit the Growth of Multidrug Resistant MCF/ADR Cancer Cells. Bioorg Med Chem Lett 9:1843-1846 (1999).
Melngaile et al., Diastereoselective Monofluorocyclopropanation Using Fluoromethylsulfonium Salts. Organic Letters 21(17):7174-7178 (2019).
Minus et al., Rhodium(II) Proximity-Labeling Identifies a Novel Target Site on STAT3 for Inhibitors with Potent Anti-Leukemia Activity. Angew Chem Int Ed Engl 54(44):13085-13089 (2015).
Motavallizadeh et al., Synthesis and evaluation of antiproliferative activity of substituted N-(9-oxo-9H-xanthen-4-yl)benzenesulfonamides. Tetrahedron Lett. 55(2):373-375 (2014).
Nazareth et al., Electrophore-labeling and alkylation of standards of nucleic acid pyrimidine bases for analysis by gas chromatography with electron-capture detection. J Chromatogr 30(314):201-10 (1984).
Norman et al. Protein-ligand crystal structures can guide the design of selective inhibitors of the FGFR tyrosine kinase. J Med Chem 55(11):5003-5012 (2012).
Orlova et al., Reaction of Polyfluorinated Aromatic Sulfones and Sulfoxides, Novosibirsk Institute of Organic Chemistry, Siberian Branch, Academy of Sciences of the USSR. Translated from Zhurnal Organicheskoi Khimii 16(5):1029-1034 (1980).
Ostrem et al., Direct Small-Molecule Inhibitors of KRAS: From Structural Insights to Mechanism-Based Design. Nat Rev Drug Discov 15(11):771-785 (2016).
Ostrem et al., K-Ras(G12C) inhibitors allosterically control GTP affinity and effector interactions. Nature 503:548-551 (2013).
PCT/IB2020/000670 International Search Report and Written Opinion dated Dec. 1, 2020.
PCT/IB2020/000981 International Search Report and Written Opinion dated Mar. 5, 2021.
PCT/IB2021/000805 International Search Report and Written Opinion dated May 31, 2022.
PCT/IB2021/000813 International Search Report and Written Opinion dated Jul. 15, 2022.
PCT/IB2021/000813 Invitation to Pay Additional Fees dated May 24, 2022.
Poteat et al., Controlled α-mono- and α,α-di-halogenation of alkyl sulfones using reagent-solvent halogen bonding. Chem Comm 55:2912-2915 (2019).
Qin et al., Identification of a novel family of BRAF(V600E) inhibitors. J Med Chem 55(11):5220-5230 (2012).
Rashad et al., Facile Synthesis and Preliminary Structure-Activity Analysis of New Sulfonamides Against Trypanosoma brucei. ACS Med Chem Lett 5(5):496-500 (2014).
Romines et al., Structure-Activity Relationship Studies of Novel Benzophenones Leading to the Discovery of a Potent, Next Generation HIV Nonnucleoside Reverse Transcriptase Inhibitor. J Med Chem 49(2):727-739 (2006).
Sandford et al., Product Class 1: Fluoroarenese: Arene-X (X=Hal, O, S, Se, Te). In: Science of Synthesis: Houben-Weyl Methods of Molecular Transformations, vol. 31a: Arene-X (X=Hal, O, S, Se, Te), Jan. 1, 2007, Georg Thieme Verlag, Stuttgart, p. 73.
Scozzafava et al., The Antifungal Activity of 2,2-Diamino-4,4-Dithiazole Derivatives is Due to the PossibleInhibition of Lanosterol-14-α-Demethylase. J. Enzyme Inhihrtiun 14(1):49-48 (1998).
Shan et al., Selective, covalent modification of B-tubulin residue Cys-239 by T138067, an antitumor agent with in vivo efficacy against multidrug-resistant tumors. PNAS USA 96(10):5686-5691 (1999).
Supuran et al., The antifungal activity of sulfonylamido derivatives of 2-aminophenoxathiin and related compounds. European Journal of Medicinal Chemistry 33(10):821-830 (1998).
Ward et al., Structure-Guided Design of Highly Selective and Potent Covalent Inhibitors of ERK1/2. J. Med. Chem 58:4790-4801 (2015).
Weiwer et al., Development of small-molecule probes that selectively kill cells induced to express mutant RAS. Bioorg Med Chem Lett 22(4):1822-1826 (2012).
Yang et al., Covalent modification of Cys-239 in B-tubulin by small molecules as a strategy to promote tubulin heterodimer degradation. J Biol Chem 294(20):8161-8170 (2019).
Zhang et al., Synthesis and Characterization of a Series of Highly Fluorogenic Substrates for Glutathione Transferases, a General Strategy. J. Am. Chem. Soc. 133(35): 14109-14119 (2011).
Zhu et al., Dipyrimidine Amines: A Novel Class of Chemokine Receptor Type 4 Antagonists with High Specificity. J. Med Chem 53(24):8556-8568 (2010).
Zhu et al., New and Convergent Synthesis of Osimertinib. Journal of Heterocyclic Chemistry, 54(5):2898-2901 (2017).
Dean, “Recent Advances in the Synthesis and Applications of Radiolabeled Compounds for Drug Discovery and Development”, Curr. Pharm. Des., 6(10):110 (Preface only), 2000.
Evans, “Synthesis of radiolabeled compounds”, J Radioanal Chem, 64(1-2), 1981, 9-32.

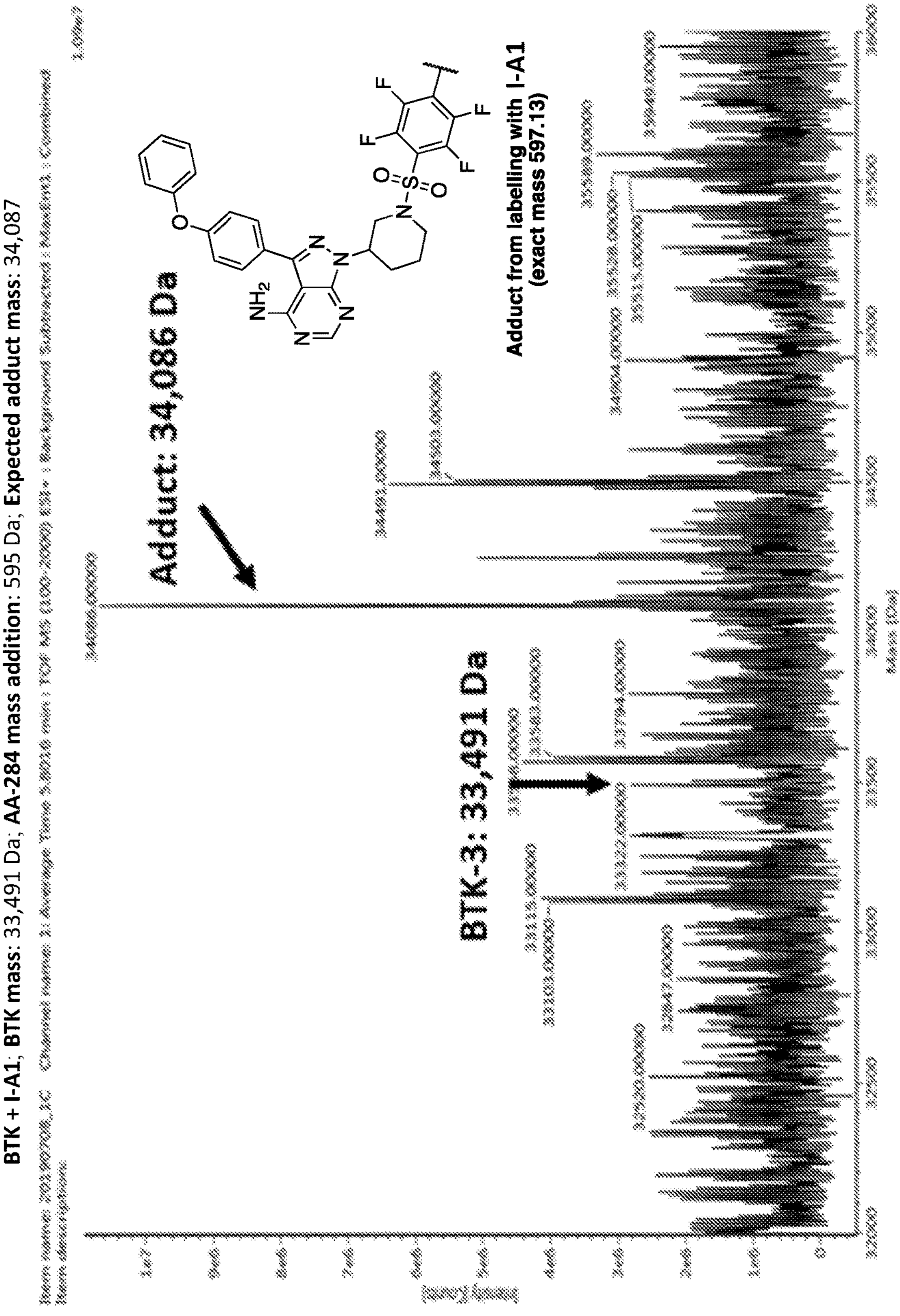
FIG. 7 CON'T

BENZENESULFONAMIDE DERIVATIVES AND USES THEREOF

RELATED APPLICATIONS

This application is filed pursuant to 35 U.S.C. § 371 as a United States National Phase Application of International Application Ser. No. PCT/IB2020/000670, filed Jul. 17, 2020, which claims the benefit of U.S. Provisional Patent Application No. 62/875,456, filed on Jul. 17, 2019 and U.S. Provisional Patent Application No. 62/875,457, filed on Jul. 17, 2019. The contents of these applications are hereby incorporated by reference in their entirety.

BACKGROUND

Microtubules are composed of alpha/beta-tubulin heterodimers and constitute a crucial component of the cell cytoskeleton. In addition, microtubules play a pivotal role during cell division, in particular when the replicated chromosomes are separated during mitosis. Interference with the ability to form microtubules from alpha/beta-tubulin heterodimeric subunits generally leads to cell cycle arrest. This event can, in certain cases, induce programmed cell death.

BRIEF SUMMARY OF THE DISCLOSURE

In some instances, compounds having fluorinated benzene sulfonamide structures are shown to have activity against (e.g., covalently bind to, inhibit (e.g., with long-lasting action), disrupt (e.g., with long-lasting action), and/or degrade) tubulins. Provided in some embodiments herein are various compounds, e.g., as described herein, comprising such fluorinated benzene structures. In some instances, compounds provided herein have tunable and/or improved properties (e.g., improved potency, improved selectivity, improved (reduced) toxicity, and/or other beneficial properties), such as compared to compounds lacking such fluorinated benzene structures. Further, in some instances, linkage of fluorinated benzene structures provided herein are further demonstrated to provide activity against (e.g., bind to, inhibit (e.g., with long-lasting action), disrupt (e.g., with long-lasting action), and/or degrade) a (e.g., target) protein (or polypeptide)(e.g., generally), when such fluorinated benzene moieties (warheads) are linked (e.g., directly or through a linker (e.g., covalent linker)) to a ligand of the (e.g., target) protein (or peptide). Provided herein are compounds (e.g., protein inhibitors), pharmaceutical compositions comprising said compounds, and methods for using said compounds (e.g., for disrupting proteins (or polypeptides), disrupting protein (or polypeptide) function, for the treatment of diseases (e.g., through the disruption of proteins or polypeptides involved in the etiology of the disease).

In one aspect, described herein is a compound of Formula (III), wherein the compound of Formula (III) is represented by the structure:

Formula (III)

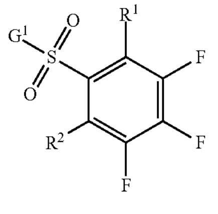

wherein, $R^1$ is —CN, —$OR^3$, —$SR^3$, —S(═O)$R^3$, —$S(═O)_2R^3$, —S(═O)(═$NR^3$)$R^3$, —$S(═O)_2N(R^3)_2$, —$OS(═O)_2R^3$, —$N(R^3)_2$, —$NR^3C(═O)R^3$, —$NR^3C(═O)N(R^3)_2$, —$NR^3C(═NR^3)N(R^3)_2$, —C(═O)$R^3$, —OC(═O)$R^3$, —C(═O)$OR^3$, —OC(═O)$OR^3$, —OC(═O)$N(R^3)_2$, —$NR^3C(═O)OR^3$, —C(═O)$N(R^3)_2$, $NO_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

$R^2$ is hydrogen, halogen, —CN, —$OR^3$, —$SR^3$, —S(═O)$R^3$, —$S(═O)_2R^3$, —$S(═O)_2N(R^3)_2$, —$N(R^3)_2$, —C(═O)$R^3$, —OC(═O)$R^3$, —C(═O)$OR^3$, —OC(═O)$N(R^3)_2$, —$NR^3C(═O)OR^3$, or —C(═O)$N(R^3)_2$;

$G^1$ is a nitrogen containing organic residue;

each $R^3$ is independently hydrogen, —C(═O)($C_2$-$C_6$ alkenyl), —C(═O)($C_2$-$C_6$ alkynyl), substituted or unsubstituted $C_1$-$C_4$ alkyl, —($C_1$-$C_4$ alkylene)-$R^4$, substituted or unsubstituted $C_1$-$C_4$ haloalkyl, substituted or unsubstituted $C_1$-$C_4$ heteroalkyl, substituted or unsubstituted $C_2$-$C_6$ alkenyl, substituted or unsubstituted $C_2$-$C_5$ alkynyl, substituted or unsubstituted $C_3$-$C_5$ cycloalkyl, substituted or unsubstituted $C_2$-$C_7$ heterocycloalkyl, substituted or unsubstituted aryl, or substituted or unsubstituted heteroaryl;

or two $R^3$ on the same nitrogen atom are joined together to form substituted or unsubstituted $C_2$-$C_7$ heterocycloalkyl; and $R^4$ is substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl, or a salt or solvate thereof.

In another aspect, described herein is a compound wherein the compound is a compound from Table 1.

In another aspect, described herein is a compound wherein the compound is a compound from Table 2.

In another aspect, described herein is a compound wherein the compound is a compound from Table 3.

In another aspect, described herein is a compound wherein the compound is a compound from Table 3A.

In another aspect, described herein is a compound wherein the compound is a compound from Table 4.

In another aspect, described herein is a compound wherein the compound is a compound from Table 5.

In another aspect, described herein is a pharmaceutical composition comprising a compound of any one of the preceding claims, or a salt or solvate thereof and one or more of pharmaceutically acceptable excipients.

In another aspect, described herein is a protein modified with a compound of any one of the preceding claims, wherein the compound forms a covalent bond with a sulfur atom of a cysteine residue of the protein.

In another aspect, described herein is a method of modifying a polypeptide with a compound, comprising contacting the polypeptide with a compound of any one of the preceding claims, to form a covalent bond with a sulfur atom of a cysteine residue of the polypeptide.

In another aspect, described herein is a method of binding a compound to a polypeptide, comprising contacting the polypeptide with a compound of any one of the preceding claims, or a salt or solvate thereof.

In another aspect, described herein is a method of disrupting a polypeptide (e.g., the function thereof), comprising contacting the polypeptide with a compound of any one of the preceding claims, or a salt or solvate thereof.

INCORPORATION BY REFERENCE

All publications, patents, and patent applications mentioned in this specification are herein incorporated by reference for the specific purposes identified herein.

BRIEF DESCRIPTION OF THE DRAWINGS

The accompanying figures, which are incorporated in and constitute a part of this specification, illustrate several aspects and together with the description serve to explain and not to limit the scope of current disclosure.

DETAILED DESCRIPTION OF THE DISCLOSURE

Figure 1:
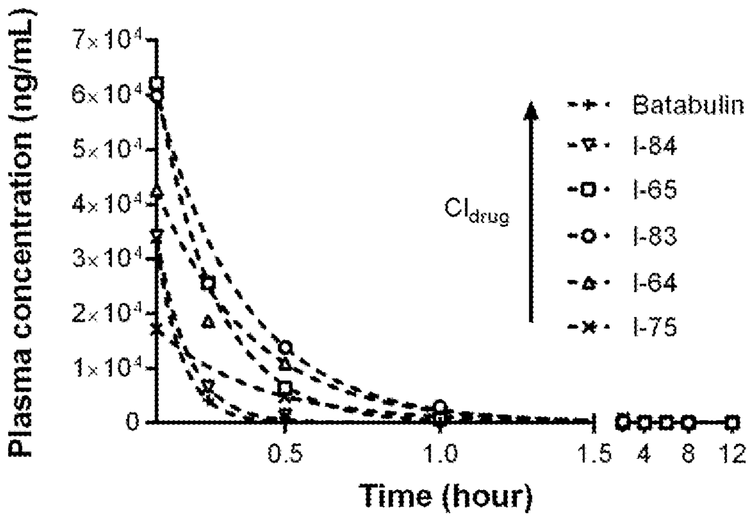
FIG. 1 illustrates representative plasma concentration of exemplary compounds in Balb/C Nude mice.
Figure 2:
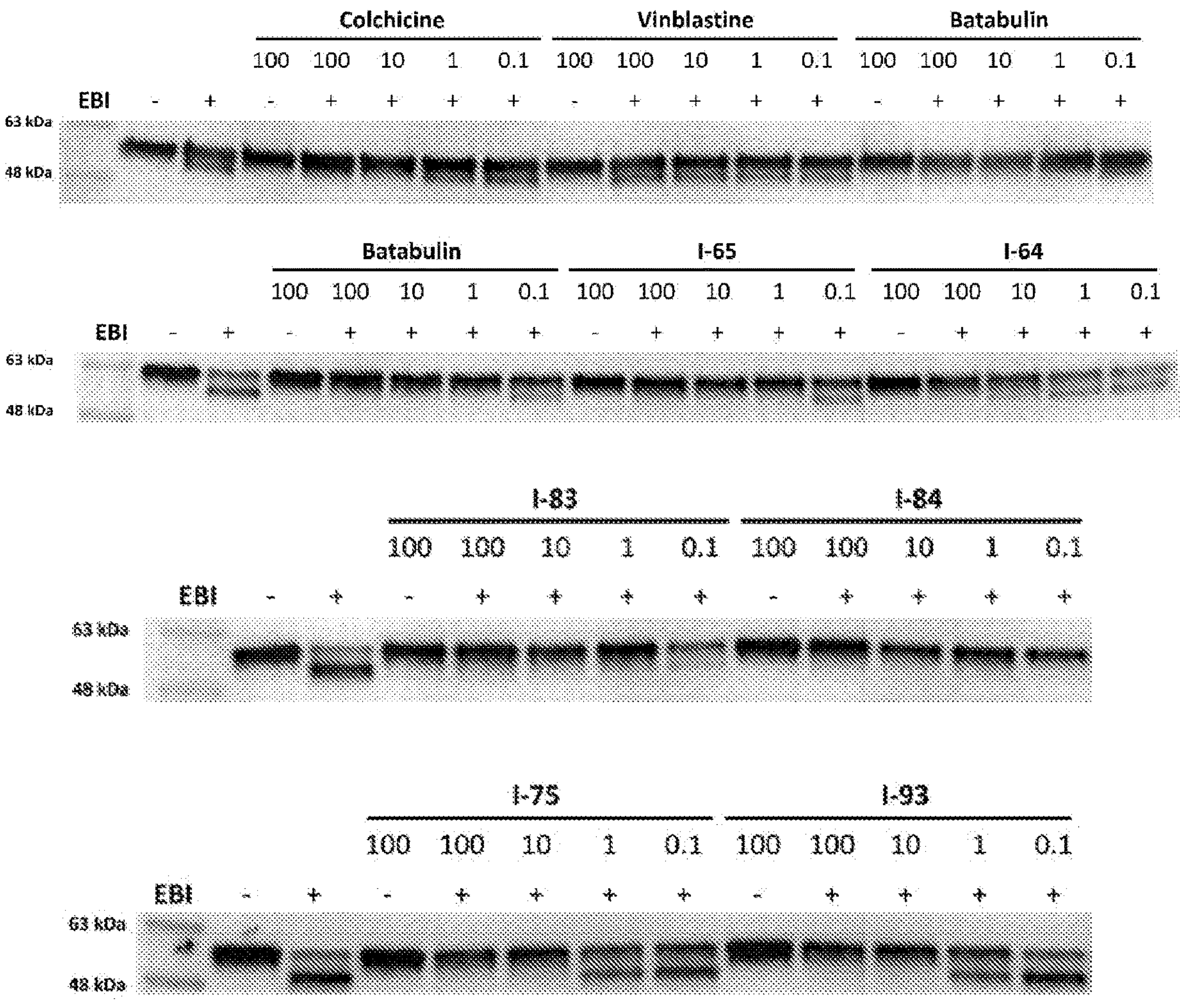
FIG. 2 illustrates representative electrophoretic mobility of porcine brain tubulin treated with different exemplary compounds and a cross-linking agent.
Figure 3A:
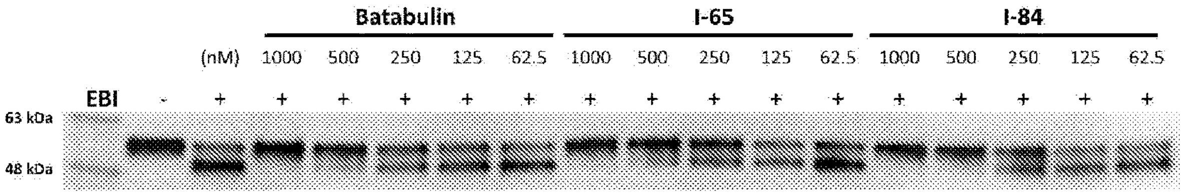
FIG. 3A illustrates representative electrophoretic mobility of porcine brain tubulin treated with different exemplary compounds and a cross-linking agent.
Figure 3B:
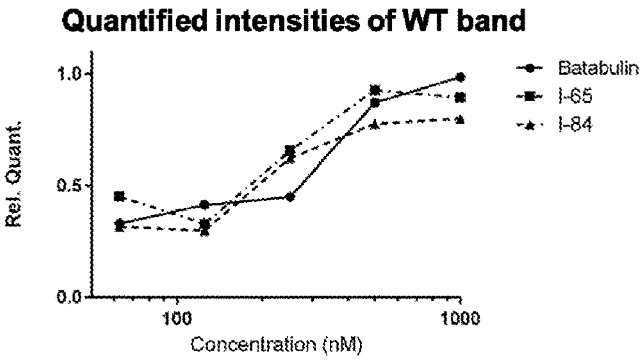
FIG. 3B illustrates representative quantified intensities of the WT band over a range of exemplary compounds. Measured intensities are relative to the initial WT band.
Figure 4A:
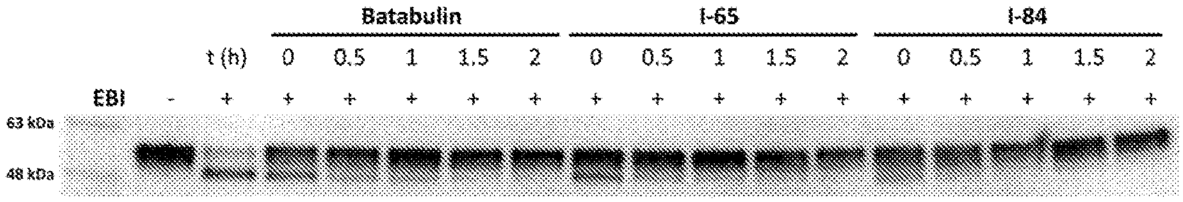
FIG. 4A illustrates representative electrophoretic mobility of porcine brain tubulin treated with different pre-incubation time with exemplary compounds.
Figure 4B:
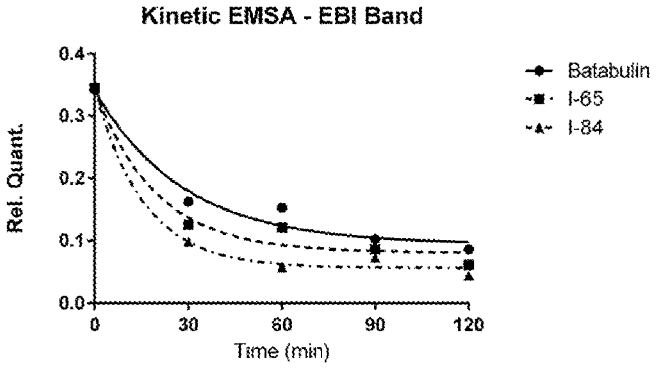
FIG. 4B illustrates representative quantified intensities of the EBI band. Measured intensities are relative to the initial EBI band.
Figure 5A:
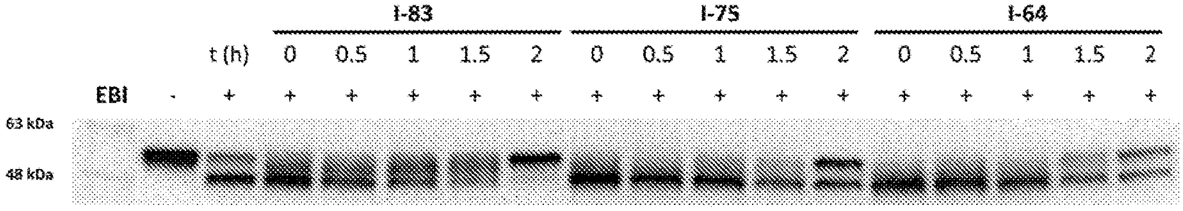
FIG. 5A illustrates representative electrophoretic mobility of porcine brain tubulin treated with different pre-incubation time with exemplary compounds.
Figure 5B:
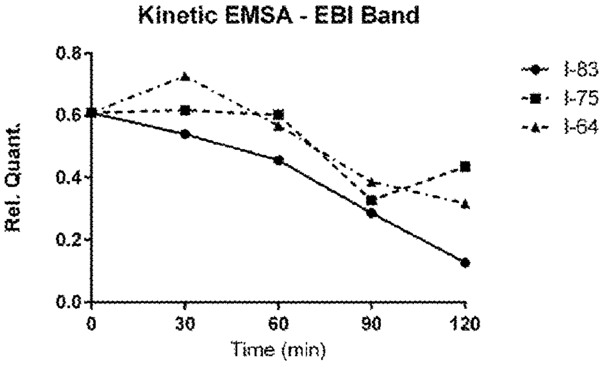
FIG. 5B illustrates representative quantified intensities of the EBI band. Measured intensities are relative to the initial EBI band.
Figure 6:
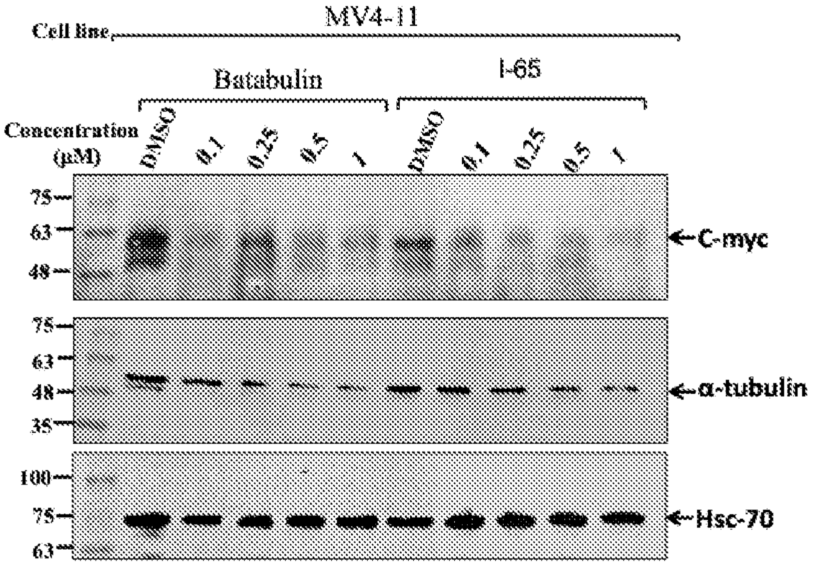
FIG. 6 illustrates representative western blot analysis of alpha tubulin and c-myc in MV-4-11 cell line after the treatment of Batabulin and exemplary compound for 6 hours.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the $—NH_2$ radical.

"Cyano" refers to the —CN radical.

"Nitro" refers to the $—NO_2$ radical.

"Oxa" refers to the —O— radical.

"Oxo" refers to the =O radical.

"Thioxo" refers to the =S radical.

"Imino" refers to the =N—H radical.

"Oximo" refers to the =N—OH radical.

"Hydrazino" refers to the $=N—NH_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)$N(R^a)_2$, —$N(R^a)$C(O)O$R^a$, —OC(O)—$N(R^a)_2$, —$N(R^a)$C(O)$R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)$N(R^a)_2$, —$N(R^a)$C(O)O$R^a$, —OC(O)—$N(R^a)_2$, —$N(R^a)$C(O)$R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)$N(R^a)_2$, —$N(R^a)$C(O)O$R^a$, —OC(O)—$N(R^a)_2$, —$N(R^a)$C(O)$R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)$N(R^a)_2$, —$N(R^a)$C(O)O$R^a$, —OC(O)—$N(R^a)_2$, —$N(R^a)$C(O)$R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises two carbon atoms (e.g., $C_2$ alkenylene). In other embodiments, an alkenylene comprises five to eight carbon atoms (e.g., $C_5$-$C_8$ alkenylene). In other embodiments, an alkenylene comprises three to five carbon atoms (e.g., $C_3$-$C_5$ alkenylene). Unless stated otherwise specifically in the specification, an alkenylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —OC(O)—$N(R^a)_2$, —$N(R^a)$C(O)$R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —OC(O)—$N(R^a)_2$, —$N(R^a)$C(O)$R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)S(O)_tR^a$ (where t is 1 or 2), —$R^b$—S(O)$R^a$ (where t is 1 or 2), —$R^b$—S(O)$OR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)O$R^a$, —$R^b$—C(O)N$(R^a)_2$, —$R^b$—O—$R^c$—C(O)N$(R^a)_2$, —$R^b$—N$(R^a)$C(O)O$R^a$, —$R^b$—N$(R^a)$C(O)$R^a$, —$R^b$—N$(R^a)$S(O)$_t$$R^a$ (where t is 1 or 2), —$R^b$—S(O)$R^a$ (where t is 1 or 2), —$R^b$—S(O)O$R^a$ (where t is 1 or 2) and —$R^b$—S(O)$_t$N$(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

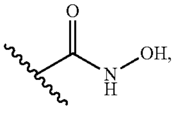 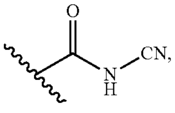 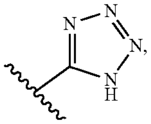 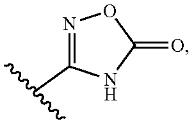 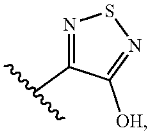 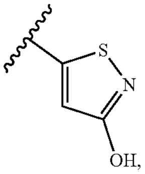 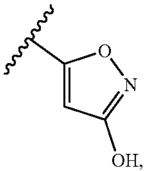 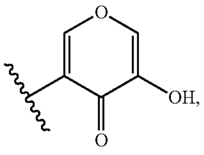

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

The term "heteroalkyl" refers to an alkyl group in which one or more skeletal atoms of the alkyl are selected from an atom other than carbon, e.g., oxygen, nitrogen (e.g. —NH—, —N(alkyl)-, or —N(aryl)-), sulfur (e.g. —S—, —S(═O)—, or —S(═O)$_2$—), or combinations thereof. In some embodiments, a heteroalkyl is attached to the rest of the molecule at a carbon atom of the heteroalkyl. In some embodiments, a heteroalkyl is attached to the rest of the molecule at a heteroatom of the heteroalkyl. In some embodiments, a heteroalkyl is a $C_1$-$C_6$ heteroalkyl. Representative heteroalkyl groups include, but are not limited to —$OCH_2OMe$, —$OCH_2CH_2OH$, —$CH_2CH_2OMe$, or —$OCH_2CH_2OCH_2CH_2NH_2$. In some embodiments, heteroalkyl includes alkoxy.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$R^a$ (where t is 1 or 2), —$R^b$—S(O)$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term “heteroaryl” is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)S(O)_tR^a$ (where t is 1 or 2), —$R^b$—S(O)$R^a$ (where t is 1 or 2), —$R^b$—S(O)$OR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

“Heteroarylalkyl” refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term “geometric isomer” refers to E or Z geometric isomers (e.g., cis or trans) of an alkene double bond. The term “positional isomer” refers to structural isomers around a central ring, such as ortho-, meta-, and para-isomers around a benzene ring.

A “tautomer” refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

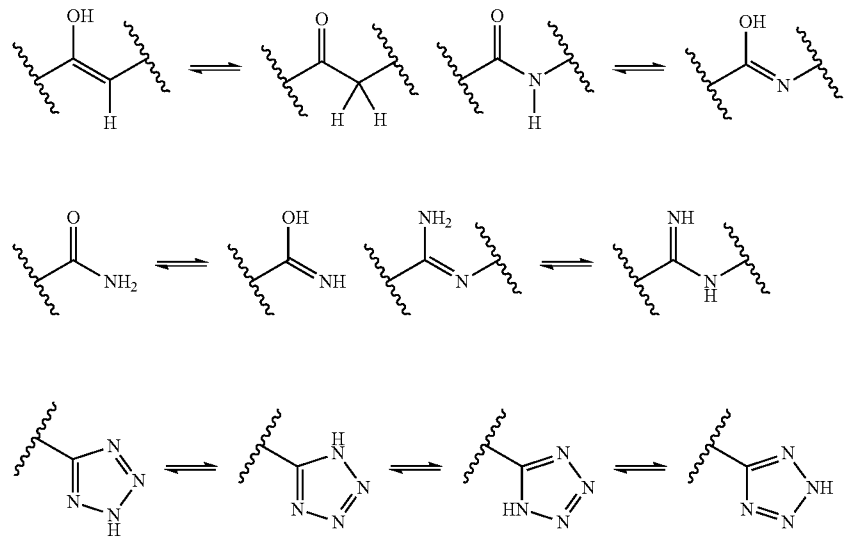

-continued

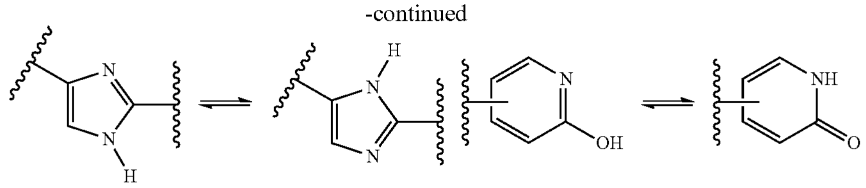

The compounds disclosed herein, in some embodiments, are used in different enriched isotopic forms, e.g., enriched in the content of $^{2}H$, $^{3}H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^{2}H$), tritium ($^{3}H$), iodine-125 ($^{125}I$) or carbon-14 ($^{14}C$). Isotopic substitution with $^{2}H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. In some embodiments, isotopic substitution with $^{18}F$ is contemplated. All isotopic variations of the compounds of the present disclosure, whether radioactive or not, are encompassed within the scope of the present disclosure.

In certain embodiments, the compounds disclosed herein have some or all of the $^{1}H$ atoms replaced with $^{2}H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-$d_3$ ($CD_3I$), are readily available and may be employed to transfer a deuterium-substituted carbon atom under nucleophilic substitution reaction conditions to the reaction substrate. The use of $CD_3I$ is illustrated, by way of example only, in the reaction schemes below.

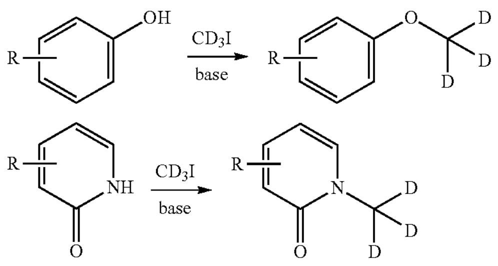

Deuterium-transfer reagents, such as lithium aluminum deuteride ($LiAlD_4$), are employed to transfer deuterium under reducing conditions to the reaction substrate. The use of $LiAlD_4$ is illustrated, by way of example only, in the reaction schemes below.

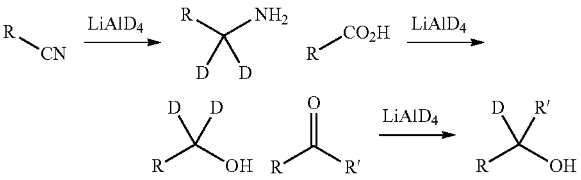

Deuterium gas and palladium catalyst are employed to reduce unsaturated carbon-carbon linkages and to perform a reductive substitution of aryl carbon-halogen bonds as illustrated, by way of example only, in the reaction schemes below.

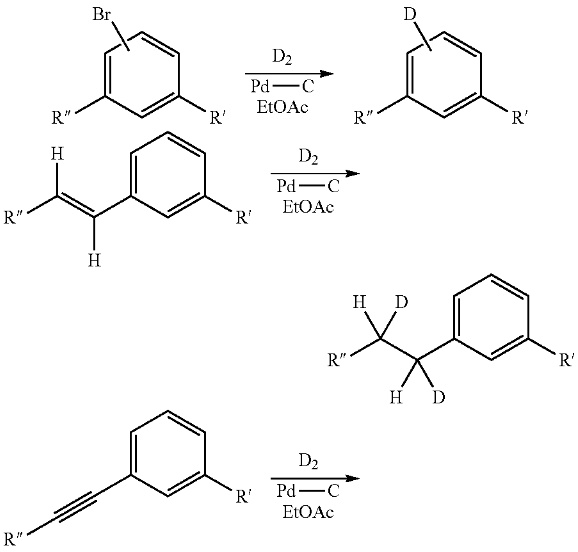

-continued

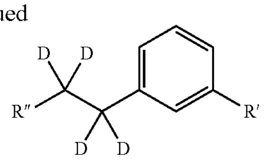

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1$H hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. The compounds provided herein optionally exist in either unsolvated as well as solvated forms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

Tubulin

Microtubules are subcellular organelles located in most eukaryotic cells and are involved in a variety of cell functions including mitosis, intracellular movement, cell movement and maintenance of cell shape. Microtubule assembly involves polymerization of tubulin and additional construction with other components of the microtubule (referred to as "microtubule-associated proteins" or MAPs).

Tubulin itself consists of two 50 kDa subunits (alpha- and beta-tubulin) which combine in a heterodimer. The heterodimer binds two molecules of guanosine triphosphate (GTP). One of the GTP molecules is tightly bound and cannot be removed without denaturing the heterodimer, while the other GTP molecule is freely exchangeable with other GTPs. This exchangeable GTP is believed to be involved in tubulin function. In particular, the tubulin heterodimer can combine in a head-to-tail arrangement in the presence of GTP to form a long protein fiber, known as a protofilament. These protofilaments can then group together to form a protein sheet which then curls into a tube-like structure known as a microtubule. Interference with this process of microtubule construction affects the downstream processes of mitosis and maintenance of cell shape. Most of the naturally-occurring antimitotic agents have been shown to exert their effect by binding to tubulin, rather than MAPs or other proteins involved in mitosis. For example, tubulin is the biochemical target for several clinically useful anticancer drugs, including vincristine, vinblastine and paclitaxel. Another natural product, colchicine, was instrumental in the purification of tubulin as a result of its potent binding, with beta-tubulin being the target for colchicine. Colchicine and other colchicine site agents bind at a site on beta-tubulin that results in inhibition of a cross-link between cys-239 and cys-354 (wherein the numbering refers to the (2 isotype) by such non-specific divalent sulfhydryl reactive agents as N,N'-ethylenebis-iodoacetamide. However, simple alkylation of cys-239 does not appear to inhibit colchicine binding to tubulin. In addition to colchicine, other natural products are known that bind at the colchicine site and inhibit microtubule assembly, for example, podophyllotoxin, steganacin and combretastatin. Still other agents bind to sites on tubulin referred to as the Vinca alkaloid site and the Rhizoxin/Maytansine site. However, none of the noted natural products are thought to operate by covalent modification of tubulin.

Based on the essential role of tubulin in the processes of cell transport and cell division, compounds which alter the tubulin activity are considered to be useful in treating or preventing various disorders. In some embodiments, described herein is a small molecule inhibitor of tubulin. In some embodiments, described herein is a pharmaceutical composition comprising a small molecule inhibitor of tubulin and one or more of pharmaceutically acceptable excipients. In other embodiments, a small molecule inhibitor of tubulin is used to treat or prevent a disease or condition in a subject in need thereof.

In some embodiments, a small molecule inhibitor of tubulin is a benzenesulfonamide derivative compound. In some embodiments, a benzenesulfonamide derivative compound as described herein is used to treat or prevent a disease or condition in a subject in need thereof.

In other embodiments, a pharmaceutical composition comprising a benzenesulfonamide derivative compound as described herein and one or more of pharmaceutically acceptable excipients is used to treat or prevent a disease or condition in a subject in need thereof.

In some embodiments, disclosed herein is a method of treating a disease comprising administering to a subject in need thereof a therapeutically effective amount of a benzenesulfonamide derivative compound as described herein.

In other embodiments, disclosed herein is a method of treating a disease comprising administering to a subject in need thereof a therapeutically effective amount of a pharmaceutical composition comprising a benzenesulfonamide derivative compound as described herein and one or more of pharmaceutically acceptable excipients.

In some embodiments, disclosed herein is a protein modified with a benzenesulfonamide derivative compound as described herein, wherein the compound forms a covalent bond with a sulfur atom of a cysteine residue of the protein. In some embodiments, disclosed herein is a method of modifying a polypeptide with a benzenesulfonamide derivative compound as described herein, comprising contacting the polypeptide with the compound to form a covalent bond with a sulfur atom of a cysteine residue of the polypeptide. In some embodiments, disclosed herein is a method of binding a compound to a polypeptide, comprising contacting the polypeptide with a benzenesulfonamide derivative compound as described herein. In some embodiments, the protein or polypeptide described herein is tubulin, JAK3, BTK, and/or BMX.

Benzenesulfonamide Derivative Compounds

In one aspect, provided herein is a benzenesulfonamide derivative compound. In some embodiments, a benzenesulfonamide derivative compound is a tubulin inhibitory compound.

One embodiment provides a compound, or pharmaceutically acceptable salt or solvate thereof, having the structure of Formula (III):

Formula (III)

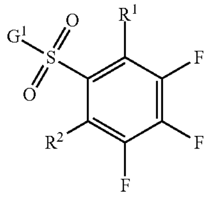

wherein, $R^1$ is —CN, —$OR^3$, —$SR^3$, —S(═O)$R^3$, —S(═O)$_2R^3$, —S(═O)(═$NR^3$)$R^3$, —S(═O)$_2$N($R^3$)$_2$, —OS(═O)$_2$ $R^3$, —N($R^3$)$_2$, —$NR^3$C(═O)$R^3$, —$NR^3$C(═O)N($R^3$)$_2$, —$NR^3$C(═$NR^3$)N($R^3$)$_2$, —C(═O)$R^3$, —OC(═O)$R^3$, —C(═O)O$R^3$, —OC(═O)O$R^3$, —OC(═O)N($R^3$)$_2$, —$NR^3$C(═O)O$R^3$, —C(═O)N($R^3$)$_2$, $NO_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

$R^2$ is hydrogen, halogen, —CN, —$OR^3$, —$SR^3$, —S(═O)$R^3$, —S(═O)$_2R^3$, —S(═O)$_2$N($R^3$)$_2$, —N($R^3$)$_2$, —C(═O)$R^3$, —OC(═O)$R^3$, —C(═O)O$R^3$, —OC(═O)N($R^3$)$_2$, —$NR^3$C(═O)O$R^3$, or —C(═O)N($R^3$)$_2$;

$G^1$ is a nitrogen containing organic residue;

each $R^3$ is independently hydrogen, —C(═O)($C_2$-$C_6$ alkenyl), —C(═O)($C_2$-$C_6$ alkynyl), substituted or unsubstituted $C_1$-$C_4$ alkyl, —($C_1$-$C_4$ alkylene)-$R^4$, substituted or unsubstituted $C_1$-$C_4$ haloalkyl, substituted or unsubstituted $C_1$-$C_4$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

or two $R^3$ on the same nitrogen atom are joined together to form substituted or unsubstituted $C_2$-$C_7$ heterocycloalkyl; and $R^4$ is substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl, or a salt or solvate thereof.

In some embodiments, $G^1$ is -L-G, L is a nitrogen containing linker, and G is an organic residue.

In some embodiments, L is —$NR^5$—, —$NR^5$-(substituted or unsubstituted alkyl), —$NR^5$-(substituted or unsubstituted heteroalkyl), —$NR^5$-(substituted or unsubstituted cycloalkyl), —$NR^5$-(substituted or unsubstituted heterocycloalkyl), —$NR^5$-(substituted or unsubstituted aryl), or —$NR^5$-(substituted or unsubstituted heteroaryl); wherein $R^5$ is hydrogen, —CN, —C(═O)$R^6$, —C(═O)O$R^6$, substituted or unsubstituted $C_1$-$C_4$ alkyl, substituted or unsubstituted $C_1$-$C_4$ haloalkyl, substituted or unsubstituted $C_1$-$C_4$ heteroalkyl, —$C_1$-$C_4$ alkylene-O$R^6$, substituted or unsubstituted $C_3$-$C_5$ cycloalkyl, or substituted or unsubstituted $C_2$-$C_4$ heterocycloalkyl; and $R^6$ is hydrogen, substituted or unsubstituted $C_1$-$C_4$ alkyl, substituted or unsubstituted $C_1$-$C_4$ fluoroalkyl, or substituted or unsubstituted $C_1$-$C_4$ heteroalkyl.

In some embodiments, the compound is represented by the structure of Formula (I):

Formula (I)

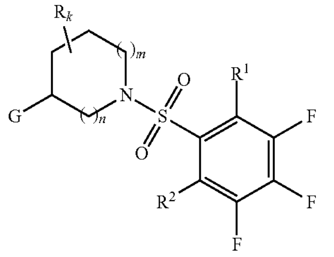

wherein, $R^1$ is —CN, —O$R^3$, —S$R^3$, —S(═O)$R^3$, —S(═O)$_2R^3$, —S(═O)(═N$R^3$)$R^3$, —S(═O)$_2$N($R^3$)$_2$, —OS(═O)$_2$ $R^3$, —N($R^3$)$_2$, —N$R^3$C(═O)$R^3$, —N$R^3$C(═O)N($R^3$)$_2$, —N$R^3$C(═N$R^3$)N($R^3$)$_2$, —C(═O)$R^3$, —OC(═O)$R^3$, —C(═O)O$R^3$, —OC(═O)O$R^3$, —OC(═O)N($R^3$)$_2$, —C(═O)N($R^3$)$_2$, —$NO_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

$R^2$ is hydrogen, halogen, —CN, —O$R^3$, —S$R^3$, —S(═O)$R^3$, —S(═O)$_2R^3$, —S(═O)$_2$N($R^3$)$_2$, —N($R^3$)$_2$, —C(═O)$R^3$, —OC(═O)$R^3$, —C(═O)O$R^3$, —OC(═O)N($R^3$)$_2$, —N$R^3$C(═O)O$R^3$, or —C(═O)N($R^3$)$_2$;

R is fluorine, substituted or unsubstituted $C_1$-$C_4$ alkyl, substituted or unsubstituted $C_1$-$C_4$ haloalkyl, or substituted or unsubstituted $C_1$-$C_4$ heteroalkyl;

G is an organic residue;

each $R^3$ is independently hydrogen, —C(═O)($C_2$-$C_6$ alkenyl), —C(═O)($C_2$-$C_6$ alkynyl), substituted or unsubstituted $C_1$-$C_4$ alkyl, —($C_1$-$C_4$ alkylene)-$R^4$, substituted or unsubstituted $C_1$-$C_4$ haloalkyl, substituted or unsubstituted $C_1$-$C_4$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

or two $R^3$ on the same nitrogen atom are joined together to form substituted or unsubstituted $C_2$-$C_7$ heterocycloalkyl;

$R^4$ is substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

k is 0, 1, 2, 3, 4, 5, 6, 7, or 8;

n is 0, 1, or 2; and m is 0, 1, or 2.

In some embodiments, the compound is represented by the structure of Formula (II):

Formula (II)

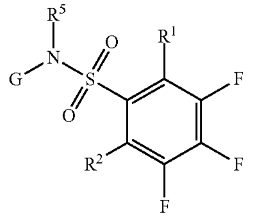

wherein, $R^1$ is —CN, —O$R^3$, —S$R^3$, —S(═O)$R^3$, —S(═O)$_2R^3$, —S(═O)(═N$R^3$)$R^3$, —S(═O)$_2$N($R^3$)$_2$, —OS(═O)$_2$ $R^3$, —N($R^3$)$_2$, —N$R^3$C(═O)$R^3$, —N$R^3$C(═O)N($R^3$)$_2$, —N$R^3$C(═N$R^3$)N($R^3$)$_2$, —C(═O)$R^3$, —OC(═O)$R^3$, —C(═O)O$R^3$, —OC(═O)O$R^3$, —OC(═O)N($R^3$)$_2$, —N$R^3$C(═O)O$R^3$, —C(═O)N($R^3$)$_2$, —$NO_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

$R^2$ is hydrogen, halogen, —CN, —O$R^3$, —S$R^3$, —S(═O)$R^3$, —S(═O)$_2R^3$, —S(═O)$_2$N($R^3$)$_2$, —N($R^3$)$_2$, —C(═O)$R^3$, —OC(═O)$R^3$, —C(═O)O$R^3$, —OC(═O)N($R^3$)$_2$, —N$R^3$C(═O)O$R^3$, or —C(═O)N($R^3$)$_2$;

each $R^3$ is independently hydrogen, —C(═O)($C_2$-$C_6$ alkenyl), —C(═O)($C_2$-$C_6$ alkynyl), substituted or unsubstituted $C_1$-$C_4$ alkyl, —($C_1$-$C_4$ alkylene)-$R^4$, substituted or unsubstituted $C_1$-$C_4$ haloalkyl, substituted or unsubstituted $C_1$-$C_4$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

or two $R^3$ on the same nitrogen atom are joined together to form substituted or unsubstituted $C_2$-$C_7$ heterocycloalkyl;

$R^4$ is substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

G is organic residue;

$R^5$ is hydrogen, —CN, —C(=O)$R^6$, —C(=O)O$R^6$, substituted or unsubstituted $C_1$-$C_4$ alkyl, substituted or unsubstituted $C_1$-$C_4$ haloalkyl, substituted or unsubstituted $C_1$-$C_4$ heteroalkyl, —$C_1$-$C_4$ alkylene-O$R^6$, substituted or unsubstituted $C_3$-$C_5$ cycloalkyl, or substituted or unsubstituted $C_2$-$C_4$ heterocycloalkyl; and $R^6$ is hydrogen, substituted or unsubstituted $C_1$-$C_4$ alkyl, substituted or unsubstituted $C_1$-$C_4$ fluoroalkyl, or substituted or unsubstituted $C_1$-$C_4$ heteroalkyl.

In some embodiments, $R^1$ is —O$R^3$, —S$R^3$, —OS(=O)$_2$ $R^3$, —N($R^3$)$_2$, —N$R^3$C(=O)$R^3$, —N$R^3$C(=O)N($R^3$)$_2$, —OC(=O)$R^3$, —OC(=O)O$R^3$, —OC(=O)N($R^3$)$_2$, —N$R^3$C(=O)O$R^3$, substituted or unsubstituted $C_1$-$C_6$ alkyl (e.g., cycloalkyl-alkyl or heterocycloalkyl-alkyl), substituted or unsubstituted $C_1$-$C_6$ haloalkyl, substituted or unsubstituted $C_1$-$C_6$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, or substituted or unsubstituted $C_2$-$C_7$ heterocycloalkyl.

In some embodiments, $R^1$ is —$CH_3$, —$CH_2CH_3$, cyclopropyl, cyclobutyl, cyclopentyl, —$CH_2OH$, —$CH_2CH_2OH$, —$CH_2CN$, —$CH_2NH_2$, —$CH_2NHCH_3$, —$CH_2N(CH_3)_2$, —$CH_2F$, —$CHF_2$, —$CF_3$, —CH=$CH_2$, —C≡CH, —OH, —$OCH_3$, —$OCH_2CH_3$, —$OCH_2CH_2OH$, —$OCH_2CN$, —$OCH_2F$, —$OCHF_2$, —$OCF_3$, —$OCH_2CH_2F$, —$OCH_2CHF_2$, —$OCH_2CF_3$, cyclopropyloxy, cyclobutyloxy, cyclopentyloxy, oxetanyl, tetrahydrofuranyl, tetrahydro-2H-pyranyl, azetidinyl, pyrrolidinyl, piperidinyl, triazolyl, tetrazolyl, phenyl, benzyl, —$NH_2$, —$NHCH_3$, —$N(CH_3)_2$, —$NHCH_2F$, —$NHCHF_2$, —$NHCF_3$, —$NHCH_2CH_2F$, —$NHCH_2CHF_2$, or —$NHCH_2CF_3$ (e.g., —$CH_3$, —$CH_2CH_3$, cyclopropyl, cyclobutyl, —$CH_2NH_2$, —$CH_2NHCH_3$, —$CH_2N(CH_3)_2$, —$CH_2F$, —$CHF_2$, —$CF_3$, —OH, —$OCH_3$, —$OCH_2CH_3$, —$OCH_2CH_2OH$, —$OCH_2CN$, —$OCH_2F$, —$OCHF_2$, —$OCF_3$, —$OCH_2CH_2F$, —$OCH_2CHF_2$, —$OCH_2CF_3$, cyclopropyloxy, cyclobutyloxy, azetidinyl, pyrrolidinyl, —$NH_2$, —$NHCH_3$, —$N(CH_3)_2$, —$NHCH_2F$, —$NHCHF_2$, —$NHCF_3$, —$NHCH_2CH_2F$, —$NHCH_2CHF_2$, or —$NHCH_2CF_3$)(e.g., —$CH_3$, cyclopropyl, cyclobutyl, —$CH_2F$, —$CHF_2$, —$CF_3$, —OH, —$OCH_3$, —$OCH_2CH_3$, —$OCH_2F$, —$OCHF_2$, —$OCF_3$, —$OCH_2CH_2F$, —$OCH_2CHF_2$, —$OCH_2CF_3$, cyclopropyloxy, cyclobutyloxy, —$NH_2$, —$NHCH_3$, —$N(CH_3)_2$, —$NHCH_2F$, —$NHCHF_2$, —$NHCF_3$, —$NHCH_2CH_2F$, —$NHCH_2CHF_2$, or —$NHCH_2CF_3$)(e.g., —$OCH_3$, —$OCH_2CH_2F$, —$OCH_2CHF_2$, —$OCH_2CF_3$, cyclopropyloxy, —$NH_2$, —$NHCH_3$, —$NHCF_3$, or —$NHCH_2CF_3$).

In some embodiments, $R^1$ is $CH_3$, —$CH_2CH_3$, cyclopropyl, cyclobutyl, cyclopentyl, —$CH_2OH$, —$CH_2CH_2OH$, —$CH_2CN$, —$CH_2NH_2$, —$CH_2NHCH_3$, —$CH_2N(CH_3)_2$, —$CH_2F$, —$CHF_2$, —$CF_3$, —CH=$CH_2$, —C≡CH, —OH, —$OCH_3$, —$OCH_2CH_3$, —$OCH_2CH_2OH$, —$OCH_2CN$, —$OCH_2F$, —$OCHF_2$, —$OCF_3$, —$OCH_2CH_2F$, —$OCH_2CHF_2$, —$OCH_2CF_3$, cyclopropyloxy, cyclobutyloxy, cyclopentyloxy, azetidinyl, pyrrolidinyl, piperidinyl, triazolyl, tetrazolyl, phenyl, benzyl, —$NH_2$, —$NHCH_3$, —$N(CH_3)_2$, —$NHCH_2F$, —$NHCHF_2$, —$NHCF_3$, —$NHCH_2CH_2F$, —$NHCH_2CHF_2$, or —$NHCH_2CF_3$ (e.g., —$CH_3$, —$CH_2CH_3$, cyclopropyl, cyclobutyl, —$CH_2NH_2$, —$CH_2NHCH_3$, —$CH_2N(CH_3)_2$, —$CH_2F$, —$CHF_2$, —$CF_3$, —OH, —$OCH_3$, —$OCH_2CH_3$, —$OCH_2CH_2OH$, —$OCH_2CN$, —$OCH_2F$, —$OCHF_2$, —$OCF_3$, —$OCH_2CH_2F$, —$OCH_2CHF_2$, —$OCH_2CF_3$, cyclopropyloxy, cyclobutyloxy, azetidinyl, pyrrolidinyl, —$NH_2$, —$NHCH_3$, —$N(CH_3)_2$, —$NHCH_2F$, —$NHCHF_2$, —$NHCF_3$, —$NHCH_2CH_2F$, —$NHCH_2CHF_2$, or —$NHCH_2CF_3$)(e.g., —$CH_3$, cyclopropyl, cyclobutyl, —$CH_2F$, —$CHF_2$, —$CF_3$, —OH, —$OCH_3$, —$OCH_2CH_3$, —$OCH_2F$, —$OCHF_2$, —$OCF_3$, —$OCH_2CH_2F$, —$OCH_2CHF_2$, —$OCH_2CF_3$, cyclopropyloxy, cyclobutyloxy, —$NH_2$, —$NHCH_3$, —$N(CH_3)_2$, —$NHCH_2F$, —$NHCHF_2$, —$NHCF_3$, —$NHCH_2CH_2F$, —$NHCH_2CHF_2$, or —$NHCH_2CF_3$)(e.g., —$OCH_3$, —$OCH_2CH_2F$, —$OCH_2CHF_2$, —$OCH_2CF_3$, cyclopropyloxy, —$NH_2$, —$NHCH_3$, —$NHCF_3$, or —$NHCH_2CF_3$)(e.g., —$OCH_2F$, —$OCHF_2$, —$OCF_3$, —$OCH_2CH_2F$, —$OCH_2CHF_2$, —$OCH_2CF_3$, —$NHCF_3$, or —$NHCH_2CF_3$)(e.g., —$OCH_3$, —$OCH_2CH_3$, —$OCH_2F$, —$OCHF_2$, —$OCF_3$, —$OCH_2CH_2F$, —$OCH_2CHF_2$, —$OCH_2CF_3$, cyclopropyloxy, or cyclobutyloxy)(e.g., —$NH_2$, —$NHCH_3$, —N $(CH_3)_2$, —$NHCH_2F$, —$NHCHF_2$, —$NHCF_3$, —$NHCH_2CH_2F$, —$NHCH_2CHF_2$, or —$NHCH_2CF_3$).

In some embodiments, $R^2$ is halogen, —CN, —S(=O)$R^3$, —S(=O)$_2R^3$, —S(=O)$_2$N($R^3$)$_2$, —C(=O)$R^3$, —OC(=O) $R^3$, —C(=O)O$R^3$, —OC(=O)N($R^3$)$_2$, —N$R^3$C(=O)O$R^3$, or —C(=O)N($R^3$)$_2$ (e.g., F, Cl, —CN, —S(=O)$R^3$, —S(=O)$_2R^3$, —S(=O)$_2$N($R^3$)$_2$, —C(=O)$R^3$, —OC(=O) $R^3$, —C(=O)O$R^3$, —OC(=O)N($R^3$)$_2$, —N$R^3$C(=O)O$R^3$, or —C(=O)N($R^3$)$_2$)(e.g., F, Cl, —CN, —S(=O)$CH_3$, —S(=O)$_2CH_3$, —S(=O)$_2$N($CH_3$)$_2$, —C(=O)$CH_3$, —OC (=O)$CH_3$, —C(=O)O$CH_3$, —OC(=O)N($CH_3$)$_2$, —N$CH_3$C(=O)O$CH_3$, or —C(=O)N($CH_3$)$_2$)(e.g., F, Cl, or —CN)(e.g., F).

In some embodiments, k is 0, 1, 2, or 3 (e.g., 1 or 2)(e.g., 0).

In some embodiments, n is 0, 1, or 2 (e.g., 1)(e.g., 0).

In some embodiments, m is 0, 1, or 2 (e.g., 1)(e.g., 0).

In some embodiments, $R^5$ is hydrogen, —CN, substituted or unsubstituted $C_1$-$C_4$ alkyl, substituted or unsubstituted $C_1$-$C_4$ haloalkyl, or substituted or unsubstituted $C_3$-$C_5$ cycloalkyl (e.g., hydrogen, —CN, —$CH_3$, —$CH_2CH_3$, —$CH_2NH_2$, —$CH_2NHCH_3$, —$CH_2N(CH_3)_2$, —$CH_2F$, —$CHF_2$, —$CF_3$, cyclopropyl, cyclobutyl, or cyclopentyl) (e.g., hydrogen, —CN, —$CH_3$, —$CF_3$, or cyclopropyl)(e.g., hydrogen).

In some embodiments, G comprises one or more cyclic ring systems selected from carbocycles and heterocycles (e.g., two or more cyclic ring systems selected from carbocycles and heterocycles)(e.g., one or more fused ring systems selected from carbocycles and heterocycles).

In some embodiments, $G^1$ comprises one or more cyclic ring systems selected from carbocycles and heterocycles (e.g., two or more cyclic ring systems selected from carbocycles and heterocycles)(e.g., one or more fused ring systems selected from carbocycles and heterocycles).

In some embodiments, the two or more cyclic ring systems are connected via a bond.

In some embodiments, the two or more cyclic ring systems are connected via a linker.

In some embodiments, the linker is —O—, —N$R^7$—, —N($R^7$)$_2^+$—, —S—, —S(=O)—, —S(=O)$_2$—, —CH=CH—, =CH—, —C≡C—, —C(=O)—, —C(=O) O—, —OC(=O)—, —OC(=O)O—, —C(=O)N$R^7$—, —N$R^7$C(=O)—, —OC(=O)N$R^7$—, —N$R^7$C(=O)O—, —N$R^7$C(=O)N$R^7$—, —N$R^7$S(=O)$_2$—, —S(=O)$_2$N$R^7$—, —C(=O)N$R^7$S(=O)$_2$—, —S(=O)$_2$N$R^7$C(=O)—, substituted or unsubstituted $C_1$-$C_4$ alkylene, substituted or unsubstituted $C_1$-$C_8$heteroalkylene, —($C_1$-$C_4$ alkylene)-O—, —O—($C_1$-$C_4$ alkylene)-, —($C_1$-$C_4$ alkylene)-$NR^7$—, —$NR^7$—($C_1$-$C_4$ alkylene)-, —($C_1$-$C_4$ alkylene)-$N(R^7)_2^+$—, or —$N(R^7)_2^+$—($C_1$-$C_4$ alkylene)-; and each $R^7$ is independently hydrogen, substituted or unsubstituted $C_1$-$C_4$ alkyl, substituted or unsubstituted $C_1$-$C_4$ haloalkyl, substituted or unsubstituted $C_1$-$C_4$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl.

In some embodiments, G comprises monocyclic aryl or monocyclic heteroaryl; or wherein G comprises bicyclic aryl or bicyclic heteroaryl.

In some embodiments, $G^1$ comprises monocyclic aryl or monocyclic heteroaryl; or wherein G comprises bicyclic aryl or bicyclic heteroaryl.

In some embodiments, G is or comprises a ligand that binds to a protein (e.g., tubulin, JAK3, BTK, and/or BMX).

In some embodiments, $G^1$ is or comprises a ligand that binds to a protein (e.g., tubulin, JAK3, BTK, and/or BMX).

In some embodiments, the compound is represented by the structure of Formula (IV):

Formula (IV)

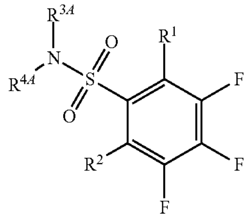

wherein, $R^1$ is —CN, —$OR^{5A}$, —$SR^{5A}$, —$S(=O)R^{5A}$, —$S(=O)_2R^{5A}$, —$S(=O)(=NR^{5A})R^{5A}$, —$S(=O)_2N(R^{5A})_2$, —$OS(=O)_2R^{5A}$, —$N(R^{5A})_2$, —$NR^{5A}C(=O)R^{5A}$, —$NR^{5A}C(=O)N(R^{5A})_2$, —$NR^{5A}C(=NR^{5A})N(R^{5A})_2$, —$C(=O)R^{5A}$, —$OC(=O)R^{5A}$, —$C(=O)OR^{5A}$, —$OC(=O)OR^{5A}$, —$OC(=O)N(R^{5A})_2$, —$NR^{5A}C(=O)OR^{5A}$, —$C(=O)N(R^{5A})_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

$R^2$ is hydrogen, halogen, —CN, —$OR^{5A}$, —$SR^{5A}$, —$S(=O)R^{5A}$, —$S(=O)_2R^{5A}$, —$S(=O)_2N(R^{5A})_2$—$N(R^{5A})_2$, —$C(=O)R^{5A}$, —$OC(=O)R^{5A}$, —$C(=O)OR^{5A}$, —$OC(=O)N(R^{5A})_2$, —$NR^5C(=O)OR^{5A}$, or —$C(=O)N(R^{5A})_2$;

$R^{3A}$ is hydrogen, —$OR^{5A}$, —$S(=O)R^{5A}$, —$S(=O)_2R^{5A}$, —$C(=O)R^{5A}$, —$C(=O)OR^{5A}$, —$C(=O)N(R^{5A})_2$, substituted or unsubstituted $C_1$-$C_4$ alkyl, substituted or unsubstituted $C_1$-$C_6$ haloalkyl, substituted or unsubstituted $C_1$-$C_6$ heteroalkyl, substituted or unsubstituted $C_2$-$C_5$ alkenyl, substituted or unsubstituted $C_2$-$C_5$ alkynyl, substituted or unsubstituted aryl, or substituted or unsubstituted heteroaryl;

$R^{4A}$ is —$OR^{6A}$, —$S(=O)R^{5A}$, —$S(=O)_2R^{5A}$, —$C(=O)R^{5A}$, —$C(=O)OR^{5A}$, —$C(=O)N(R^{5A})_2$, substituted or unsubstituted $C_1$-$C_4$ alkyl, substituted or unsubstituted $C_1$-$C_6$ haloalkyl, substituted or unsubstituted $C_1$-$C_6$ heteroalkyl, substituted or unsubstituted $C_2$-$C_5$ alkenyl, substituted or unsubstituted $C_2$-$C_5$ alkynyl, substituted or unsubstituted aryl, or substituted or unsubstituted heteroaryl;

each $R^{5A}$ is independently hydrogen, —$C(=O)(C_2$-$C_6$ alkenyl), —$C(=O)(C_2$-$C_6$ alkynyl), substituted or unsubstituted $C_1$-$C_4$ alkyl, —($C_1$-$C_4$ alkylene)-$R^{7A}$, substituted or unsubstituted $C_1$-$C_4$ haloalkyl, substituted or unsubstituted $C_1$-$C_4$ heteroalkyl, substituted or unsubstituted $C_2$-$C_5$ alkenyl, substituted or unsubstituted $C_2$-$C_5$ alkynyl, substituted or unsubstituted $C_3$-$C_6$cycloalkyl, substituted or unsubstituted $C_2$-$C_5$ heterocycloalkyl, substituted or unsubstituted aryl, or substituted or unsubstituted heteroaryl;

or two $R^{5A}$ on the same nitrogen atom are joined together to form substituted or unsubstituted $C_2$-$C_7$ heterocycloalkyl;

$R^{6A}$ is substituted or unsubstituted $C_1$-$C_4$ alkyl, —($C_1$-$C_4$ alkylene)-$R^{7A}$, substituted or unsubstituted $C_1$-$C_4$ haloalkyl, substituted or unsubstituted $C_1$-$C_4$ heteroalkyl, substituted or unsubstituted $C_2$-$C_5$ alkenyl, substituted or unsubstituted $C_2$-$C_5$ alkynyl, substituted or unsubstituted $C_3$-$C_6$cycloalkyl, substituted or unsubstituted $C_2$-$C_5$ heterocycloalkyl, substituted or unsubstituted aryl, or substituted or unsubstituted heteroaryl; and each $R^{7A}$ is independently substituted or unsubstituted $C_3$-$C_6$cycloalkyl, substituted or unsubstituted $C_2$-$C_5$ heterocycloalkyl, substituted or unsubstituted aryl, or substituted or unsubstituted heteroaryl.

In some embodiments, $R^1$ is —$OR^{5A}$, —$SR^{5A}$, —$OS(=O)_2R^{5A}$, —$N(R^{5A})_2$, $NR^{5A}C(=O)R^{5A}$, —$NR^{5A}C(=O)N(R^{5A})_2$, —$OC(=O)R^{5A}$, —$OC(=O)OR^{5A}$, —$OC(=O)N(R^{5A})_2$, —$NR^{5A}C(=O)OR^{5A}$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, or substituted or unsubstituted $C_2$-$C_7$ heterocycloalkyl (e.g., —$OR^{5A}$, —$SR^{5A}$—$N(R^{5A})_2$—$OC(=O)R^{5A}$, —$OC(=O)OR^{5A}$, substituted or unsubstituted $C_1$-$C_6$ alkyl, substituted or unsubstituted $C_1$-$C_6$ haloalkyl, substituted or unsubstituted $C_3$-$C_8$ cycloalkyl, substituted or unsubstituted $C_2$-$C_7$ heterocycloalkyl)(e.g., —$OR^{5A}$, —$N(R^{5A})_2$, substituted or unsubstituted $C_1$-$C_6$ alkyl, substituted or unsubstituted $C_1$-$C_6$ haloalkyl, substituted or unsubstituted $C_3$-$C_8$ cycloalkyl, or substituted or unsubstituted $C_2$-$C_7$ heterocycloalkyl)(e.g., —$OR^{5A}$, and $R^{5A}$ is substituted or unsubstituted $C_1$-$C_4$ alkyl, substituted or unsubstituted $C_1$-$C_4$ haloalkyl, or substituted or unsubstituted $C_3$-$C_5$ cycloalkyl)(e.g., —$OR^{5A}$, and $R^{5A}$ is substituted or unsubstituted $C_2$-$C_5$ heterocycloalkyl, substituted or unsubstituted phenyl, or substituted or unsubstituted benzyl)(e.g., —$N(R^{5A})_2$, and each $R^{5A}$ is independently hydrogen, substituted or unsubstituted $C_1$-$C_4$ alkyl, substituted or unsubstituted $C_1$-$C_4$ haloalkyl, or substituted or unsubstituted $C_3$-$C_5$ cycloalkyl; or wherein two $R^{5A}$ are joined together to form substituted or unsubstituted $C_2$-$C_5$ heterocycloalkyl).

In some embodiments, $R^1$ is —$CH_3$, —$CH_2CH_3$, cyclopropyl, cyclobutyl, cyclopentyl, —$CH_2OH$, —$CH_2CH_2OH$, —$CH_2CN$, —$CH_2NH_2$, —$CH_2NHCH_3$, —$CH_2N(CH_3)_2$, —$CH_2F$, —$CHF_2$, —$CF_3$, —$CH{=}CH_2$, —$C{\equiv}CH$, —OH, —$OCH_3$, —$OCH_2CH_3$, —$OCH_2CH_2OH$, —$OCH_2CN$, —$OCH_2F$, —$OCHF_2$, —$OCF_3$, —$OCH_2CH_2F$, —$OCH_2CHF_2$, —$OCH_2CF_3$, cyclopropyloxy, cyclobutyloxy, cyclopentyloxy, oxetanyl, tetrahydrofuranyl, tetrahydro-2H-pyranyl, azetidinyl, pyrrolidinyl, piperidinyl, triazolyl, tetrazolyl, phenyl, benzyl, —$NH_2$, —$NHCH_3$, —$N(CH_3)_2$, —$NHCH_2F$, —$NHCHF_2$, —$NHCF_3$, —$NHCH_2CH_2F$, —$NHCH_2CHF_2$, or —$NHCH_2CF_3$ (e.g., —$CH_3$, cyclopropyl, cyclobutyl, —$CH_2F$, —$CHF_2$, —$CF_3$, —OH, —$OCH_3$, —$OCH_2CH_3$, —$OCH_2F$, —$OCHF_2$, —$OCF_3$, —$OCH_2CH_2F$, —$OCH_2CHF_2$, —$OCH_2CF_3$, cyclopropyloxy, cyclobutyloxy, —$NH_2$, —$NHCH_3$, —$N(CH_3)_2$, —$NHCH_2F$, —$NHCHF_2$, —$NHCF_3$, —$NHCH_2CH_2F$, —$NHCH_2CHF_2$, or —$NHCH_2CF_3$) (e.g., —$OCH_3$, —$OCH_2CH_3$, —$OCH_2CH_2OH$, —$OCH_2CN$, —$OCH_2F$, —$OCHF_2$, —$OCF_3$, —$OCH_2CH_2F$, —$OCH_2CHF_2$, —$OCH_2CF_3$, cyclopropyloxy, or cyclobutyloxy)(e.g., —$OCH_3$, —$OCH_2CH_3$, cyclopropyloxy, or cyclobutyloxy)(e.g., —$OCH_2F$, —$OCHF_2$, —$OCF_3$, —$OCH_2CH_2F$, —$OCH_2CHF_2$, or —$OCH_2CF_3$)(e.g., —$NH_2$, —$NHCH_3$, —$N(CH_3)_2$, —$NHCH_2F$, —$NHCHF_2$, —$NHCF_3$, —$NHCH_2CH_2F$, —$NHCH_2CHF_2$, or —$NHCH_2CF_3$).

In some embodiments, $R^1$ is —$CH_3$, —$CH_2CH_3$, cyclopropyl, cyclobutyl, cyclopentyl, —$CH_2OH$, —$CH_2CH_2OH$, —$CH_2CN$, —$CH_2NH_2$, —$CH_2NHCH_3$, —$CH_2N(CH_3)_2$, —$CH_2F$, —$CHF_2$, —$CF_3$, —CH═$CH_2$, —C≡CH, —OH, —$OCH_3$, —$OCH_2CH_3$, —$OCH_2CH_2OH$, —$OCH_2CN$, —$OCH_2F$, —$OCHF_2$, —$OCF_3$, —$OCH_2CH_2F$, —$OCH_2CHF_2$, —$OCH_2CF_3$, cyclopropyloxy, cyclobutyloxy, cyclopentyloxy, azetidinyl, pyrrolidinyl, piperidinyl, triazolyl, tetrazolyl, phenyl, benzyl, —$NH_2$, —$NHCH_3$, —$N(CH_3)_2$, —$NHCH_2F$, —$NHCHF_2$, —$NHCF_3$, —$NHCH_2CH_2F$, —$NHCH_2CHF_2$, or —$NHCH_2CF_3$ (e.g., —$CH_3$, cyclopropyl, cyclobutyl, —$CH_2F$, —$CHF_2$, —$CF_3$, —OH, —$OCH_3$, —$OCH_2CH_3$, —$OCH_2F$, —$OCHF_2$, —$OCF_3$, —$OCH_2CH_2F$, —$OCH_2CHF_2$, —$OCH_2CF_3$, cyclopropyloxy, cyclobutyloxy, —$NH_2$, —$NHCH_3$, —$N(CH_3)_2$, —$NHCH_2F$, —$NHCHF_2$, —$NHCF_3$, —$NHCH_2CH_2F$, —$NHCH_2CHF_2$, or —$NHCH_2CF_3$)(e.g., —$OCH_3$, —$OCH_2CH_3$, —$OCH_2CH_2OH$, —$OCH_2CN$, —$OCH_2F$, —$OCHF_2$, —$OCF_3$, —$OCH_2CH_2F$, —$OCH_2CHF_2$, —$OCH_2CF_3$, cyclopropyloxy, or cyclobutyloxy)(e.g., —$OCH_3$, —$OCH_2CH_3$, cyclopropyloxy, or cyclobutyloxy)(e.g., —$OCH_2F$, —$OCHF_2$, —$OCF_3$, —$OCH_2CH_2F$, —$OCH_2CHF_2$, or —$OCH_2CF_3$)(e.g., —$NH_2$, —$NHCH_3$, —$N(CH_3)_2$, —$NHCH_2F$, —$NHCHF_2$, —$NHCF_3$, —$NHCH_2CH_2F$, —$NHCH_2CHF_2$, or —$NHCH_2CF_3$).

In some embodiments, $R^2$ is halogen, —CN, —S(═O)$R^{1A}$, —S(═O)$_2R^{5A}$, —S(═O)$_2N(R^{5A})_2$—C(═O)$R^{5A}$, —OC(═O)$R^{5A}$, —C(═O)O$R^{5A}$, —OC(═O)N$(R^{5A})_2$, —N$R^{5A}$C(═O)O$R^{5A}$, or —C(═O)N$(R^{5A})_2$ (e.g., F, Cl, —CN, —S(═O)$R^{5A}$, —S(═O)$_2R^{5A}$, —S(═O)$_2N(R^{5A})_2$, —C(═O)$R^{5A}$, —OC(═O)$R^{5A}$, —C(═O)O$R^{5A}$, —OC(═O)N$(R^{5A})_2$, —N$R^{5A}$C(═O)O$R^{5A}$, or —C(═O)N$(R^{5A})_2$) (e.g., F, Cl, —CN, —S(═O)$CH_3$, —S(═O)$_2CH_3$, —S(═O)$_2N(CH_3)_2$, —C(═O)$CH_3$, —OC(═O)$CH_3$, —C(═O)O$CH_3$, —OC(═O)N$(CH_3)_2$, —N$CH_3$C(═O)O$CH_3$, or —C(═O)N$(CH_3)_2$)(e.g., $R^2$ is F, Cl, or —CN) (e.g., F). In some embodiments, $R^2$ is hydrogen.

In some embodiments, $R^{3A}$ is hydrogen, substituted or unsubstituted $C_1$-$C_4$ alkyl, substituted or unsubstituted $C_1$-$C_6$ haloalkyl, substituted or unsubstituted $C_1$-$C_6$ heteroalkyl, substituted or unsubstituted $C_2$-$C_5$ alkenyl, or substituted or unsubstituted $C_2$-$C_5$ alkynyl (e.g., hydrogen, substituted or unsubstituted $C_1$-$C_4$ alkyl, substituted or unsubstituted $C_2$-$C_5$ alkenyl, or substituted or unsubstituted $C_2$-$C_5$ alkynyl)(e.g., hydrogen, —$CH_3$, —$CH_2CH_3$, —$CH_2(CH_3)_2$, cyclopropyl, cyclobutyl, —$CH_2OH$, —$CH_2CH_2OH$, —$CH_2CN$, —$CH_2NH_2$, —$CH_2NHCH_3$, —$CH_2N(CH_3)_2$, —$CH_2F$, —$CHF_2$, —$CF_3$, —CH═$CH_2$, —$CH_2$CH═$CH_2$, —C≡CH, or —$CH_2$C≡CH)(e.g., hydrogen, —$CH_3$, —$CH_2CH_3$, —$CH_2(CH_3)_2$, or cyclopropyl) (e.g., hydrogen or —$CH_3$)(e.g., hydrogen)(e.g., —$CH_2OH$, —$CH_2CH_2OH$, —$CH_2CN$, —$CH_2NH_2$, —$CH_2NHCH_3$, or —$CH_2N(CH_3)_2$) (e.g., —$CH_2F$, —$CHF_2$, —$CF_3$, —CH═$CH_2$, —$CH_2$CH═$CH_2$, —C≡CH, or —$CH_2$C≡CH).

In some embodiments, $R^{4A}$ is substituted or unsubstituted $C_1$-$C_4$ alkyl, substituted or unsubstituted $C_1$-$C_6$ haloalkyl, substituted or unsubstituted $C_1$-$C_6$ heteroalkyl, substituted or unsubstituted aryl, or substituted or unsubstituted heteroaryl (e.g., substituted or unsubstituted $C_1$-$C_4$ alkyl, substituted or unsubstituted aryl, or substituted or unsubstituted heteroaryl)(e.g., —$CH_3$, —$CH_2CH_3$, cyclopropyl, cyclobutyl, —$CH_2OH$, —$CH_2CH_2OH$, —$CH_2CN$, substituted or unsubstituted phenyl, or substituted or unsubstituted benzyl)(e.g., —$CH_3$, —$CH_2CH_3$, cyclopropyl, cyclobutyl, —$CH_2OH$, —$CH_2CH_2OH$, —$CH_2CN$, substituted or unsubstituted phenyl, or substituted or unsubstituted benzyl) (e.g., —$CH_3$, —$CH_2CH_3$, —$CH_2(CH_3)_2$, or cyclopropyl) (e.g., —$CH_3$).

In some embodiments, $R^{4A}$ is (e.g., substituted or unsubstituted aryl or substituted or unsubstituted heteroaryl)(e.g., substituted or unsubstituted aryl)(e.g., aryl substituted with 1, 2, 3, 4, or 5 substituents independently selected from halogen, —CN, $NO_2$, —O$R^{8A}$, —S$R^{8A}$, —OS(═O)$_2R^{8A}$, —N$(R^{8A})_2$, —C(═O)$R^{8A}$, —OC(═O)$R^{8A}$, —C(═O)O$R^{8A}$, —OC(═O)O$R^{8A}$, —C(═O)N$(R^{8A})_2$, substituted or unsubstituted $C_1$-$C_6$ alkyl, substituted or unsubstituted $C_1$-$C_6$ haloalkyl; and each $R^{8A}$ is independently hydrogen, substituted or unsubstituted $C_1$-$C_4$ alkyl, substituted or unsubstituted $C_1$-$C_4$ haloalkyl, substituted or unsubstituted $C_1$-$C_4$ heteroalkyl, substituted or unsubstituted $C_3$-$C_6$cycloalkyl, substituted or unsubstituted $C_2$-$C_5$ heterocycloalkyl, substituted or unsubstituted aryl, or substituted or unsubstituted heteroaryl) (e.g., aryl substituted with 1, 2, 3, 4, or 5 substituents independently selected from halogen, —CN, $NO_2$, —O$R^{8A}$, —N$(R^{8A})_2$, —C(═O)$R^{8A}$, —OC(═O)$R^{8A}$, —C(═O)O$R^{8A}$, —OC(═O)O$R^{8A}$, —C(═O)N$(R^{8A})_2$, substituted or unsubstituted $C_1$-$C_6$ alkyl, substituted or unsubstituted $C_1$-$C_6$ haloalkyl; and each $R^{8A}$ is independently hydrogen, substituted or unsubstituted $C_1$-$C_4$ alkyl, substituted or unsubstituted $C_1$-$C_4$ haloalkyl, substituted or unsubstituted $C_1$-$C_4$ heteroalkyl, substituted or unsubstituted $C_3$-$C_6$cycloalkyl, substituted or unsubstituted $C_2$-$C_5$ heterocycloalkyl, substituted or unsubstituted aryl, or substituted or unsubstituted heteroaryl) (e.g., aryl substituted with 1, 2, 3, 4, or 5 substituents independently selected from F, Cl, Br, —$CH_3$, —$CH_2CH_3$, —$CH_2CH_2CH_3$, —$CH(CH_3)_2$, —$CH_2F$, —$CHF_2$, —$CF_3$, —$CH_2CF_3$, —$CH_2OH$, —$CH_2CH_2OH$, —$CH_2CN$, —$CH_2$C(═O)OH, —$CH_2$C(═O)O$CH_3$, —$CH_2$C(═O)O$CH_2CH_3$, —$CH_2$C(═O)$NH_2$, —$CH_2$C(═O)NH$CH_3$, —$CH_2$C(═O)N$(CH_3)_2$, —$CH_2NH_2$, —$CH_2NHCH_3$, —$CH_2N(CH_3)_2$, —CH═$CH_2$, —C≡CH, cyclopropyl, cyclobutyl, cyclopentyl, cyclopropyloxy, cyclobutyloxy, cyclopentyloxy, oxetanyloxy, tetrahydrofuranyloxy, tetrahydropyranyloxy, azetidinyl, pyrrolidinyl, tetrazolyl, —CN, —OH, —$OCH_3$, —$OCH_2CH_3$, —$OCH_2CH_2OH$, —$OCH_2CN$, —$OCH_2F$, —$OCHF_2$, —$OCF_3$, —$OCH_2CF_3$, —$CO_2H$, —$CO_2CH_3$, —$CO_2CH_2CH_3$, —C(═O)$NH_2$, —C(═O)NH$CH_3$, —C(═O)N$(CH_3)_2$, —$NH_2$, —$NHCH_3$, —$N(CH_3)_2$, —NHC(═O)$CH_3$, —N$CH_3$C(═O)$CH_3$, —NHC(═O)O$CH_3$, —N$CH_3$C(═O)O$CH_3$, —S(═O)$CH_3$, —S(═O)$_2CH_3$, —NHS(═O)$_2CH_3$, or —N$(CH_3)$S(═O)$_2CH_3$)(e.g., aryl substituted with 1, 2, 3, 4, or 5 substituents independently selected from F, Cl, $—CH_3$, $—CH_2F$, $—CHF_2$, $—CF_3$, $—CH_2OH$, cyclopropyl, cyclopropyloxy, oxetanyloxy, azetidinyl, —CN, —OH, $—OCH_3$, $—OCH_2F$, $—OCHF_2$, $—OCF_3$, $—CO_2CH_3$, $—C(=O)NH_2$, $—C(=O)NHCH_3$, $—C(=O)N(CH_3)_2$, $—NH_2$, $—NHCH_3$, $—N(CH_3)_2$, $—NHC(=O)CH_3$, $—NCH_3C(=O)CH_3$, $—NHC(=O)OCH_3$, $—NCH_3C(=O)OCH_3$, $—S(=O)CH_3$, $—S(=O)_2CH_3$, $—NHS(=O)_2CH_3$, or $—N(CH_3)S(=O)_2CH_3$)(e.g., aryl substituted with 1, 2, 3, 4, or 5 substituents independently selected from F, Cl, $—CH_3$, $—CH_2F$, $—CHF_2$, $—CF_3$, cyclopropyl, cyclopropyloxy, oxetanyloxy, azetidinyl, —CN, —OH, $—OCH_3$, $—OCH_2F$, $—OCHF_2$, or $—OCF_3$) (e.g., aryl substituted with 1, 2, 3, 4, or 5 substituents independently selected from F, Cl, $—CH_3$, $—CH_2F$, $—CHF_2$, $—CF_3$, cyclopropyl, cyclopropyloxy, oxetanyloxy, azetidinyl, —CN, —OH, $—OCH_3$, $—OCH_2F$, $—OCHF_2$, or $—OCF_3$)(e.g., aryl substituted with 1, 2, 3, 4, or 5 substituents independently selected from F, Cl, $—CH_3$, $—CH_2F$, $—CHF_2$, $—CF_3$, —CN, $—OCH_3$, $—OCH_2F$, $—OCHF_2$, or $—OCF_3$)(e.g., aryl substituted with 1, 2, or 3 substituents independently selected from F, Cl, $—CH_3$, $—CH_2F$, $—CHF_2$, $—CF_3$, —CN, $—OCH_3$, $—OCH_2F$, $—OCHF_2$, or $—OCF_3$). In some embodiments, the aryl is phenyl.

In some embodiments, the benzenesulfonamide derivative compound described herein has a structure provided in Table 1.

TABLE 1

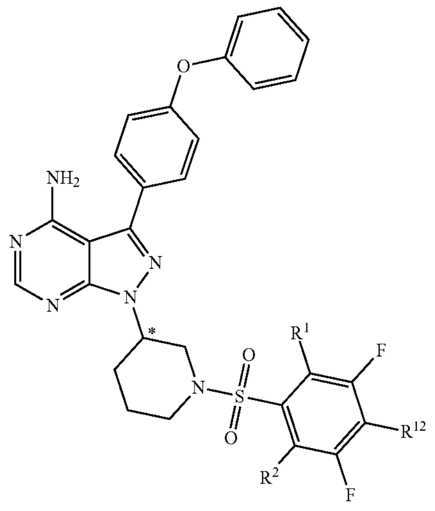

| Synthetic Chemistry Example | * | $R^1$ | $R^2$ | $R^{12}$ |
|---|---|---|---|---|
| A1 | R | F | F | F |
| A2 | S | F | F | F |
| A4 | R | H | F | F |
| A5 | R | F | F | H |
| A6 | R | —O-cyclopropyl | F | F |
| A7 | R | —O-cyclopropyl | —O-cyclopropyl | F |

In some embodiments, disclosed herein is a pharmaceutically acceptable salt, solvate, or stereoisomer of a compound of Table 1.

In some embodiments, the benzenesulfonamide derivative compound described herein has a structure provided in Table 2.

TABLE 2

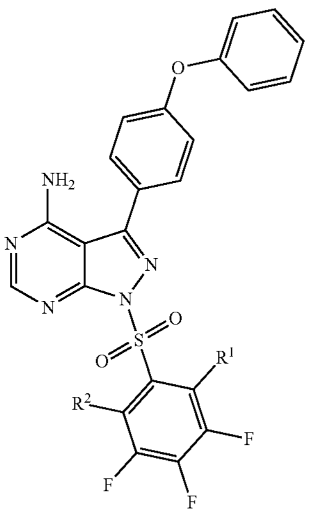

| Synthetic Chemistry Example | $R^1$ | $R^2$ |
|---|---|---|
| A3 | F | F |

In some embodiments, disclosed herein is a pharmaceutically acceptable salt or solvate of a compound of Table 2.

In some embodiments, the benzenesulfonamide derivative compound described herein has a structure provided in Table 3.

TABLE 3

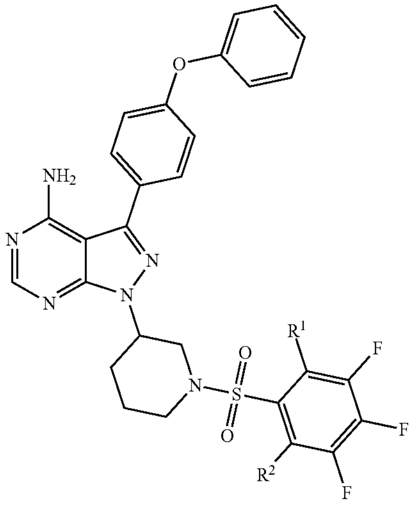

| $R^1$ | $R^2$ |
|---|---|
| $—OCH_2CHF_2$ | F |
| $—OCH_2CH_2F$ | F |
| $—OCF_3$ | F |

TABLE 3-continued

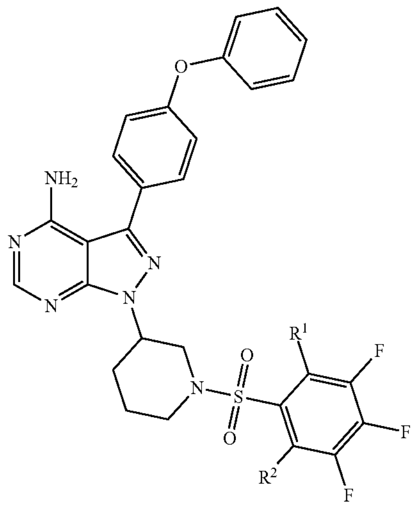

| $R^1$ | $R^2$ |
|---|---|
| —$OCHF_2$ | F |
| —$OCH_2F$ | F |
| —$OCH_3$ | F |
| —OH | F |
| —$NH_2$ | F |
| —$NHCH_3$ | F |
| 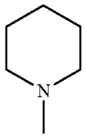 | F |
| —$NHCF_3$ | F |
| —$NHCH_2CF_3$ | F |
| —$CH_3$ | F |
| cyclopropyl | F |
| benzyl | F |

In some embodiments, disclosed herein is a pharmaceutically acceptable salt, solvate, or stereoisomer of a compound of Table 3.

In some embodiments, the benzenesulfonamide derivative compound described herein has a structure provided in Table 3A.

TABLE 3A

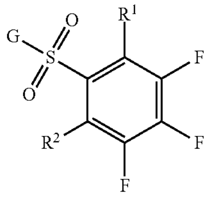

| Compound | G | $R^1$ | $R^2$ |
|---|---|---|---|
| Ibrutinib - $R^1$ and $R^2$ variant | | | |
| 3A-1 | 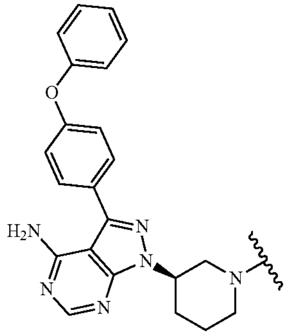 [SMILES: *N1CCC[C@@H](n2nc(-c3ccc(Oc4ccccc4)cc3)c3c(N)ncnc32)C1] | F | 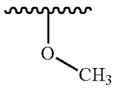 |
| 3A-2 | | F | 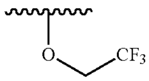 |
| 3A-3 | | F | 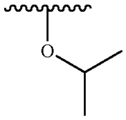 |
| 3A-4 | | F | H |
| 3A-5 | | F | $CF_3$ |
| 3A-6 | 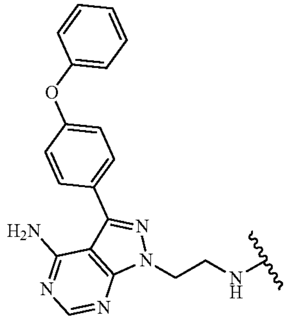 [SMILES: *NCCn1nc(-c2ccc(Oc3ccccc3)cc2)c2c(N)ncnc21] | F | 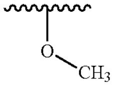 |
| 3A-7 | | F | $CF_3$ |
| 3A-8 | | F | OH |
| 3A-9 | | F | F |
| 3A-10 | 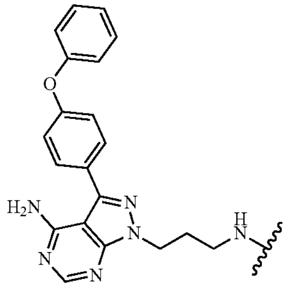 [SMILES: *NCCCn1nc(-c2ccc(Oc3ccccc3)cc2)c2c(N)ncnc21] | F | F |
| 3A-11 | 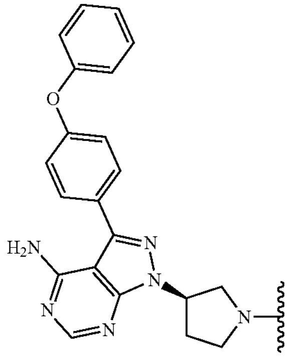 [SMILES: *N1CC[C@@H](n2nc(-c3ccc(Oc4ccccc4)cc3)c3c(N)ncnc32)C1] | F | F |
| 3A-12 | | F | $CF_3$ |
| 3A-13 | | F | OH |
| 3A-14 | | F | $OCFH_2$ |
| 3A-15 | | F | $OCF_2H$ |
| 3A-16 | | F | $OCF_3$ |
| 3A-17 | | F | CN |
| 3A-18 | | F | $NO_2$ |
| 3A-19 | | F | $SO_2CH_3$ |
| 3A-20 | | F | SOR |
| 3A-21 | | F | $SO_2R$ |
| 3A-22 | | F | $SO_2NRR$ |
| 3A-23 | | Br | OH |

TABLE 3A-continued
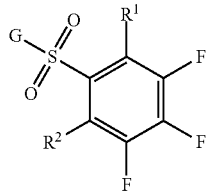
| Compound | G | $R^1$ | $R^2$ |
|---|---|---|---|
| 3A-24 | 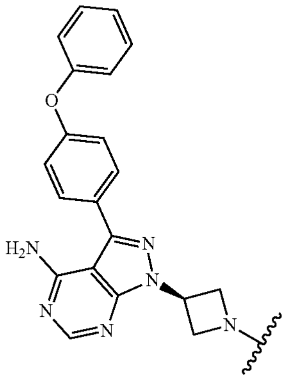 | F | F |
| JAK3 - $R^1$ and $R^2$ variant | | | |
| 3A-25 | 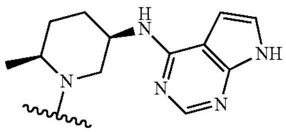 [SMILES: *N1C[C@H](Nc2ncnc3[nH]ccc23)CC[C@@H]1C] | F | F |
| 3A-26 | 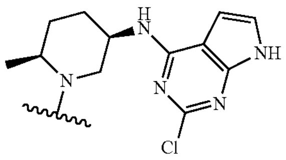 [SMILES: *N1C[C@H](Nc2nc(Cl)nc3[nH]ccc23)CC[C@@H]1C] | F | F |
| 3A-27 | 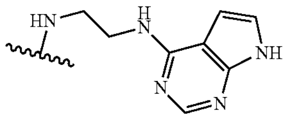 [SMILES: *NCCNc1ncnc2[nH]ccc12] | F | F |
| 3A-28 | 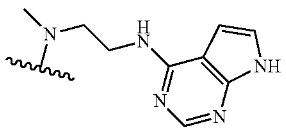 [SMILES: *N(C)CCNc1ncnc2[nH]ccc12] | F | F |
| 3A-30 | 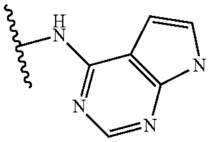 [SMILES: *Nc1ncnc2[nH]ccc12] | F | $CF_3$ |
| 3A-31 | | F | $CF_2H$ |
| 3A-32 | | F | $OCH_2F$ |
| 3A-33 | | F | $OCHF_2$ |
| 3A-34 | | F | $OCF_3$ |
| 3A-35 | | F | CN |
| 3A-36 | | F | $NO_2$ |
TABLE 3A-continued
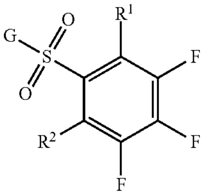
| Compound | G | $R^1$ | $R^2$ |
|---|---|---|---|
| Spebrutinib - $R^1$ and $R^2$ variant | | | |
| 3A-37 | 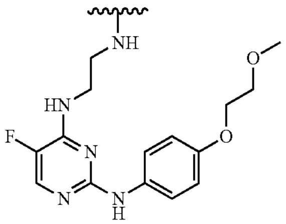 [SMILES: *NCCNc1nc(Nc2ccc(OCCOC)cc2)ncc1F] | F | F |
| 3A-38 | 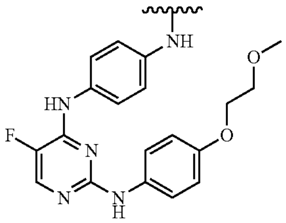 [SMILES: *Nc1ccc(Nc2nc(Nc3ccc(OCCOC)cc3)ncc2F)cc1] | F | F |
| 3A-39 | 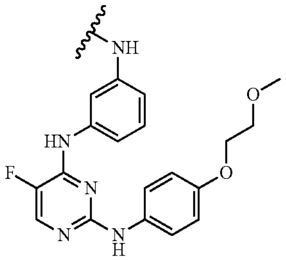 [SMILES: *Nc1cccc(Nc2nc(Nc3ccc(OCCOC)cc3)ncc2F)c1] | F | F |
| 3A-40 | | F | $CF_3$ |
| 3A-41 | 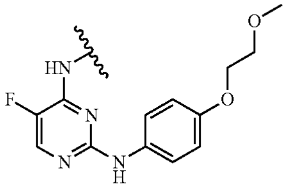 [SMILES: *Nc1nc(Nc2ccc(OCCOC)cc2)ncc1F] | F | F |
| 3A-42 | | F | $CF_3$ |
| Direct Attachement to Hinge binder | | | |
| 3A-43 | 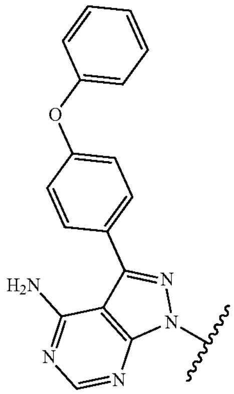 [SMILES: *n1nc(-c2ccc(Oc3ccccc3)cc2)c2c(N)ncnc21] | F | F |
| 3A-44 | | F | $CF_3$ |
| 3A-45 | | F | OMe |
| 3A-46 | | F | $OCFH_2$ |
| 3A-47 | | F | $OCF_2H$ |
| 3A-48 | | F | $OCF_3$ |
| 3A-49 | | F | $CF_2$ |

In some embodiments, disclosed herein is a pharmaceutically acceptable salt, solvate, or stereoisomer of a compound of Table 3A.

In some embodiments, the benzenesulfonamide derivative compound described herein has a structure provided in Table 4.

TABLE 4

| Synthetic Chemistry Example | Compound Structure | Compound Name |
|---|---|---|
| 2 | 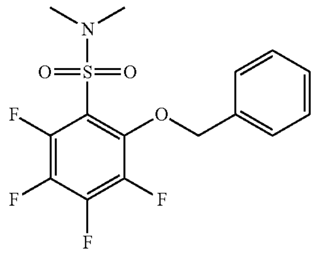 | 2-(benzyloxy)-3,4,5,6-tetrafluoro-N,N-dimethylbenzenesulfonamide |
| 3 | 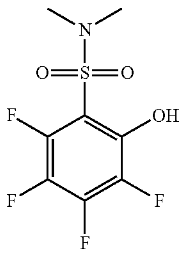 | 2,3,4,5-tetrafluoro-6-hydroxy-N,N-dimethylbenzenesulfonamide |
| 4 | 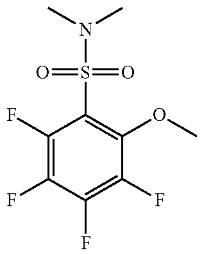 [SMILES: COc1c(F)c(F)c(F)c(F)c1S(=O)(=O)N(C)C] | 2,3,4,5-tetrafluoro-6-methoxy-N,N-dimethylbenzenesulfonamide |
| 5 | 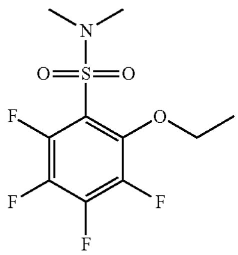 | 2-ethoxy-3,4,5,6-tetrafluoro-N,N-dimethylbenzenesulfonamide |
| 6 | 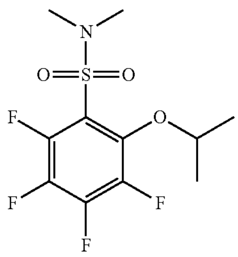 | 2,3,4,5-tetrafluoro-6-isopropoxy-N,N-dimethylbenzenesulfonamide |

TABLE 4-continued

| Synthetic Chemistry Example | Compound Structure | Compound Name |
|---|---|---|
| 7 | 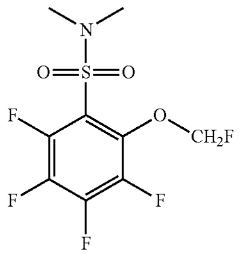 | 2,3,4,5-tetrafluoro-6-(fluoromethoxy)-N,N-dimethylbenzenesulfonamide |
| 8 | 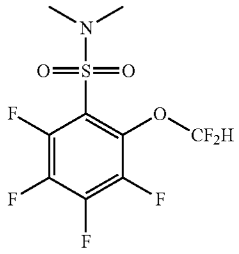 [SMILES: CN(C)S(=O)(=O)c1c(F)c(F)c(F)c(F)c1OC(F)F] | 2-(difluoromethoxy)-3,4,5,6-tetrafluoro-N,N-dimethylbenzenesulfonamide |
| 9 | 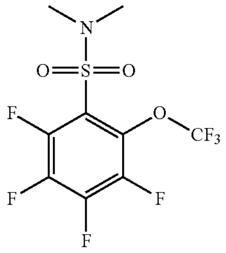 | 2,3,4,5-tetrafluoro-N,N-dimethyl-6-(trifluoromethoxy)benzenesulfonamide |
| 10 | 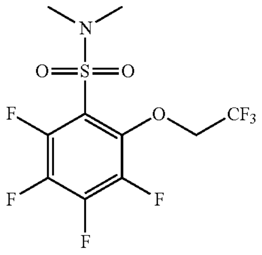 [SMILES: CN(C)S(=O)(=O)c1c(F)c(F)c(F)c(F)c1OCC(F)(F)F] | 2,3,4,5-tetrafluoro-N,N-dimethyl-6-(2,2,2-trifluoroethoxy)benzenesulfonamide |
| 11 | 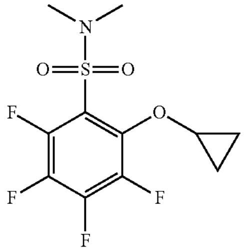 [SMILES: CN(C)S(=O)(=O)c1c(F)c(F)c(F)c(F)c1OC1CC1] | 2-cyclopropoxy-3,4,5,6-tetrafluoro-N,N-dimethylbenzenesulfonamide |

TABLE 4-continued

| Synthetic Chemistry Example | Compound Structure | Compound Name |
|---|---|---|
| 12 | 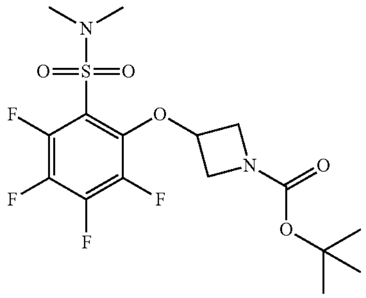 [SMILES: CN(C)S(=O)(=O)c1c(F)c(F)c(F)c(F)c1OC1CN(C(=O)OC(C)(C)C)C1] | 3-(2-(N,N-dimethylsulfamoyl)-3,4,5,6-tetrafluorophenoxy)azetidine-1-carboxylate |
| 13 | 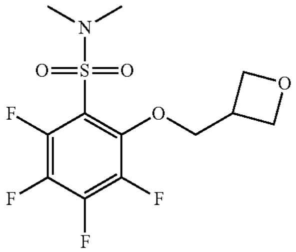 [SMILES: CN(C)S(=O)(=O)c1c(F)c(F)c(F)c(F)c1OCC1COC1] | 2,3,4,5-tetrafluoro-N,N-dimethyl-6-(oxetan-3-ylmethoxy)benzenesulfonamide |
| 14 | 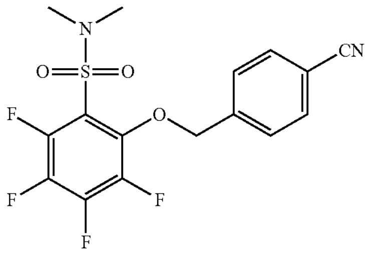 [SMILES: CN(C)S(=O)(=O)c1c(F)c(F)c(F)c(F)c1OCc1ccc(C#N)cc1] | 2-((4-cyanobenzyl)oxy)-3,4,5,6-tetrafluoro-N,N-dimethylbenzenesulfonamide |
| 15 | 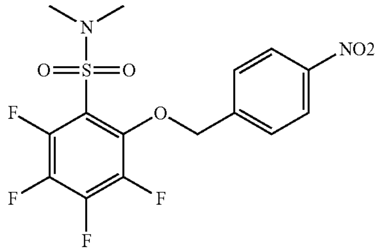 [SMILES: CN(C)S(=O)(=O)c1c(F)c(F)c(F)c(F)c1OCc1ccc([N+](=O)[O-])cc1] | 2,3,4,5-tetrafluoro-N,N-dimethyl-6-((4-nitrobenzyl)oxy)benzenesulfonamide |
| 16 | 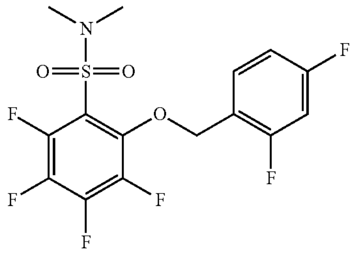 [SMILES: CN(C)S(=O)(=O)c1c(F)c(F)c(F)c(F)c1OCc1ccc(F)cc1F] | 2-((2,4-difluorobenzyl)oxy)-3,4,5,6-tetrafluoro-N,N-dimethylbenzenesulfonamide |

TABLE 4-continued

| Synthetic Chemistry Example | Compound Structure | Compound Name |
|---|---|---|
| 17 | 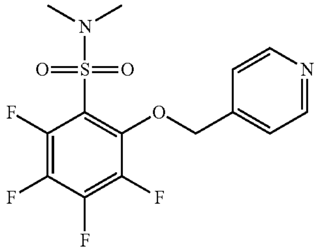 [SMILES: CN(C)S(=O)(=O)c1c(F)c(F)c(F)c(F)c1OCc1ccncc1] | 2,3,4,5-tetrafluoro-N,N-dimethyl-6-(pyridin-4-ylmethoxy)benzenesulfonamide |
| 18 | 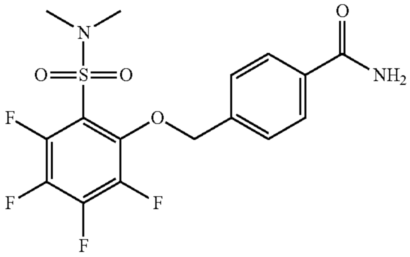 [SMILES: CN(C)S(=O)(=O)c1c(F)c(F)c(F)c(F)c1OCc1ccc(C(N)=O)cc1] | 4-((2-(N,N-dimethylsulfamoyl)-3,4,5,6-tetrafluorophenoxy)methyl)benzamide |
| 19 | 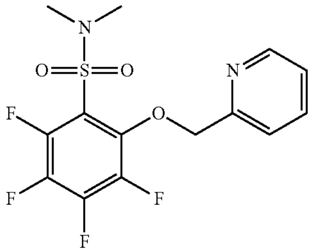 [SMILES: CN(C)S(=O)(=O)c1c(F)c(F)c(F)c(F)c1OCc1ccccn1] | 2,3,4,5-tetrafluoro-N,N-dimethyl-6-(pyridin-2-ylmethoxy)benzenesulfonamide |
| 20 | 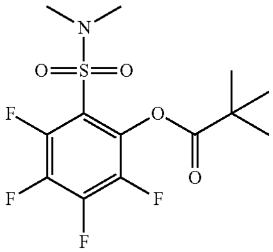 [SMILES: CN(C)S(=O)(=O)c1c(F)c(F)c(F)c(F)c1OC(=O)C(C)(C)C] | 2-(N,N-dimethylsulfamoyl)-3,4,5,6-tetrafluorophenyl pivalate |
| 21 | 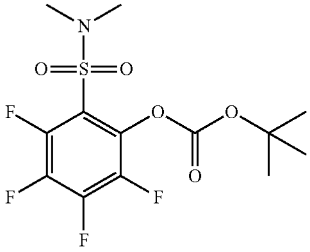 [SMILES: CN(C)S(=O)(=O)c1c(F)c(F)c(F)c(F)c1OC(=O)OC(C)(C)C] | tert-butyl (2-(N,N-dimethylsulfamoyl)-3,4,5,6-tetrafluorophenyl) carbonate |
| 22 | 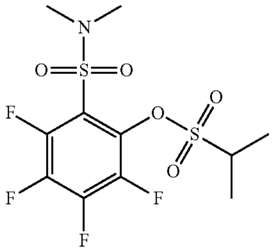 [SMILES: CC(C)S(=O)(=O)Oc1c(F)c(F)c(F)c(F)c1S(=O)(=O)N(C)C] | 2-(N,N-dimethylsulfamoyl)-3,4,5,6-tetrafluorophenyl propane-2-sulfonate |

TABLE 4-continued

| Synthetic Chemistry Example | Compound Structure | Compound Name |
|---|---|---|
| 23 | 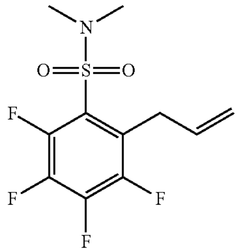 | 2-allyl-3,4,5,6-tetrafluoro-N,N-dimethylbenzenesulfonamide |
| 24 | 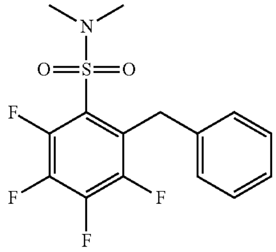 [SMILES: CN(C)S(=O)(=O)c1c(F)c(F)c(F)c(F)c1Cc1ccccc1] | 2-benzyl-3,4,5,6-tetrafluoro-N,N-dimethylbenzenesulfonamide |
| 25 | 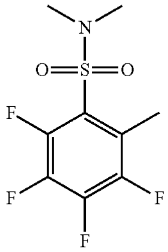 | 2,3,4,5-tetrafluoro-N,N,6-trimethylbenzenesulfonamide |
| 26 | 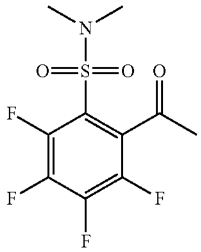 [SMILES: CC(=O)c1c(F)c(F)c(F)c(F)c1S(=O)(=O)N(C)C] | 2-acetyl-3,4,5,6-tetrafluoro-N,N-dimethylbenzenesulfonamide |
| 27 | 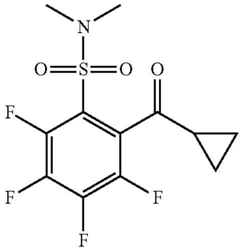 | 2-(cyclopropanecarbonyl)-3,4,5,6-tetrafluoro-N,N-dimethylbenzenesulfonamide |
| 28 | 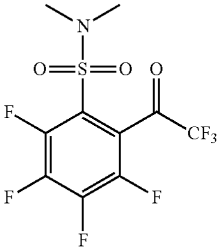 [SMILES: CN(C)S(=O)(=O)c1c(F)c(F)c(F)c(F)c1C(=O)C(F)(F)F] | 2,3,4,5-tetrafluoro-N,N-dimethyl-6-(2,2,2-trifluoroacetyl)benzenesulfonamide |

TABLE 4-continued

| Synthetic Chemistry Example | Compound Structure | Compound Name |
|---|---|---|
| 29 | 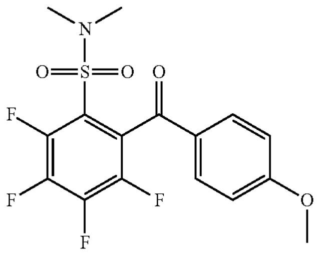 [SMILES: COc1ccc(C(=O)c2c(F)c(F)c(F)c(F)c2S(=O)(=O)N(C)C)cc1] | 2,3,4,5-tetrafluoro-6-(4-methoxybenzoyl)-N,N-dimethylbenzenesulfonamide |
| 30 | 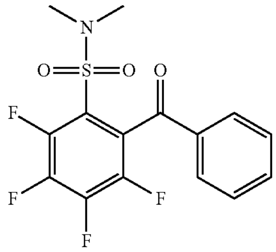 [SMILES: CN(C)S(=O)(=O)c1c(F)c(F)c(F)c(F)c1C(=O)c1ccccc1] | 2-benzoyl-3,4,5,6-tetrafluoro-N,N-dimethylbenzenesulfonamide |
| 31 | 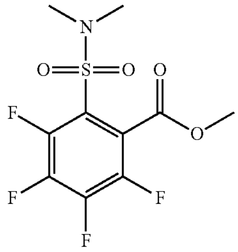 [SMILES: COC(=O)c1c(F)c(F)c(F)c(F)c1S(=O)(=O)N(C)C] | 2-(N,N-dimethylsulfamoyl)-3,4,5,6-tetrafluorobenzoate |
| 32 | 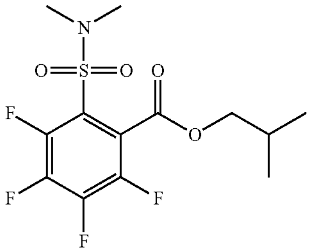 [SMILES: CC(C)COC(=O)c1c(F)c(F)c(F)c(F)c1S(=O)(=O)N(C)C] | 2-(N,N-dimethylsulfamoyl)-3,4,5,6-tetrafluorobenzoate |
| 33 | 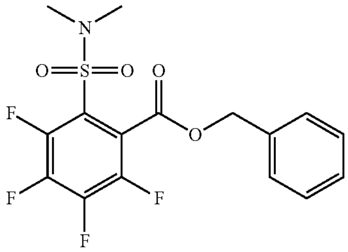 [SMILES: CN(C)S(=O)(=O)c1c(F)c(F)c(F)c(F)c1C(=O)OCc1ccccc1] | 2-(N,N-dimethylsulfamoyl)-3,4,5,6-tetrafluorobenzoate |
| 34 | 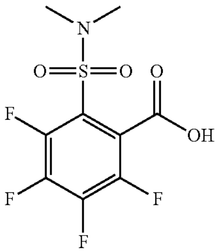 | 2-(N,N-dimethylsulfamoyl)-3,4,5,6-tetrafluorobenzoic acid |

TABLE 4-continued

| Synthetic Chemistry Example | Compound Structure | Compound Name |
|---|---|---|
| 35 | 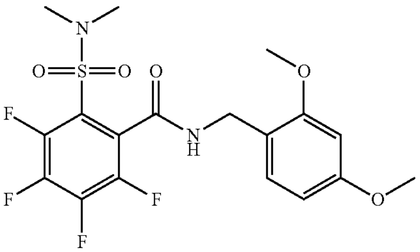 [SMILES: COc1ccc(CNC(=O)c2c(F)c(F)c(F)c(F)c2S(=O)(=O)N(C)C)c(OC)c1] | N-(2,4-dimethoxybenzyl)-2-(N,N-dimethylsulfamoyl)-3,4,5,6-tetrafluorobenzamide |
| 36 | 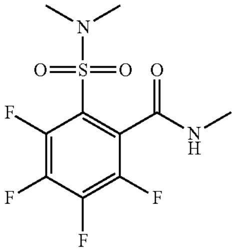 [SMILES: CNC(=O)c1c(F)c(F)c(F)c(F)c1S(=O)(=O)N(C)C] | 2-(N,N-dimethylsulfamoyl)-3,4,5,6-tetrafluoro-N-methylbenzamide |
| 37 | 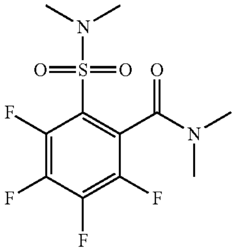 [SMILES: CN(C)C(=O)c1c(F)c(F)c(F)c(F)c1S(=O)(=O)N(C)C] | 2-(N,N-dimethylsulfamoyl)-3,4,5,6-tetrafluoro-N,N-dimethylbenzamide |
| 38 | 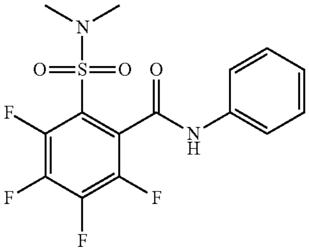 [SMILES: CN(C)S(=O)(=O)c1c(F)c(F)c(F)c(F)c1C(=O)Nc1ccccc1] | 2-(N,N-dimethylsulfamoyl)-3,4,5,6-tetrafluoro-N-phenylbenzamide |
| 39 | 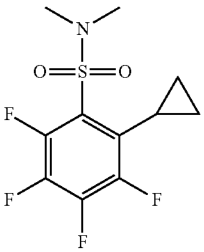 [SMILES: CN(C)S(=O)(=O)c1c(F)c(F)c(F)c(F)c1C1CC1] | 2-cyclopropyl-3,4,5,6-tetrafluoro-N,N-dimethylbenzenesulfonamide |
| 40 | 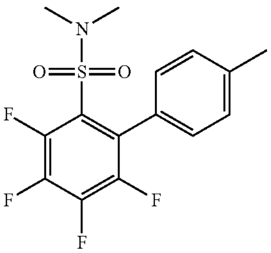 [SMILES: Cc1ccc(-c2c(F)c(F)c(F)c(F)c2S(=O)(=O)N(C)C)cc1] | 3,4,5,6-tetrafluoro-N,N,4'-trimethyl-[1,1'-biphenyl]-2-sulfonamide |

TABLE 4-continued

| Synthetic Chemistry Example | Compound Structure | Compound Name |
|---|---|---|
| 41 | 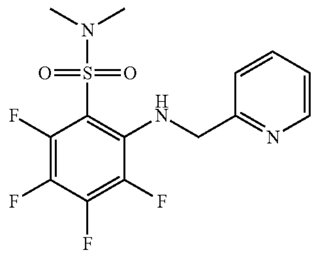 [SMILES: CN(C)S(=O)(=O)c1c(F)c(F)c(F)c(F)c1NCc1ccccn1] | 2,3,4,5-tetrafluoro-N,N-dimethyl-6-((pyridin-2-ylmethyl)amino)benzenesulfonamide |
| 42 | 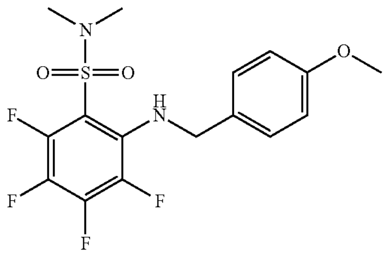 | 2,3,4,5-tetrafluoro-6-((4-methoxybenzyl)amino)-N,N-dimethylbenzenesulfonamide |
| 43 | 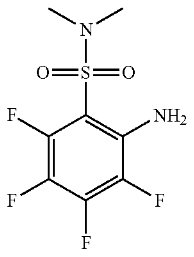 [SMILES: CN(C)S(=O)(=O)c1c(N)c(F)c(F)c(F)c1F] | 2-amino-3,4,5,6-tetrafluoro-N,N-dimethylbenzenesulfonamide |
| 44 | 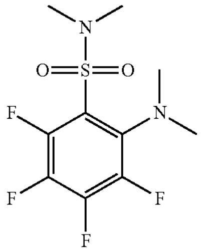 [SMILES: CN(C)c1c(F)c(F)c(F)c(F)c1S(=O)(=O)N(C)C] | 2-(dimethylamino)-3,4,5,6-tetrafluoro-N,N-dimethylbenzenesulfonamide |
| 45 | 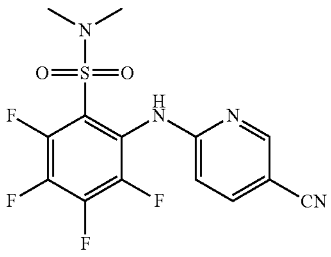 [SMILES: CN(C)S(=O)(=O)c1c(F)c(F)c(F)c(F)c1Nc1ccc(C#N)cn1] | 2,3,4,5-tetrafluoro-6-((3-fluoro-4-methoxybenzyl)amino)-N,N-dimethylbenzenesulfonamide |
| 46 | 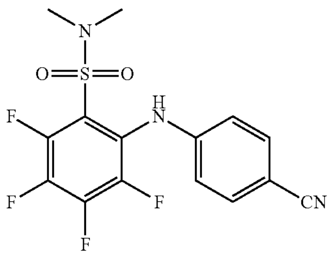 [SMILES: CN(C)S(=O)(=O)c1c(F)c(F)c(F)c(F)c1Nc1ccc(C#N)cc1] | 2-((4-cyanophenyl)amino)-3,4,5,6-tetrafluoro-N,N-dimethylbenzenesulfonamide |

TABLE 4-continued

| Synthetic Chemistry Example | Compound Structure | Compound Name |
|---|---|---|
| 47 | 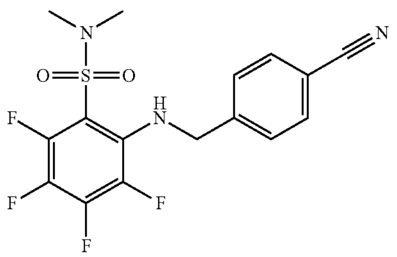 [SMILES: CN(C)S(=O)(=O)c1c(F)c(F)c(F)c(F)c1NCc1ccc(C#N)cc1] | 2-((4-cyanobenzyl)amino)-3,4,5,6-tetrafluoro-N,N-dimethylbenzenesulfonamide |
| 48 | 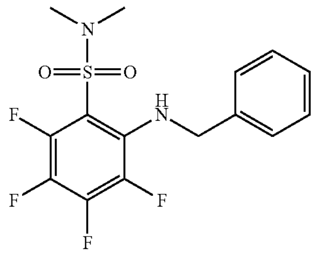 [SMILES: CN(C)S(=O)(=O)c1c(F)c(F)c(F)c(F)c1NCc1ccccc1] | 2-(benzylamino)-3,4,5,6-tetrafluoro-N,N-dimethylbenzenesulfonamide |
| 49 | 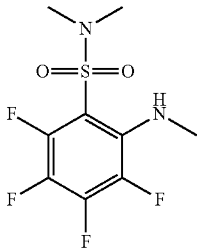 [SMILES: CNc1c(F)c(F)c(F)c(F)c1S(=O)(=O)N(C)C] | 2,3,4,5-tetrafluoro-N,N-dimethyl-6-(methylamino)benzenesulfonamide |
| 50 | 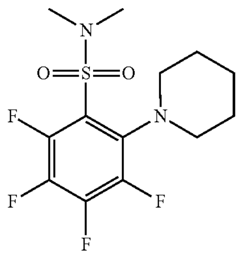 | 2,3,4,5-tetrafluoro-N,N-dimethyl-6-(piperidin-1-yl)benzenesulfonamide |
| 51 | 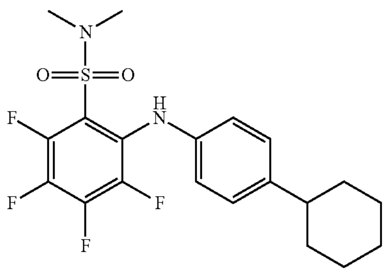 [SMILES: CN(C)S(=O)(=O)c1c(F)c(F)c(F)c(F)c1Nc1ccc(C2CCCCC2)cc1] | 2-((4-cyclohexylphenyl)amino)-3,4,5,6-tetrafluoro-N,N-dimethylbenzenesulfonamide |

TABLE 4-continued

| Synthetic Chemistry Example | Compound Structure | Compound Name |
|---|---|---|
| 52 | 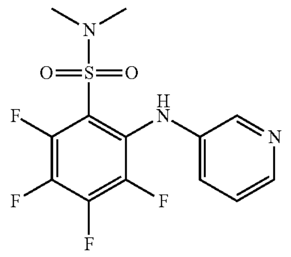 | 2,3,4,5-tetrafluoro-N,N-dimethyl-6-(pyridin-3-ylamino)benzenesulfonamide |
| 53 | 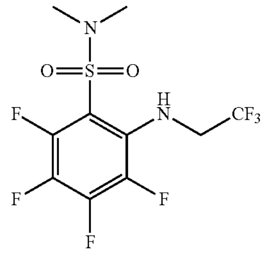 [SMILES: CN(C)S(=O)(=O)c1c(F)c(F)c(F)c(F)c1NCC(F)(F)F] | 2,3,4,5-tetrafluoro-N,N-dimethyl-6-(pyridin-2-ylamino)benzenesulfonamide |
| 54 | 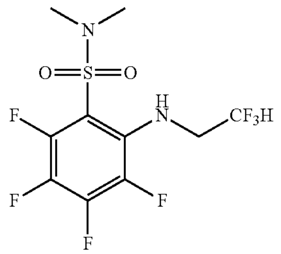 | 2-((2,2-difluoroethyl)amino)-3,4,5,6-tetrafluoro-N,N-dimethylbenzenesulfonamide |
| 55 | 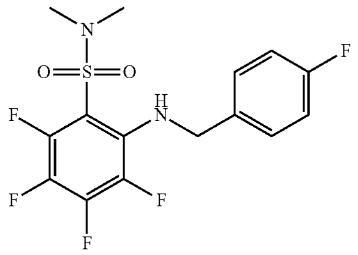 [SMILES: CN(C)S(=O)(=O)c1c(F)c(F)c(F)c(F)c1NCc1ccc(F)cc1] | 2,3,4,5-tetrafluoro-6-((4-fluorobenzyl)amino)-N,N-dimethylbenzenesulfonamide |
| 56 | 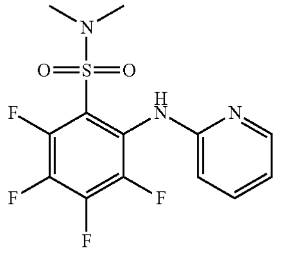 [SMILES: CN(C)S(=O)(=O)c1c(F)c(F)c(F)c(F)c1Nc1ccccn1] | 2,3,4,5-tetrafluoro-N,N-dimethyl-6-(pyridin-2-ylamino)benzenesulfonamide |
| 57 | 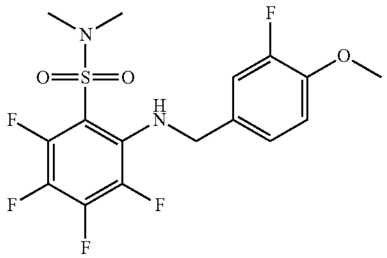 [SMILES: COc1ccc(CNc2c(F)c(F)c(F)c(F)c2S(=O)(=O)N(C)C)cc1F] | 2,3,4,5-tetrafluoro-6-((3-fluoro-4-methoxybenzyl)amino)-N,N-dimethylbenzenesulfonamide |

TABLE 4-continued

| Synthetic Chemistry Example | Compound Structure | Compound Name |
|---|---|---|
| 58 | 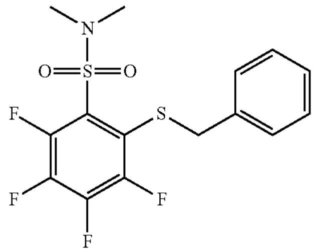 | 2-(benzylthio)-3,4,5,6-tetrafluoro-N,N-dimethylbenzenesulfonamide |
| 59 | 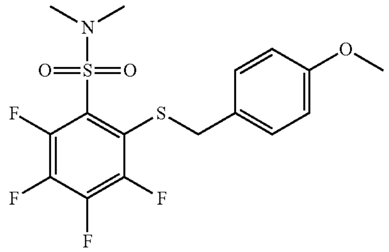 | 2,3,4,5-tetrafluoro-6-((4-methoxybenzyl)thio)-N,N-dimethylbenzenesulfonamide |
| 60 | 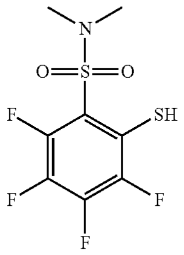 [SMILES: CN(C)S(=O)(=O)c1c(F)c(F)c(F)c(F)c1S] | 2,3,4,5-tetrafluoro-6-((4-methoxybenzyl)thio)-N,N-dimethylbenzenesulfonamide |
| 61 | 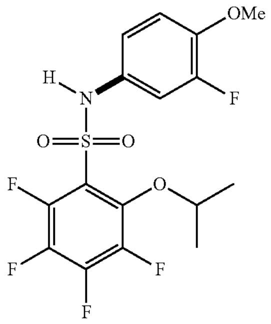 | 2,3,4,5-tetrafluoro-N-(3-fluoro-4-methoxyphenyl)-6-isopropoxybenzenesulfonamide |
| 62 | 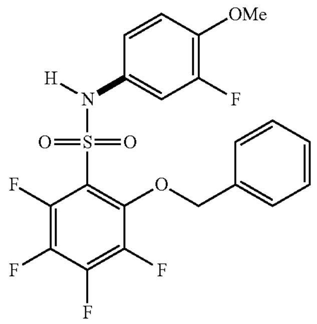 | 2-(benzyloxy)-3,4,5,6-tetrafluoro-N-(3-fluoro-4-methoxyphenyl)benzenesulfonamide |

TABLE 4-continued

| Synthetic Chemistry Example | Compound Structure | Compound Name |
|---|---|---|
| 63 | 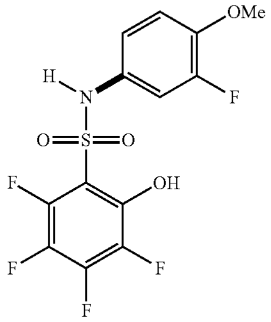 | 2,3,4,5-tetrafluoro-N-(3-fluoro-4-methoxyphenyl)-6-hydroxybenzenesulfonamide |
| 64 | 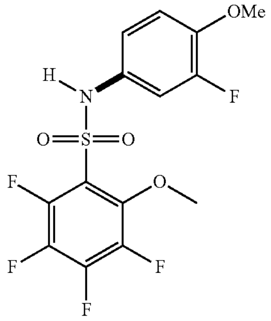 | 2,3,4,5-tetrafluoro-N-(3-fluoro-4-methoxyphenyl)-6-methoxybenzenesulfonamide |
| 65 | 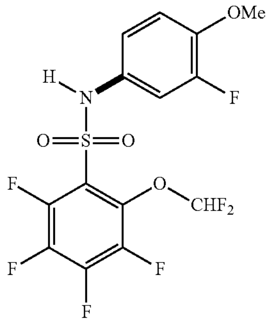 | 2-(difluoromethoxy)-3,4,5,6-tetrafluoro-N-(3-fluoro-4-methoxyphenyl)benzenesulfonamide |
| 66 | 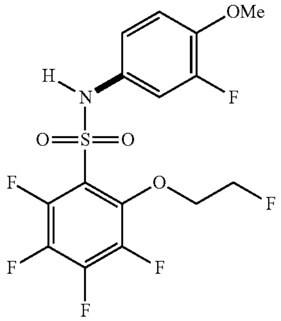 | 2,3,4,5-tetrafluoro-N-(3-fluoro-4-methoxyphenyl)-6-(2-fluoroethoxy)benzenesulfonamide |

TABLE 4-continued

| Synthetic Chemistry Example | Compound Structure | Compound Name |
|---|---|---|
| 67 | 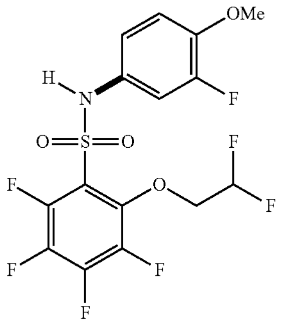 | 2-(2,2-difluoroethoxy)-3,4,5,6-tetrafluoro-N-(3-fluoro-4-methoxyphenyl)benzenesulfonamide |
| 68 | 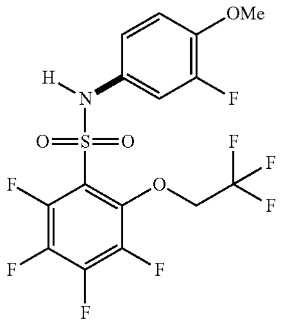 | 2,3,4,5-tetrafluoro-N-(3-fluoro-4-methoxyphenyl)-6-(2,2,2-trifluoroethoxy)benzenesulfonamide |
| 69 | 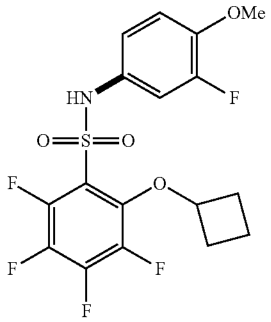 | 2-cyclobutoxy-3,4,5,6-tetrafluoro-N-(3-fluoro-4-methoxyphenyl)benzenesulfonamide |
| 70 | 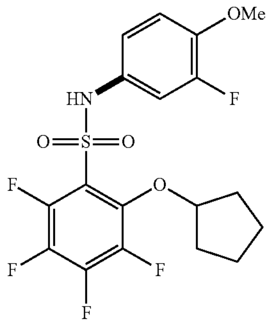 | 2-(cyclopentyloxy)-3,4,5,6-tetrafluoro-N-(3-fluoro-4-methoxyphenyl)benzenesulfonamide |

TABLE 4-continued

| Synthetic Chemistry Example | Compound Structure | Compound Name |
|---|---|---|
| 71 | 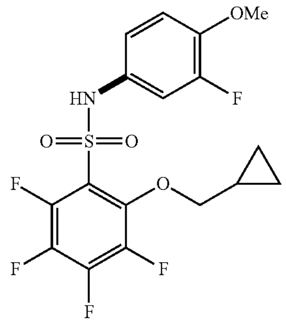 | 2-(cyclopropylmethoxy)-3,4,5,6-tetrafluoro-N-(3-fluoro-4-methoxyphenyl)benzenesulfonamide |
| 72 | 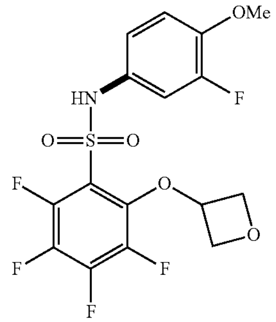 | 2,3,4,5-tetrafluoro-N-(3-fluoro-4-methoxyphenyl)-6-(oxetan-3-yloxy)benzenesulfonamide |
| 73 | 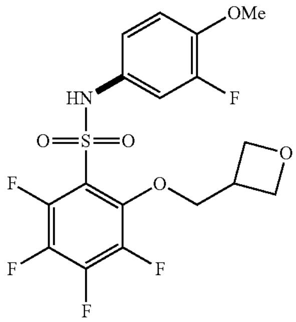 | 2,3,4,5-tetrafluoro-N-(3-fluoro-4-methoxyphenyl)-6-(oxetan-3-ylmethoxy)benzenesulfonamide |
| 74 | 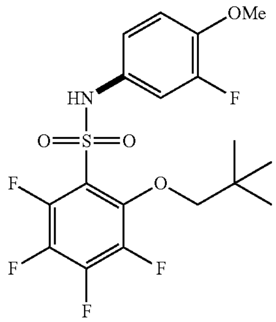 | 2,3,4,5-tetrafluoro-N-(3-fluoro-4-methoxyphenyl)-6-(neopentyloxy)benzenesulfonamide |

TABLE 4-continued

| Synthetic Chemistry Example | Compound Structure | Compound Name |
|---|---|---|
| 75 | 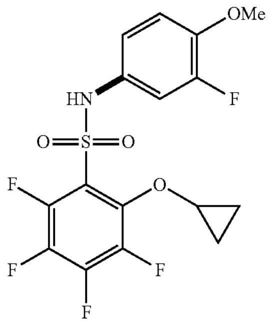 | 2-cyclopropoxy-3,4,5,6-tetrafluoro-N-(3-fluoro-4-methoxyphenyl)benzenesulfonamide |
| 76 | 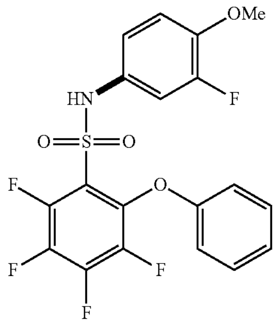 | 2,3,4,5-tetrafluoro-N-(3-fluoro-4-methoxyphenyl)-6-phenoxybenzenesulfonamide |
| 77 | 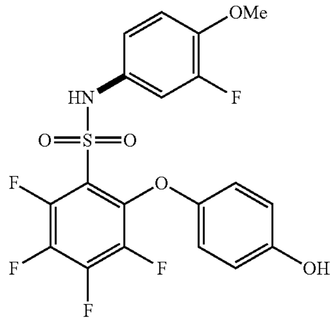 | 2,3,4,5-tetrafluoro-N-(3-fluoro-4-methoxyphenyl)-6-(4-hydroxyphenoxy)benzenesulfonamide |
| 78 | 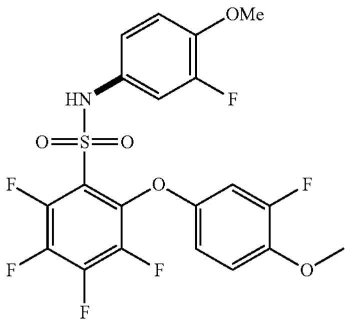 | 2,3,4,5-tetrafluoro-6-(3-fluoro-4-methoxyphenoxy)-N-(3-fluoro-4-methoxyphenyl)benzenesulfonamide |

TABLE 4-continued

| Synthetic Chemistry Example | Compound Structure | Compound Name |
| --- | --- | --- |
| 79 | 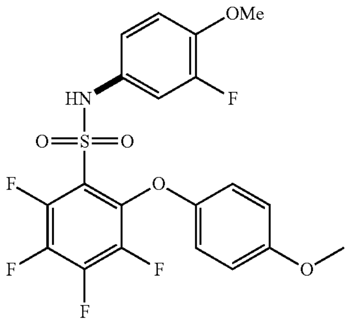 | 2,3,4,5-tetrafluoro-N-(3-fluoro-4-methoxyphenyl)-6-(4-methoxyphenoxy)benzenesulfonamide |
| 80 | 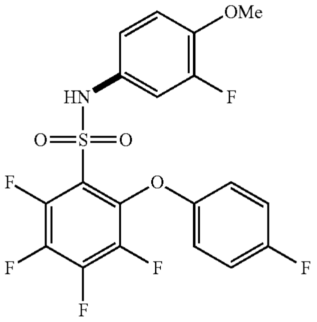 | 2,3,4,5-tetrafluoro-N-(3-fluoro-4-methoxyphenyl)-6-(4-fluorophenoxy)benzenesulfonamide |
| 81 | 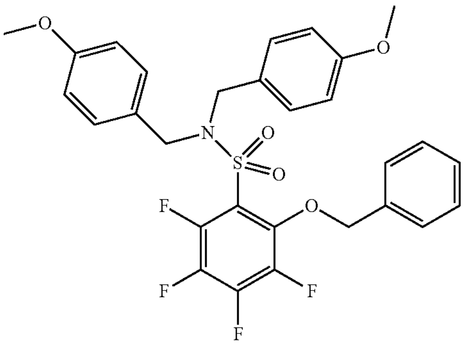 [SMILES: COc1ccc(CN(Cc2ccc(OC)cc2)S(=O)(=O)c2c(F)c(F)c(F)c(F)c2OCc2ccccc2)cc1] | 2-(benzyloxy)-3,4,5,6-tetrafluoro-N,N-bis(4-methoxybenzyl)benzenesulfonamide |
| 82 | 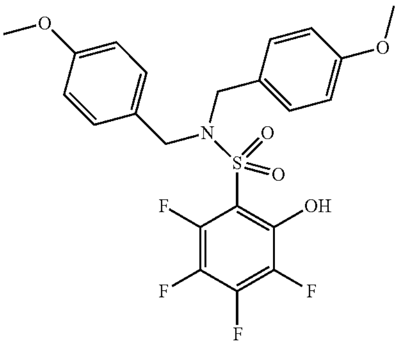 | 2,3,4,5-tetrafluoro-6-hydroxy-N,N-bis(4-methoxybenzyl)benzenesulfonamide |

TABLE 4-continued

| Synthetic Chemistry Example | Compound Structure | Compound Name |
| --- | --- | --- |
| 83 | 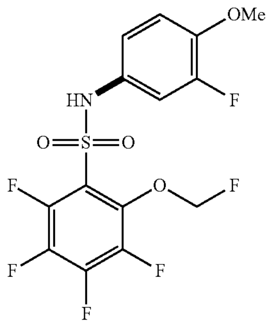 | 2,3,4,5-tetrafluoro-N-(3-fluoro-4-methoxyphenyl)-6-(fluoromethoxy)benzenesulfonamide |
| 84 | 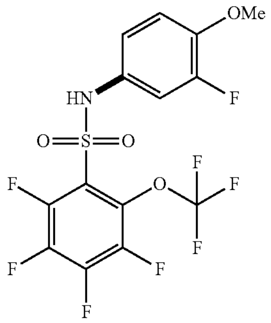 | 2,3,4,5-tetrafluoro-N-(3-fluoro-4-methoxyphenyl)-6-(trifluoromethoxy)benzenesulfonamide |
| 85 | 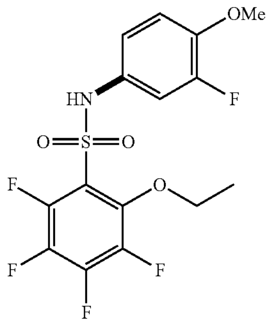 | 2-ethoxy-3,4,5,6-tetrafluoro-N-(3-fluoro-4-methoxyphenyl)benzenesulfonamide |
| 86 | 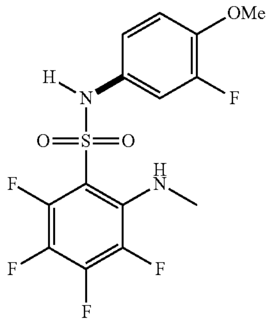 | 2,3,4,5-tetrafluoro-N-(3-fluoro-4-methoxyphenyl)-6-(methylamino)benzenesulfonamide |

TABLE 4-continued

| Synthetic Chemistry Example | Compound Structure | Compound Name |
|---|---|---|
| 87 | 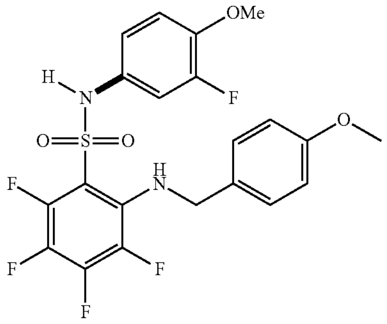 | 2,3,4,5-tetrafluoro-N-(3-fluoro-4-methoxyphenyl)-6-((4-methoxybenzyl)amino)benzenesulfonamide |
| 88 | 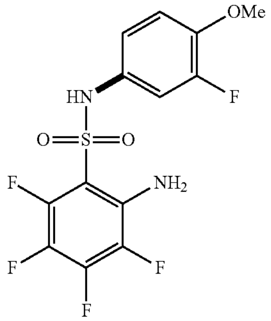 | 2-amino-3,4,5,6-tetrafluoro-N-(3-fluoro-4-methoxyphenyl)benzenesulfonamide |
| 89 | 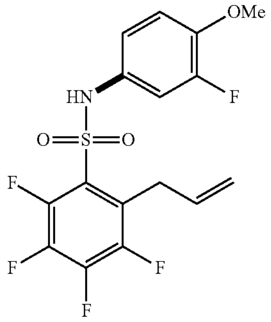 | 2-allyl-3,4,5,6-tetrafluoro-N-(3-fluoro-4-methoxyphenyl)benzenesulfonamide |
| 90 | 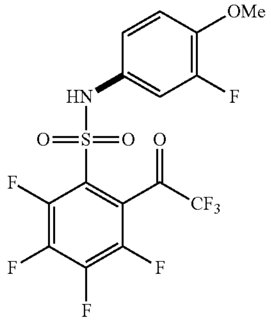 | 2,3,4,5-tetrafluoro-N-(3-fluoro-4-methoxyphenyl)-6-(2,2,2-trifluoroacetyl)benzenesulfonamide |

TABLE 4-continued
| Synthetic Chemistry Example | Compound Structure | Compound Name |
| --- | --- | --- |
| 91 | 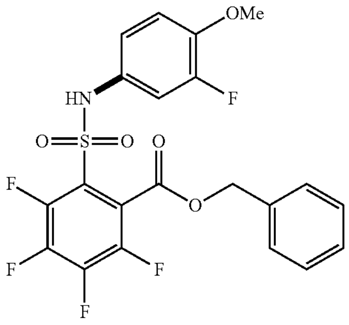 | benzyl 2,3,4,5-tetrafluoro-6-(N-(3-fluoro-4-methoxyphenyl)sulfamoyl)benzoate |
| 92 | 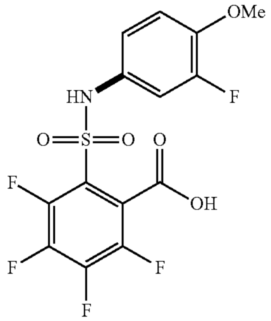 | 2,3,4,5-tetrafluoro-6-(N-(3-fluoro-4-methoxyphenyl)sulfamoyl)benzoic acid |
| 93 | 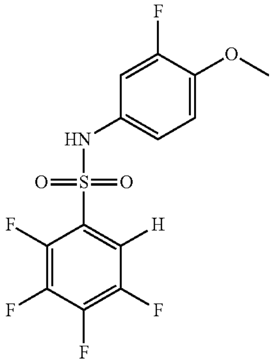 [SMILES: COc1ccc(NS(=O)(=O)c2cc(F)c(F)c(F)c2F)cc1F] | 2,3,4,5-tetrafluoro-N-(3-fluoro-4-methoxyphenyl)benzenesulfonamide |
| 94 | 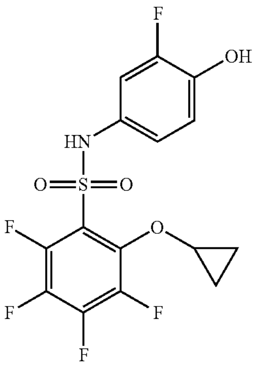 [SMILES: O=S(=O)(Nc1ccc(O)c(F)c1)c1c(F)c(F)c(F)c(F)c1OC1CC1] | 2-cyclopropoxy-3,4,5,6-tetrafluoro-N-(3-fluoro-4-hydroxyphenyl)benzenesulfonamide |

TABLE 4-continued
| Synthetic Chemistry Example | Compound Structure | Compound Name |
| --- | --- | --- |
| 95 | 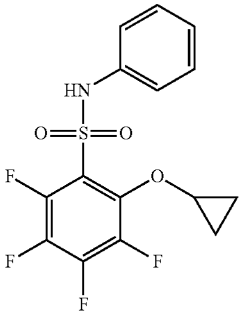 [SMILES: O=S(=O)(Nc1ccccc1)c1c(F)c(F)c(F)c(F)c1OC1CC1] | 2-cyclopropoxy-3,4,5,6-tetrafluoro-N-phenylbenzenesulfonamide |
| 96 | 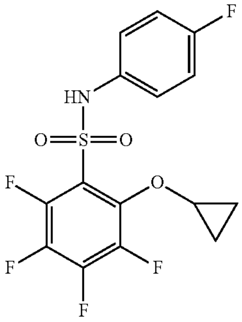 [SMILES: O=S(=O)(Nc1ccc(F)cc1)c1c(F)c(F)c(F)c(F)c1OC1CC1] | 2-cyclopropoxy-3,4,5,6-tetrafluoro-N-(4-fluorophenyl)benzenesulfonamide |
| 97 | 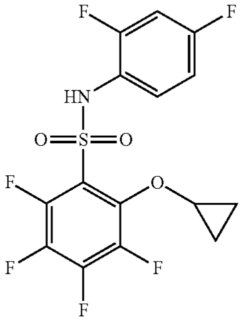 [SMILES: O=S(=O)(Nc1ccc(F)cc1F)c1c(F)c(F)c(F)c(F)c1OC1CC1] | 2-cyclopropoxy-N-(2,4-difluorophenyl)-3,4,5,6-tetrafluorobenzenesulfonamide |
| 98 | 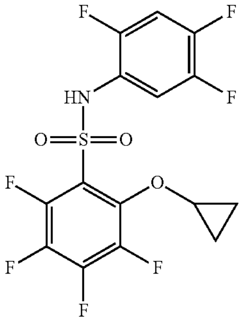 [SMILES: O=S(=O)(Nc1cc(F)c(F)cc1F)c1c(F)c(F)c(F)c(F)c1OC1CC1] | 2-cyclopropoxy-3,4,5,6-tetrafluoro-N-(2,4,5-trifluorophenyl)benzenesulfonamide |

TABLE 4-continued
| Synthetic Chemistry Example | Compound Structure | Compound Name |
|---|---|---|
| 99 | 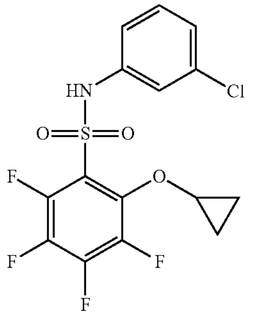 [SMILES: O=S(=O)(Nc1cccc(Cl)c1)c1c(F)c(F)c(F)c(F)c1OC1CC1] | N-(3-chlorophenyl)-2-cyclopropoxy-3,4,5,6-tetrafluorobenzenesulfonamide |
| 100 | 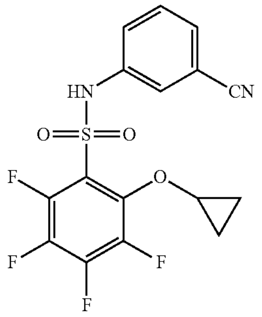 [SMILES: N#Cc1cccc(NS(=O)(=O)c2c(F)c(F)c(F)c(F)c2OC2CC2)c1] | N-(3-cyanophenyl)-2-cyclopropoxy-3,4,5,6-tetrafluorobenzenesulfonamide |
| 101 | 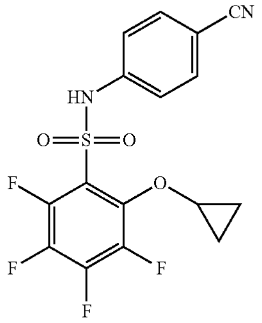 [SMILES: N#Cc1ccc(NS(=O)(=O)c2c(F)c(F)c(F)c(F)c2OC2CC2)cc1] | N-(4-cyanophenyl)-2-cyclopropoxy-3,4,5,6-tetrafluorobenzenesulfonamide |
| 102 | 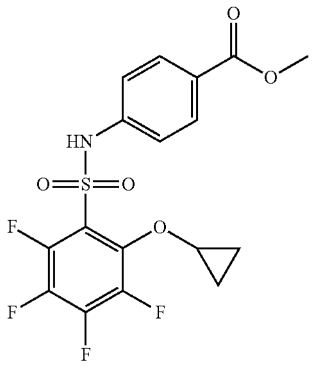 [SMILES: COC(=O)c1ccc(NS(=O)(=O)c2c(F)c(F)c(F)c(F)c2OC2CC2)cc1] | methyl 4-((2-cyclopropoxy-3,4,5,6-tetrafluorophenyl)sulfonamido)benzoate |

TABLE 4-continued
| Synthetic Chemistry Example | Compound Structure | Compound Name |
|---|---|---|
| 103 | 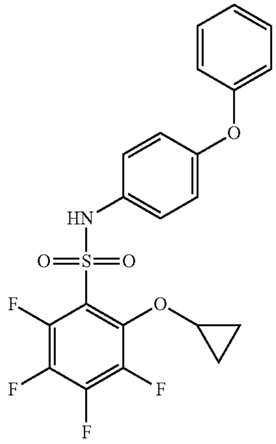 [SMILES: O=S(=O)(Nc1ccc(Oc2ccccc2)cc1)c1c(F)c(F)c(F)c(F)c1OC1CC1] | 2-cyclopropoxy-3,4,5,6-tetrafluoro-N-(4-phenoxyphenyl)benzenesulfonamide |
| 104 | 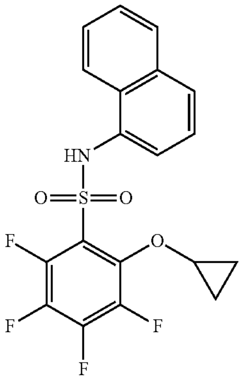 [SMILES: O=S(=O)(Nc1cccc2ccccc12)c1c(F)c(F)c(F)c(F)c1OC1CC1] | 2-cyclopropoxy-3,4,5,6-tetrafluoro-N-(naphthalen-1-yl)benzenesulfonamide |
| 105 | 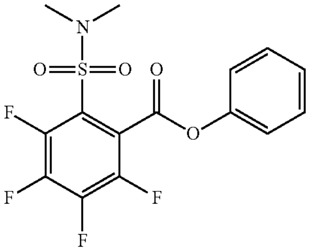 [SMILES: CN(C)S(=O)(=O)c1c(F)c(F)c(F)c(F)c1C(=O)Oc1ccccc1] | phenyl 2-(N,N-dimethylsulfamoyl)-3,4,5,6-tetrafluorobenzoate |
| 106 | 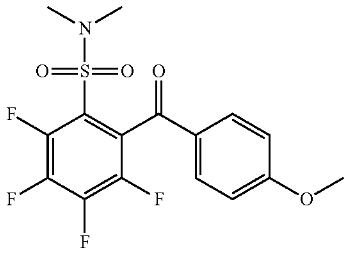 [SMILES: COc1ccc(C(=O)c2c(F)c(F)c(F)c(F)c2S(=O)(=O)N(C)C)cc1] | 2,3,4,5-tetrafluoro-6-(4-methoxybenzoyl)-N,N-dimethylbenzenesulfonamide |

TABLE 4-continued

| Synthetic Chemistry Example | Compound Structure | Compound Name |
| --- | --- | --- |
| 107 | 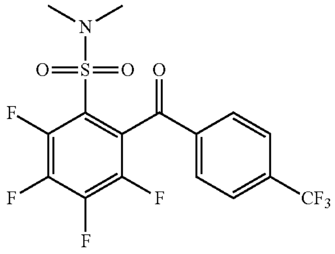 [SMILES: CN(C)S(=O)(=O)c1c(F)c(F)c(F)c(F)c1C(=O)c1ccc(C(F)(F)F)cc1] | 2,3,4,5-tetrafluoro-N,N-dimethyl-6-(4-(trifluoromethyl)benzoyl)benzenesulfonamide |
| 108 | 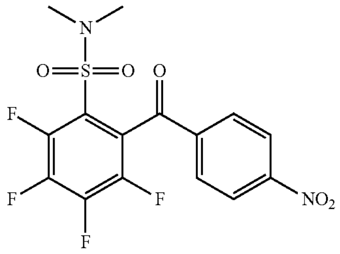 [SMILES: CN(C)S(=O)(=O)c1c(F)c(F)c(F)c(F)c1C(=O)c1ccc([N+](=O)[O-])cc1] | 2,3,4,5-tetrafluoro-N,N-dimethyl-6-(4-nitrobenzoyl)benzenesulfonamide |
| 109 | 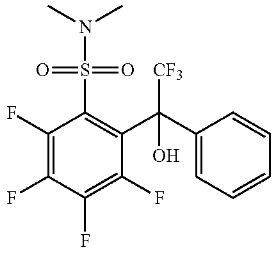 [SMILES: CN(C)S(=O)(=O)c1c(F)c(F)c(F)c(F)c1C(O)(c1ccccc1)C(F)(F)F] | 2,3,4,5-tetrafluoro-N,N-dimethyl-6-(2,2,2-trifluoro-1-hydroxy-1-phenylethyl)benzenesulfonamide |
| 110 | 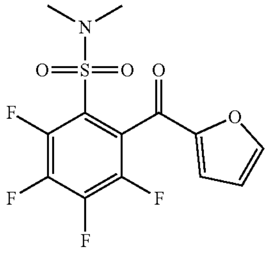 [SMILES: CN(C)S(=O)(=O)c1c(F)c(F)c(F)c(F)c1C(=O)c1ccco1] | 2,3,4,5-tetrafluoro-6-(furan-2-carbonyl)-N,N-dimethylbenzenesulfonamide |
| 111 | 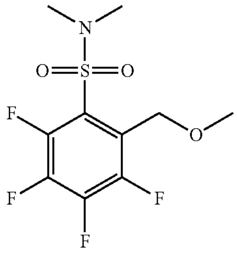 [SMILES: COCc1c(F)c(F)c(F)c(F)c1S(=O)(=O)N(C)C] | 2,3,4,5-tetrafluoro-6-(methoxymethyl)-N,N-dimethylbenzenesulfonamide |
| 112 | 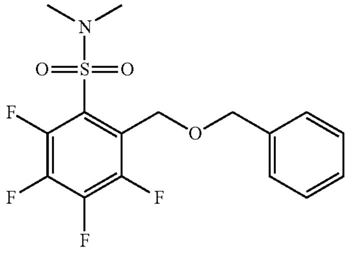 [SMILES: CN(C)S(=O)(=O)c1c(F)c(F)c(F)c(F)c1COCc1ccccc1] | 2,3,4,5-tetrafluoro-6-(methoxymethyl)-N,N-dimethylbenzenesulfonamide |

TABLE 4-continued
| Synthetic Chemistry Example | Compound Structure | Compound Name |
|---|---|---|
| 113 | 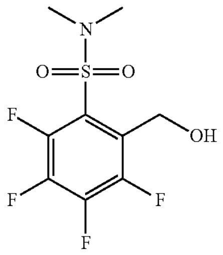 | 2,3,4,5-tetrafluoro-6-(hydroxymethyl)-N,N-dimethylbenzenesulfonamide |
| 114 | 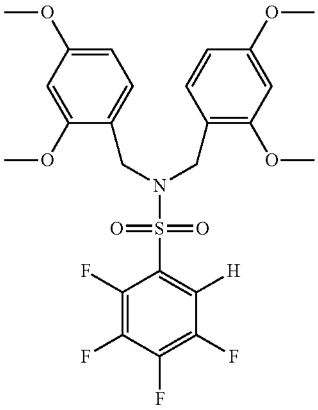 | N,N-bis(2,4-dimethoxybenzyl)-2,3,4,5-tetrafluorobenzenesulfonamide |
| 115 | 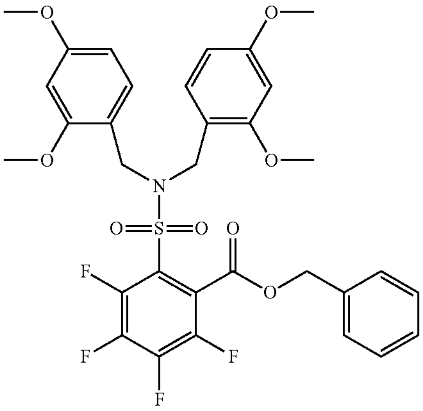 [SMILES: COc1ccc(CN(Cc2ccc(OC)cc2OC)S(=O)(=O)c2c(F)c(F)c(F)c(F)c2C(=O)OCc2ccccc2)c(OC)c1] | benzyl 2-(N,N-bis(2,4-dimethoxybenzyl)sulfamoyl)-3,4,5,6-tetrafluorobenzoate |
| 116 | 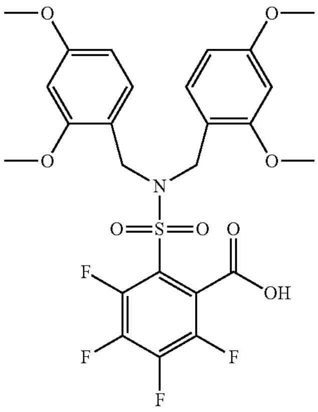 | 2-(N,N-bis(2,4-dimethoxybenzyl)sulfamoyl)-3,4,5,6-tetrafluorobenzoic acid |

TABLE 4-continued
| Synthetic Chemistry Example | Compound Structure | Compound Name |
|---|---|---|
| 117 | 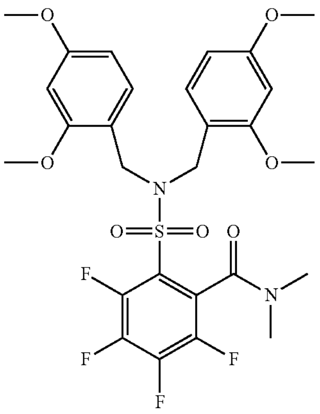 | 2-(N,N-bis(2,4-dimethoxybenzyl)sulfamoyl)-3,4,5,6-tetrafluoro-N,N-dimethylbenzamide |
| 118 | 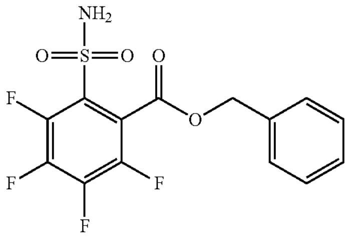 [SMILES: NS(=O)(=O)c1c(F)c(F)c(F)c(F)c1C(=O)OCc1ccccc1] | benzyl 2,3,4,5-tetrafluoro-6-sulfamoylbenzoate |
| 119 | 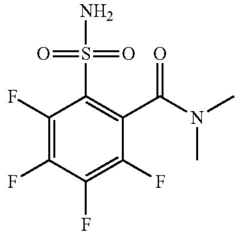 [SMILES: CN(C)C(=O)c1c(F)c(F)c(F)c(F)c1S(N)(=O)=O] | 2,3,4,5-tetrafluoro-N,N-dimethyl-6-sulfamoylbenzamide |
| 120 | 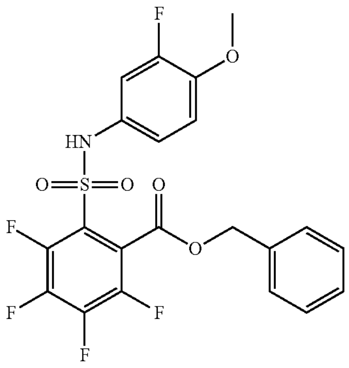 [SMILES: COc1ccc(NS(=O)(=O)c2c(F)c(F)c(F)c(F)c2C(=O)OCc2ccccc2)cc1F] | benzyl 2,3,4,5-tetrafluoro-6-(N-(3-fluoro-4-methoxyphenyl)sulfamoyl)benzoate |

TABLE 4-continued

| Synthetic Chemistry Example | Compound Structure | Compound Name |
|---|---|---|
| 121 | 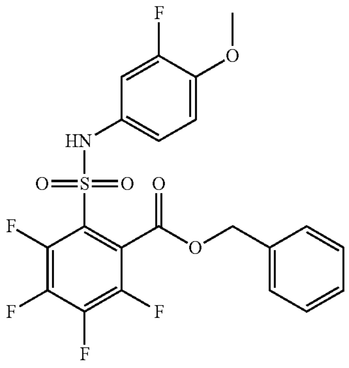 [SMILES: COc1ccc(NS(=O)(=O)c2c(F)c(F)c(F)c(F)c2C(=O)OCc2ccccc2)cc1F] | 2,3,4,5-tetrafluoro-6-(N-(3-fluoro-4-methoxyphenyl)sulfamoyl)-N,N-dimethylbenzamide |
| 122 | 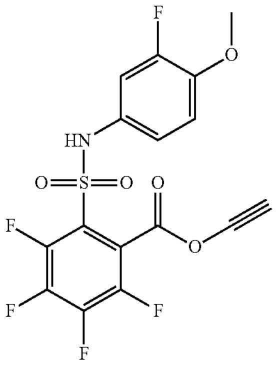 [SMILES: C#COC(=O)c1c(F)c(F)c(F)c(F)c1S(=O)(=O)Nc1ccc(OC)c(F)c1] | 2,3,4,5-tetrafluoro-N-(3-fluoro-4-methoxyphenyl)-6-(prop-2-yn-1-yloxy)benzenesulfonamide |
| 123 | 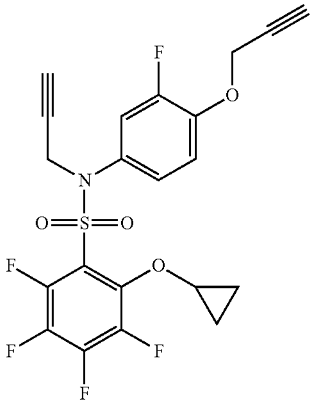 [SMILES: C#CCOc1ccc(N(CC#C)S(=O)(=O)c2c(F)c(F)c(F)c(F)c2OC2CC2)cc1F] | 2-cyclopropoxy-3,4,5,6-tetrafluoro-N-(3-fluoro-4-(prop-2-yn-1-yloxy)phenyl)-N-(prop-2-yn-1-yl)benzenesulfonamide |
| 124 | 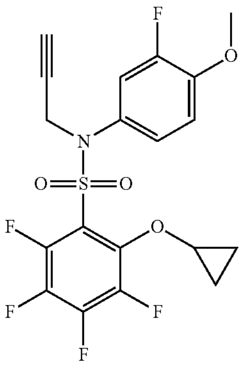 [SMILES: C#CCN(c1ccc(OC)c(F)c1)S(=O)(=O)c1c(F)c(F)c(F)c(F)c1OC1CC1] | 2-cyclopropoxy-3,4,5,6-tetrafluoro-N-(3-fluoro-4-methoxyphenyl)-N-(prop-2-yn-1-yl)benzenesulfonamide |

TABLE 4-continued

| Synthetic Chemistry Example | Compound Structure | Compound Name |
|---|---|---|
| 125 | 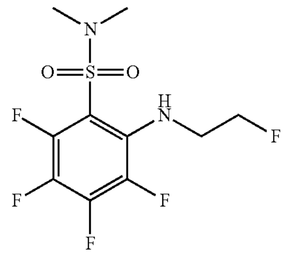 [SMILES: CN(C)S(=O)(=O)c1c(F)c(F)c(F)c(F)c1NCCF] | 2,3,4,5-tetrafluoro-6-(2-fluoroethoxy)-N,N-dimethylbenzenesulfonamide |

In some embodiments, disclosed herein is a pharmaceutically acceptable salt, solvate, or stereoisomer of a compound of Table 4.

In some embodiments, the benzenesulfonamide derivative compound described herein has a structure provided in Table 5.

TABLE 5

| Compound Structure | Compound Name |
|---|---|
| 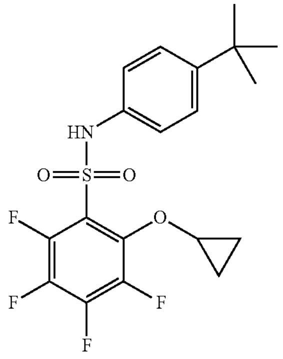 [SMILES: CC(C)(C)c1ccc(NS(=O)(=O)c2c(F)c(F)c(F)c(F)c2OC2CC2)cc1] | N-(4-(tert-butyl)phenyl)-2-cyclopropoxy-3,4,5,6-tetrafluoro-benzenesulfonamide |
| 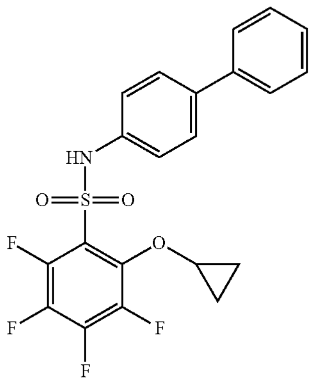 [SMILES: O=S(=O)(Nc1ccc(-c2ccccc2)cc1)c1c(F)c(F)c(F)c(F)c1OC1CC1] | N-([1,1'-biphenyl]-4-yl)-2-cyclopropoxy-3,4,5,6-tetrafluoro-benzenesulfonamide |

TABLE 5-continued

| Compound Structure | Compound Name |
|---|---|
| 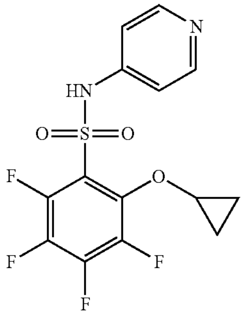 [SMILES: O=S(=O)(Nc1ccncc1)c1c(F)c(F)c(F)c(F)c1OC1CC1] | 2-cyclopropoxy-3,4,5,6-tetrafluoro-N-(pyridin-4-yl) benzenesulfonamide |
| 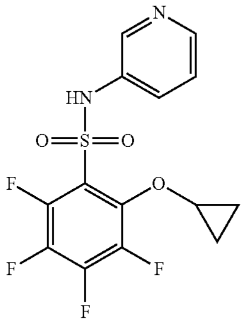 [SMILES: O=S(=O)(Nc1cccnc1)c1c(F)c(F)c(F)c(F)c1OC1CC1] | 2-cyclopropoxy-3,4,5,6-tetrafluoro-N-(pyridin-3-yl) benzenesulfonamide |
| 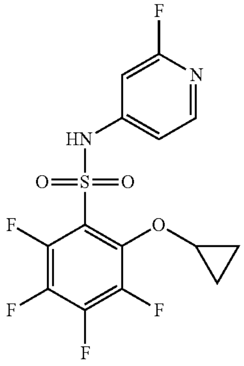 [SMILES: O=S(=O)(Nc1ccnc(F)c1)c1c(F)c(F)c(F)c(F)c1OC1CC1] | 2-cyclopropoxy-3,4,5,6-tetrafluoro-N-(2-fluoropyridin-4-yl)benzenesulfonamide |

TABLE 5-continued

| Compound Structure | Compound Name |
|---|---|
| 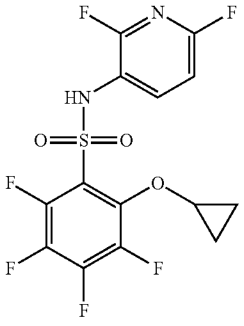 [SMILES: O=S(=O)(Nc1ccc(F)nc1F)c1c(F)c(F)c(F)c(F)c1OC1CC1] | 2-cyclopropoxy-N-(2,6-difluoropyridin-3-yl)-3,4,5,6-tetrafluoro-benzenesulfonamide |
| 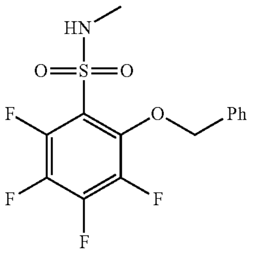 [SMILES: CNS(=O)(=O)c1c(F)c(F)c(F)c(F)c1OCc1ccccc1] | 2-(benzyloxy)-3,4,5,6-tetrafluoro-N-methyl-benzenesulfonamide |
| 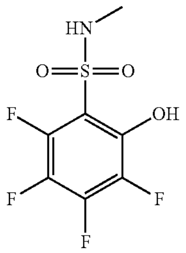 [SMILES: CNS(=O)(=O)c1c(O)c(F)c(F)c(F)c1F] | 2,3,4,5-tetrafluoro-6-hydroxy-N-methyl-benzenesulfonamide |
| 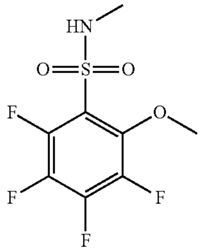 [SMILES: CNS(=O)(=O)c1c(F)c(F)c(F)c(F)c1OC] | 2,3,4,5-tetrafluoro-6-methoxy-N-methyl-benzenesulfonamide |
| 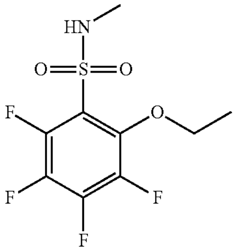 [SMILES: CCOc1c(F)c(F)c(F)c(F)c1S(=O)(=O)NC] | 2-ethoxy-3,4,5,6-tetrafluoro-N-methyl-benzenesulfonamide |

TABLE 5-continued

| Compound Structure | Compound Name |
|---|---|
| 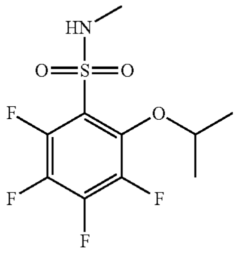 [SMILES: CNS(=O)(=O)c1c(F)c(F)c(F)c(F)c1OC(C)C] | 2,3,4,5-tetrafluoro-6-isopropoxy-N-methyl-benzenesulfonamide |
| 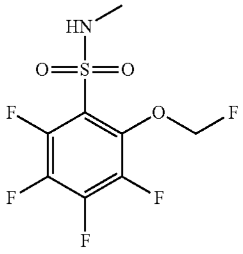 [SMILES: CNS(=O)(=O)c1c(F)c(F)c(F)c(F)c1OCF] | 2,3,4,5-tetrafluoro-6-(fluoromethoxy)-N-methyl-benzenesulfonamide |
| 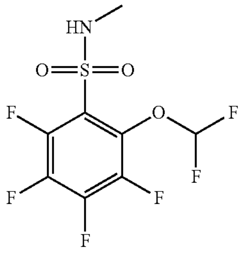 [SMILES: CNS(=O)(=O)c1c(F)c(F)c(F)c(F)c1OC(F)F] | 2-(difluoromethoxy)-3,4,5,6-tetrafluoro-N-methylbenzene-sulfonamide |
| 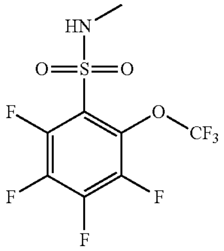 [SMILES: CNS(=O)(=O)c1c(F)c(F)c(F)c(F)c1OC(F)(F)F] | 2,3,4,5-tetrafluoro-N-methyl-6-(trifluoromethoxy) benzenesulfonamide |
| 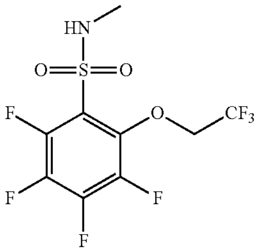 [SMILES: CNS(=O)(=O)c1c(F)c(F)c(F)c(F)c1OCC(F)(F)F] | 2,3,4,5-tetrafluoro-N-methyl-6-(2,2,2-trifluoroethoxy) benzenesulfonamide |
| 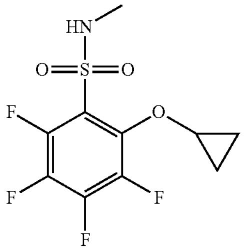 [SMILES: CNS(=O)(=O)c1c(F)c(F)c(F)c(F)c1OC1CC1] | 2-cyclopropoxy-3,4,5,6-tetrafluoro-N-methyl-benzenesulfonamide |

TABLE 5-continued

| Compound Structure | Compound Name |
|---|---|
| 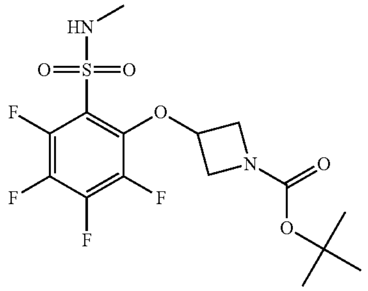 [SMILES: CNS(=O)(=O)c1c(F)c(F)c(F)c(F)c1OC1CN(C(=O)OC(C)(C)C)C1] | tert-butyl 3-(2,3,4,5-tetrafluoro-6-(N-methylsulfamoyl) phenoxy)azetidine-1-carboxylate |
| 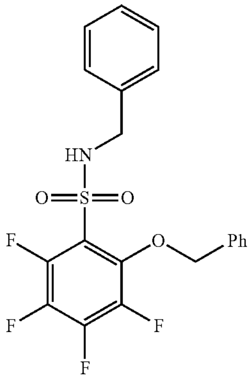 [SMILES: O=S(=O)(NCc1ccccc1)c1c(F)c(F)c(F)c(F)c1OCc1ccccc1] | N-benzyl-2-(benzyloxy)-3,4,5,6-tetrafluoro-benzenesulfonamide |
| 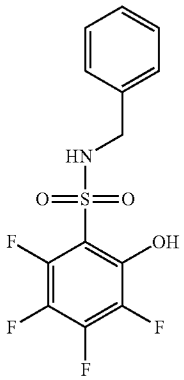 [SMILES: O=S(=O)(NCc1ccccc1)c1c(O)c(F)c(F)c(F)c1F] | N-benzyl-2,3,4,5-tetrafluoro-6-hydroxy-benzenesulfonamide |
| 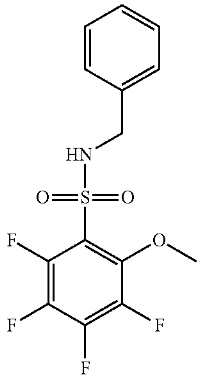 [SMILES: COc1c(F)c(F)c(F)c(F)c1S(=O)(=O)NCc1ccccc1] | N-benzyl-2,3,4,5-tetrafluoro-6-methoxy-benzenesulfonamide |

TABLE 5-continued

| Compound Structure | Compound Name |
|---|---|
| 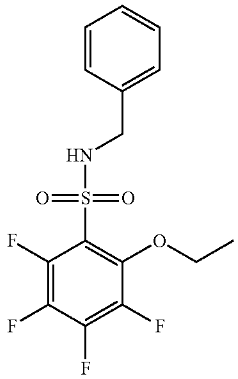 [SMILES: CCOc1c(F)c(F)c(F)c(F)c1S(=O)(=O)NCc1ccccc1] | N-benzyl-2-ethoxy-3,4,5,6-tetrafluoro-benzenesulfonamide |
| 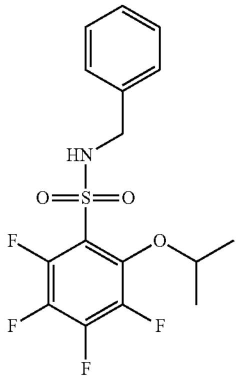 | N-benzyl-2,3,4,5-tetrafluoro-6-isopropoxy-benzenesulfonamide |
| 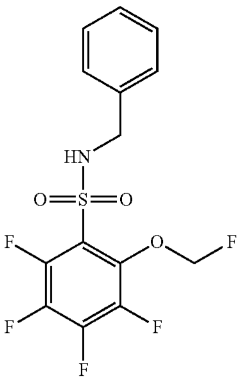 [SMILES: O=S(=O)(NCc1ccccc1)c1c(F)c(F)c(F)c(F)c1OCF] | N-benzyl-2,3,4,5-tetrafluoro-6-(fluoromethoxy) benzenesulfonamide |
| 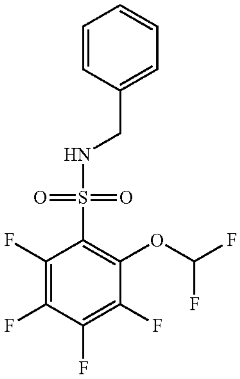 [SMILES: O=S(=O)(NCc1ccccc1)c1c(F)c(F)c(F)c(F)c1OC(F)F] | N-benzyl-2-(difluoromethoxy)-3,4,5,6-tetrafluoro-benzenesulfonamide |

TABLE 5-continued

| Compound Structure | Compound Name |
|---|---|
| 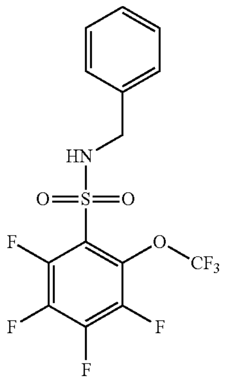 [SMILES: O=S(=O)(NCc1ccccc1)c1c(F)c(F)c(F)c(F)c1OC(F)(F)F] | N-benzyl-2,3,4,5-tetrafluoro-6-(trifluoromethoxy) benzenesulfonamide |
| 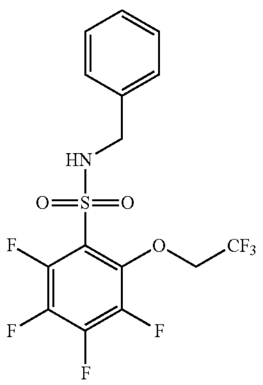 [SMILES: O=S(=O)(NCc1ccccc1)c1c(F)c(F)c(F)c(F)c1OCC(F)(F)F] | N-benzyl-2,3,4,5-tetrafluoro-6-(2,2,2-trifluoroethoxy) benzenesulfonamide |
| 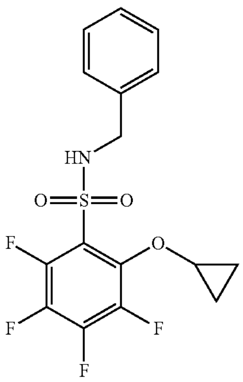 [SMILES: O=S(=O)(NCc1ccccc1)c1c(F)c(F)c(F)c(F)c1OC1CC1] | N-benzyl-2-cyclopropoxy-3,4,5,6-tetrafluoro-benzenesulfonamide |
| 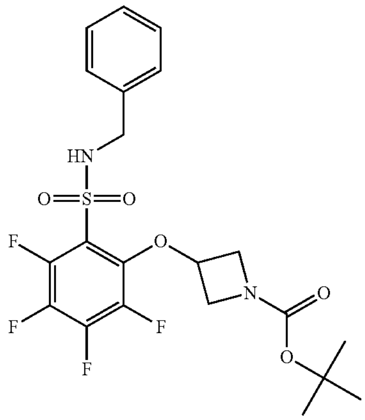 [SMILES: CC(C)(C)OC(=O)N1CC(Oc2c(F)c(F)c(F)c(F)c2S(=O)(=O)NCc2ccccc2)C1] | tert-butyl 3-(2-(N-benzylsulfamoyl)-3,4,5,6-tetrafluorophenoxy) azetidine-1-carboxylate |

In some embodiments, disclosed herein is a pharmaceutically acceptable salt, solvate, or stereoisomer of a compound of Table 5.

In some embodiments, the benzenesulfonamide derivative compound described herein is a compound from Examples section.

In some embodiments, disclosed herein is a pharmaceutically acceptable salt, solvate, or stereoisomer of a compound from Examples section.

Methods of Synthesis

In one aspect, provided herein is a method for synthesizing a compound of Formula (V) comprising: reacting a compound of Formula (VI) or a salt or solvate thereof with a compound of Formula (VII) or a salt or solvate thereof Formula (VI)

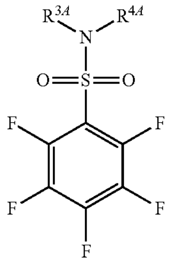

Formula (VII)

$R^{11}$—H

Formula (V)

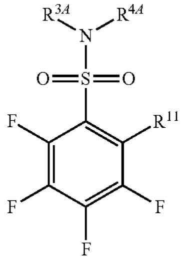

wherein, $R^{11}$ is —$OR^{5A}$, —$SR^{5A}$, —$OS(=O)_2R^{5A}$, —$N(R^{5A})_2$, —$C(=O)R^{5A}$, —$OC(=O)R^{5A}$, —$C(=O)OR^{5A}$, —$OC(=O)OR^{5A}$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_2$-$C_6$ alkenyl, substituted or unsubstituted $C_2$-$C_5$ alkynyl, substituted or unsubstituted $C_3$-$C_6$ cycloalkyl, substituted or unsubstituted $C_2$-$C_5$ heterocycloalkyl, substituted or unsubstituted aryl, or substituted or unsubstituted heteroaryl;

$R^{3A}$ is hydrogen, —$OR^{5A}$, —$S(=O)R^{5A}$, —$S(=O)_2R^{5A}$, —$C(=O)R^{5A}$, —$C(=O)OR^{5A}$, —$C(=O)N(R^{5A})_2$, substituted or unsubstituted $C_1$-$C_4$ alkyl, substituted or unsubstituted $C_1$-$C_6$ haloalkyl, substituted or unsubstituted $C_1$-$C_6$ heteroalkyl, substituted or unsubstituted $C_2$-$C_5$ alkenyl, substituted or unsubstituted $C_2$-$C_5$ alkynyl, substituted or unsubstituted aryl, or substituted or unsubstituted heteroaryl;

$R^{4A}$ is —$OR^{6A}$, —$S(=O)R^{5A}$, —$S(=O)_2R^{5A}$, —$C(=O)R^{5A}$, —$C(=O)OR^{5A}$, —$C(=O)N(R^{5A})_2$, substituted or unsubstituted $C_1$-$C_4$ alkyl, substituted or unsubstituted $C_1$-$C_6$ haloalkyl, substituted or unsubstituted $C_1$-$C_6$ heteroalkyl, substituted or unsubstituted $C_2$-$C_5$ alkenyl, substituted or unsubstituted $C_2$-$C_5$ alkynyl, substituted or unsubstituted aryl, or substituted or unsubstituted heteroaryl;

each $R^{5A}$ is independently hydrogen, —C(=O)($C_2$-$C_6$ alkenyl), —C(=O)($C_2$-$C_6$ alkynyl), substituted or unsubstituted $C_1$-$C_4$ alkyl, —($C_1$-$C_4$ alkylene)-$R^{7A}$, substituted or unsubstituted $C_1$-$C_4$ haloalkyl, substituted or unsubstituted $C_1$-$C_4$ heteroalkyl, substituted or unsubstituted $C_2$-$C_5$ alkenyl, substituted or unsubstituted $C_2$-$C_5$ alkynyl, substituted or unsubstituted $C_3$-$C_6$cycloalkyl, substituted or unsubstituted $C_2$-$C_5$ heterocycloalkyl, substituted or unsubstituted aryl, or substituted or unsubstituted heteroaryl;

or two $R^{5A}$ on the same nitrogen atom are joined together to form substituted or unsubstituted $C_2$-$C_7$ heterocycloalkyl;

$R^{6A}$ is substituted or unsubstituted $C_1$-$C_4$ alkyl, —($C_1$-$C_4$ alkylene)-$R^{7A}$, substituted or unsubstituted $C_1$-$C_4$ haloalkyl, substituted or unsubstituted $C_1$-$C_4$ heteroalkyl, substituted or unsubstituted $C_2$-$C_5$ alkenyl, substituted or unsubstituted $C_2$-$C_5$ alkynyl, substituted or unsubstituted $C_3$-$C_6$cycloalkyl, substituted or unsubstituted $C_2$-$C_5$ heterocycloalkyl, substituted or unsubstituted aryl, or substituted or unsubstituted heteroaryl; and each $R^{7A}$ is independently substituted or unsubstituted $C_3$-$C_6$cycloalkyl, substituted or unsubstituted $C_2$-$C_5$ heterocycloalkyl, substituted or unsubstituted aryl, or substituted or unsubstituted heteroaryl.

In some embodiments, $R^{11}$ is —$OR^{5A}$, —$SR^{5A}$, —OS(=O)$_2R^{5A}$, —N($R^{5A}$)$_2$, —OC(=O)$R^{5A}$, —OC(=O)O$R^{5A}$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl.

In some embodiments, $R^{11}$ is —$OR^{5A}$, —$SR^{5A}$, —N($R^{5A}$)$_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, or substituted or unsubstituted $C_2$-$C_7$ heterocycloalkyl.

In some embodiments, $R^{11}$ is —OS(=O)$_2R^{5A}$, —C(=O)$R^{5A}$, —OC(=O)$R^{5A}$, —C(=O)O$R^{5A}$, or —OC(=O)O$R^{5A}$; and each $R^{5A}$ is independently hydrogen, substituted or unsubstituted $C_1$-$C_4$ alkyl, substituted or unsubstituted $C_1$-$C_4$ haloalkyl, substituted or unsubstituted $C_1$-$C_4$ heteroalkyl, substituted or unsubstituted aryl, or substituted or unsubstituted heteroaryl.

In some embodiments, $R^{11}$ is —$OR^{5A}$, —$SR^{5A}$, —N($R^{5A}$)$_2$, substituted or unsubstituted $C_1$-$C_6$ alkyl, substituted or unsubstituted $C_1$-$C_6$ haloalkyl, substituted or unsubstituted $C_3$-$C_8$ cycloalkyl, or substituted or unsubstituted $C_2$-$C_7$ heterocycloalkyl.

In some embodiments, $R^{11}$ is —$OR^{5A}$, —$SR^{5A}$, or —N($R^{5A}$)$_2$; and each $R^{5A}$ is substituted or unsubstituted $C_1$-$C_4$ alkyl, substituted or unsubstituted $C_1$-$C_4$ haloalkyl, or substituted or unsubstituted $C_3$-$C_5$ cycloalkyl.

In some embodiments, $R^{11}$ is —$OR^{5A}$, and $R^{5A}$ is substituted or unsubstituted $C_2$-$C_5$ heterocycloalkyl, substituted or unsubstituted phenyl, or substituted or unsubstituted benzyl.

In some embodiments, $R^{11}$ is —N($R^{5A}$)$_2$, and each $R^{5A}$ is independently hydrogen, substituted or unsubstituted $C_1$-$C_4$ alkyl, substituted or unsubstituted $C_1$-$C_4$ haloalkyl, or substituted or unsubstituted $C_3$-$C_5$ cycloalkyl; or wherein two $R^{5A}$ are joined together to form substituted or unsubstituted $C_2$-$C_5$ heterocycloalkyl.

In some embodiments, $R^{11}$ is —$OCH_3$, —$OCH_2CH_3$, —$OCH_2CH_2OH$, —$OCH_2CN$, —$OCH_2F$, —$OCHF_2$, —$OCF_3$, —$OCH_2CH_2F$, —$OCH_2CHF_2$, —$OCH_2CF_3$, cyclopropyloxy, or cyclobutyloxy.

In some embodiments, $R^{11}$ is —$OCH_3$, —$OCH_2CH_3$, cyclopropyloxy, or cyclobutyloxy.

In some embodiments, $R^{11}$ is —$OCH_2F$, —$OCHF_2$, —$OCF_3$, —$OCH_2CH_2F$, —$OCH_2CHF_2$, or —$OCH_2CF_3$.

In some embodiments, $R^{11}$ is —$NH_2$, —$NHCH_3$, —N($CH_3$)$_2$, —$NHCH_2F$, —$NHCHF_2$, —$NHCF_3$, —$NHCH_2CH_2F$, —$NHCH_2CHF_2$, or —$NHCH_2CF_3$.

In some embodiments, $R^{3A}$ is hydrogen, substituted or unsubstituted $C_1$-$C_4$ alkyl, substituted or unsubstituted $C_1$-$C_6$ haloalkyl, substituted or unsubstituted $C_1$-$C_6$ heteroalkyl, substituted or unsubstituted $C_2$-$C_5$ alkenyl, or substituted or unsubstituted $C_2$-$C_5$ alkynyl.

In some embodiments, $R^{3A}$ is hydrogen, substituted or unsubstituted $C_1$-$C_4$ alkyl, substituted or unsubstituted $C_2$-$C_5$ alkenyl, or substituted or unsubstituted $C_2$-$C_5$ alkynyl.

In some embodiments, $R^{3A}$ is hydrogen, —$CH_3$, —$CH_2CH_3$, —$CH_2(CH_3)_2$, cyclopropyl, cyclobutyl, —$CH_2OH$, —$CH_2CH_2OH$, —$CH_2CN$, —$CH_2NH_2$, —$CH_2NHCH_3$, —$CH_2N(CH_3)_2$, —$CH_2F$, —$CHF_2$, —$CF_3$, —CH=$CH_2$, —$CH_2$CH=$CH_2$, —C≡CH, or —$CH_2$C≡CH.

In some embodiments, $R^{3A}$ is hydrogen, —$CH_3$, —$CH_2CH_3$, —$CH_2(CH_3)_2$, or cyclopropyl.

In some embodiments, $R^{3A}$ is hydrogen or —$CH_3$.

In some embodiments, $R^{3A}$ is hydrogen.

In some embodiments, $R^{3A}$ is —$CH_2OH$, —$CH_2CH_2OH$, —$CH_2CN$, —$CH_2NH_2$, —$CH_2NHCH_3$, or —$CH_2N(CH_3)_2$.

In some embodiments, $R^{3A}$ is —$CH_2F$, —$CHF_2$, —$CF_3$, —CH=$CH_2$, —$CH_2$CH=$CH_2$, —C≡CH, or —$CH_2$C≡CH.

In some embodiments, $R^{4A}$ is substituted or unsubstituted $C_1$-$C_4$ alkyl, substituted or unsubstituted $C_1$-$C_6$ haloalkyl, substituted or unsubstituted $C_1$-$C_6$ heteroalkyl, substituted or unsubstituted aryl, or substituted or unsubstituted heteroaryl.

In some embodiments, $R^{4A}$ is substituted or unsubstituted $C_1$-$C_4$ alkyl, substituted or unsubstituted aryl, or substituted or unsubstituted heteroaryl.

In some embodiments, $R^{4A}$ is —$CH_3$, —$CH_2CH_3$, cyclopropyl, cyclobutyl, —$CH_2OH$, —$CH_2CH_2OH$, —$CH_2CN$, substituted or unsubstituted phenyl, or substituted or unsubstituted benzyl.

In some embodiments, $R^{4A}$ is —$CH_3$, —$CH_2CH_3$, cyclopropyl, cyclobutyl, —$CH_2OH$, —$CH_2CH_2OH$, —$CH_2CN$, substituted or unsubstituted phenyl, or substituted or unsubstituted benzyl.

In some embodiments, $R^{4A}$ is —$CH_3$, —$CH_2CH_3$, —$CH_2(CH_3)_2$, or cyclopropyl.

In some embodiments, $R^{4A}$ is —$CH_3$.

In some embodiments, $R^{4A}$ is substituted or unsubstituted aryl or substituted or unsubstituted heteroaryl.

In some embodiments, $R^{4A}$ is substituted or unsubstituted aryl.

In some embodiments, $R^{4A}$ is aryl substituted with 1, 2, 3, 4, or 5 substituents independently selected from halogen, —CN, $NO_2$, —$OR^8$, —$SR^8$, —OS(=O)$_2R^8$, —N($R^8$)$_2$, —C(=O)$R^8$, —OC(=O)$R^8$, —C(=O)O$R^8$, —OC(=O)O$R^8$, —C(=O)N($R^8$)$_2$, substituted or unsubstituted $C_1$-$C_6$ alkyl, substituted or unsubstituted $C_1$-$C_6$ haloalkyl; and each $R^8$ is independently hydrogen, substituted or unsubstituted $C_1$-$C_4$ alkyl, substituted or unsubstituted $C_1$-$C_4$ haloalkyl, substituted or unsubstituted $C_1$-$C_4$ heteroalkyl, substituted or unsubstituted $C_3$-$C_6$cycloalkyl, substituted or unsubstituted $C_2$-$C_5$ heterocycloalkyl, substituted or unsubstituted aryl, or substituted or unsubstituted heteroaryl.

In some embodiments, $R^{4A}$ is aryl substituted with 1, 2, 3, 4, or 5 substituents independently selected from halogen, —CN, $NO_2$, —$OR^8$, —$N(R^8)_2$, —C(═O)$R^8$, —OC(═O)$R^8$, —C(═O)$OR^8$, —OC(═O)$OR^8$, —C(═O)$N(R^8)_2$, substituted or unsubstituted $C_1$-$C_6$ alkyl, substituted or unsubstituted $C_1$-$C_6$ haloalkyl; and each $R^8$ is independently hydrogen, substituted or unsubstituted $C_1$-$C_4$ alkyl, substituted or unsubstituted $C_1$-$C_4$ haloalkyl, substituted or unsubstituted $C_1$-$C_4$ heteroalkyl, substituted or unsubstituted $C_3$-$C_6$cycloalkyl, substituted or unsubstituted $C_2$-$C_5$ heterocycloalkyl, substituted or unsubstituted aryl, or substituted or unsubstituted heteroaryl.

In some embodiments, $R^{4A}$ is aryl substituted with 1, 2, 3, 4, or 5 substituents independently selected from F, Cl, Br, —$CH_3$, —$CH_2CH_3$, —$CH_2CH_2CH_3$, —$CH(CH_3)_2$, —$CH_2F$, —$CHF_2$, —$CF_3$, —$CH_2CF_3$, —$CH_2OH$, —$CH_2CH_2OH$, —$CH_2CN$, —$CH_2C$(═O)OH, —$CH_2C$(═O)$OCH_3$, —$CH_2C$(═O)$OCH_2CH_3$, —$CH_2C$(═O)$NH_2$, —$CH_2C$(═O)$NHCH_3$, —$CH_2C$(═O)$N(CH_3)_2$, —$CH_2NH_2$, —$CH_2NHCH_3$, —$CH_2N(CH_3)_2$, —CH═$CH_2$, —C≡CH, cyclopropyl, cyclobutyl, cyclopentyl, cyclopropyloxy, cyclobutyloxy, cyclopentyloxy, oxetanyloxy, tetrahydrofuranyloxy, tetrahydropyranyloxy, azetidinyl, pyrrolidinyl, tetrazolyl, —CN, —OH, —$OCH_3$, —$OCH_2CH_3$, —$OCH_2CH_2OH$, —$OCH_2CN$, —$OCH_2F$, —$OCHF_2$, —$OCF_3$, —$OCH_2CF_3$, —$CO_2H$, —$CO_2CH_3$, —$CO_2CH_2CH_3$, —C(═O)$NH_2$, —C(═O)$NHCH_3$, —C(═O)$N(CH_3)_2$, —$NH_2$, —$NHCH_3$, —$N(CH_3)_2$, —NHC(═O)$CH_3$, —$NCH_3C$(═O)$CH_3$, —NHC(═O)$OCH_3$, —$NCH_3C$(═O)$OCH_3$, —S(═O)$CH_3$, —S(═O)$_2CH_3$, —NHS(═O)$_2CH_3$, or —$N(CH_3)$S(═O)$_2CH_3$.

In some embodiments, $R^{4A}$ is aryl substituted with 1, 2, 3, 4, or 5 substituents independently selected from F, Cl, —$CH_3$, —$CH_2F$, —$CHF_2$, —$CF_3$, —$CH_2OH$, cyclopropyl, cyclopropyloxy, oxetanyloxy, azetidinyl, —CN, —OH, —$OCH_3$, —$OCH_2F$, —$OCHF_2$, —$OCF_3$, —$CO_2CH_3$, —C(═O)$NH_2$, —C(═O)$NHCH_3$, —C(═O)$N(CH_3)_2$, —$NH_2$, —$NHCH_3$, —$N(CH_3)_2$, —NHC(═O)$CH_3$, —$NCH_3C$(═O)$CH_3$, —NHC(═O)$OCH_3$, —$NCH_3C$(═O)$OCH_3$, —S(═O)$CH_3$, —S(═O)$_2CH_3$, —NHS(═O)$_2CH_3$, or —$N(CH_3)$S(═O)$_2CH_3$.

In some embodiments, $R^{4A}$ is aryl substituted with 1, 2, 3, 4, or 5 substituents independently selected from F, Cl, —$CH_3$, —$CH_2F$, —$CHF_2$, —$CF_3$, cyclopropyl, cyclopropyloxy, oxetanyloxy, azetidinyl, —CN, —OH, —$OCH_3$, —$OCH_2F$, —$OCHF_2$, or —$OCF_3$.

In some embodiments, $R^{4A}$ is aryl substituted with 1, 2, 3, 4, or 5 substituents independently selected from F, Cl, —$CH_3$, —$CH_2F$, —$CHF_2$, —$CF_3$, cyclopropyl, cyclopropyloxy, oxetanyloxy, azetidinyl, —CN, —OH, —$OCH_3$, —$OCH_2F$, —$OCHF_2$, or —$OCF_3$.

In some embodiments, $R^{4A}$ is aryl substituted with 1, 2, 3, 4, or 5 substituents independently selected from F, Cl, —$CH_3$, —$CH_2F$, —$CHF_2$, —$CF_3$, —CN, —$OCH_3$, —$OCH_2F$, —$OCHF_2$, or —$OCF_3$.

In some embodiments, $R^{4A}$ is aryl substituted with 1, 2, or 3 substituents independently selected from F, Cl, —$CH_3$, —$CH_2F$, —$CHF_2$, —$CF_3$, —CN, —$OCH_3$, —$OCH_2F$, —$OCHF_2$, or —$OCF_3$.

In some embodiments, the aryl is phenyl.

Preparation of Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, PA), Aldrich Chemical (Milwaukee, WI, including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Spectrum Quality Product, Inc. (New Brunswick, NJ), TCI America (Portland, OR), Trans World Chemicals, Inc. (Rockville, MD), and Wako Chemicals USA, Inc. (Richmond, VA).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference useful for the preparation and selection of pharmaceutical salts of the benzenesulfonamide derivative compounds described herein is P. H. Stahl & C. G. Wermuth "Handbook of Pharmaceutical Salts", Verlag Helvetica Chimica Acta, Zurich, 2002.

Pharmaceutical Compositions

In certain embodiments, the benzenesulfonamide derivative compound described herein is administered as a pure chemical. In other embodiments, the benzenesulfonamide derivative compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21st Ed. Mack Pub. Co., Easton, PA (2005)).

Provided herein is a pharmaceutical composition comprising at least one benzenesulfonamide derivative compound as described herein, or a stereoisomer, pharmaceutically acceptable salt, hydrate, or solvate thereof, together with one or more pharmaceutically acceptable carriers. The carrier(s)(or excipient(s)) is acceptable or suitable if the carrier is compatible with the other ingredients of the composition and not deleterious to the recipient (i.e., the subject or the patient) of the composition.

One embodiment provides a pharmaceutical composition comprising a pharmaceutically acceptable excipient and a compound of Formula (I), Formula (II), Formula (III), Formula (IV), or Formula (V), or a compound disclosed in Table 1, Table 2, Table 3, Table 3A, Table 4, or Table 5, or a pharmaceutically acceptable salt or solvate thereof.

One embodiment provides a method of preparing a pharmaceutical composition comprising mixing a compound of Formula (I), Formula (II), Formula (III), Formula (IV), or Formula (V), or a compound disclosed in Table 1, Table 2, Table 3, Table 3A, Table 4, or Table 5, or a pharmaceutically acceptable salt or solvate thereof, and a pharmaceutically acceptable carrier.

In certain embodiments, the benzenesulfonamide derivative compound as described by Formula (I), Formula (II), Formula (III), Formula (IV), or Formula (V), or a compound disclosed in Table 1, Table 2, Table 3, Table 3A, Table 4, or Table 5, is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21st Ed. Mack Pub. Co., Easton, PA (2005)).

In some embodiments, the benzenesulfonamide derivative compound as described by Formula (I), Formula (II), Formula (III), Formula (IV), or Formula (V), or a compound disclosed in Table 1, Table 2, Table 3, Table 3A, Table 4, or Table 5, or pharmaceutically acceptable salt or solvate thereof, is formulated for administration by injection. In some instances, the injection formulation is an aqueous formulation. In some instances, the injection formulation is a non-aqueous formulation. In some instances, the injection formulation is an oil-based formulation, such as sesame oil, or the like.

The dose of the composition comprising at least one benzenesulfonamide derivative compound as described herein differs depending upon the subject or patient's (e.g., human) condition. In some embodiments, such factors include general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Methods of Treatment

One embodiment provides a compound of Formula (I), Formula (II), Formula (III), Formula (IV), or Formula (V), or a compound disclosed in Table 1, Table 2, Table 3, Table 3A, Table 4, or Table 5, or a pharmaceutically acceptable salt or solvate thereof, for use in a method of treatment of the human or animal body.

One embodiment provides a compound of Formula (I), Formula (II), Formula (III), Formula (IV), or Formula (V), or a compound disclosed in Table 1, Table 2, Table 3, Table 3A, Table 4, or Table 5, or a pharmaceutically acceptable salt or solvate thereof, for use in a method of treatment of cancer or neoplastic disease.

One embodiment provides a use of a compound of Formula (I), Formula (II), Formula (III), Formula (IV), or Formula (V), or a compound disclosed in Table 1, Table 2, Table 3, Table 3A, Table 4, or Table 5, or a pharmaceutically acceptable salt or solvate thereof, in the manufacture of a medicament for the treatment of cancer or neoplastic disease.

In some embodiments, described herein is a method of treating cancer in a patient in need thereof comprising administering to the patient a compound of Formula (I), Formula (II), Formula (III), Formula (IV), or Formula (V), or a pharmaceutically acceptable salt or solvate thereof.

In some embodiments, described herein is a method of treating cancer in a patient in need thereof comprising administering to the patient a compound disclosed in Table 1, Table 2, Table 3, Table 3A, Table 4, or Table 5, or a pharmaceutically acceptable salt or solvate thereof.

In some embodiments, also described herein is a method of treating cancer in a patient in need thereof comprising administering to the patient a pharmaceutical composition comprising a compound of Formula (I), Formula (II), Formula (III), Formula (IV), or Formula (V), or a pharmaceutically acceptable salt or solvate thereof, and a pharmaceutically acceptable excipient.

In some embodiments, also described herein is a method of treating cancer in a patient in need thereof comprising administering to the patient a pharmaceutical composition comprising a compound disclosed in Table 1, Table 2, Table 3, Table 3A, Table 4, or Table 5, or a pharmaceutically acceptable salt or solvate thereof, and a pharmaceutically acceptable excipient. In some embodiments, the cancer is selected from chronic and acute myeloid leukemia. In some embodiments, the cancer is selected from chronic lymphocytic leukemia and small lymphocytic lymphoma.

Provided herein is the method wherein the pharmaceutical composition is administered orally. Provided herein is the method wherein the pharmaceutical composition is administered by injection.

One embodiment provides a protein modified with a benzenesulfonamide derivative compound as described herein, wherein the compound forms a covalent bond with a sulfur atom of a cysteine residue of the protein.

One embodiment provides a method of modifying a polypeptide with a benzenesulfonamide derivative compound as described herein, comprising contacting the polypeptide with the compound to form a covalent bond with a sulfur atom of a cysteine residue of the polypeptide.

One embodiment provides a method of binding a compound to a polypeptide, comprising contacting the polypeptide with a benzenesulfonamide derivative compound as described herein.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

In some embodiments, the benzenesulfonamide derivative compounds disclosed herein are synthesized according to the following examples. As used below, and throughout the description of the disclosure, the following abbreviations, unless otherwise indicated, shall be understood to have the following meanings:

° C. degrees Celsius
$\delta_H$ chemical shift in parts per million downfield from tetramethylsilane
DCM dichloromethane ($CH_2Cl_2$)
DMF dimethylformamide
DMSO dimethylsulfoxide
EA ethyl acetate
ESI electrospray ionization
Et ethyl
g gram(s)
h hour(s)
HPLC high performance liquid chromatography
Hz hertz
J coupling constant (in NMR spectrometry)
LCMS liquid chromatography mass spectrometry
μ micro
m multiplet (spectral); meter(s); milli
M molar
$M^+$ parent molecular ion
Me methyl
MHz megahertz
min minute(s)
mol mole(s); molecular (as in mol wt)
mL milliliter
MS mass spectrometry
nm nanometer(s)
NMR nuclear magnetic resonance
pH potential of hydrogen; a measure of the acidity or basicity of an aqueous solution
PE petroleum ether
RT room temperature
s singlet (spectral)
t triplet (spectral)
T temperature
TFA trifluoroacetic acid
THF tetrahydrofuran Exemplary compounds of the application were synthesized using the methods described herein, or other methods, which are known in the art. Unless otherwise noted, reagents and solvents were obtained from commercial suppliers Anhydrous solvents, methanol, acetonitrile, dichloromethane, tetrahydrofuran and dimethylformamide, were purchased from Sigma Aldrich and used directly from Sure-Seal bottles. Reactions were performed under an atmosphere of dry nitrogen in oven-dried glassware and were monitored for completeness by thin-layer chromatography (TLC) using silica gel (visualized by UV light, or developed by treatment with $KMnO_4$ stain and ninhydrin stain). NMR spectra were recorded in Bruker Avance III spectrometer at 23° C., operating at 400 MHz for $^1H$ NMR and 100 MHz $^{13}C$ NMR spectroscopy either in $CDCl_3$, $CD_3OD$ or $d_6$-DMSO. Chemical shifts (d) are reported in parts per million (ppm) after calibration to residual isotopic solvent. Coupling constants (J) are reported in Hz. Mass spectrometry was performed with an AB/Sciex QStar mass spectrometer with an ESI source, MS/MS and accurate mass capabilities, associated with an Agilent 1100 capillary LC system. Before biological testing, inhibitor purity was evaluated by reversed-phase HPLC (rpHPLC). Analysis by rpHPLC was performed using a Phenomenex Luna 5u C18 150 mm×4.6 mm column run at 1.2 mL/min, and using gradient mixtures. The linear gradient consisted of a changing solvent composition of either $(I)_{15}$% MeCN and 85% $H_2O$ with 0.1% TFA (v/v) to 100% MeCN over 30 minutes and $(II)_{15}$% MeCN and 85% $H_2O$ with 0.1% TFA (v/v) to 100% MeCN over 60 minutes, UV detection at 250 nm. For reporting HPLC data, percentage purity is given in parentheses after the retention time for each condition. All biologically evaluated compounds are >95% chemical purity as measured by HPLC. The HPLC traces for all tested compounds are provided in supporting information.

General Procedure A

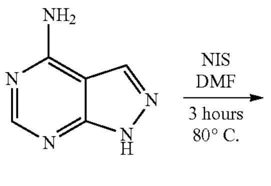

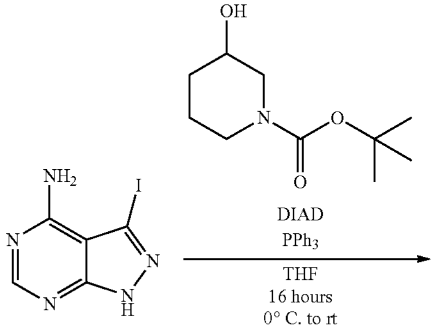

A-1

-continued

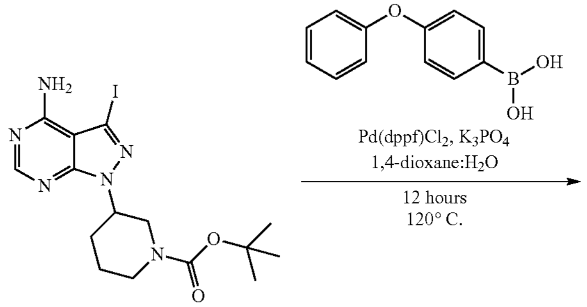

A-2

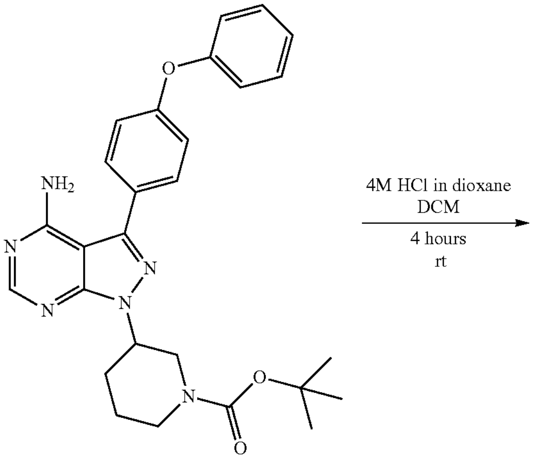

A-3

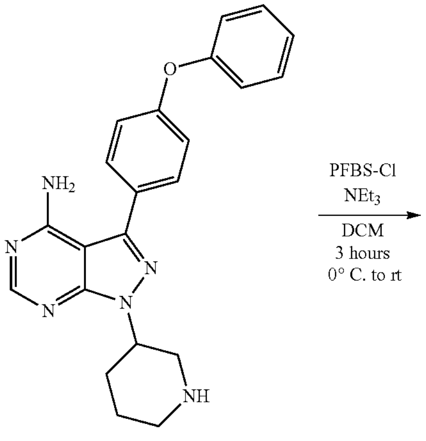

A-4

-continued

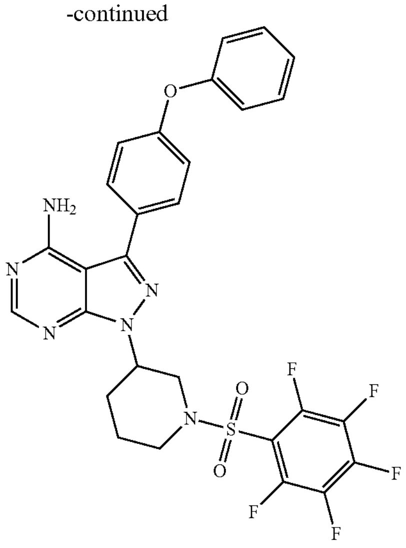

Step 1: 3-iodo-1H-pyrazolo[3,4-d]pyrimidin-4-amine (A-1)

1H-Pyrazolo[3,4-d]pyrimidin-4-amine (1.5 g, 11.1 mmol) was dissolved in dimethylformamide (12 mL) and the resulting solution was stirred at 25° C. After 5 minutes, the solution was added with N-Iodosuccinimide (3.7 g, 16.7 mmol). The resulting mixture was stirred at 80° C. After 4 hours, the resulting solid was filtered and rinsed with cold ethanol and concentrated in vacuo to yield the desired product (2.8 g, 97% yield). The isolated product was used for subsequent reactions. $^1$H NMR (400 MHz, DMSO-$d_6$) δ 11.07 (b, 1H), 8.17 (s, 1H).

Step 2: tert-butyl 3-(4-amino-3-iodo-1H-pyrazolo[3,4-d]pyrimidin-1-yl)piperidine-1-carboxylate (A-2)

3-Iodo-1H-pyrazolo[3,4-d]pyrimidin-4-amine (450 mg, 1.72 mmol) was dissolved in tetrahydrofuran (0.05 M). The resulting solution was treated with triphenylphosphine (904 mg, 3.45 mmol) and tert-butyl(S/R)-3-hydroxypiperidine-1-carboxylate (694 mg, 3.45 mmol). The reaction mixture was stirred for 10 min at 0° C. followed by the dropwise addition of diisopropyl azodicarboxylate (0.684 ml, 3.45 mmol). The solution was stirred at room temperature. After 20 hours, the solution was added with dichloromethane and water. The resulting solution was extracted thrice with 10% methanol in dichloromethane. The combined organic layers were dried over magnesium sulfate and concentrated in vacuo. The crude sample was absorbed onto silica gel and purified using flash chromatography using a 1-3% methanol:dichloromethane gradient. The desired product was isolated as off-white solid. (410 mg, 53% yield). The desired product was used for subsequent reactions $^1$H NMR (400 MHz, Chloroform-d) δ 1.46 (d, J=4.8 Hz, 9H), 1.67 (qd, J=17.1, 15.3, 4.5 Hz, 1H), 1.84-1.93 (m, 1H), 2.10-2.21 (m, 2H), 2.84 (t, J=12.5 Hz, 1H), 3.35 (d, J=11.7 Hz, 1H), 4.13 (q, J=7.2 Hz, 2H), 4.76 (tt, J=10.8, 4.5 Hz, 1H), 6.31-6.52 (m, 2H), 8.33 (d, J=3.9 Hz, 1H).

Step 3: tert-butyl 3-(4-amino-3-(4-phenoxyphenyl)-1H-pyrazolo[3,4-d]pyrimidin-1-yl)piperidine-1-carboxylate (A-3)

tert-Butyl 3-(4-amino-3-iodo-1H-pyrazolo[3,4-d]pyrimidin-1-yl)piperidine-1-carboxylate (144 mg, 0.324 mmol)

was dissolved in 1,4-dioxane:$H_2O$ (3:1, 0.05 M), and the resulting solution was stirred at room temperature. The solution was added with 4-phenoxyphenylboronic acid (97.1 mg, 0.454 mmol) and potassium carbonate (89.6 mg, 0.648 mmol). The resulting solution was purged under nitrogen. After 15 minutes, the solution was added with [1,1'-Bis(diphenylphosphino)ferrocene]dichloropalladium(II)(11.9 mg, 0.0162 mmol). The solution was bubble-purged with nitrogen for 10 min. The reaction mixture was then heated to 120° C. and left to stir for 21 hours. The solution was filtered through the Celite and the collected filtrate was concentrated in vacuo. Filtrate was re-dissolved in ethyl acetate, washed three times with water, dried over magnesium sulfate and concentrated in vacuo. The crude sample was absorbed onto silica gel and purified using flash chromatography using a 1-4% methanol:dichloromethane gradient. The desired product was isolated as off-white solid. (120 mg, 76% yield). $^1H$ NMR (400 MHz, Chloroform-d) δ 1.45 (d, J=2.9 Hz, 9H), 1.66-1.80 (m, 1H), 1.84-1.94 (m, 1H), 2.16-2.28 (m, 2H), 2.86 (td, J=12.8, 2.9 Hz, 1H), 3.49 (d, J=15.2 Hz, 1H), 4.12 (q, J=7.1 Hz, 2H), 4.85 (tt, J=10.8, 4.5 Hz, 1H), 5.99 (s, 2H), 7.09 (d, J=8.2 Hz, 2H), 7.13-7.21 (m, 3H), 7.39 (t, J=7.9 Hz, 2H), 7.64-7.69 (m, 2H), 8.36 (s, 1H).

Step 4: 3-(4-phenoxyphenyl)-1-(piperidin-3-yl)-1H-pyrazolo[3,4-d]pyrimidin-4-amine (A-4)

tert-Butyl 3-(4-amino-3-(4-phenoxyphenyl)-1H-pyrazolo[3,4-d]pyrimidin-1-yl)piperidine-1-carboxylate was dissolved in dichloromethane (0.14 M). The solution was then treated with 4 M hydrochloric acid in dioxane (0.14 M). The reaction mixture was stirred at room temperature. After 12 hours, the reaction mixture was concentrated in vacuo. The crude product was diluted with ethyl acetate and water, and the aqueous layer was added with saturated sodium bicarbonate solution. The mixture was extracted with ethyl acetate, and the collected organic layer was washed with saturated sodium chloride solution, dried over magnesium sulfate and concentrated in vacuo to afford the crude intermediate A-4 which was used in the next step without further purification (92 mg, 89% yield).

Step 5: 1-(1-((perfluorophenyl)sulfonyl)piperidin-3-yl)-3-(4-phenoxyphenyl)-1H-pyrazolo[3,4-d]pyrimidin-4-amine 3-(4-Phenoxyphenyl)-1-(piperidin-3-yl)-1H-pyrazolo[3,4-d]pyrimidin-4-amine (1 eq.) was dissolved in dichloromethane (0.1 M). The resulting solution was stirred at 0° C. After 10 minutes, the solution was added with pentafluorobenzenesulfonyl chloride (1.5 eq) in a dropwise manner. The resulting mixture was left to stir at 0° C. for 15 minutes followed by the dropwise addition of triethylamine (1.5 eq). The resulting solution was stirred for 3 hours and the mixture was subsequently quenched with 0.1 M hydrochloric acid at 0° C. The aqueous layer was extracted thrice with dichloromethane, dried over magnesium sulfate and concentrated in vacuo. The crude sample was absorbed onto silica gel and purified using flash chromatography. 1-(1-((perfluorophenyl)sulfonyl)piperidin-3-yl)-3-(4-phenoxyphenyl)-1H-pyrazolo[3,4-d]pyrimidin-4-amine was isolated as white solid and was lyophilized from water/acetonitrile. (52-65%)

General Procedure B

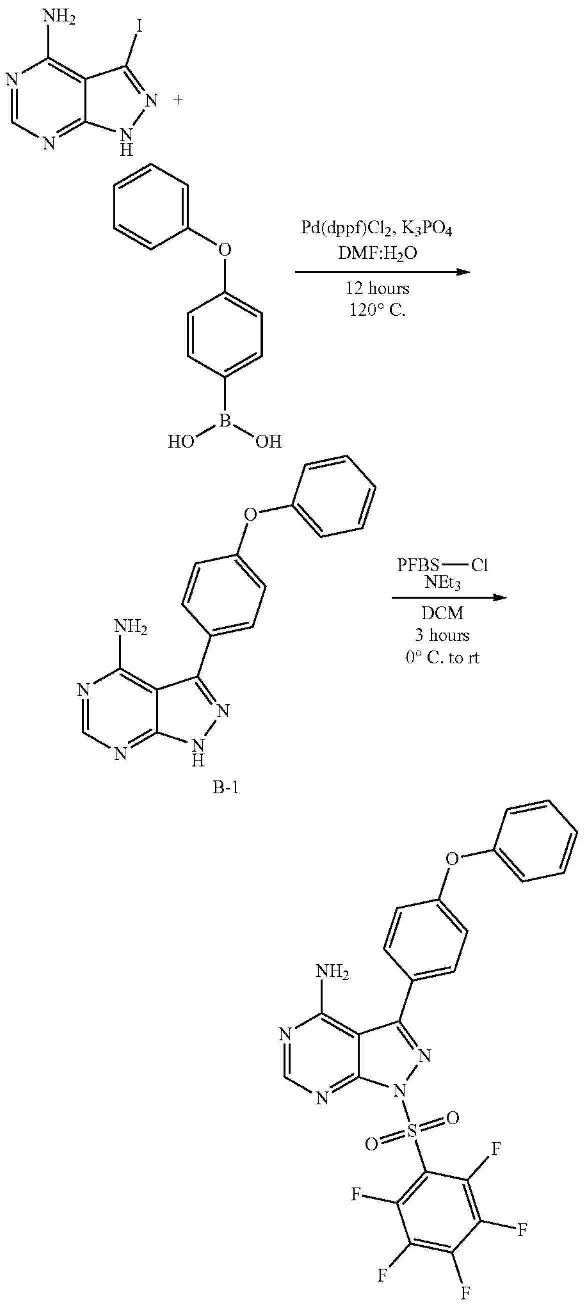

B-1

Step 1: 3-(4-phenoxyphenyl)-1H-pyrazolo[3,4-d]pyrimidin-4-amine (B-1)

1H-Pyrazolo[3,4-d]pyrimidin-4-amine was dissolved in dimethylformamide and water (3:2, 0.26 M). The resulting solution was added with 4-phenoxyphenylboronic acid (214 mg, 1 mmol) and potassium phosphate (266 mg, 1.25 mmol). The resulting solution was purged once with nitrogen and then added with [1,1'-Bis(diphenylphosphino)ferrocene]dichloropalladium(II)(30.6 mg, 0.0418 mmol). The reaction was stirred at 120° C. for 16 hours. The resulting mixture was allowed to cool to room temperature and subsequently filtered through celite. The filtrate was washed five times with saturated sodium chloride, dried over magnesium sulfate and concentrated in vacuo. The crude product was then recrystallized from methanol to afford the desired off-white solid 5 (100 mg, 40%). The isolated product was used for subsequent reactions. $^1$H NMR (400 MHz, DMSO-$d_6$) δ 7.13-7.19 (m, 5H), 7.36-7.48 (m, 2H), 7.63-7.70 (m, 2H), 8.23 (s, 1H), 13.56 (s, 1H).

Step 2: 1-((perfluorophenyl)sulfonyl)-3-(4-phenoxyphenyl)-1H-pyrazolo[3,4-d]pyrimidin-4-amine 3-(4-Phenoxyphenyl)-1H-pyrazolo[3,4-d]pyrimidin-4-amine (5)(1 eq.) was dissolved in dichloromethane (0.1 M). The resulting solution was stirred at 0° C. After 10 minutes, the solution was added with pentafluorobenzenesulfonyl chloride (1.5 eq) in a dropwise manner. The resulting mixture was left to stir at 0° C. for 15 minutes followed by the dropwise addition of triethylamine (1.5 eq). The resulting solution was stirred for 3 hours and the mixture was subsequently quenched with 0.1 M hydrochloric acid at 0° C. The aqueous layer was extracted thrice with dichloromethane, dried over magnesium sulfate and concentrated in vacuo. The crude sample was absorbed onto silica gel and purified using flash chromatography. 1-((perfluorophenyl) sulfonyl)-3-(4-phenoxyphenyl)-1H-pyrazolo[3,4-d]pyrimidin-4-amine was isolated as white solid and was lyophilized from water/acetonitrile. (52-65%)

General Procedure C

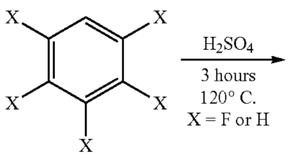

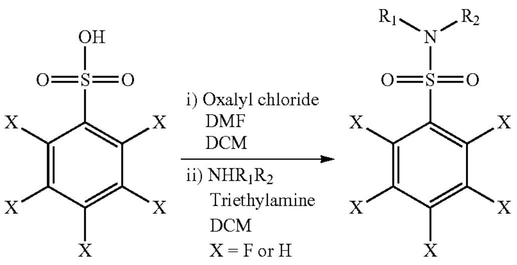

C-1

Step 1: Sulfonic Acid (C-1)

Chlorosulfonic acid (5 eq.) was added with the appropriate fluorobenzene compound (1 eq). The reaction mixture was then heated to reflux at 150° C. for 3 hours. The reaction was quenched with ice. The aqueous mixture was further diluted with 1 M hydrochloric acid and extracted thrice with ethyl acetate, the collected organic layers were washed once with saturated sodium chloride and concentrated in vacuo to yield brownish/yellow solid which was used without further purification.

Step 2: Sulfonamide

An appropriate sulfonic acid (1.1 eq) was added with dichloromethane (0.15M) and oxalyl chloride (2 eq.) dropwise at 0° C. The solution was then added with three drops of dimethylformamide. After 1 hour, the reaction mixture was evaporated in vacuo. The crude mixture was re-dissolved in dichloromethane (0.15M) and stirred at 0° C. After 10 minutes, 3-(4-phenoxyphenyl)-1-(piperidin-3-yl)-1H-pyrazolo[3,4-d]pyrimidin-4-amine (4)(1 eq.) was added, followed by the dropwise addition of triethylamine (1.1 eq). After 12 hours, the reaction was quenched with water and extracted three times with dichloromethane. The collected organic layers were washed once with saturated sodium chloride, dried over magnesium sulfate, filtered and evaporated in vacuo. The crude sample was absorbed onto silica gel and purified using flash chromatography (45-67%).

General Procedure D

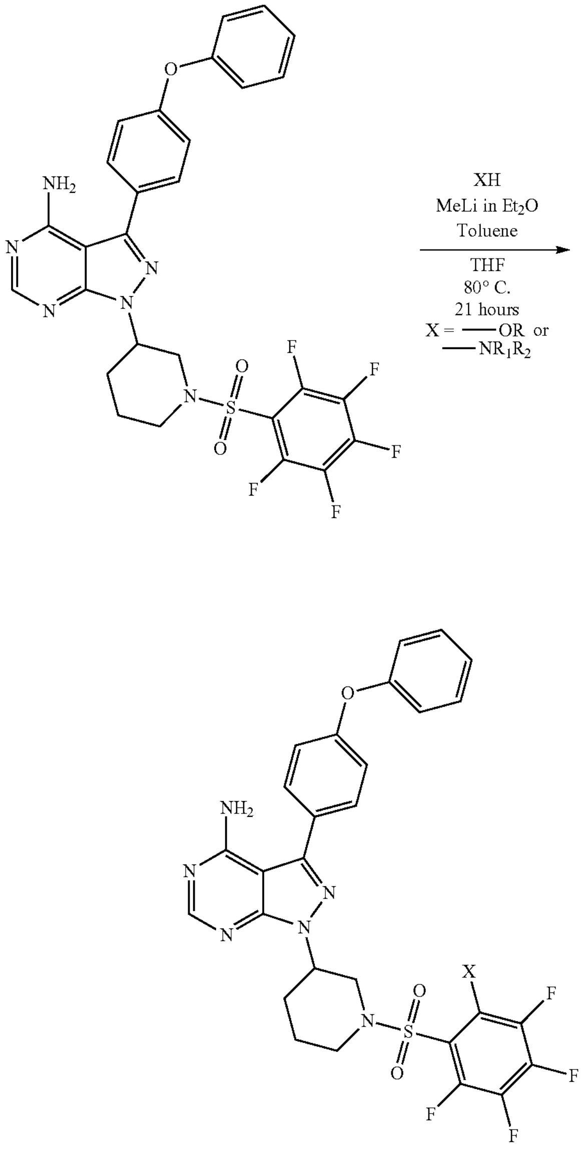

An appropriate alcohol (1.5 eq) was dissolved in toluene (0.1 M) and tetrahydrofuran (1 M). The solution was stirred at 0° C. After 10 minutes, the solution was added with 1.5 M methyllithium in ethyl ether (1.5 eq.) in a dropwise manner. The resulting mixture was stirred at 0° C. for 30 minutes and then added to a solution of (R)-1-(1-((perfluorophenyl)sulfonyl)piperidin-3-yl)-3-(4-phenoxyphenyl)-1H-pyrazolo[3,4-d]pyrimidin-4-amine (1 eq.) in toluene (0.1 M) and tetrahydrofuran (1 M). The reaction was left to stir at room temperature. After 12 hours, the reaction was quenched with 1 M hydrochloric acid and extracted thrice with dichloromethane. The collected organic layers were washed once with saturated sodium chloride solution, dried over magnesium sulfate, filtered and concentrated in vacuo. The product was purified using preparative HPLC using a water (+0.1% v/v formic acid):acetonitrile (+0.1% v/v formic acid) gradient.

Example A1 Synthesis of (R)-1-(1-((perfluorophenyl)sulfonyl)piperidin-3-yl)-3-(4-phenoxyphenyl)-1H-pyrazolo[3,4-d]pyrimidin-4-amine (I-A1)

I-A1

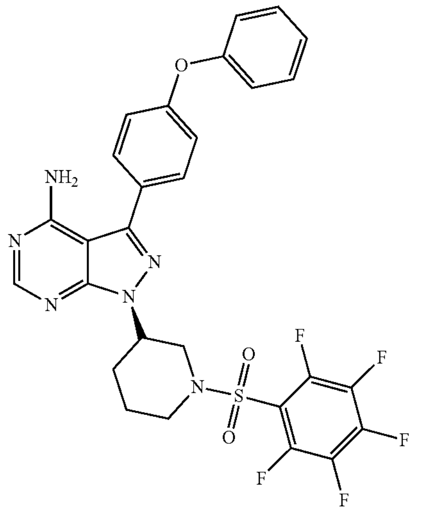

The title compound I-A1, (R)-1-(1-((perfluorophenyl)sulfonyl)piperidin-3-yl)-3-(4-phenoxyphenyl)-1H-pyrazolo[3,4-d]pyrimidin-4-amine, was prepared via general route of synthesis A. $^1$H NMR (400 MHz, Chloroform-d) δ 1.96 (dt, J=12.8, 7.4 Hz, 1H), 2.02-2.14 (m, 1H), 2.22-2.31 (m, 2H), 2.86 (t, J=12.0 Hz, 1H), 3.40 (t, J=11.3 Hz, 1H), 4.05 (d, J=12.3 Hz, 1H), 4.19 (dd, J=12.0, 4.5 Hz, 1H), 5.05 (tt, J=10.4, 5.0 Hz, 1H), 5.70 (s, 2H), 7.06-7.13 (m, 2H), 7.13-7.24 (m, 3H), 7.39-7.47 (m, 2H), 7.60-7.69 (m, 2H), 8.39 (s, 1H). $^{19}$F NMR (376 MHz, Chloroform-d) δ −159.32--157.72 (m), −145.32 (tt, J=21.2, 6.5 Hz), −134.36 (qd, J=13.8, 7.8 Hz).

Example A2 Synthesis of (S)-1-(1-((perfluorophenyl)sulfonyl)piperidin-3-yl)-3-(4-phenoxyphenyl)-1H-pyrazolo[3,4-d]pyrimidin-4-amine (I-A2)

I-A2

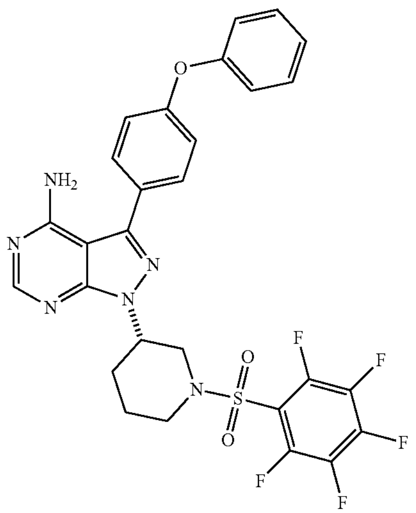

The title compound I-A2, (S)-1-(1-((perfluorophenyl)sulfonyl)piperidin-3-yl)-3-(4-phenoxyphenyl)-1H-pyrazolo[3,4-d]pyrimidin-4-amine, was prepared via general route of synthesis A. $^1$H NMR (400 MHz, Chloroform-d) δ 1.88-2.00 (m, 1H), 2.03-2.13 (m, 1H), 2.22-2.32 (m, 2H), 2.78-2.91 (m, 1H), 3.40 (t, J=11.3 Hz, 1H), 4.04 (d, J=12.4 Hz, 1H), 4.18 (dd, J=12.2, 4.4 Hz, 1H), 5.05 (dt, J=10.5, 5.5 Hz, 1H), 5.80 (s, 2H), 7.05-7.13 (m, 2H), 7.13-7.25 (m, 3H), 7.36-7.47 (m, 2H), 7.59-7.67 (m, 2H), 8.39 (s, 1H). 19F NMR (376 MHz, Chloroform-d) δ −158.20 (tt, J=21.3, 6.9 Hz), −145.39 (tt, J=21.1, 6.5 Hz), −134.41 (qd, J=13.8, 7.8 Hz).

Example A3 Synthesis of 1-((perfluorophenyl)sulfonyl)-3-(4-phenoxyphenyl)-1H-pyrazolo[3,4-d]pyrimidin-4-amine (I-A3)

I-A3

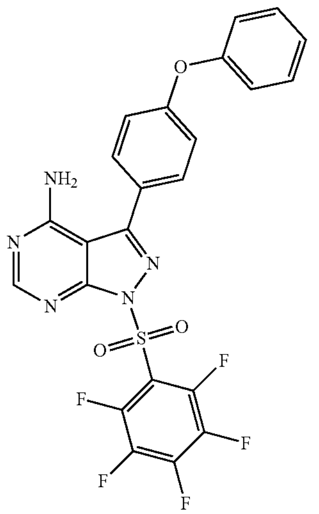

The title compound I-A3, 1-((perfluorophenyl)sulfonyl)-3-(4-phenoxyphenyl)-1H-pyrazolo[3,4-d]pyrimidin-4-amine, was prepared via general route of synthesis B. $^{1}$H NMR (400 MHz, Chloroform-d) h 7.13 (d, J=8.0 Hz, 2H), 7.21 (s, 2H), 7.25 (d, J=7.5 Hz, 1H), 7.46 (t, J=7.9 Hz, 2H), 7.65 (d, J=8.3 Hz, 2H), 8.58 (s, 1H). $^{19}$F NMR (376 MHz, Chloroform-d) δ −156.78−−156.25 (m), −139.14 (q, J=16.8, 14.9 Hz), −132.58−−131.88 (m).

Example A4 Synthesis of (R)-3-(4-phenoxyphenyl)-1-(1-((2,3,4,5-tetrafluorophenyl)sulfonyl)piperidin-3-yl)-1H-pyrazolo[3,4-d]pyrimidin-4-amine (I-A4)

I-A4

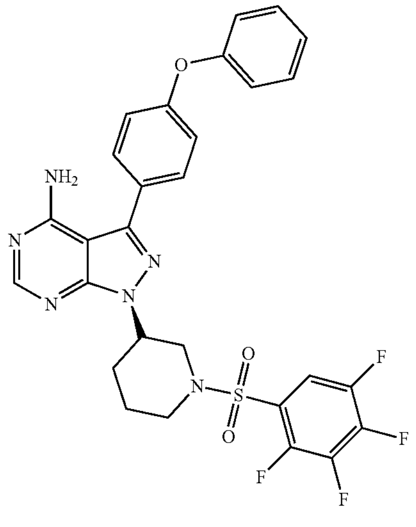

The title compound I-A4, (R)-3-(4-phenoxyphenyl)-1-(1-((2,3,4,5-tetrafluorophenyl)sulfonyl)piperidin-3-yl)-1H-pyrazolo[3,4-d]pyrimidin-4-amine, was prepared via general route of synthesis C. $^{1}$H NMR (400 MHz, Chloroform-d) δ 1.86-1.98 (m, 1H), 2.06 (d, J=10.4 Hz, 1H), 2.17-2.31 (m, 2H), 2.82 (t, J=2.3 Hz, 1H), 3.33 (ddd, J=12.0, 10.7, 1.4 Hz, 1H), 3.98 (d, J=12.3 Hz, 1H), 4.10 (dd, J=11.9, 4.4 Hz, 1H), 4.97-5.08 (m, 1H), 5.58 (s, 2H), 7.06-7.14 (m, 2H), 7.15-7.24 (m, 3H), 7.38-7.45 (m, 2H), 7.62-7.67 (m, 2H), 8.40 (s, 1H). $^{19}$F NMR (376 MHz, Chloroform-d) δ −150.65 (ddd, J=22.3, 19.1, 3.3 Hz), −145.90 (tt, J=20.1, 8.0 Hz), −135.60−−135.15 (m), −132.71 (ddt, J=21.1, 13.7, 7.0 Hz).

Example A5 Synthesis of (R)-3-(4-phenoxyphenyl)-1-(1-((2,3,5,6-tetrafluorophenyl)sulfonyl)piperidin-3-yl)-1H-pyrazolo[3,4-d]pyrimidin-4-amine (I-A5)

I-A5

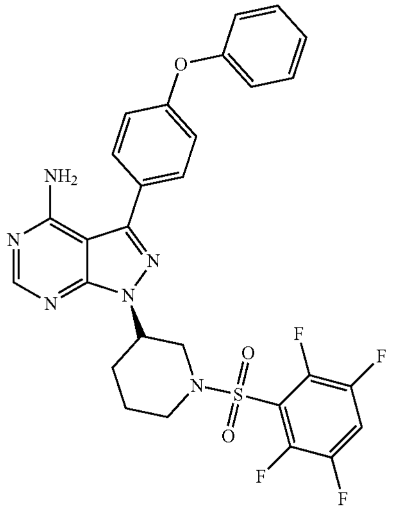

The title compound I-A5, (R)-3-(4-phenoxyphenyl)-1-(1-((2,3,5,6-tetrafluorophenyl)sulfonyl)piperidin-3-yl)-1H-pyrazolo[3,4-d]pyrimidin-4-amine, was prepared via general route of synthesis C. $^{1}$H NMR (400 MHz, Chloroform-d) δ 1.87-2.00 (m, OH), 2.07 (ddd, J=14.6, 8.9, 5.6 Hz, 1H), 2.21-2.31 (m, 2H), 2.79-2.90 (m, 1H), 3.39 (t, J=11.3 Hz, 1H), 4.06 (d, J=12.5 Hz, 1H), 4.16-4.24 (m, 1H), 5.06 (dt, J=10.6, 5.6 Hz, 1H), 7.06-7.14 (m, 2H), 7.14-7.24 (m, 3H), 7.33 (dt, J=9.1, 7.3 Hz, 1H), 7.39-7.46 (m, 2H), 7.61-7.68 (m, 2H), 8.35 (s, 1H). $^{19}$F NMR (376 MHz, Chloroform-d) δ −135.98−−134.87 (m).

Example A6 Synthesis of (R)-1-(1-((2-cyclopropoxy-3,4,5,6-tetrafluorophenyl)sulfonyl)piperidin-3-yl)-3-(4-phenoxyphenyl)-1H-pyrazolo[3,4-d]pyrimidin-4-amine (I-A6)

I-A6

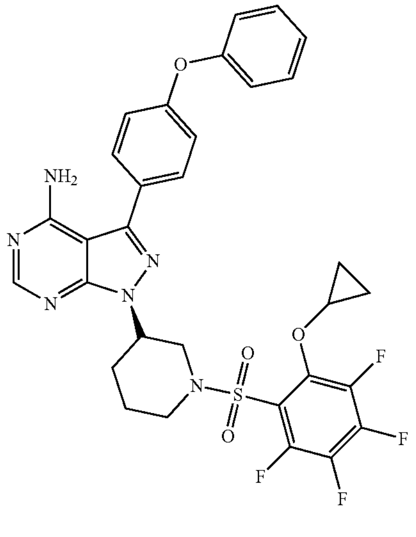

The title compound I-A6, (R)-1-(1-((2-cyclopropoxy-3,4,5,6-tetrafluorophenyl)sulfonyl)piperidin-3-yl)-3-(4-phenoxyphenyl)-1H-pyrazolo[3,4-d]pyrimidin-4-amine, was prepared via general route of synthesis D. $^{1}H$ NMR (400 MHz, Chloroform-d) δ 0.63 (dtd, J=6.1, 3.9, 2.3 Hz, 2H), 0.97-1.12 (m, 2H), 1.80-1.94 (m, 1H), 2.02 (dd, J=13.7, 3.4 Hz, 1H), 2.22 (td, J=9.7, 8.2, 3.9 Hz, 2H), 2.84 (td, J=12.4, 2.9 Hz, 1H), 3.37 (t, J=11.4 Hz, 1H), 3.95 (d, J=12.6 Hz, 1H), 4.11 (dd, J=12.0, 4.6 Hz, 1H), 4.44 (tq, J=6.4, 3.1 Hz, 1H), 5.01 (tt, J=10.5, 4.7 Hz, 1H), 5.86 (s, 2H), 7.07-7.13 (m, 2H), 7.15-7.24 (m, 3H), 7.37-7.46 (m, 2H), 7.60-7.68 (m, 2H), 8.37 (s, 1H). $^{19}F$ NMR (376 MHz, Chloroform-d) δ−160.40 (dd, J=24.2, 21.1 Hz), −150.19 (ddd, J=20.3, 9.4, 3.8 Hz), −147.46 (td, J=20.9, 7.0 Hz), −135.65-−134.51 (m).

Example A7 Synthesis of (R)-1-(1-((2,6-dicyclopropoxy-3,4,5-trifluorophenyl)sulfonyl)piperidin-3-yl)-3-(4-phenoxyphenyl)-1H-pyrazolo[3,4-d]pyrimidin-4-amine (I-A7)

I-A7

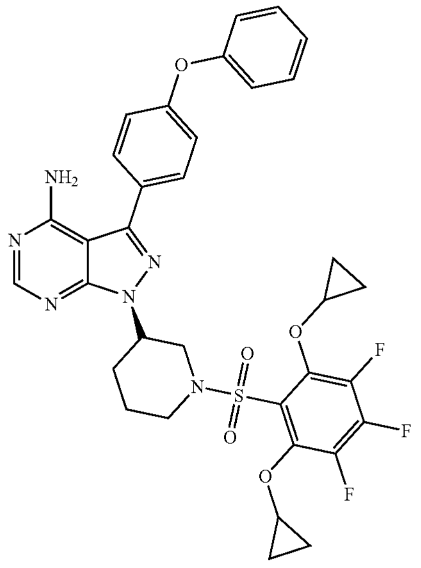

The title compound I-A7, (R)-1-(1-((2,6-dicyclopropoxy-3,4,5-trifluorophenyl)sulfonyl)piperidin-3-yl)-3-(4-phenoxyphenyl)-1H-pyrazolo[3,4-d]pyrimidin-4-amine, was prepared via general route of synthesis D. $^{1}H$ NMR (400 MHz, Chloroform-d) δ 0.52-0.64 (m, 4H), 1.00-1.09 (m, 4H), 1.82 (s, 1H), 1.95 (d, J=13.2 Hz, 1H), 2.17 (dt, J=8.3, 4.7 Hz, 2H), 2.71-2.82 (m, 1H), 3.27-3.37 (m, 1H), 3.88 (d, J=12.7 Hz, 1H), 4.05 (dd, J=12.2, 4.4 Hz, 1H), 4.36 (tt, J=6.2, 3.2 Hz, 2H), 4.97 (s, 1H), 5.53 (s, 2H), 7.06-7.13 (m, 2H), 7.16-7.24 (m, 3H), 7.38-7.46 (m, 2H), 7.65 (d, J=8.5 Hz, 2H), 8.40 (s, 1H). $^{19}F$ NMR (376 MHz, Chloroform-d) δ −151.28 (dd, J=20.5, 3.3 Hz), −149.26 (t, J=21.0 Hz).

Synthesis of (1S)-3-(4-phenoxyphenyl)-1-pyrrolidin-3-yl-pyrazolo[3,4-d]pyrimidin-4-amine To a solution of 3-(4-phenoxyphenyl)-1H-pyrazolo[3,4-d]pyrimidin-4-amine (2 g, 6.59 mmol) in anhydrous tetrahydrofuran (100 mL) were added tert-butyl (3S)-3-hydroxypyrrolidine-1-carboxylate (2.47 g, 13.19 mmol) and triphenylphosphine (3.46 g, 13.19 mmol) at room temperature. The mixture was cooled down to 0° C. in an ice bath and a solution of diisopropyl azodicarboxylate (2.67 g, 13.19 mmol, 2.59 mL) in 20 mL of anhydrous THF was added dropwise over 2 hours. The mixture was allowed to warm gradually to room temperature and stirred overnight. After 16 hours, concentrated HCl (13 mL) was added to the mixture and it was stirred at 50° C. for 3 hrs (bubbling was observed during the first 1.5 hours) and then cooled down to room temperature. THF was evaporated, 10 mL of water was added and the aqueous phase was extracted with DCM to remove all undesired organic materials (monitored by TLC, Ethyl Acetate/DCM 1:1). 10% NaOH was added to the aqueous phase dropwise until a pH of 9 was achieved. The aqueous solution was extracted with 10% MeOH/DCM. The combined organic layers were dried over sodium sulfate and evaporated, providing the crude product as brown semi-solid (0.89 g). The crude was purified by column chromatography on silica gel eluting with 0-25% MeOH/DCM providing the anticipated product as yellowish solid (0.53 g, 21% yield).

$^{1}H$ NMR (400 MHz, DMSO-$d_6$) δ 9.69 (s, 2H), 8.28 (s, 1H), 7.72 (d, J=8.7 Hz, 2H), 7.44 (dd, J=8.6, 7.3 Hz, 2H), 7.26-7.10 (m, 5H), 5.60 (tt, J=7.2, 4.7 Hz, 1H), 3.82-3.30 (m, 5H), 2.49-2.27 (m, 2H). ESI-MS: measured m/z 372.90 $[M+H]^+$

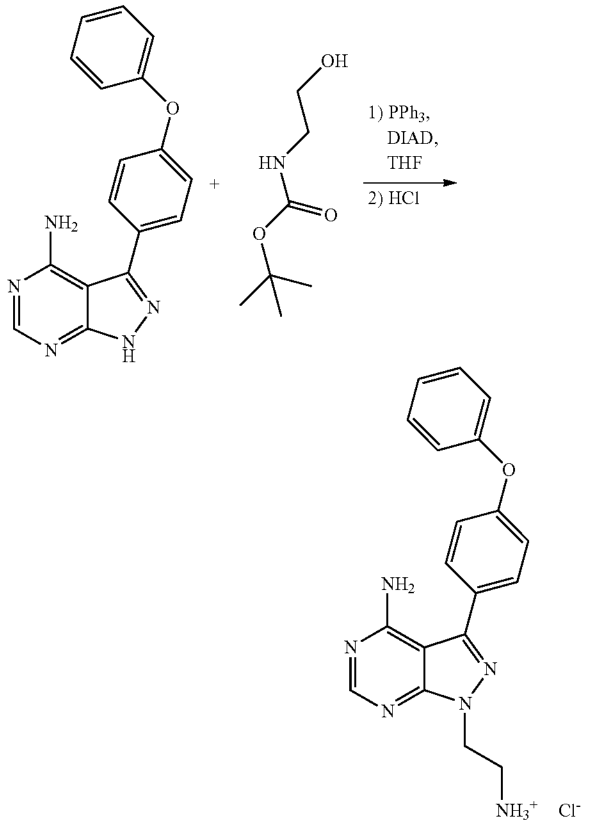

Synthesis of 1-(2-aminoethyl)-3-(4-phenoxyphenyl)pyrazolo[3,4-d]pyrimidin-4-amine hydrochloride To a solution of 3-(4-phenoxyphenyl)-1H-pyrazolo[3,4-d]pyrimidin-4-amine (20 g, 65.94 mmol) in tetrahydrofuran, anhydrous (900 mL) were added tert-butyl N-(2-hydroxyethyl)carbamate (21.26 g, 131.88 mmol, 20.44 mL) and triphenylphosphine (34.59 g, 131.88 mmol). The mixture was cooled down to 0° C. in an ice bath and a solution of diisopropyl azodicarboxylate (26.67 g, 131.88 mmol, 25.89 mL) in 100 mL of anhydrous THF was added dropwise over 5 hours. The solution was allowed to warm slowly in the ice bath and stirred overnight at room temperature.

Concentrated HCl (130 mL) was added to the reaction mixture slowly and it was stirred at 50° C. for 4 hrs (gas evolving during the first 2.5 hours observed) and then cooled down to 0° C. in an ice bath. After 1 hour at 0° C., a beige solid precipitated from the solution. It was filtered off, washed with THF, and dried under vacuum to afford the anticipated product as a beige solid (14.79 g, 56.82% yield). $^1$H NMR (400 MHz, DMSO-$d_6$) δ 8.61 (s, 1H), 8.38 (s, 3H), 7.70 (d, J=8.7 Hz, 2H), 7.46 (dd, J=8.6, 7.3 Hz, 2H), 7.27-7.06 (m, 5H), 4.70 (t, J=6.1 Hz, 2H), 3.36 (q, J=6.0 Hz, 2H). ESI-MS: measured m/z 346.90 [M+H]$^+$.

Synthesis of Intermediate D

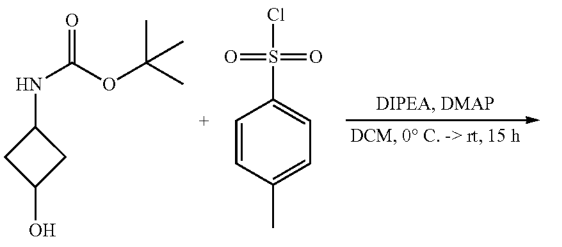

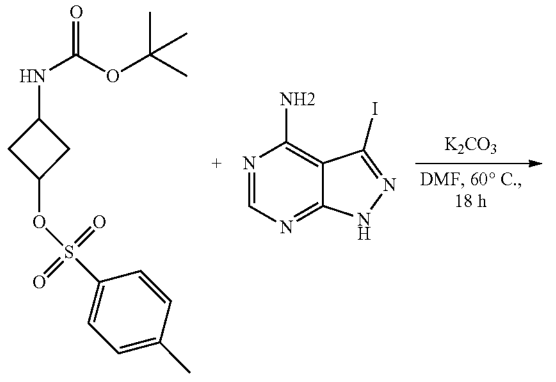

A

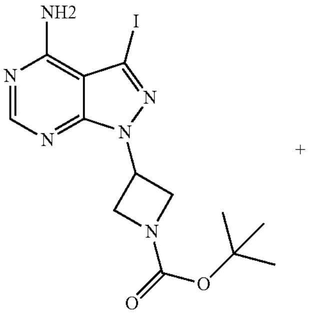

B

-continued

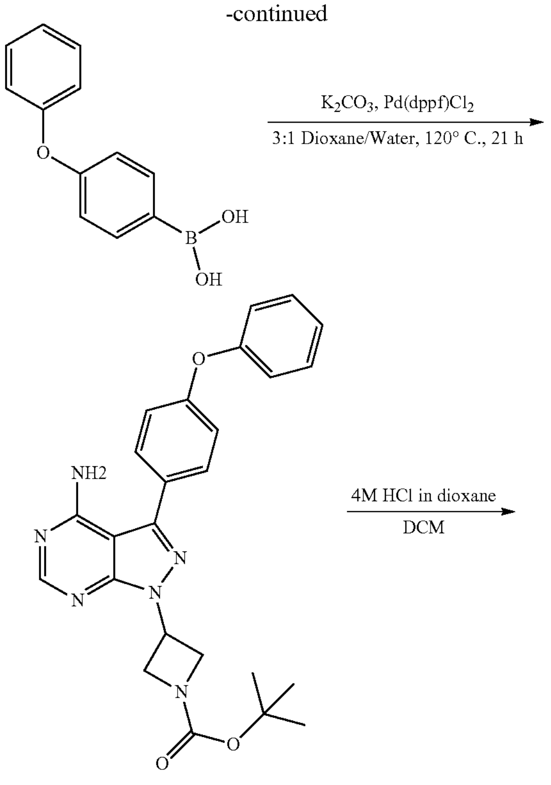

C

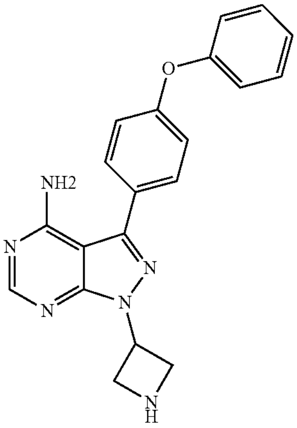

D

Intermediate A: 3-((tert-butoxycarbonyl)amino)cyclobutyl 4-methylbenzenesulfonate. To a oven dried microwave vial was added 1-(tert-Butoxycarbonyl)-3-hydroxyazetidine (500 mg, 2.89 mmol) in Dichloromethane (28.9 mL, 0.1M). The solution was cooled to 0° C. and N,N-Diisopropylethylamine (1.5 mL, 8.66 mmol) and 4-(Dimethylamino)pyridine (35.3 mg, 0.289 mmol) were added and the solution was stirred at 0° C. for 10 min. p-Toluenesulfonyl Chloride (248 mg, 1.3 mmol) was then added to the mixture which was left to stir at room temperature for 15 h. The reaction was subsequently quenched on ice with 1M HCl, and washed 3× with water. Combined organic layers were dried over $Mg_2SO_4$ and concentrated in vacuo to yield tert-butyl 3-(tosyloxy)azetidine-1-carboxylate as a white solid (283 mg, 99%). Product used as crude in the next step. $^1$H NMR (400 MHz, Chloroform-d) δ 7.77-7.72 (m, 2H), 7.34 (d, J=8.0 Hz, 2H), 4.97 (tt, J=6.7, 4.3 Hz, 1H), 4.07 (dd, J=10.1, 6.7 Hz, 2H), 3.89 (dd, J=10.6, 4.2 Hz, 2H), 2.43 (s, 3H), 1.38 (s, 9H).

Intermediate B: tert-butyl 3-(4-amino-3-iodo-1H-pyrazolo[3,4-d]pyrimidin-1-yl)azetidine-1-carboxylate To an oven dried round bottom flask was added 3-iodo-1H-pyrazolo[3,4-d]pyrimidin-4-amine (631 mg, 2.42 mmol)(intermediate A). The vial was subsequently purged once with nitrogen followed by the addition of DMF (12.1 mL, 0.2 M). The reaction was cooled to 0° C. and potassium carbonate (668 mg, 4.84 mmol) was then added on ice followed by the addition of tert-butyl 3-(tosyloxy)azetidine-1-carboxylate (950 mg, 2.9 mmol). The reaction was then heated to 60° C. for 18 h and subsequently quenched over 1M HCl, extracted thrice with ethyl acetate and washed four times with brine. Combined organic layers were dried over $Mg_2SO_4$, and evaporated. Crude product purified on a Biotage Isolera using a 100 g cartridge and a 1-5% MeOH/DCM gradient to obtain tert-butyl 3-(4-amino-3-iodo-1H-pyrazolo[3,4-d]pyrimidin-1-yl)azetidine-1-carboxylate as an off-white solid (232 mg, 20%). $^1H$ NMR (400 MHz, Chloroform-d) δ 8.32 (s, 1H), 6.22 (s, 2H), 5.61 (tt, J=8.1, 5.7 Hz, 1H), 4.16 (ddd, J=9.6, 6.7, 1.2 Hz, 2H), 3.82 (ddd, J=9.5, 4.4, 1.1 Hz, 2H).). MS (ESI, $[M+H]^+$) m/z 417.23.

Intermediate C: tert-butyl 3-(4-amino-3-(4-phenoxyphenyl)-1H-pyrazolo[3,4-d]pyrimidin-1-yl)azetidine-1-carboxylate. A sealed microwave vial containing intermediate B (232 mg, 0.557 mmol), 4-methoxyphenylboronic acid (167 mg, 0.78 mmol), potassium carbonate (154 mg, 1.11 mmol) in 3:1 1,4-dioxane:$H_2O$ (0.05 M) was purged under nitrogen for 15 min. [1,1'-Bis(diphenylphosphino)ferrocene] dichloropalladium(II)(20.4 mg, 0.0279 mmol) was subsequently added and nitrogen was bubbled through the solution for 10 min. The reaction mixture was then heated to 120° C. and left to stir for 21 h. The solution was filtered through celite and the filtrate concentrated. Filtrate was re-dissolved in ethyl acetate and extracted three times with water and the combined organic layers were dried over $Mg_2SO_4$ and concentrated. Silica gel chromatography (1-4% MeOH/DCM) yielded the desired tert-butyl 3-(4-amino-3-(4-phenoxyphenyl)-1H-pyrazolo[3,4-d]pyrimidin-1-yl)azetidine-1-carboxylate product as an off-white solid (254 mg, 98%). $^1H$ NMR (400 MHz, Chloroform-d) δ 8.30 (s, 1H), 7.70-7.64 (m, 2H), 7.41-7.34 (m, 2H), 7.19-7.11 (m, 3H), 7.10-7.04 (m, 2H), 5.69 (tt, J=8.1, 5.7 Hz, 1H), 4.61-4.50 (m, 2H), 4.40 (t, J=8.6 Hz, 2H), 1.46 (s, 9H). MS (ESI, $[M+H]^+$) m/z 459.3.

Intermediate D: 1-(azetidin-3-yl)-3-(4-phenoxyphenyl)-1H-pyrazolo[3,4-d]pyrimidin-4-amine. In a 25 mL round bottom was dissolved intermediate C in DCM and treated with 4M HCl in dioxane (total concentration 0.07 M, 1:1 4M HCl:DCM). The reaction mixture was stirred at room temperature for 12 h. The solvent was subsequently evaporated off under vacuum and co-distilled twice using chloroform to afford 1-(azetidin-3-yl)-3-(4-phenoxyphenyl)-1H-pyrazolo[3,4-d]pyrimidin-4-amine as a yellow, off-white solid which was used without further purification. MS (ESI, $[M+H]^+$) m/z 359.6.

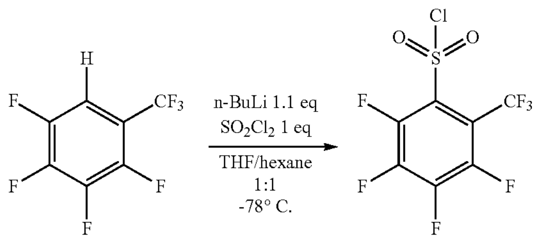 [SMILES: Fc1cc(C(F)(F)F)c(F)c(F)c1F ; O=S(=O)(Cl)c1c(F)c(F)c(F)c(F)c1C(F)(F)F]

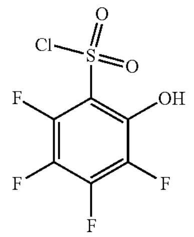

Synthesis of 2,3,4,5-tetrafluoro-6-(trifluoromethyl)benzenesulfonyl chloride

To a solution of 1,2,3,4-tetrafluoro-5-(trifluoromethyl)benzene (1.87 g, 8.58 mmol) in anhydrous THF cooled to −78° C. was added n-butyllithium (2.5 M in hexane, 3.77 mL) dropwise over a period of 10 min under argon. The resulting dark violet solution was slowly added to a hexane (5 mL) solution of sulfuryl chloride (1.16 g, 8.58 mmol, 693.05 uL) at −78° C. via cannula. After stirring for 3 h, the mixture was quenched with 5 mL of water at −78° C. and the bath was removed. The mixture was partitioned between ethyl acetate and cold water and the organic phase was separated. The organic phase was washed with cold water twice, dried over sodium sulfate and concentrated in vacuo to afford the anticipated product as brown oil (1.43 g, 52.68% yield). $^{19}F$ NMR (376 MHz, $CDCl_3$) δ −50.67 (d, J=37.7 Hz), −122.70 (ddd, J=23.5, 14.6, 8.8 Hz), −129.90 (ddt, J=37.7, 20.4, 9.6 Hz), −138.15 (td, J=20.6, 13.9 Hz), −142.22 (ddd, J=22.9, 19.8, 10.7 Hz).

General Procedure AA

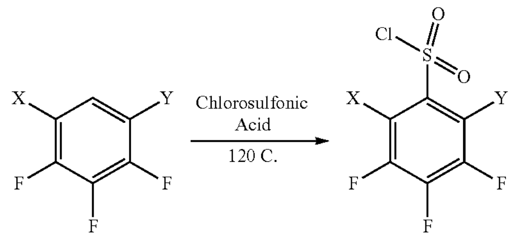

A substituted fluoro-arene (1 eq) was added to a cold solution of chlorosulfonic acid cooled to 0° C. The reaction vessel was outfitted with a water jacketed reflux condenser and subsequently heated to 120° C. using a sand bath for 1-16 hrs. Once starting material was consumed, the reaction was cooled to room temperature then poured slowly over crushed ice. The resulting mixture was partitioned between DCM and 1M HCl and the organic phase separated. The remaining aqueous phase was extracted twice more with DCM. The combined organic phases were washed with brine, dried over sodium sulfate, and concentrated in vacuo to afford the desired arylsulfonyl chloride.

2,3,4,5-tetrafluoro-6-hydroxybenzene-1-sulfonyl chloride

Using potassium 2,3,4,5-tetrafluorophenoxide as a starting material, 2,3,4,5-tetrafluoro-6-hydroxybenzene-1-sulfonyl chloride was prepared according to the protocol described in general procedure AA. (red oil, 52-60% yield). $^{19}$F NMR (376 MHz, $CDCl_3$) δ −134.49--134.89 (m), −140.19--140.39 (m), −156.03--156.45 (m), −164.26--164.38 (m).

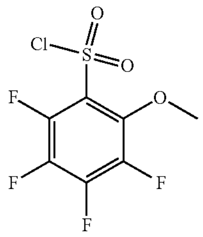 [SMILES: COc1c(F)c(F)c(F)c(F)c1S(=O)(=O)Cl]

2,3,4,5-tetrafluoro-6-methoxybenzene-1-sulfonyl chloride

Using 1,2,3,4-tetrafluoro-5-methoxybenzene as a starting material, 2,3,4,5-tetrafluoro-6-methoxybenzene-1-sulfonyl chloride was prepared according to the protocol described in general procedure AA. (red oil, 40% yield). $^{19}$F NMR (376 MHz, $CDCl_3$) δ −134.21--134.81 (m), −141.73--141.93 (m), −151.49--151.89 (m), −159.14--159.54 (m).

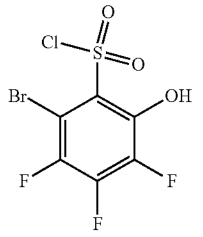 [SMILES: O=S(=O)(Cl)c1c(O)c(F)c(F)c(F)c1Br]

2-bromo-3,4,5-trifluoro-6-hydroxybenzene-1-sulfonyl chloride

Using 5-bromo-2,3,4-trifluorophenol as a starting material, 2-bromo-3,4,5-trifluoro-6-hydroxybenzene-1-sulfonyl chloride was prepared according to the protocol described in general procedure AA. (white solid, 63% yield). $^{19}$F NMR (376 MHz, $CDCl_3$) δ −137.08--137.15 (m), −155.80--155.92 (m), −156.48--156.53 (m).

General Procedure BA

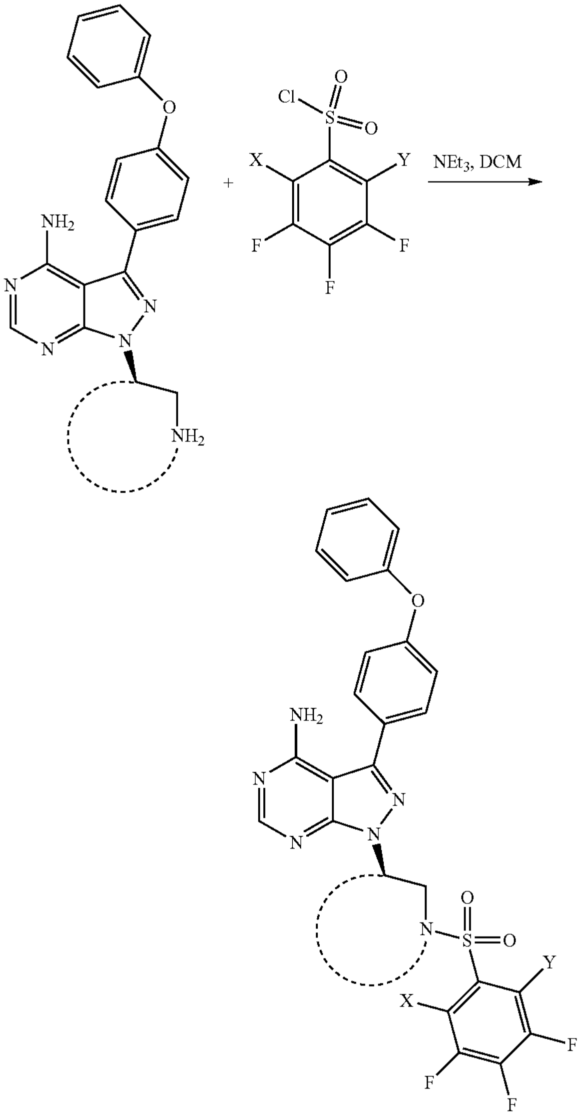

An appropriate sulfonyl chloride (0.9-1.2 eq) was incubated with its corresponding pyrazololopyrimidine (1 eq) in anhydrous DCM (0.1 M-0.25 M) under an atmosphere of argon. The resulting mixture was cooled to 0° C. and stirred for 15 minutes. Neat triethylamine (3-5 eq) was slowly added to the mixture and it was stirred at 0° C. for a further 3-16 hrs. The reaction quenched with 0.1M HCl (aq) and vigorously stirred for 10-15 min, after which the organic layer was separated. The aqueous layer was extracted with DCM one further time. The combined organic layers were dried over sodium sulfate, filtered, and evaporated. The crude material was purified by either flash column chromatography, eluting with a solvent system comprised of ethyl acetate/DCM, or reverse-phase chromatography employing a solvent system comprised of ACN/Water containing 0.1% formic acid. The isolated material was lyophilized from ACN and water to afford the desired product as a free flowing off-white solid.

Example AA-1 N-[2-[4-amino-3-(4-phenoxyphenyl)pyrazolo[3,4-d]pyrimidin-1-yl]ethyl]-2,3,4,5,6-pentafluoro-benzenesulfonamide (3A-9)

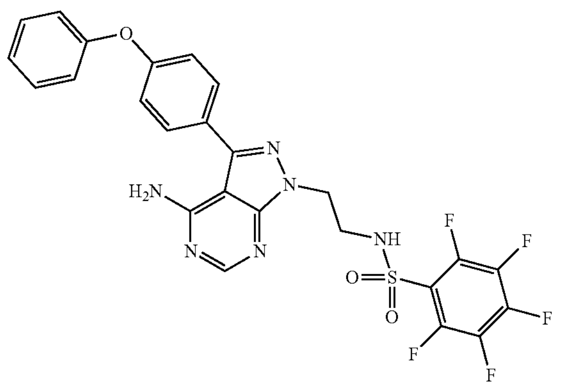 [SMILES: Nc1ncnc2c1c(-c1ccc(Oc3ccccc3)cc1)nn2CCNS(=O)(=O)c1c(F)c(F)c(F)c(F)c1F]

The title compound N-[2-[4-amino-3-(4-phenoxyphenyl)pyrazolo[3,4-d]pyrimidin-1-yl]ethyl]-2,3,4,5,6-pentafluoro-benzenesulfonamide, was prepared using the protocol described in general procedure BA (1.68 g, 74% yield). $^1$H NMR (400 MHz, $CDCl_3$) δ 8.26 (s, 1H), 7.69 (s, 1H), 7.60-7.51 (m, 2H), 7.40 (dd, J=8.6, 7.4 Hz, 2H), 7.23-7.02 (m, 5H), 5.78 (s, 2H), 4.66-4.52 (m, 2H), 3.89-3.75 (m, 2H). $^{19}$F NMR (376 MHz, CDCl3) δ −136.77 (d, J=20.7 Hz), −146.13--146.66 (m), −158.33--158.77 (m). ESI-MS: measured m/z 576.70 [M+H]$^+$.

Example AA-2 3-(4-phenoxyphenyl)-1-[(3R)-1-(2,3,4,5-tetrafluorophenyl)sulfonylpyrrolidin-3-yl]pyrazolo[3,4-d]pyrimidin-4-amine (3A-4)

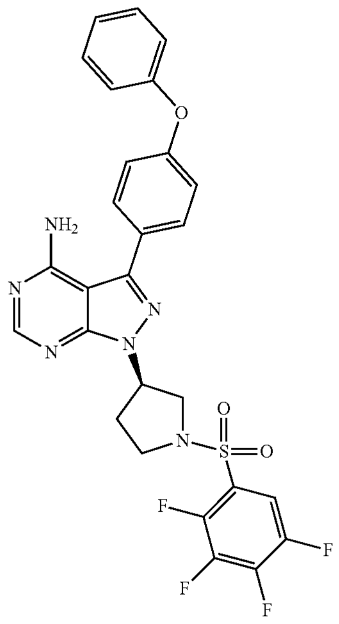 [SMILES: Nc1ncnc2c1c(-c1ccc(Oc3ccccc3)cc1)nn2[C@@H]1CCN(S(=O)(=O)c2cc(F)c(F)c(F)c2F)C1]

The title compound 3-(4-phenoxyphenyl)-1-[(3R)-1-(2,3,4,5-tetrafluorophenyl)sulfonyl pyrrolidin-3-yl]pyrazolo[3,4-d]pyrimidin-4-amine, was prepared using the protocol described in general procedure BA (0.55 g, 17% yield). $^1$H NMR (400 MHz, $CDCl_3$) δ 8.33 (s, 1H), 7.54 (dtd, J=11.0, 5.5, 2.7 Hz, 1H), 7.50-7.35 (m, 4H), 7.25-7.16 (m, 1H), 7.12 (d, J=8.4 Hz, 4H), 5.56 (td, J=6.5, 3.3 Hz, 3H), 4.10-3.91 (m, 2H), 3.85 (q, J=8.5 Hz, 1H), 3.75 (ddd, J=9.4, 7.7, 4.4 Hz, 1H), 2.61-2.41 (m, 2H). $^{19}$F NMR (376 MHz, $CDCl_3$) δ −131.99 (dd, J=14.4, 8.4 Hz), −136.25 (dd, J=12.3, 8.8 Hz), −146.05--146.53 (m), −151.11 (dd, J=22.9, 19.4 Hz). ESI-MS: measured m/z 584.70 [M+H]$^+$.

Example AA-3 3-(4-phenoxyphenyl)-1-[(3R)-1-[2,3,4,5-tetrafluoro-6-(trifluoromethyl)phenyl]sulfonylpyrrolidin-3-yl]pyrazolo[3,4-d]pyrimidin-4-amine (3A-12)

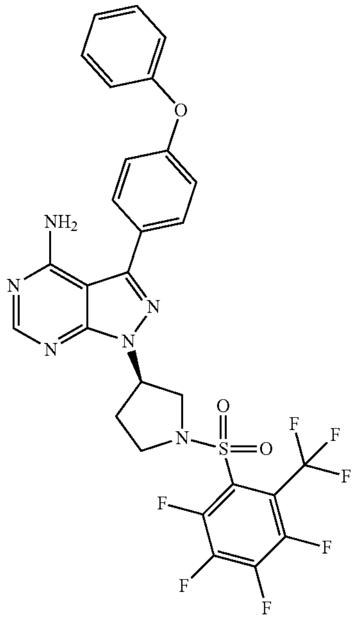 [SMILES: Nc1ncnc2c1c(-c1ccc(Oc3ccccc3)cc1)nn2[C@@H]1CCN(S(=O)(=O)c2c(F)c(F)c(F)c(F)c2C(F)(F)F)C1]

The title compound 3-(4-phenoxyphenyl)-1-[(3R)-1-[2,3,4,5-tetrafluoro-6-(trifluoromethyl)phenyl]sulfonylpyrrolidin-3-yl]pyrazolo[3,4-d]pyrimidin-4-amine, was prepared using the protocol described in general procedure BA (0.030 g, 17% yield). $^1$H NMR (400 MHz, $CDCl_3$) δ 8.36 (s, 1H), 7.52 (d, J=8.6 Hz, 2H), 7.42 (dd, J=8.5, 7.4 Hz, 2H), 7.24-7.16 (m, 1H), 7.16-7.04 (m, 4H), 5.69-5.47 (m, 3H), 4.12-3.94 (m, 3H), 3.78 (td, J=9.3, 8.8, 5.1 Hz, 1H), 2.74-2.46 (m, 2H). $^{19}$F NMR (376 MHz, $CDCl_3$) δ −51.34 (d, J=36.9 Hz), −129.06--129.44 (m), −131.20--131.63 (m), −144.93--145.15 (m), −145.20--145.39 (m). ESI-MS: measured m/z 652.6 [M+H]$^+$.

Example AA-4 N-(2-(4-amino-3-(4-phenoxyphenyl)-1H-pyrazolo[3,4-d]pyrimidin-1-yl)ethyl)-2,3,4,5-tetrafluoro-6-methoxybenzenesulfonamide (3A-6)

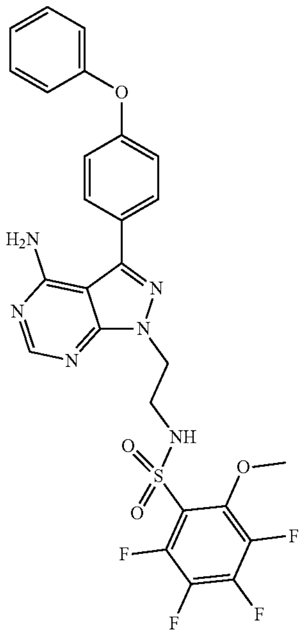 [SMILES: COc1c(F)c(F)c(F)c(F)c1S(=O)(=O)NCCn1nc(-c2ccc(Oc3ccccc3)cc2)c2c(N)ncnc21]

The title compound N-(2-(4-amino-3-(4-phenoxyphenyl)-1H-pyrazolo[3,4-d]pyrimidin-1-yl)ethyl)-2,3,4,5-tetrafluoro-6-methoxybenzenesulfonamide, was prepared using the protocol described in general procedure BA (0.029 g, 13% yield). $^1$H NMR (400 MHz, $CDCl_3$) δ 8.37 (s, 1H), 7.69-7.60 (m, 2H), 7.48-7.38 (m, 2H), 7.27-7.16 (m, 3H), 7.16-7.09 (m, 2H), 6.47 (t, J=5.7 Hz, 1H), 5.59 (s, 2H), 4.61-4.58 (m, 2H), 4.59 (s, 1H), 3.92 (d, J=1.5 Hz, 3H), 3.76 (q, J=5.5 Hz, 2H). $^{19}$F NMR (376 MHz, $CDCl_3$) δ −137.27−−138.79 (m), −147.88−−148.00 (m), −152.99−−153.05 (m), −159.60−−159.73 (m). ESI-MS: measured m/z 588.70 $[M+H]^+$.

Example AA-5 N-(3-(4-amino-3-(4-phenoxyphenyl)-1H-pyrazolo[3,4-d]pyrimidin-1-yl)propyl)-2,3,4,5,6-pentafluorobenzenesulfonamide (3A-10)

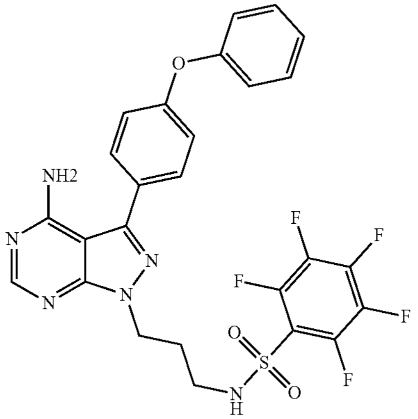 [SMILES: Nc1ncnc2c1c(-c1ccc(Oc3ccccc3)cc1)nn2CCCNS(=O)(=O)c1c(F)c(F)c(F)c(F)c1F]

The title compound N-(3-(4-amino-3-(4-phenoxyphenyl)-1H-pyrazolo[3,4-d]pyrimidin-1-yl)propyl)-2,3,4,5,6-pentafluorobenzenesulfonamide, was prepared using the protocol described in general procedure BA (0.011 g, 17% yield). $^1$H NMR (400 MHz, $CD_3CN$)$_{\delta\ 8.29}$ (s, 1H), 7.72-7.63 (m, 2H), 7.49-7.41 (m, 2H), 7.27-7.12 (m, 5H), 5.94 (s, 2H), 4.45 (t, J=6.4 Hz, 2H), 3.11 (t, J=6.7 Hz, 2H), 2.12 (p, J=6.6 Hz, 2H). $^{19}$F NMR (376 MHz, $CDCl_3$) δ −138.96−−139.33 (m), −149.75−−149.98 (m), −161.32−−161.75 (m). ESI-MS: measured m/z 590.7 $[M+H]^+$.

Example AA-6 1-(1-((perfluorophenyl)sulfonyl)azetidin-3-yl)-3-(4-phenoxyphenyl)-1H-pyrazolo[3,4-d]pyrimidin-4-amine (3A-24)

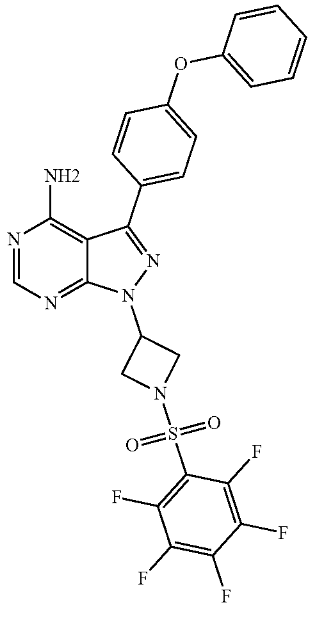 [SMILES: Nc1ncnc2c1c(-c1ccc(Oc3ccccc3)cc1)nn2C1CN(S(=O)(=O)c2c(F)c(F)c(F)c(F)c2F)C1]

The title compound 1-(1-((perfluorophenyl)sulfonyl)azetidin-3-yl)-3-(4-phenoxyphenyl)-1H-pyrazolo[3,4-d]pyrimidin-4-amine, was prepared using the protocol described in general procedure BA (0.068 g, 18% yield). $^1$H NMR (400 MHz, DMSO-$d_6$) δ 8.20 (s, 1H), 7.56-7.44 (m, 5H), 7.23 (td, J=7.4, 1.2 Hz, 1H), 7.20-7.13 (m, 4H), 5.81-5.68 (m, 1H), 4.58 (t, J=8.6 Hz, 2H), 4.46 (dd, J=9.2, 6.0 Hz, 2H). $^{19}$F NMR (376 MHz, DMSO-$d_6$) δ −133.55−−134.01 (m), −145.23−−145.69 (m), −159.10 (tt, J=22.5, 6.2 Hz). ESI-MS: measured m/z 588.7 $[M+H]^+$.

Example AA-7 (R)-3-(4-phenoxyphenyl)-1-(1-((2,3,4,5-tetrafluoro-6-(trifluoromethyl)phenyl) sulfonyl) pyrrolidin-3-yl)-1H-pyrazolo[3,4-d]pyrimidin-4-amine (3A-12)

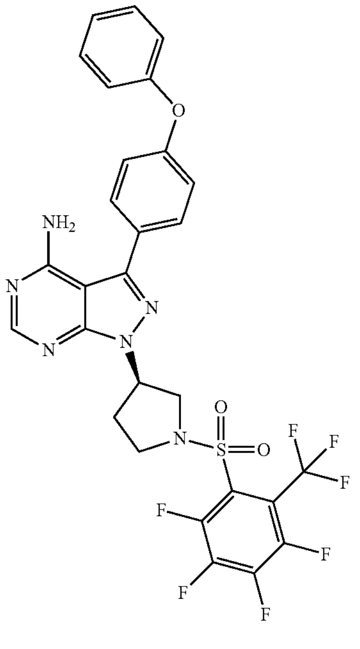 [SMILES: Nc1ncnc2c1c(-c1ccc(Oc3ccccc3)cc1)nn2[C@@H]1CCN(S(=O)(=O)c2c(F)c(F)c(F)c(F)c2C(F)(F)F)C1]

The title compound (R)-3-(4-phenoxyphenyl)-1-(1-((2,3,4,5-tetrafluoro-6-(trifluoromethyl)phenyl) sulfonyl)pyrrolidin-3-yl)-1H-pyrazolo[3,4-d]pyrimidin-4-amine, was prepared using the protocol described in general procedure BA (0.030 g, 17% yield). $^1$H NMR (400 MHz, $CDCl_3$) δ 8.36 (s, 1H), 7.52 (d, J=8.6 Hz, 2H), 7.42 (dd, J=8.5, 7.4 Hz, 2H), 7.24-7.16 (m, 1H), 7.16-7.04 (m, 4H), 5.69-5.47 (m, 3H), 4.12-3.94 (m, 3H), 3.78 (td, J=9.3, 8.8, 5.1 Hz, 1H), 2.74-2.46 (m, 2H). $^{19}$F NMR (376 MHz, $CDCl_3$) δ −51.34 (d, J=36.9 Hz), −129.06-−129.44 (m), −131.20-−131.63 (m), −144.93-−145.15 (m), −145.20-−145.39 (m). ESI-MS: measured m/z 652.6 $[M+H]^+$.

Example AA-8 (R)-2-((3-(4-amino-3-(4-phenoxyphenyl)-1H-pyrazolo[3,4-d]pyrimidin-1-yl)pyrrolidin-1-yl)sulfonyl)-3-bromo-4,5,6-trifluorophenol (3A-23)

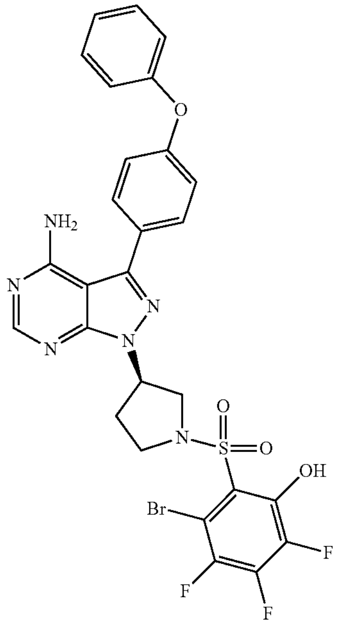 [SMILES: Nc1ncnc2c1c(-c1ccc(Oc3ccccc3)cc1)nn2[C@@H]1CCN(S(=O)(=O)c2c(O)c(F)c(F)c(F)c2Br)C1]

The title compound (R)-2-((3-(4-amino-3-(4-phenoxyphenyl)-1H-pyrazolo[3,4-d]pyrimidin-1-yl)pyrrolidin-1-yl) sulfonyl)-3-bromo-4,5,6-trifluorophenol, was prepared using the protocol described in general procedure BA (0.006 g, 5% yield). $^1$H NMR (400 MHz, $CDCl_3$) δ 8.37 (s, 1H), 7.59 (d, J=8.6 Hz, 2H), 7.44 (t, J=7.9 Hz, 2H), 7.27-7.13 (m, 3H), 7.17-7.10 (m, 2H), 5.68 (bs, 2H), 5.60 (p, J=6.2 Hz, 1H), 4.04 (m, 3H), 3.77 (td, J=8.7, 5.0 Hz, 1H), 2.79-2.68 (m, 1H), 2.56 (dq, J=14.5, 7.5 Hz, 1H). $^{19}$F NMR (376 MHz, $CDCl_3$) δ −130.33-−130.40 (m), −146.34-−146.46 (m), −151.35-−151.41 (m). MS: measured m/z 660.6 $[M+H]^+$.

Example AA-9 (R)-3-(4-phenoxyphenyl)-1-(1-((2,3,4,5-tetrafluoro-6-(trifluoromethyl)phenyl) sulfonyl) piperidin-3-yl)-1H-pyrazolo[3,4-d]pyrimidin-4-amine

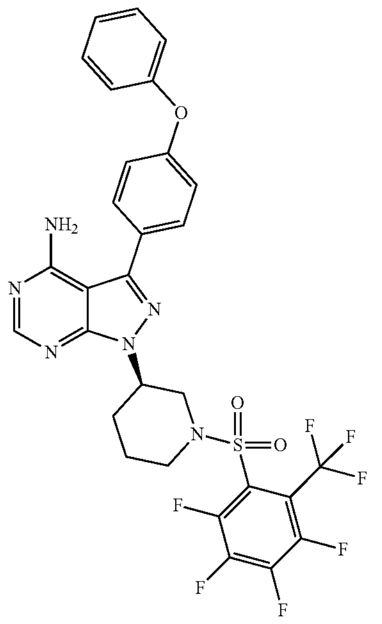 [SMILES: Nc1ncnc2c1c(-c1ccc(Oc3ccccc3)cc1)nn2[C@@H]1CCCN(S(=O)(=O)c2c(F)c(F)c(F)c(F)c2C(F)(F)F)C1]

The title compound (R)-3-(4-phenoxyphenyl)-1-(1-((2,3,4,5-tetrafluoro-6-(trifluoromethyl)phenyl)sulfonyl)piperidin-3-yl)-1H-pyrazolo[3,4-d]pyrimidin-4-amine, was prepared using the protocol described in general procedure BA (0.008 g, 5% yield). $^1$H NMR (400 MHz, Methanol-$d_4$) δ 8.27 (s, 1H), 7.74-7.64 (m, 2H), 7.49-7.37 (m, 2H), 7.24-7.07 (m, 5H), 4.93-4.97 (dq, J=10.2, 4.9 Hz, 1H), 4.60 (s, 2H), 4.05 (dd, J=12.8, 4.2 Hz, 1H), 3.89 (d, J=13.3 Hz, 1H), 3.76-3.65 (m, 1H), 3.23 (t, J=12.0 Hz, 1H), 2.45-2.29 (m, 1H), 2.27-2.10 (m, 2H), 1.90 (t, J=12.2 Hz, 1H). $^{19}$F NMR (376 MHz, Methanol-$d_4$) δ −52.93 (d, J=37.1 Hz), −132.59-−132.90 (m), −134.74 (ddd, J=37.4, 19.6, 9.6 Hz), −147.88-−148.17 (m), −148.48 (td, J=19.7, 10.7 Hz). MS: measured m/z 666.7 [M+H]$^+$.

Example AA-10 N-(2-(4-amino-3-(4-phenoxyphenyl)-1H-pyrazolo[3,4-d]pyrimidin-1-yl)ethyl)-2,3,4,5-tetrafluoro-6-hydroxybenzenesulfonamide

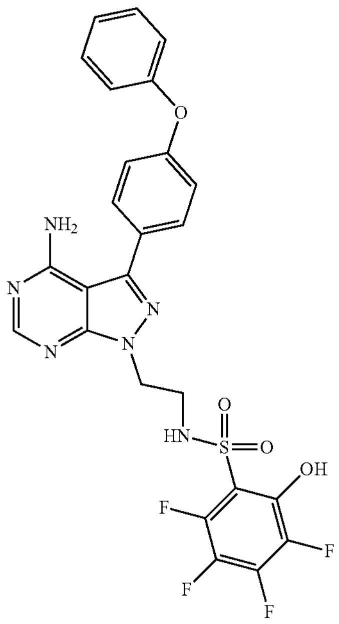 [SMILES: Nc1ncnc2c1c(-c1ccc(Oc3ccccc3)cc1)nn2CCNS(=O)(=O)c1c(O)c(F)c(F)c(F)c1F]

The title compound N-(2-(4-amino-3-(4-phenoxyphenyl)-1H-pyrazolo[3,4-d]pyrimidin-1-yl)ethyl)-2,3,4,5-tetrafluoro-6-hydroxybenzenesulfonamide, was prepared using the protocol described in general procedure BA (0.030 g, 21% yield). $^1$H NMR (400 MHz, $CDCl_3$) δ 8.34 (s, 1H), 8.12 (s, 1H), 7.66-7.58 (m, 2H), 7.48-7.39 (m, 2H), 7.27-7.16 (m, 3H), 7.20-7.09 (m, 2H), 6.11 (s, 2H), 4.67-4.59 (m, 2H), 3.75 (s, 1H), 3.75 (d, J=10.3 Hz, 1H). $^{19}$F NMR (376 MHz, $CDCl_3$) δ −138.48-−138.58 (m), −146.96-−147.09 (m), −158.50-−158.59 (m), −166.87-−167.00 (m). ESI-MS: measured m/z 574.6 [M+H]$^+$.

Example AA-11 N-(2-(4-amino-3-(4-phenoxyphenyl)-1H-pyrazolo[3,4-d]pyrimidin-1-yl)ethyl)-2,3,4,5-tetrafluoro-6-(trifluoromethyl)benzenesulfonamide

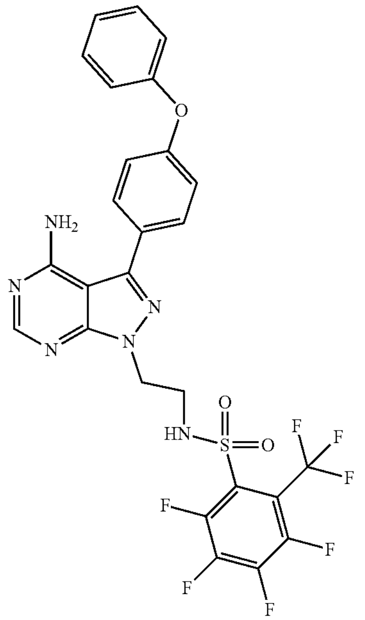 [SMILES: Nc1ncnc2c1c(-c1ccc(Oc3ccccc3)cc1)nn2CCNS(=O)(=O)c1c(F)c(F)c(F)c(F)c1C(F)(F)F]

The title compound N-(2-(4-amino-3-(4-phenoxyphenyl)-1H-pyrazolo[3,4-d]pyrimidin-1-yl)ethyl)-2,3,4,5-tetrafluoro-6-hydroxybenzenesulfonamide, was prepared using the protocol described in general procedure BA (0.030 g, 21% yield). $^1$H NMR (400 MHz, $CDCl_3$) δ 8.30 (s, 1H), 7.64-7.59 (m, 2H), 7.47-7.40 (m, 2H), 7.21 (t, J=7.4 Hz, 1H), 7.19-7.15 (m, 2H), 7.15-7.09 (m, 2H), 5.78 (s, 2H), 4.67-4.58 (m, 2H), 3.85 (d, J=5.7 Hz, 2H). $^{19}$F NMR (376 MHz, $CDCl_3$) δ −51.69 (d, J=35.2 Hz), −130.31 (dt, J=22.9, 9.6 Hz), −131.61 (qdt, J=35.6, 19.8, 9.4 Hz), −144.84--145.04 (m), −145.14 (td, J=20.2, 9.8 Hz). ESI-MS: measured m/z 625.27 $[M+H]^+$.

Example AA-12 (R)-2-((3-(4-amino-3-(4-phenoxyphenyl)-1H-pyrazolo[3,4-d]pyrimidin-1-yl)pyrrolidin-1-yl)sulfonyl)-3,4,5,6-tetrafluorophenol)

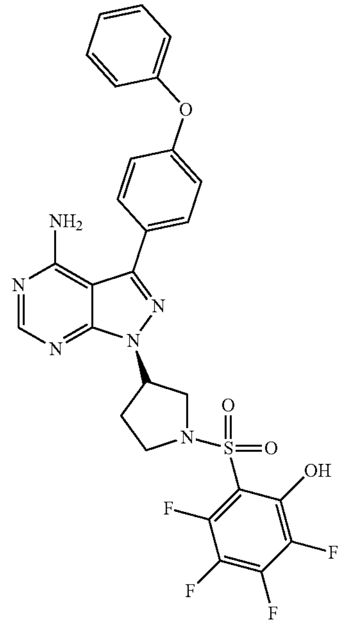

The title compound (R)-2-((3-(4-amino-3-(4-phenoxyphenyl)-1H-pyrazolo[3,4-d]pyrimidin-1-yl)pyrrolidin-1-yl)sulfonyl)-3,4,5,6-tetrafluorophenol, was prepared using the protocol described in general procedure BA (0.008 g, 5% yield). $^1$H NMR (400 MHz, $CDCl_3$) $^1$H NMR (400 MHz, $CDCl_3$) δ 8.34 (s, 1H), 8.12 (s, 1H), 7.50-7.43 (m, 4H), 7.26-7.22 (m, 1H), 7.17-7.13 (m, 4H), 6.78-5.97 (bs, 2H), 5.63 (p, J=6.2 Hz, 1H), 4.08-4.00 (m, 2H), 3.98-3.91 (m, 1H), 3.82-3.76 (m, 1H), 2.63-2.55 (m, 2H). $^{19}$F NMR (376 MHz, $CDCl_3$) δ −135.09--135.16 (m), −146.37--146.50 (m), −158.81--158.88 (m), −166.81--166.94 (m). ESI-MS: measured m/z 598.7 $[M+H]^+$.

General Procedure CA: Ortho-Substitution Protocol

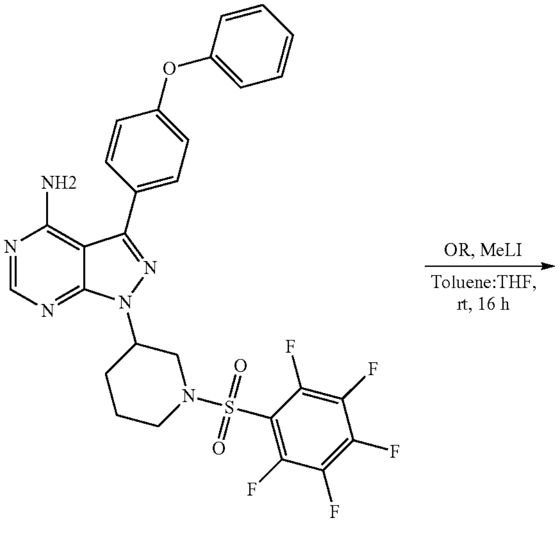

-continued

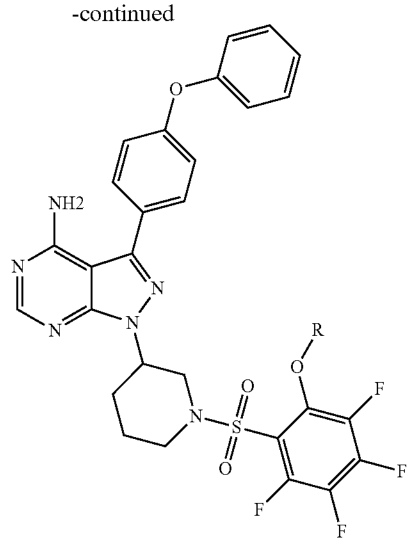

To a dried, nitrogen-purged round-bottom flask was added the appropriate alcohol (1.1-2 eq) in half the volume of Toluene (0.05M) and THF (1M). The solution was cooled to 0° C. and methyllithium (1.1-2 eq, 1.5 M in hexane) was then added in a dropwise manner. The resulting mixture was stirred at 0° C. for 30 min and then added to a solution of (R)-1-(1-((perfluorophenyl)sulfonyl)piperidin-3-yl)-3-(4-phenoxyphenyl)-1H-pyrazolo[3,4-d]pyrimidin-4-amine (1 eq) in the remaining volume of toluene and THF. The reaction was left to stir at room temperature for 16 hours and then quenched with 1 M HCl and extracted thrice with DCM. The collected organic layers were washed once with brine, dried over magnesium sulfate, filtered and evaporated under reduced pressure. Products were purified by Prep-HPLC using a 45-75% ACN (0.1% FA)/$H_2O$ (0.1% FA) as the solvent gradient.

Example AA-13 (R)-3-(4-phenoxyphenyl)-1-(1-((2,3,4,5-tetrafluoro-6-methoxyphenyl)sulfonyl) piperidin-3-yl)-1H-pyrazolo[3,4-d]pyrimidin-4-amine (3A-1)

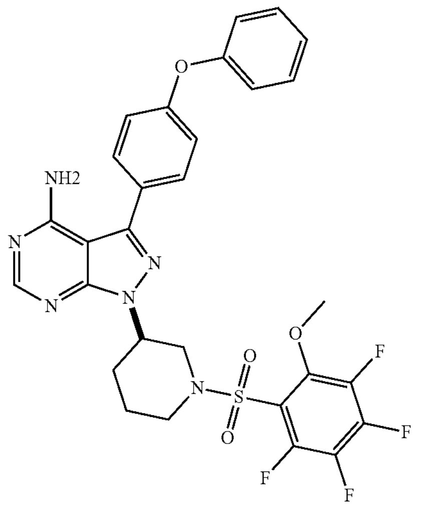

The title compound (R)-3-(4-phenoxyphenyl)-1-(1-((2,3,4,5-tetrafluoro-6-methoxyphenyl) sulfonyl)piperidin-3-yl)-1H-pyrazolo[3,4-d]pyrimidin-4-amine, was prepared using the protocol described in general procedure CA using (R)-1-(1-((perfluorophenyl)sulfonyl)piperidin-3-yl)-3-(4-phenoxyphenyl)-1H-pyrazolo[3,4-d]pyrimidin-4-amine (60 mg, 0.0973 mmol), methanol (4.33 μL, 0.107 mmol) and 1.5 M methyllithium solution in hexane (71.3 μL, 0.107 mmol). The compound was isolated as an off-white solid (4.8 mg, 7.85%). $^{1}H$ NMR (400 MHz, $CDCl_3$) δ 8.39 (s, 1H), 7.68-7.61 (m, 2H), 7.45-7.37 (m, 2H), 7.24-7.15 (m, 3H), 7.14-7.06 (m, 2H), 5.69 (s, 2H), 5.04 (tt, J=10.5, 4.8 Hz, 1H), 4.17 (dd, J=12.0, 4.5 Hz, 1H), 4.04 (d, J=1.3 Hz, 3H), 3.99 (d, J=2.9 Hz, 1H), 3.38 (t, J=11.4 Hz, 1H), 2.91-2.80 (m, 1H), 2.24 (td, J=11.0, 10.2, 4.0 Hz, 2H), 2.05-1.85 (m, 3H). $^{19}F$ NMR (376 MHz, $CDCl_3$) δ −134.84 (dt, J=24.3, 8.2 Hz), −147.43 (td, J=20.8, 6.9 Hz), −152.62 (dd, J=21.2, 9.6 Hz), −159.66 (dd, J=24.1, 20.9 Hz). ESI-MS: measured m/z 628.7 $[M+H]^+$.

Example AA-14 (R)-3-(4-phenoxyphenyl)-1-(1-((2,3,4,5-tetrafluoro-6-(2,2,2 trifluoroethoxy)phenyl) sulfonyl) piperidin-3-yl)-1H-pyrazolo[3,4-d]pyrimidin-4-amine (3A-2)

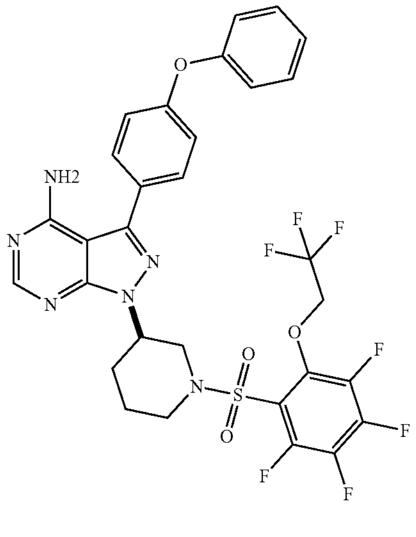

The title compound (R)-3-(4-phenoxyphenyl)-1-(1-((2,3,4,5-tetrafluoro-6-methoxyphenyl) sulfonyl)piperidin-3-yl)-1H-pyrazolo[3,4-d]pyrimidin-4-amine, was prepared using the protocol described in general procedure CA using (R)-1-(1-((perfluorophenyl)sulfonyl)piperidin-3-yl)-3-(4-phenoxyphenyl)-1H-pyrazolo[3,4-d]pyrimidin-4-amine (75 mg, 0.122 mmol), 2,2,2-Trifluoroethanol (13.1 μL, 0.182 mmol) and 1.5 M methyllithium solution in hexane (121.3 μL, 0.182 mmol). The compound was isolated as a white solid (5 mg, 5.88%). $^{1}H$ NMR (400 MHz, $CDCl_3$) δ 8.40 (s, 1H), 7.68-7.61 (m, 2H), 7.46-7.39 (m, 2H), 7.24-7.15 (m, 3H), 7.14-7.06 (m, 2H), 5.59 (bs, 2H), 5.00 (s, 1H), 4.51 (p, J=7.9 Hz, 2H), 4.14 (dd, J=12.1, 4.5 Hz, 1H), 4.02 (d, J=12.5 Hz, 1H), 3.41 (t, J=11.4 Hz, 1H), 2.86 (t, J=11.5 Hz, 1H), 2.24 (q, J=5.4, 4.5 Hz, 2H), 2.05 (d, J=14.4 Hz, 2H). $^{19}F$ NMR (376 MHz, $CDCl_3$) δ −74.20-−74.28 (m), −133.27 (dt, J=24.3, 8.6 Hz), −145.95 (td, J=20.9, 7.4 Hz), −151.09 (ddd, J=21.1, 10.1, 5.3 Hz), −156.14 (dd, J=24.2, 20.9 Hz). ESI-MS: measured m/z 696.6 $[M+H]^+$.

Example AA-15 (R)-3-(4-phenoxyphenyl)-1-(1-((2,3,4,5-tetrafluoro-6-isopropoxyphenyl) sulfonyl)piperidin-3-yl)-1H-pyrazolo[3,4-d]pyrimidin-4-amine (3A-3)

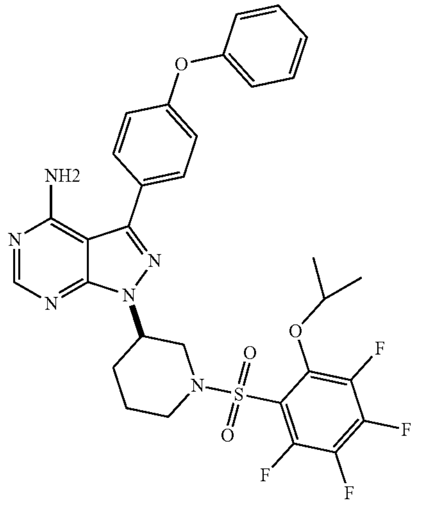

The title compound (R)-3-(4-phenoxyphenyl)-1-(1-((2,3,4,5-tetrafluoro-6-isopropoxyphenyl) sulfonyl)piperidin-3-yl)-1H-pyrazolo[3,4-d]pyrimidin-4-amine, was prepared using the protocol described in general procedure CA using (R)-1-(1-((perfluorophenyl)sulfonyl)piperidin-3-yl)-3-(4-phenoxyphenyl)-1H-pyrazolo[3,4-d]pyrimidin-4-amine (60 mg, 0.0973 mmol), 2-propanol (9.69 μL, 0.127 mmol) and 1.5 M methyllithium solution in hexane (84.7 μL, 0.127 mmol). The compound was isolated as a white solid (4.8 mg, 7.51%). $^{1}$H NMR (400 MHz, $CDCl_3$) δ 8.39 (s, 1H), 7.67-7.61 (m, 2H), 7.47-7.37 (m, 2H), 7.24-7.14 (m, 3H), 7.14-7.06 (m, 2H), 5.65 (bs, 2H), 5.05-4.94 (m, 1H), 4.93-4.81 (m, 1H), 4.16 (dd, J=12.0, 4.2 Hz, 1H), 4.03-3.93 (m, 1H), 3.40 (t, J=11.4 Hz, 1H), 2.88-2.77 (m, 1H), 2.22 (q, J=5.9, 5.5 Hz, 2H), 2.05-1.97 (m, 1H), 1.90 (d, J=22.4 Hz, 2H), 1.38 (ddd, J=11.8, 6.2, 1.1 Hz, 6H).). $^{19}$F NMR (376 MHz, $CDCl_3$) δ −134.41 (dt, J=24.5, 8.1 Hz), −148.17 (td, J=21.1, 7.0 Hz), −150.85 (dd, J=20.9, 8.9 Hz), −160.90–−161.30 (m). ESI-MS: measured m/z 656.7 $[M+H]^+$.

Testing JAK3 Compound

General Procedure DA:

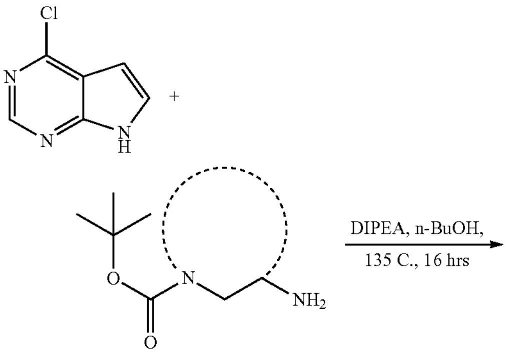

-continued

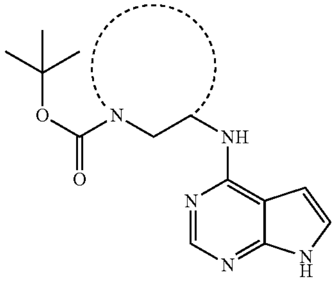

Neat diisopropylethylamine (DIPEA) was added to a mixture of 4-Chloro-7H-pyrrolo[2,3-d]pyrimidine (1 eq), aminocarbamate (1 eq) and n-butanol (0.5-1 M). The reaction vessel was equipped with a water jacketed condenser and the apparatus heated at 135° C. in an oil bath overnight. After 16 hours, the reaction was cooled to room temperature and partitioned between ethyl acetate and brine. The aqueous phase was separated and the organic phase washed with water, dilute HCl (done 4 times), and brine. The organic phase was dried over anhydrous sodium sulfate, filtered, concentrated and purified using flash column chromatography techniques (DCM/MeOH mobile phase) to afford the desired product.

General Procedure EA:

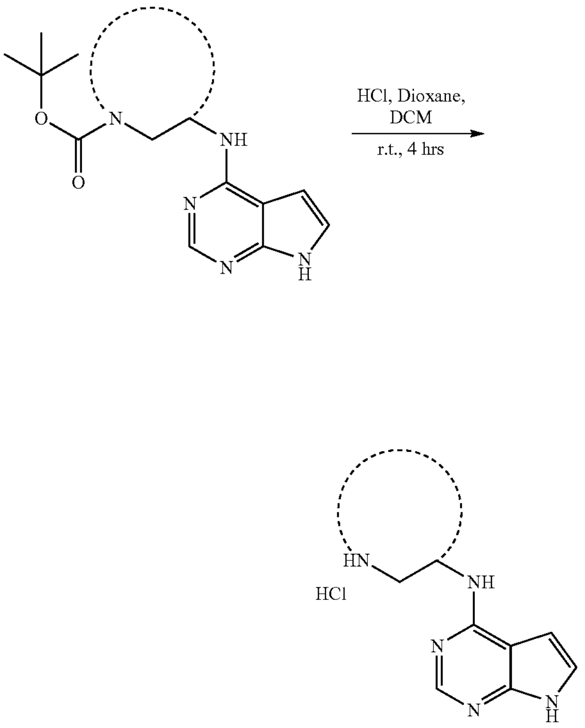

To a mixture of boc-protected pyrrolopyrimidine (1 eq.) in DCM was added a solution of HCl in dioxane (4 M, 4 eq.). The resulting mixture was stirred at room temperature until consumption of the starting material was observed by LC/MS. Once the reaction was complete, excess solvent was removed using a rotary evaporator and the remaining residue dried in vacuo to afford the anticipated product.

General Procedure FA:

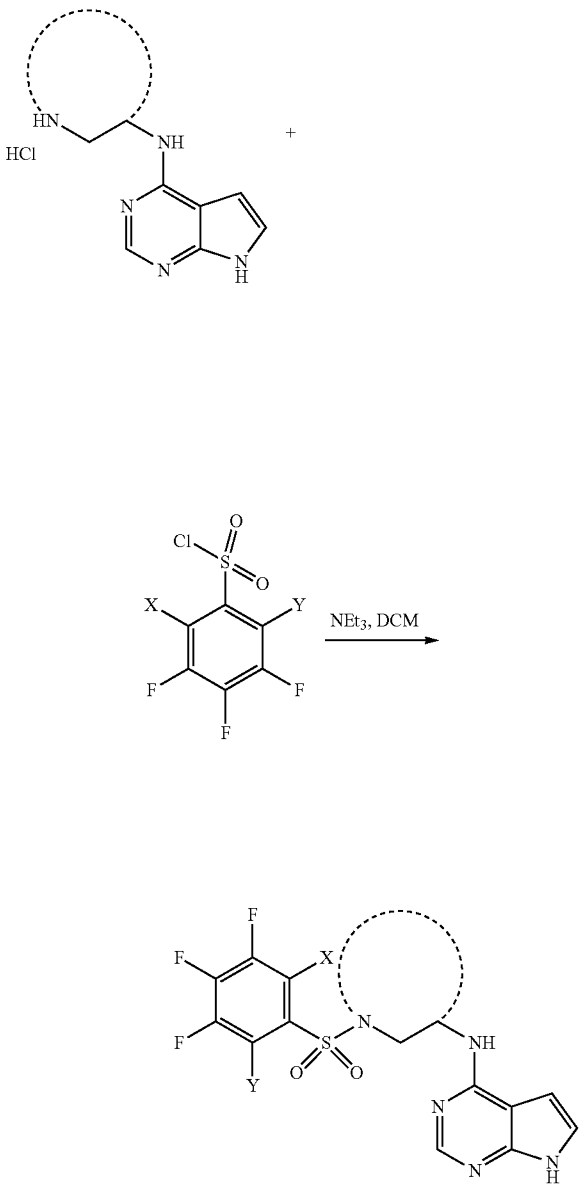

An appropriate sulfonyl chloride (0.9-1.2 eq) was incubated with its corresponding pyrrolopyrimidine (1 eq) in anhydrous DCM (0.1 M-0.25 M) under an atmosphere of argon. The resulting mixture was cooled to 0° C. and stirred for 15 minutes. Neat triethylamine (3-5 eq) was slowly added to the mixture and it was stirred at 0° C. for a further 3-16 hrs. The reaction quenched with 0.1M HCl (aq) and vigorously stirred for 10-15 min, after which the organic layer was separated. The aqueous layer was extracted with DCM one further time. The combined organic layers were dried over sodium sulfate, filtered, and evaporated. The crude material was purified by either flash column chromatography, eluting with a solvent system comprised of MeOH/DCM, or reverse-phase chromatography, employing a solvent system comprised of ACN/Water containing 0.1% formic acid. The isolated material was lyophilized from ACN and water to afford the desired product.

Synthesis of tert-butyl (2-((7H-pyrrolo[2,3-d]pyrimidin-4-yl)amino)ethyl)carbamate

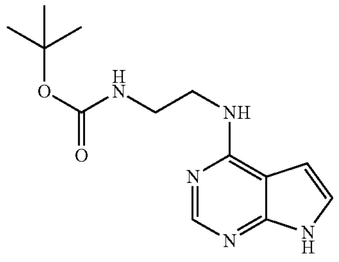 [SMILES: CC(C)(C)OC(=O)NCCNc1ncnc2[nH]ccc12]

Tert-butyl (2-((7H-pyrrolo[2,3-d]pyrimidin-4-yl)amino)ethyl)carbamate was prepared according to the protocol described in general procedure DA and isolated as an off-white powdery solid (63% yield). $^1$H NMR (400 MHz, DMSO-$d_6$) δ 12.23 (br s, 1H), 9.03 (br s, 1H), 8.26 (s, 1H), 7.32 (br s, 1H), 6.99 (s, 1H), 6.87 (s, 1H), 3.58 (q, J=8.0 Hz, 2H), 3.25 (q, J=8.0 Hz, 2H), 1.34 (s, 9H)

ESI-MS: measured m/z 277.9 $[M+H]^+$.

Synthesis of tert-butyl (2-((7H-pyrrolo[2,3-d]pyrimidin-4-yl)amino)ethyl)(methyl)carbamate

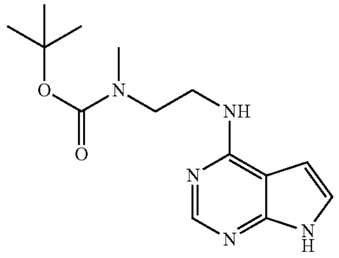 [SMILES: CN(CCNc1ncnc2[nH]ccc12)C(=O)OC(C)(C)C]

Tert-butyl (2-((7H-pyrrolo[2,3-d]pyrimidin-4-yl)amino)ethyl)(methyl)carbamate was prepared according to the protocol described in general procedure DA and isolated as a white powdery solid (1.48 g, 78% yield). $^1$H NMR (400 MHz, DMSO-$d_6$) δ 11.44 (brs, 1H), 8.08 (s, 1H), 7.53-7.38 (m, 1H), 7.08-7.01 (m, 1H), 6.53-6.44 (m, 1H), 3.61-3.48 (m, 2H), 3.46-3.33 (m, 2H), 2.80 (s, 3H), 1.41-1.07 (9H). ESI-MS: measured m/z 292.0 $[M+H]^+$.

Synthesis of $N^1$-(7H-pyrrolo[2,3-d]pyrimidin-4-yl)ethane-1,2-diamine hydrochloride

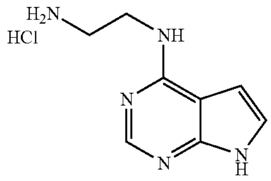 [SMILES: Cl ; NCCNc1ncnc2[nH]ccc12]

$N^1$-(7H-pyrrolo[2,3-d]pyrimidin-4-yl)ethane-1,2-diamine hydrochloride was prepared according to the protocol described in general procedure EA and isolated as a beige solid (2.1 g, 97% yield). $^1$H NMR (400 MHz, DMSO-$d_6$) δ

12.75 (br s, 1H), 10.09 (br s, 1H), 8.35 (s, 1H), 7.43 (s, 1H), 7.13 (s, 1H), 3.89 (d, J=8.0 Hz, 2H), 3.18 (d, J=8.0 Hz, 2H). ESI-MS: measured m/z 178.0 $[M+H]^+$.

Synthesis of $N^1$-methyl-$N^2$-(7H-pyrrolo[2,3-d]pyrimidin-4-yl)ethane-1,2-diamine hydrochloride

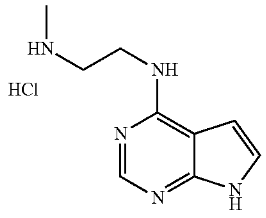

$N^1$-methyl-$N^2$-(7H-pyrrolo[2,3-d]pyrimidin-4-yl)ethane-1,2-diamine hydrochloride was prepared according to the protocol described in general procedure EA and isolated as a beige solid (1.34 g, 100% yield). $^1H$ NMR (400 MHz, DMSO-$d_6$+$D_2O$) δ 8.34 (s, 1H), 7.41-7.34 (m, 1H), 6.80-6.83 (m, 1H), 3.86-3.79 (m, 2H), 3.26-3.19 (m, 2H), 2.60 (s, 3H). ESI-MS: measured m/z 192.0 $[M+H]^+$.

Example AA-16 N-(2-((7H-pyrrolo[2,3-d]pyrimidin-4-yl)amino)ethyl)-2,3,4,5,6-pentafluorobenzene sulfonamide (3A-27)

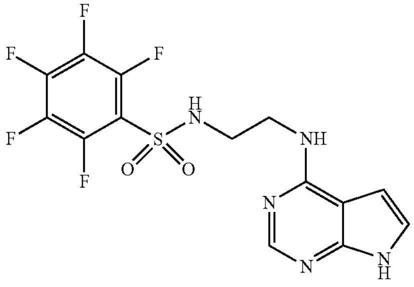 [SMILES: O=S(=O)(NCCNc1ncnc2[nH]ccc12)c1c(F)c(F)c(F)c(F)c1F]

The title compound N-(2-((7H-pyrrolo[2,3-d]pyrimidin-4-yl)amino)ethyl)-2,3,4,5,6-pentafluorobenzene sulfonamide, was prepared according to the protocol described in general procedure FA and isolated as a yellow powder (13% yield). $^1H$ NMR (400 MHz, DMSO-$d_6$) δ 11.62 (br s, 1H), 8.81 (br s, 1H), 8.05 (s, 1H), 7.35 (t, J=8.0 Hz, 1H), 7.06 (dd, J=4.0, 8.0 Hz, 1H), 6.35 (dd, J=4.0, 8.0 Hz, 1H), 3.51 (q, J=8.0 Hz, 2H), 3.42 (q, J=8.0 Hz, 2H). $^{19}F$ NMR (376 MHz, DMSO-$d_6$) δ −138.22--138.39 (m), −148.56--148.47 (m), −160.06--160.28 (m). ESI-MS: measured m/z 407.8 $[M+H]^+$.

Example AA-17 N-(2-((7H-pyrrolo[2,3-d]pyrimidin-4-yl)amino)ethyl)-2,3,4,5-tetrafluorobenzene sulfonamide

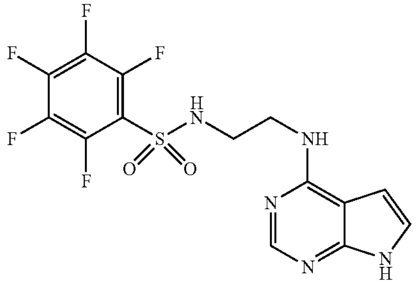 [SMILES: O=S(=O)(NCCNc1ncnc2[nH]ccc12)c1c(F)c(F)c(F)c(F)c1F]

The title compound N-(2-((7H-pyrrolo[2,3-d]pyrimidin-4-yl)amino)ethyl)-2,3,4,5-tetrafluorobenzenesulfonamide, was prepared according to the protocol described in general procedure FA and isolated as a yellow powder (0.058 g, 21% yield). $^1H$ NMR (400 MHz, $CD_3CN$) δ 9.61 (br s, 1H), 8.15 (s, 1H), 7.66-7.44 (m, 1H), 7.08 (s, 1H), 6.33-6.32 (m, 1H), 6.06 (s, 1H), 3.64 (q, J=8.0 Hz, 2H), 3.39 (q, J=8.0 Hz, 2H). $^{19}F$ NMR (376 MHz, $CD_3CN$) δ −136.86--136.90 (m), −138.92--138.97 (m), −150.24--150.35 (m), −154.14--154.28 (m). ESI-MS: measured m/z 389.8 $[M+H]^+$.

Example AA-18 N-(2-((7H-pyrrolo[2,3-d]pyrimidin-4-yl)amino)ethyl)-2,3,4,5,6-pentafluoro-N-methylbenzenesulfonamide (3A-28)

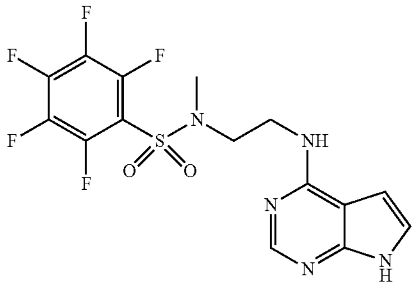 [SMILES: CN(CCNc1ncnc2[nH]ccc12)S(=O)(=O)c1c(F)c(F)c(F)c(F)c1F]

The title compound N-(2-((7H-pyrrolo[2,3-d]pyrimidin-4-yl)amino)ethyl)-2,3,4,5,6-pentafluoro-N-methylbenzenesulfonamide, was prepared according to the protocol described in general procedure FA and isolated as a yellow powder (0.075 g, 35% yield). $^1H$ NMR (400 MHz, DMSO-$d_6$) δ 11.51 (brs, 1H), 8.05 (s, 1H), 7.45-7.38 (brs, 1H), 7.07-7.02 (m, 1H), 6.33-6.28 (m, 1H), 3.65-3.56 (m, 4H), 3.10 (s, 3H). $^{19}F$ NMR (376 MHz, DMSO-$d_6$) δ −136.8 (m), −147.8 (m), −159.7 (m). ESI-MS: measured m/z 421.7 $[M+H]^+$.

Example AA-19 N-((3R,6S)-6-methyl-1-((perfluorophenyl)sulfonyl)piperidin-3-yl)-7H-pyrrolo[2,3-d]pyrimidin-4-amine (3A-25)

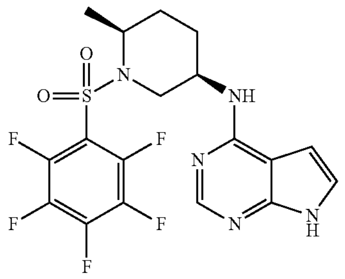 [SMILES: C[C@H]1CC[C@@H](Nc2ncnc3[nH]ccc23)CN1S(=O)(=O)c1c(F)c(F)c(F)c(F)c1F]

The title compound N-((3R,6S)-6-methyl-1-((perfluorophenyl)sulfonyl)piperidin-3-yl)-7H-pyrrolo[2,3-d]pyrimidin-4-amine, was prepared according to the protocol described in general procedure FA and isolated as a pale yellow solid (0.14 g, 31% yield). $^{1}$H NMR (400 MHz, DMSO-$d_6$) δ 11.54 (brs, 1H), 8.06 (s, 1H), 7.24 (d, J=8 Hz, 1H), 7.11-7.07 (m, 1H), 6.53-6.49 (m, 1H), 4.34-4.24 (m, 1H), 4.01-3.88 (m, 2H), 3.01-2.91 (m, 1H), 1.81-1.60 (m, 4H), 1.24-1.13 (m, 3H).

$^{19}$F NMR (376 MHz, DMSO-$d_6$) δ 136.8 (m), −147.3 (m), −159.4 (m). ESI-MS: measured m/z 461.7 [M+H]$^+$.

General Procedure GA

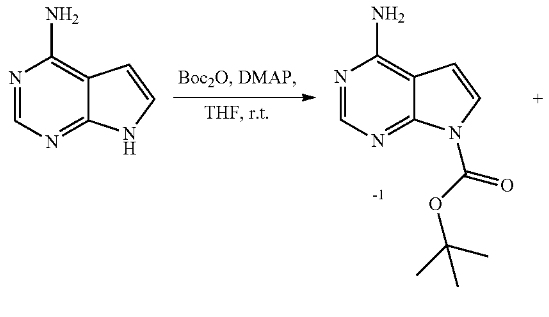

-1

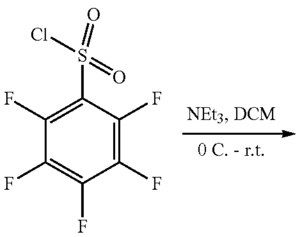

-continued

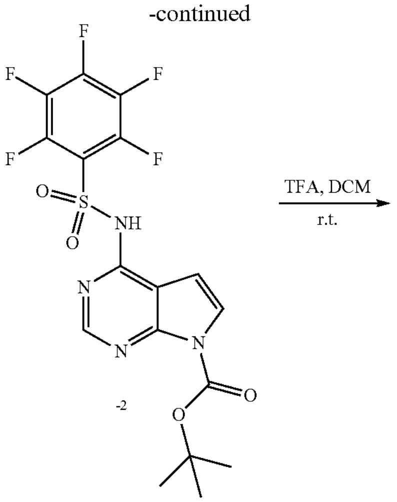

-2

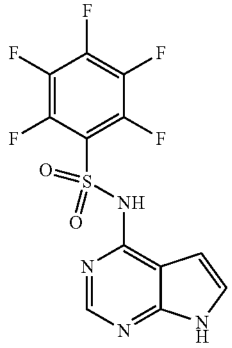

-3

Synthesis of tert-butyl 4-amino-7H-pyrrolo[2,3-d]pyrimidine-7-carboxylate (-1)

To a stirred suspension of 7H-pyrrolo[2,3-d]pyrimidin-4-amine (5 g, 37.27 mmol) and DMAP (455.38 mg, 3.73 mmol) in THF (20 mL) at room temperature under argon was added di-tert-butyl dicarbonate (8.95 g, 41.00 mmol, 9.41 mL) slowly as a solution in THF (20 mL). The mixture was stirred for at room temperature for 3 h. Once the reaction was finished, the mixture was diluted with water/brine and extracted with ethyl acetate (3×). The combined organic phases were washed with brine (2×), dried over anhydrous sodium sulfate, filtered and concentrated in vacuo. The product of interest was isolated via flash column chromatography (50-100% EtOAc in DCM) and subsequently triturated in a solution of diethyl ether and hexanes. The mixture was filtered to collect the desired product as a white solid (4.5 g, 19.21 mmol, 51.54% yield). $^{1}$H NMR (400 MHz, DMSO-$d_6$) δ 8.18 (s, 1H), 7.44 (d, J=4 Hz, 1H), 7.22 brs, 2H), 6.74 (d, J=4 Hz, 1H), 1.60 (s, 9H). ESI-MS: measured m/z 234.9 [M+H]$^+$.

Synthesis of tert-butyl 4-((perfluorophenyl)sulfonamido)-7H-pyrrolo[2,3-d]pyrimidine-7-carboxylate (-2)

To a solution of tert-butyl 4-aminopyrrolo[2,3-d]pyrimidine-7-carboxylate (0.1 g, 426.9 umol, 1 eq.) in chloroform (0.1 M)(4.2 mL) cooled to 0° C. was added neat 2,3,4,5,6-pentafluoro benzene sulfonyl chloride (113.8 mg, 426.9 umol, 63.22 uL, 1 eq.) under inert conditions (nitrogen atmosphere). The resulting solution was stirred at 0° C. for 5 minutes before neat N,N-diethylethanamine (64.8 mg, 640.3 umol, 89.25 uL, 1.5 eq.) was added slowly over a period of 2 minutes. The mixture was stirred for 5 hours while slowly warming to room temperature. Water was added to quench the reaction and the resulting mixture extracted three times with DCM. The collected organic layers were washed with brine, dried over anhydrous sodium sulfate, filtered, and evaporated under reduced pressure using a rotary evaporator. The resulting residue was separated on a pad of silica eluting with a gradient of 20% to 30% ethyl acetate in hexanes to afford the desired product (0.08 g, 172.2 umol, 40% yield). $^{1}$H NMR (400 MHz, $CDCl_3$) δ 12.46 (s, 1H), 8.25 (s, 1H), 7.56 (d, J=3.9 Hz, 1H), 6.78 (d, J=3.9 Hz, 1H). $^{19}$F NMR (376 MHz, $CDCl_3$) δ −136.95 (m), −147.48 (m), −159.22-−159.41 (m).

Synthesis of 2,3,4,5,6-pentafluoro-N-(7H-pyrrolo[2,3-d]pyrimidin-4-yl)benzene sulfonamide To a stirred solution of tert-butyl 4-[(2,3,4,5,6-pentafluorophenyl)sulfonylamino]pyrrolo[2,3-d]pyrimidine-7-carboxylate (0.05 g, 0.107 mmol) in DCM (0.1 M)(1 mL) was added TFA (0.1 M)(1 mL) in a dropwise manner. The resulting mixture was stirred at room temperature for 1 hour. Upon complete consumption of the starting material based on TLC (H:E=2:1), the mixture was concentrated under reduced pressure using rotary evaporator. The mixture was diluted with EtOAc (40 mL) and washed three times with a saturated aqueous solution of sodium bicarbonate (30 mL×3). The collected organic layers were dried with anhydrous sodium sulfate, filtered, and evaporated under reduced pressure to yield the crude product. The crude residue was purified by Prep-HPLC, running a mobile phase of 90% to 0% $H_2O$ (0.1% FA) in ACN (0.1% FA) over 60 minutes to afford the desired product. $^{1}$H NMR (400 MHz, $CD_3CN$) δ 11.90 (s, 1H), 10.38 (s, 1H), 8.20 (s, 1H), 7.27 (dd, J=3.6, 2.2 Hz, 1H), 6.72 (dd, J=3.6, 1.9 Hz, 1H). $^{19}$F NMR (376 MHz, $CD_3CN$) δ −139.51 (dt, J=20.8, 5.4 Hz, 2F), −151.68-−151.85 (m, 1F), −162.26-−162.44 (m, 2F).

Spebrutinib Compounds

General Procedure HA:

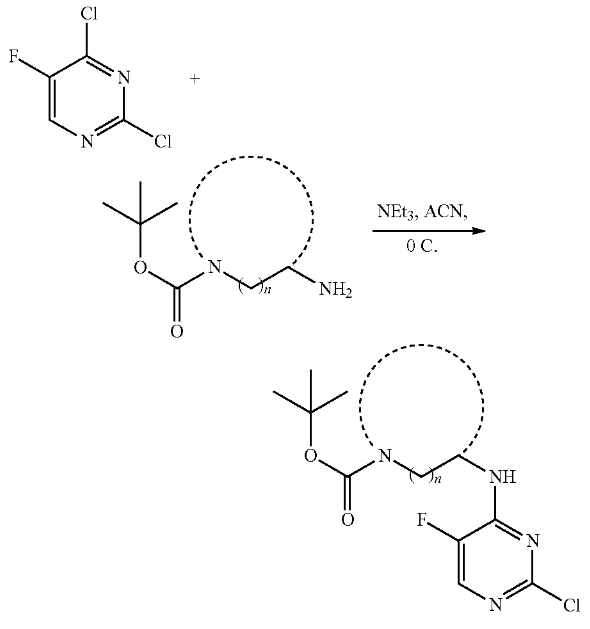

Neat triethylamine (1.6 eq.) was added dropwise to a cold solution (0° C.) of 2,4-dichloro-5-fluoro-pyrimidine (1 eq.), aminocarbamate (1.6 eq.) and acetonitrile (0.5 M). After 2-16 hours of stirring, the reaction was partitioned between water and ethyl acetate. The organic phase was removed and the remaining aqueous phase extracted a further two times with ethyl acetate. The organic phases were combined and washed with brine, dried over anhydrous magnesium sulfate, filtered, and concentrated under reduced pressure to afford the desired product.

General Procedure IA:

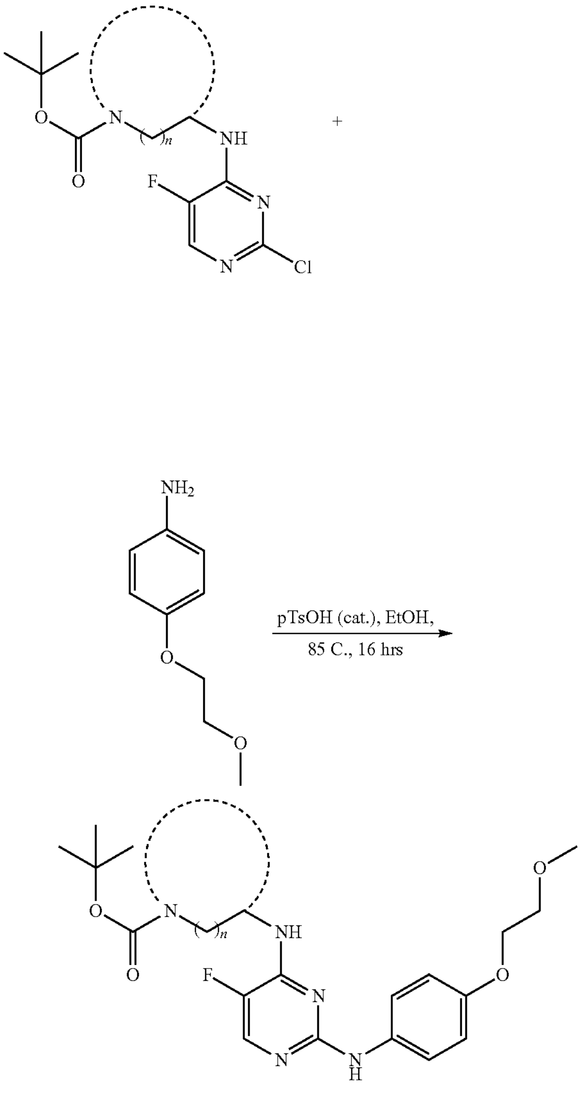

To a solution of boc-protected pyrimidine (1 eq.), 4-(2-methoxyethoxy)aniline (2 eq.), and ethanol (0.1-0.5 M) was added 4-methylbenzenesulfonic acid hydrate (0.05 eq.). The reaction vessel was fitted with a water jacketed reflux condenser and the apparatus heated at 85° C. for 18 hours. The reaction mixture was allowed to cool to room temperature and the solvent removed under reduced pressure. The compound of interest was isolated using flash column chromatography techniques employing a mobile phase of hexanes and ethyl acetate.

General Procedure JA:

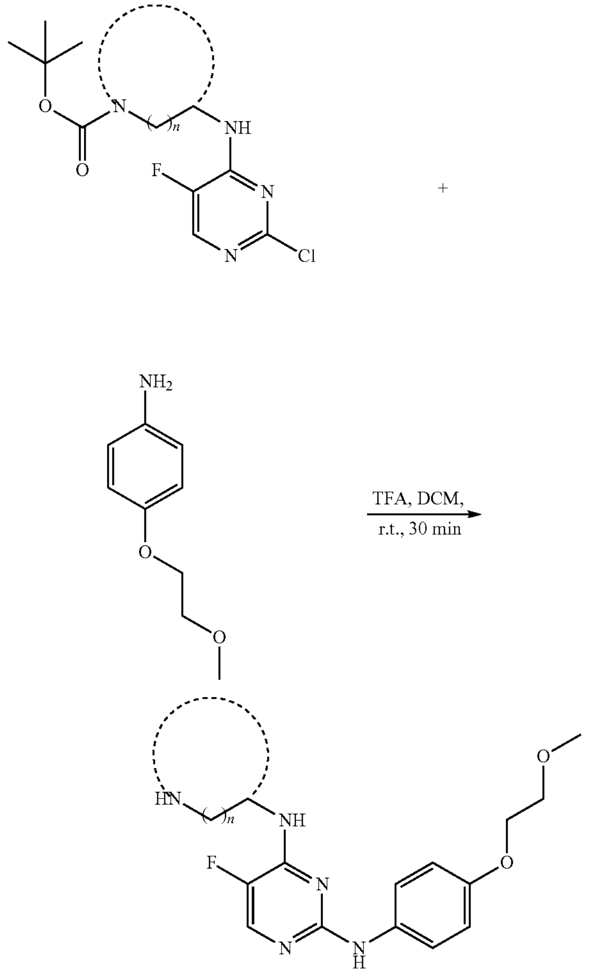

To a stirred solution of boc-protected pyrimidine (1 eq.) in DCM (0.1 M) was added TFA (3 eq.). The resulting solution was stirred at room temperature for 30 minutes and then quenched with saturated a saturated aqueous solution of sodium bicarbonate, followed by extraction with ethyl acetate (3 times). The combined organic phases were washed with brine, dried over anhydrous sodium sulfate, filtered, and evaporated under reduced pressure to afford the desired product.

General Procedure KA:

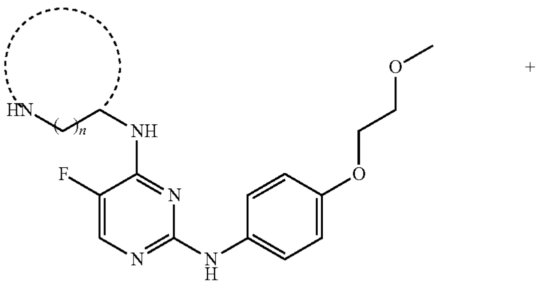

-continued

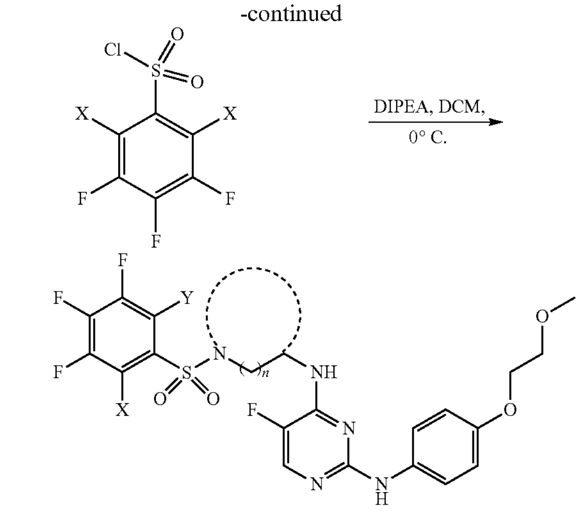

An appropriate sulfonyl chloride (0.9-1.2 eq) was incubated with its corresponding pyrimidine (1 eq) in anhydrous DCM (0.05 M-0.1 M) under an atmosphere of argon. The resulting mixture was cooled to 0° C. and stirred for 15 minutes. Neat diisopropylethylamine (3-5 eq) was slowly added to the mixture and it was stirred at 0° C. for a further 3-16 hrs. The reaction was quenched with water and extracted with ethyl acetate (3 times). The combined organic layers were washed with brine, dried over anhydrous sodium sulfate, filtered, and evaporated to dryness. The crude material was purified by either flash column chromatography, eluting with a solvent system comprised of MeOH/DCM, or reverse-phase chromatography, employing a solvent system comprised of ACN/Water containing 0.1% formic acid. The isolated material was lyophilized from ACN and water to afford the desired product.

Synthesis of 2-chloro-5-fluoro-N-(3-nitrophenyl) pyrimidin-4-amine

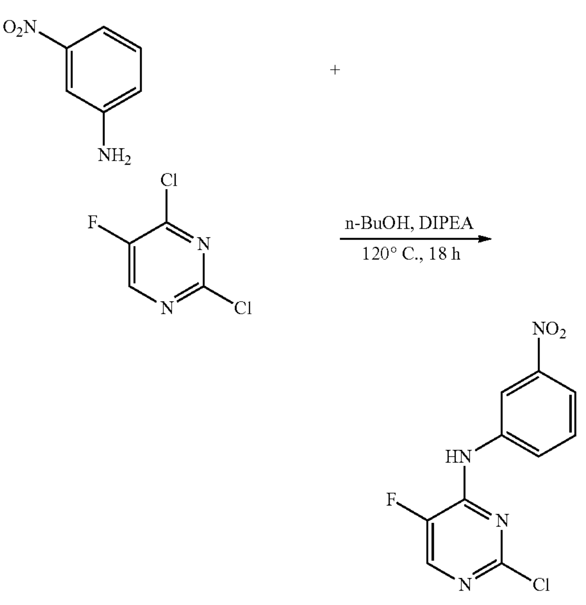

In an oven-dried 100 mL round bottom flask purged with nitrogen, 3-nitroaniline (3 g, 21.72 mmol, 1 eq.), 2,4-dichloro-5-fluoro-pyrimidine (5.44 g, 32.58 mmol, 1.5 eq.) and N-ethyl-N-isopropyl-propan-2-amine (7.57 ml, 43.44 mmol, 2 eq.) were dissolved in n-butanol (0.27M) (80 mL). The reaction mixture was heated to reflux at 120° C. for 18 h. Reaction was monitored by TLC. After completion, the reaction mixture was allowed to cool to room temperature. The reaction was poured into water and extracted with ethyl acetate (3×25 mL). The combined ethyl acetate layers were washed with brine, dried over anhydrous sodium sulfate and concentrated under reduced pressure. The resulting residue was triturated with diethyl ether three times to afford the desired product (3.7 g, 13.77 mmol, 63%). $^1$H NMR (400 MHz, DMSO-$d_6$) δ 10.43 (s, 1H), 8.75 (t, J=2.2 Hz, 1H), 8.45 (d, J=3.3 Hz, 1H), 8.17 (ddd, J=8.2, 2.3, 0.9 Hz, 1H), 8.02-7.97 (m, 1H), 7.70 (t, J=8.2 Hz, 1H). $^{19}$F NMR (376 MHz, DMSO-$d_6$) δ −152.69 (d, J=3.4 Hz, 1F).

Synthesis of 5-fluoro-$N^2$-(4-(2-methoxyethoxy)phenyl)-$N^4$-(3-nitrophenyl)pyrimidine-2,4-diamine

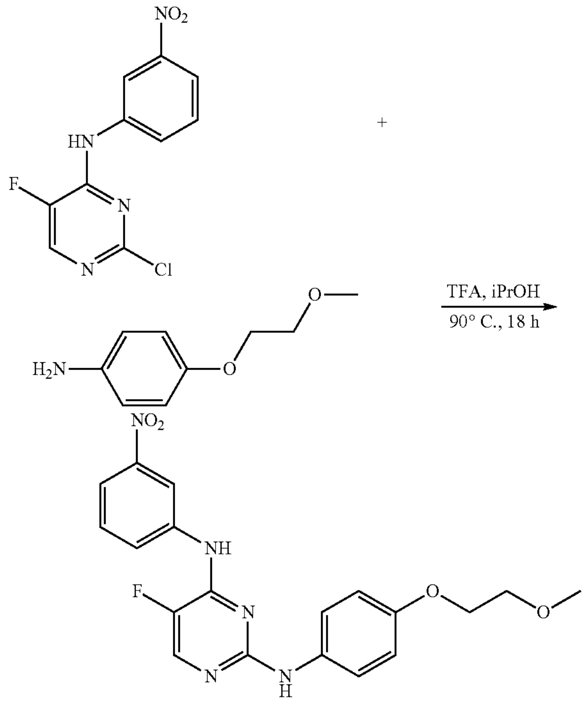

2-chloro-5-fluoro-N-(3-nitrophenyl)pyrimidin-4-amine (400 mg, 1.49 mmol) and 4-(2-methoxyethoxy)aniline (273.8 mg, 1.64 mmol) were dissolved in isopropanol (9 mL) under an inert atmosphere of argon. Neat trifluoroacetic acid (339.5 mg, 2.98 mmol, 227.90 uL) was introduced dropwise and the resulting solution was heated at 90° C. for 18 h. The reaction was permitted to cool to room temperature. Upon cooling, a solid started to precipitate from the solution. The solid was collected by vacuum filtration and triturated with ether to afford the desired product (0.386 g, 65% yield). $^1$H NMR (400 MHz, DMSO-$d_6$) δ 10.49 (s, 1H), 9.86 (s, 1H), 8.53 (t, J=2.0 Hz, 1H), 8.29 (s, 1H), 8.23 (s, 1H), 7.99 (d, J=8.2 Hz, 1H), 7.64 (t, J=8.2 Hz, 1H), 7.46-7.33 (m, 2H), 6.86 (d, J=8.9 Hz, 2H), 4.14-3.91 (m, 2H), 3.66 (dd, J=5.4, 3.8 Hz, 2H), 3.32 (s, 3H).

Synthesis of $N^4$-(3-aminophenyl)-5-fluoro-$N^2$-(4-(2-methoxyethoxy)phenyl)pyrimidine-2,4-diamine

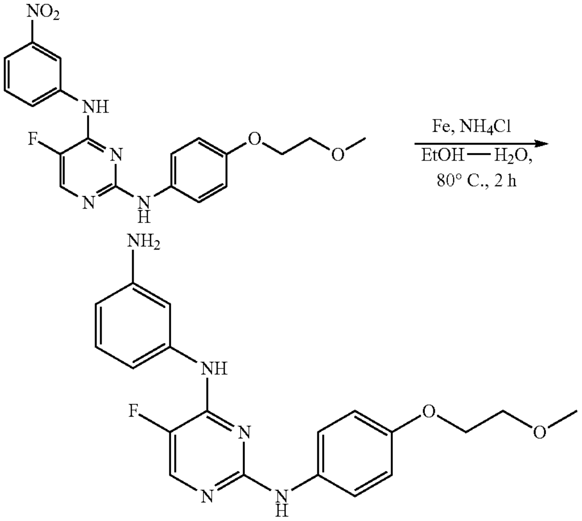

5-fluoro-$N^2$-[4-(2-methoxyethoxy)phenyl]-$N_4$-(3-nitrophenyl)pyrimidine-2,4-diamine (364.7 mg, 913.18 umol) was dissolved in ethanol (5.5 mL). Iron (254.9 mg, 4.57 mmol), ammonium chloride (73.27 mg, 1.37 mmol), and water (0.9 mL) were added and the resulting mixture heated to reflux. After 2 hours, the reaction mixture was allowed to cool to room temperature, filtered, and residue washed with ethyl acetate. The filtrate was partitioned between water and ethyl acetate. The organic phase was removed and the remaining aqueous phase extracted a further two times with ethyl acetate. The combined organic phases were washed with brine, dried over anhydrous sodium sulfate, filtered, and concentrated to dryness to afford the desired product (0.197 g, 58% yield) as a crude mixture of materials that was used without further purification. $^1$H NMR (400 MHz, DMSO-$d_6$) δ 9.00 (s, 1H), 8.90 (s, 1H), 8.01 (d, J=3.8 Hz, 1H), 7.60-7.53 (m, 2H), 7.02-6.88 (m, 3H), 6.87-6.78 (m, 2H), 6.33 (d, J=7.8 Hz, 1H), 4.98 (s, 2H), 4.06-3.99 (m, 2H), 3.67-3.61 (m, 2H), 3.31 (s, 3H).

Synthesis of 2-chloro-5-fluoro-N-(4-nitrophenyl)pyrimidin-4-amine

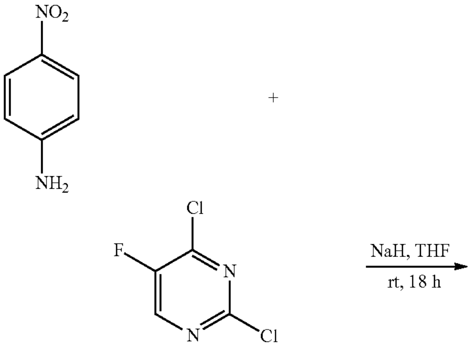

-continued

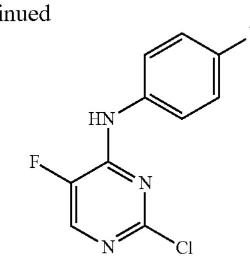

2,4-dichloro-5-fluoro-pyrimidine (1.00 g, 5.99 mmol) and 4-nitroaniline (992.7 mg, 7.19 mmol, 689.37 uL) were dissolved in THF (50 mL) and cooled to 0° C. by using an ice bath. A mineral dispersion of sodium hydride (287.4 mg, 7.19 mmol, 60% in mineral oil) was added in three portions to the cold solution. The reaction mixture was allowed to warm slowly to room temperature and stir for 18 hours. The reaction mixture was quenched with water and the bi-phasic mixture extracted three times with ethyl acetate. The combined organic layers were washed with brine, dried over anhydrous magnesium sulfate, and concentrated to dryness to afford the desired product (0.298 g, 19% yield). $^1$H NMR (400 MHz, DMSO-$d_6$) δ 10.55 (s, 1H), 8.51 (d, J=3.3 Hz, 1H), 8.34-8.23 (m, 2H), 8.11-7.97 (m, 2H).

Synthesis of 5-fluoro-N$^2$-(4-(2-methoxyethoxy)phenyl)-N$^4$-(4-nitrophenyl)pyrimidine-2,4-diamine

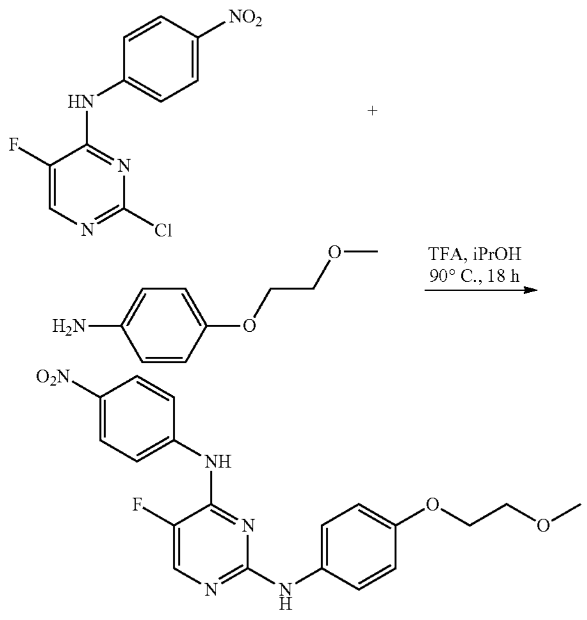

2-chloro-5-fluoro-N-(4-nitrophenyl)pyrimidin-4-amine (386.1 mg, 1.44 mmol), and 4-(2-methoxyethoxy)aniline (240 mg, 1.44 mmol) were dissolved in isopropanol (9 mL) under an inert atmosphere of argon. Neat trifluoroacetic acid (327 mg, 2.87 mmol, 221.5 uL) was added dropwise and the resulting solution heated at 90° C. for 18 h. After cooling to room temperature, a solid began to precipitate from the solution. The solid was collect via vacuum filtration and rinsed with ether to afford the desired product (0.328 g, 57% yield). $^1$H NMR (400 MHz, DMSO-$d_6$) δ 10.55 (s, 1H), 9.89 (s, 1H), 8.34 (d, J=4.0 Hz, 1H), 8.18 (d, J=8.3 Hz, 2H), 8.08 (d, J=8.5 Hz, 2H), 7.44 (d, J=8.5 Hz, 2H), 6.98 (d, J=7.6 Hz, 2H), 4.10 (d, J=3.4 Hz, 2H), 3.67 (d, J=3.3 Hz, 2H), 3.32 (d, J=3.9 Hz, 3H).

Synthesis of N$^4$-(4-aminophenyl)-5-fluoro-N$^2$-(4-(2-methoxyethoxy)phenyl)pyrimidine-2,4-diamine

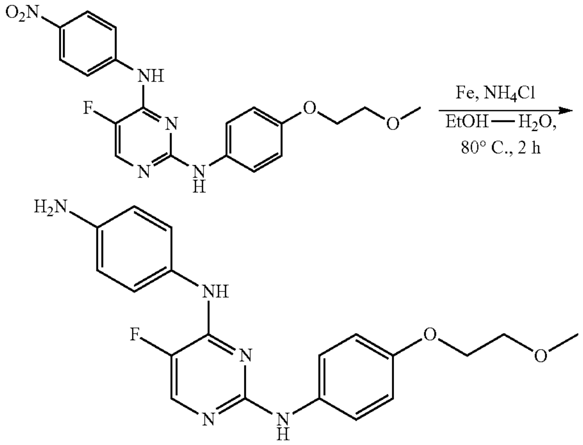

5-fluoro-N$^2$-[4-(2-methoxyethoxy)phenyl]-$N_4$-(4-nitrophenyl)pyrimidine-2,4-diamine (328 mg, 821.3 umol) was dissolved in ethanol (4.9 mL). Iron (229 mg, 4.11 mmol, 29.2 uL), ammonium chloride (65.9 mg, 1.23 mmol), and water (0.8 mL) were added and the resulting mixture heated to reflux. After 2 hours, the reaction mixture was cooled to room temperature, filtered, and the residue washed with ethyl acetate. The filtrate was partitioned between water and ethyl acetate. The organic phase was removed and the remaining aqueous phase extracted a further two times with ethyl acetate. The combined organic phases were washed with brine, dried over anhydrous sodium sulfate, filtered, and concentrated to dryness to afford the desired product (0.208 g, 69% yield) as a crude mixture of materials that was used without further purification. $^1$H NMR (400 MHz, DMSO-$d_6$) δ 8.95 (d, J=37.2 Hz, 2H), 7.97 (s, 1H), 7.46 (dd, J=62.1, 7.2 Hz, 4H), 6.72 (dd, J=58.1, 7.5 Hz, 4H), 4.03 (s, 2H), 3.53 (s, 2H), 3.32 (s, 3H).

Synthesis of N$^1$ tert-Butyl (2-((2-chloro-5-fluoropyrimidin-4-yl)amino)ethyl)carbamate

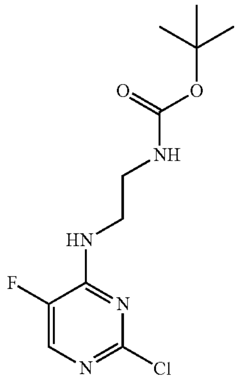 [SMILES: CC(C)(C)OC(=O)NCCNc1nc(Cl)ncc1F]

tert-Butyl (2-((2-chloro-5-fluoropyrimidin-4-yl)amino)ethyl)carbamate was prepared according to the protocol described in general procedure HA (8.46 g, 97% yield). $^1$H NMR (400 MHz, $CDCl_3$) δ 7.89 (s, 1H), 6.31 (s, 1H), 4.94 (s, 1H), 3.63 (dd, J=10.9, 5.3 Hz, 2H), 3.45 (dd, J=11.0, 5.8 Hz, 2H), 1.46 (s, 9H).

Synthesis of tert-butyl (2-((5-fluoro-2-((4-(2-methoxyethoxy)phenyl)amino)pyrimidin-4-yl)amino)ethyl)carbamate

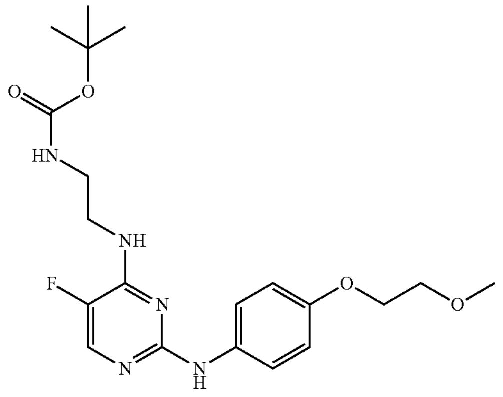 [SMILES: COCCOc1ccc(Nc2ncc(F)c(NCCNC(=O)OC(C)(C)C)n2)cc1]

tert-butyl (2-((5-fluoro-2-((4-(2-methoxyethoxy)phenyl)amino)pyrimidin-4-yl)amino)ethyl) carbamate was prepared according to the protocol described in general procedure IA (0.486 g, 67% yield). $^1$H NMR (400 MHz, $CDCl_3$) δ 7.78 (d, J=3.2 Hz, 1H), 7.47-7.40 (m, 2H), 6.95-6.88 (m, 2H), 5.50 (s, 1H), 4.92 (s, 1H), 4.13 (dd, J=5.5, 4.0 Hz, 2H), 3.80-3.74 (m, 2H), 3.60 (dd, J=11.2, 5.6 Hz, 2H), 3.48 (s, 3H), 3.42 (d, J=5.4 Hz, 2H), 1.46 (s, 9H).

Synthesis of $N^4$-(2-aminoethyl)-5-fluoro-$N^2$-(4-(2 methoxyethoxy)phenyl)pyrimidine-2,4-diamine

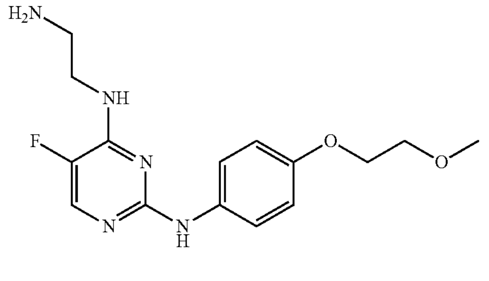 [SMILES: COCCOc1ccc(Nc2ncc(F)c(NCCN)n2)cc1]

$N^4$-(2-aminoethyl)-5-fluoro-$N^2$-(4-(2 methoxyethoxy) phenyl)pyrimidine-2,4-diamine was prepared according to the protocol described in general procedure JA. $^1$H NMR (400 MHz, DMSO-$d_6$) δ 8.86 (s, 1H), 7.87 (d, J=3.6 Hz, 1H), 7.57 (d, J=9.1 Hz, 2H), 7.39 (t, J=5.6 Hz, 1H), 6.85 (d, J=9.1 Hz, 2H), 6.16 (s, 2H), 4.05-4.01 (m, 2H), 3.66-3.62 (m, 2H), 3.50 (q, J=6.0 Hz, 2H), 3.31 (s, 3H), 2.98 (t, J=6.1 Hz, 2H). $^{19}$F NMR (376 MHz, DMSO-$d_6$) δ −75.69.

Synthesis of tert-butyl (3-((2-chloro-5-fluoropyrimidin-4-yl)amino)propyl)carbamate

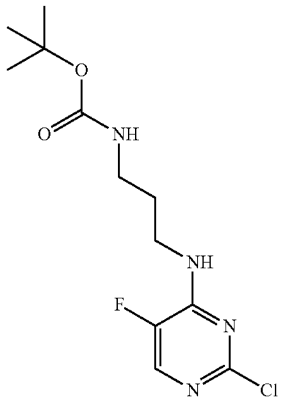 [SMILES: CC(C)(C)OC(=O)NCCCNc1nc(Cl)ncc1F]

tert-butyl (3-((2-chloro-5-fluoropyrimidin-4-yl)amino)propyl)carbamate was prepared according to the protocol described in general procedure HA (8.5 g, 93% yield). $^1$H NMR (400 MHz, $CDCl_3$) δ 7.86 (d, J=7.0 Hz, 1H), 6.31 (s, 1H), 4.94 (d, J=25.3 Hz, 1H), 3.66-3.53 (m, 2H), 3.24 (s, 2H), 1.77 (s, 2H), 1.46 (s, 9H). $^{19}$F NMR (376 MHz, $CDCl_3$) δ −159.52 (d, J=23.6 Hz).

Synthesis of tert-butyl (3-((5-fluoro-2-((4-(2-methoxyethoxy)phenyl)amino)pyrimidin-4-yl)amino)propyl)carbamate

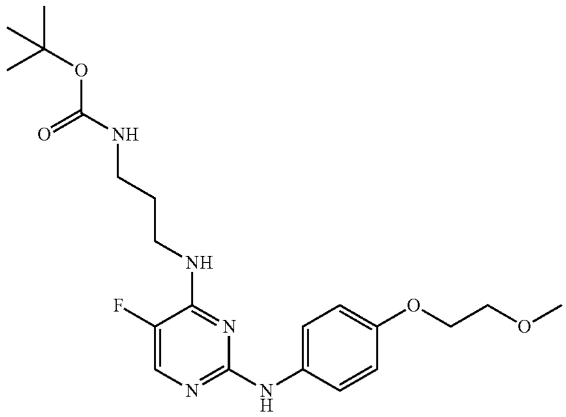 [SMILES: COCCOc1ccc(Nc2ncc(F)c(NCCCNC(=O)OC(C)(C)C)n2)cc1]

tert-butyl (3-((5-fluoro-2-((4-(2-methoxyethoxy)phenyl)amino)pyrimidin-4-yl)amino)propyl) carbamate was prepared according to the protocol described in general procedure IA (4 g, 93% yield). $^1$H NMR (400 MHz, DMSO-$d_6$) δ 10.35 (s, 1H), 9.10 (s, 1H), 8.12 (d, J=5.2 Hz, 1H), 7.46 (dd, J=21.9, 8.4 Hz, 2H), 7.03 (dd, J=24.0, 8.8 Hz, 2H), 6.87 (s, 1H), 4.19-3.89 (m, 2H), 3.68-3.53 (m, 2H), 3.41 (dd, J=12.8, 6.5 Hz, 2H), 3.32 (s, 3H), 3.14-2.76 (m, 2H), 1.71 (p, J=7.0 Hz, 2H), 1.37 (s, 9H). $^{19}$F NMR (376 MHz, DMSO-$d_6$) δ −163.25 (s).

Synthesis of $N^4$-(3-aminopropyl)-5-fluoro-$N^2$-(4-(2-methoxyethoxy)phenyl)pyrimidine-2,4-diamine

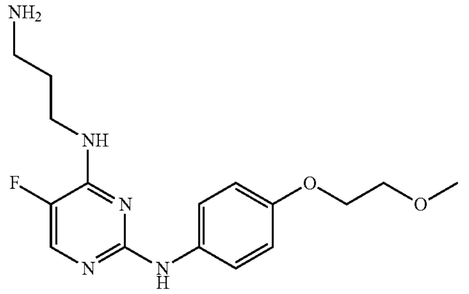 [SMILES: COCCOc1ccc(Nc2ncc(F)c(NCCCN)n2)cc1]

$N^4$-(3-aminopropyl)-5-fluoro-$N^2$-(4-(2-methoxyethoxy)phenyl)pyrimidine-2,4-diamine was prepared according to the protocol described in general procedure JA (0.192 g, 50% yield). $^1H$ NMR (400 MHz, $CD_3CN$) δ 7.74 (d, J=3.7 Hz, 1H), 7.58-7.48 (m, 2H), 7.36 (s, 1H), 6.93-6.81 (m, 2H), 6.38 (s, 1H), 4.14-4.03 (m, 2H), 3.68 (ddd, J=17.8, 7.0, 3.8 Hz, 2H), 3.58-3.47 (m, 2H), 3.38 (s, 3H), 2.78 (t, J=6.4 Hz, 2H), 1.81-1.63 (m, 2H). $^{19}F$ NMR (376 MHz, $CD_3CN$) δ −170.97 (d, J=3.4 Hz).

Synthesis of 5-fluoro-$N^2$-(4-(2-methoxyethoxy)phenyl)pyrimidine-2,4-diamine

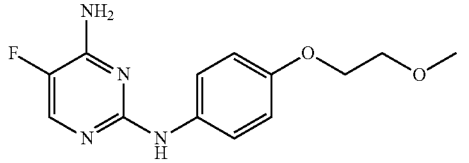 [SMILES: COCCOc1ccc(Nc2ncc(F)c(N)n2)cc1]

5-fluoro-$N^2$-(4-(2-methoxyethoxy)phenyl)pyrimidine-2,4-diamine was prepared according to the protocol described in general procedure KA (1.45 g, 77% yield). $^1H$ NMR (400 MHz, $CD_3CN$) δ 7.83 (d, J=3.4 Hz, 1H), 7.62-7.44 (m, 2H), 7.29 (s, 1H), 6.97-6.75 (m, 2H), 5.74-5.41 (m, 2H), 4.08 (dd, J=5.4, 3.8 Hz, 2H), 3.67 (ddd, J=16.9, 5.4, 3.8 Hz, 2H), 3.38 (s, 3H). $^{19}F$ NMR (376 MHz, $CD_3CN$) δ −169.77 (d, J=3.4 Hz).

Example AA-20 2,3,4,5,6-pentafluoro-N-(3-((5-fluoro-2-((4-(2-methoxyethoxy)phenyl)amino)pyrimidin-4-yl)amino)phenyl)benzenesulfonamide (3A-29)

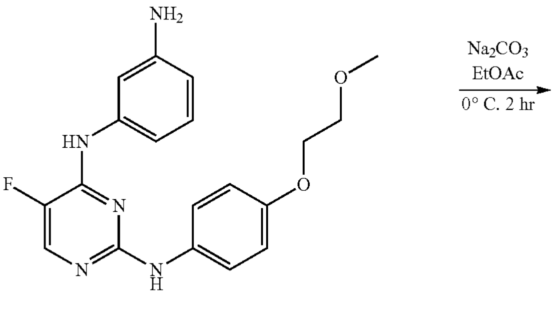

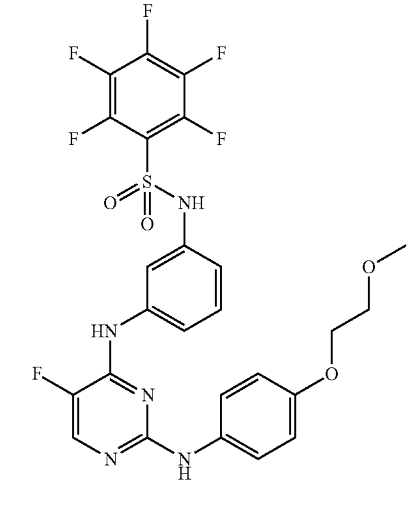

To a solution of $N^4$-(3-aminophenyl)-5-fluoro-$N^2$-[4-(2-methoxyethoxy)phenyl]pyrimidine-2,4-diamine (0.05 g, 135.3 umol, 1 eq.) in ethyl acetate (0.1 M, 1.35 mL) was added sodium carbonate (14.3 mg, 135.36 umol, 1 eq.) at 0° C. under a nitrogen atmosphere. 2,3,4,5,6 pentafluorobenzenesulfonyl chloride (21.05 uL, 142.13 umol, 1.05 eq.) was added dropwise to the stirring mixture and the reaction permitted to warm to room temperature over 2 hours. The reaction was quenched with water and extracted three times with ethyl acetate. The combined organic phases were washed with brine, dried over anhydrous sodium sulfate, filtered, and concentrated in vacuo. The crude material was purified on a Biotage Isolera equipped with a 10 g silica cartridge running a solvent gradient of 20 to 30% EtOAc in Hexanes to afford the desired product (0.052 g, 0.088 mmol, 64%). $^1H$ NMR (400 MHz, $CDCl_3$) δ 7.94 (s, 1H), 7.81 (s, 1H), 7.36 (d, J=8.9 Hz, 2H), 7.32-7.28 (m, 1H), 7.22 (t, J=8.1 Hz, 1H), 7.20 (s, 1H), 6.96 (d, J=3.0 Hz, 2H), 6.94-6.89 (m, 1H), 6.86 (d, J=8.9 Hz, 2H), 4.15-4.11 (m, 2H), 3.82-3.78 (m, 2H), 3.49 (s, 3H). $^{19}F$ NMR (376 MHz, $CDCl_3$) δ −136.37 (qd, J=13.2, 7.5 Hz), −144.32 (tt, J=21.1, 6.9 Hz), −157.96 (tt, J=21.1, 6.3 Hz), −167.58 (d, J=3.5 Hz). ESI-MS: measured m/z 597.6 $[M+H]^+$.

Example AA-21 2,3,4,5,6-pentafluoro-N-(4-((5-fluoro-2-((4-(2-methoxyethoxy)phenyl)amino)pyrimidin-4-yl)amino)phenyl)benzenesulfonamide (3A-38)

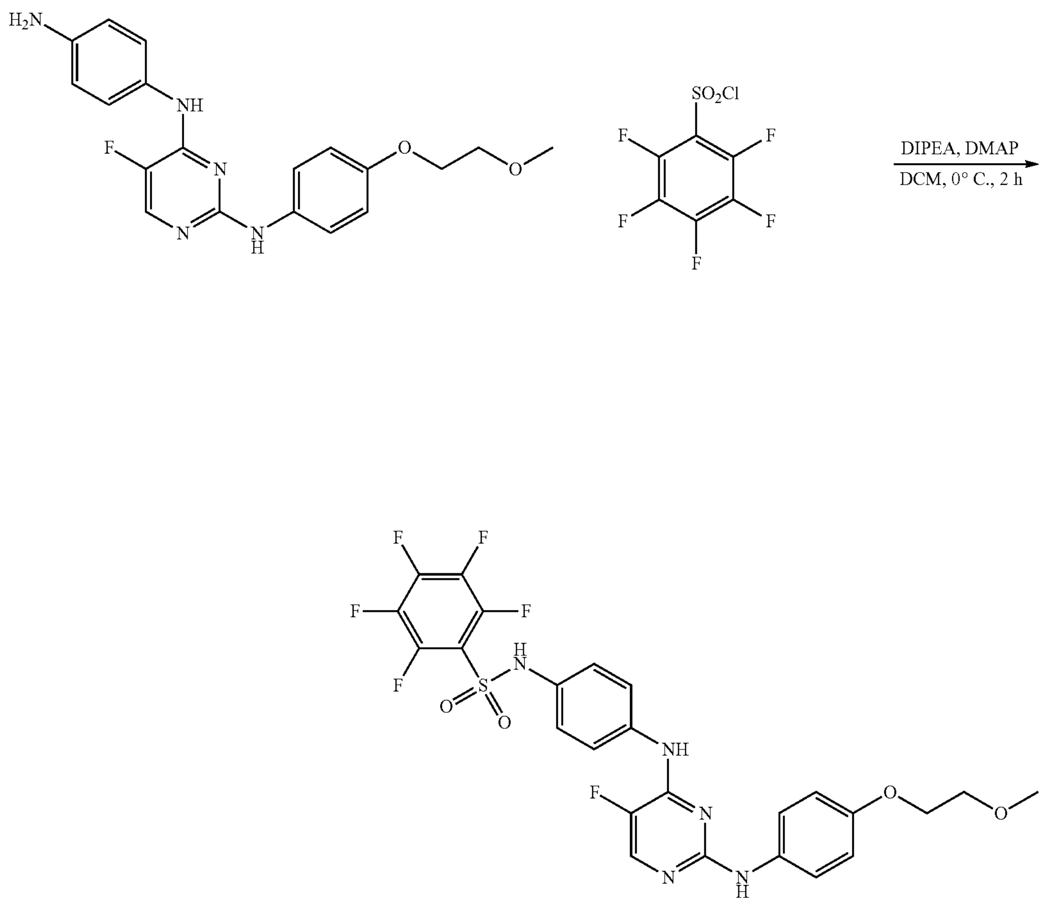

A mixture of $N^4$-(4-aminophenyl)-5-fluoro-$N^2$-[4-(2-methoxyethoxy)phenyl]pyrimidine-2,4-diamine (50.0 mg, 135.3 umol), N,N-dimethylpyridin-4-amine (3.3 mg, 27.0 umol), and DIPEA (26.2 mg, 203.0 umol, 35.37 uL) in anhydrous dichloromethane (1.25 mL) was cooled to 0° C. under a nitrogen atmosphere. Once cold, a solution of 2,3,4,5,6-pentafluorobenzenesulfonyl chloride (32.5 mg, 121.8 umol, 18.04 uL) in anhydrous dichloromethane (1.25 mL) was added dropwise and the resulting mixture stirred for 2 hours. The reaction was quenched with water and extracted 3 times with ethyl acetate. The combined organic phases were washed with brine, dried over anhydrous sodium sulfate, filtered, and concentrated to dryness. The crude residue was purified by Prep-HPLC running a mobile phase of 90% to 0% $H_2O$ (0.1% FA) in ACN (0.1% FA) over 60 minutes to afford the desired product (0.023 g, 28% yield). $^1H$ NMR (400 MHz, $CDCl_3$) δ 7.95 (d, J=3.0 Hz, 1H), 7.57 (d, J=8.9 Hz, 2H), 7.37 (d, J=8.9 Hz, 2H), 7.15 (d, J=8.8 Hz, 2H), 6.98-6.89 (m, 3H), 6.79 (s, 1H), 4.20-4.13 (m, 2H), 3.85-3.79 (m, 2H), 3.53 (s, 3H). $^{19}F$ NMR (376 MHz, $CDCl_3$) δ −136.00--136.62 (m), −144.09--144.75 (m), −157.86--158.33 (m), −167.80 (s). ESI-MS: measured m/z 599.1 $[M+H]^+$.

Example AA-22 2,3,4,5,6-pentafluoro-N-(2-((5-fluoro-2-((4-(2-methoxyethoxy)phenyl)amino)pyrimidin-4-yl)amino)ethyl)benzenesulfonamide (3A-37)

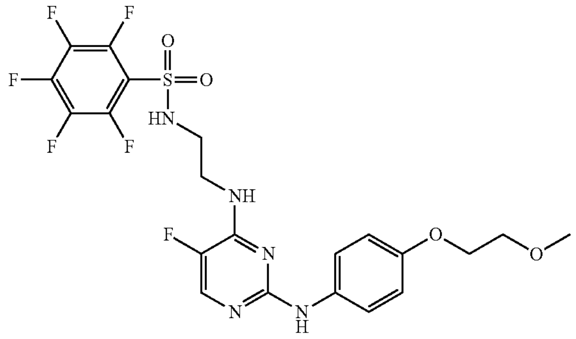 [SMILES: COCCOc1ccc(Nc2ncc(F)c(NCCNS(=O)(=O)c3c(F)c(F)c(F)c(F)c3F)n2)cc1]

The title compound 2,3,4,5,6-pentafluoro-N-(2-((5-fluoro-2-((4-(2-methoxyethoxy)phenyl)amino)pyrimidin-4-yl)amino)ethyl)benzenesulfonamide, was prepared according to the protocol described in general procedure KA and isolated as a white powder (0.037 g, 20% yield). $^{1}H$ NMR (400 MHz, $CD_3CN$) δ 7.75 (s, 1H), 7.53 (s, 1H), 7.48 (d, J=8.7 Hz, 2H), 6.88 (d, J=8.5 Hz, 2H), 6.62 (s, 1H), 6.01 (s, 1H), 4.08 (s, 2H), 3.70 (d, J=3.0 Hz, 2H), 3.54 (d, J=5.0 Hz, 2H), 3.43 (d, J=4.8 Hz, 2H), 3.38 (s, 3H). $^{19}F$ NMR (376 MHz, $CD_3CN$) δ −139.04-−139.26 (m), −149.80 (t, J=20.3 Hz), −161.48 (t, J=18.0 Hz), −170.68 (s). ESI-MS: measured m/z 551.7 $[M+H]^+$.

Example AA-23 2,3,4,5,6-pentafluoro-N-(3-((5-fluoro-2-((4-(2-methoxyethoxy)phenyl)amino)pyrimidin-4-yl)amino)propyl)benzenesulfonamide

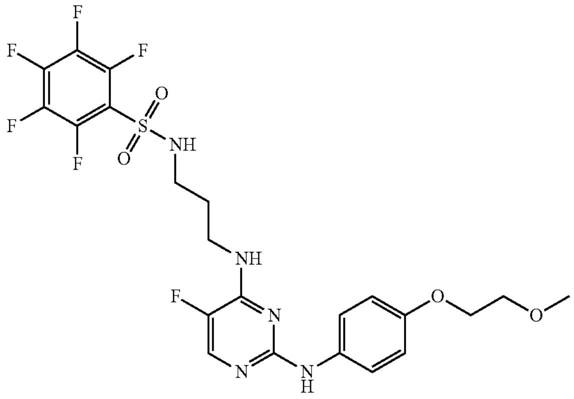 [SMILES: COCCOc1ccc(Nc2ncc(F)c(NCCCNS(=O)(=O)c3c(F)c(F)c(F)c(F)c3F)n2)cc1]

The title compound 2,3,4,5,6-pentafluoro-N-(3-((5-fluoro-2-((4-(2-methoxyethoxy)phenyl)amino)pyrimidin-4-yl)amino)propyl)benzenesulfonamide, was prepared according to the protocol described in general procedure KA and isolated as a white powder. $^{1}H$ NMR (400 MHz, $CD_3CN$) δ 8.07 (s, 1H), 7.76 (d, J=3.7 Hz, 1H), 7.56-7.48 (m, 2H), 6.93-6.85 (m, 2H), 6.66 (s, 1H), 5.98 (s, 1H), 4.08 (dd, J=5.4, 3.8 Hz, 2H), 3.70 (dd, J=5.4, 3.8 Hz, 2H), 3.50 (q, J=6.4 Hz, 2H), 3.39 (s, 3H), 3.18 (q, J=6.6 Hz, 2H), 1.86 (p, J=6.7 Hz, 2H). $^{19}F$ NMR (376 MHz, $CD_3CN$) δ −139.12, −139.24 (m), −149.59-−149.73 (m), −161.44-−161.61 (m). ESI-MS: measured m/z 566.5 $[M+H]^+$.

Example AA-24 2,3,4,5,6-pentafluoro-N-(5-fluoro-2-((4-(2-methoxyethoxy)phenyl)amino)pyrimidin-4-yl)benzenesulfonamide

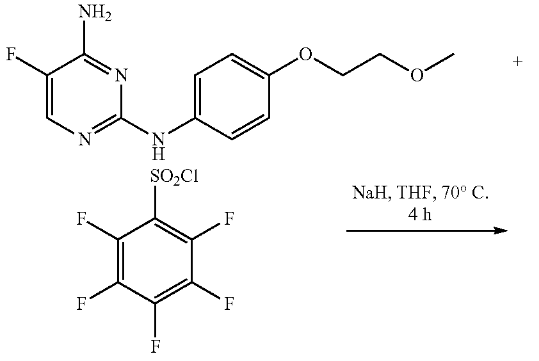

-continued

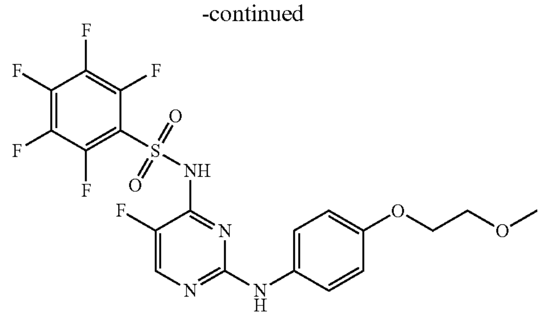

A mixture of 5-fluoro-N2-[4-(2-methoxyethoxy)phenyl]pyrimidine-2,4-diamine (49.8 mg, 178.9 umol) and a mineral dispersion of sodium hydride (7.9 mg, 196.8 umol, 60% in mineral oil) were dissolved in THF (1.8 mL) and cooled to 0° C. using an ice bath. Once sufficiently cold, a solution of 2,3,4,5,6-pentafluorobenzenesulfonyl chloride (42.9 mg, 161.01 umol, 23.8 uL) in THF (1.8 mL) was added dropwise. The resulting mixture was allowed to warm to room temperature and then refluxed for 4 h. Once the reaction was finished, excess solvent was removed under reduced pressure and the residue reconstituted in ethyl acetate. The crude material was washed with a saturated aqueous solution of sodium bicarbonate, brine, dried over anhydrous sodium sulfate, and concentrated to dryness. The crude residue was purified by Prep-HPLC running a mobile phase of 90% to 0% $H_2O$ (0.1% FA) in ACN (0.1% FA) over 60 minutes to afford the desired product. ESI-MS: measured m/z 509.3 $[M+H]^+$.

Example AA-25 Synthesis of N-(2-(4-amino-3-(4-phenoxyphenyl)-1H-pyrazolo[3,4-d]pyrimidin-1-yl)ethyl)-2,3,4,5-tetrafluoro-N-methyl-6-(trifluoromethyl)benzenesulfonamide (I-138)

I-138

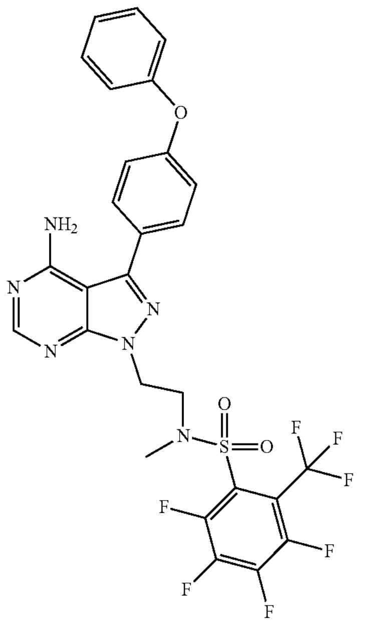

The title compound I-138, N-(2-(4-amino-3-(4-phenoxyphenyl)-1H-pyrazolo[3,4-d]pyrimidin-1-yl)ethyl)-2,3,4,5- tetrafluoro-N-methyl-6-(trifluoromethyl)benzenesulfonamide, was prepared using the protocol described in general procedure B (0.009 g, 10% yield). $^1$H NMR (400 MHz, $CD_3CN$) δ 8.29 (s, 1H), 7.67 (d, J=8.6 Hz, 2H), 7.46 (dd, J=8.6, 7.3 Hz, 2H), 7.27-7.09 (m, 5H), 5.91 (s, 2H), 4.67-4.59 (m, 2H), 3.87 (dd, J=11.2, 1.5 Hz, 2H), 3.03 (d, J=2.0 Hz, 3H). $^{19}$F NMR (376 MHz, $CD_3CN$) δ −52.34--52.71 (m), −133.68--133.92 (m), −134.00--134.21 (m), −147.05--147.30 (m), −148.26--148.43 (m). ESI-MS: measured m/z 641.3 $[M+H]^+$.

General Procedure A-1

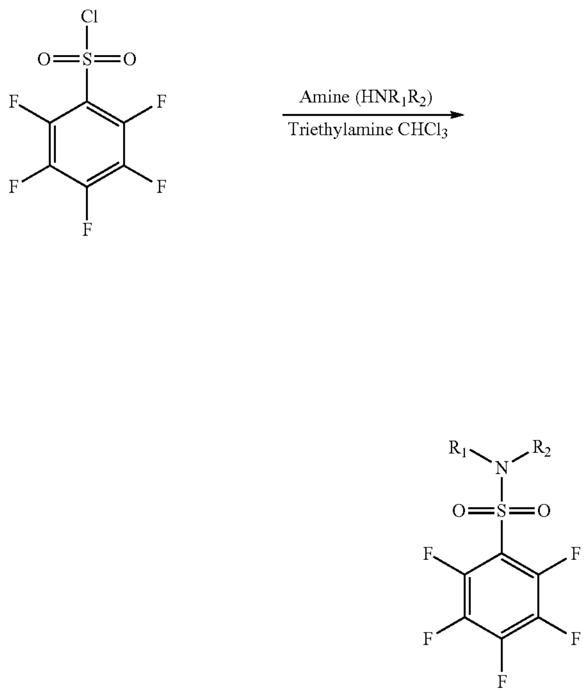

Pentafluorobenzenesulfonyl chloride (1 eq.) was added with chloroform (0.3 M). The resulting solution was stirred at 0° C., followed by dropwise addition of appropriate starting amine (1.1 eq.) and triethylamine (3 eq.). The reaction was quenched with 0.1 M HCl and the aqueous phase was extracted thrice with dichloromethane. The combined organic layer was washed once with saturated sodium chloride solution, dried with sodium sulfate, and concentrated in vacuo. The crude sample was absorbed onto silica gel and purified using flash chromatography using a Hexane: Ethyl acetate gradient.

General Procedure A-2

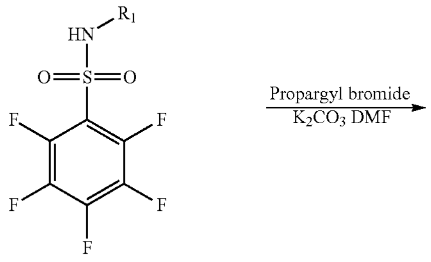

-continued

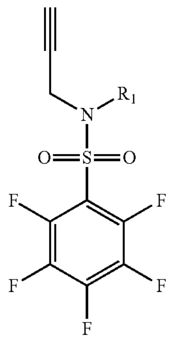

Sulfonamide (1 eq.) was added with dimethylformamide (0.3 M) and resulting solution was stirred at room temperature for 15 minutes, followed by addition of potassium carbonate (1.1 eq.). The resulting solution was stirred at 0° C. After 10 minutes, the solution was added with propargyl bromide in toluene (0.78 mL, 7 mmol) and the resulting solution was stirred at room temperature. After 12 hours, the solution was quenched with 0.1 M HCl at 0° C. and the aqueous phase was extracted thrice with dichloromethane. The combined organic layer was washed once with saturated sodium chloride solution, dried with sodium sulfate, and concentrated in vacuo. The crude sample was absorbed onto silica gel and purified using flash chromatography using a Hexane:Ethyl acetate gradient.

General Procedure A-3

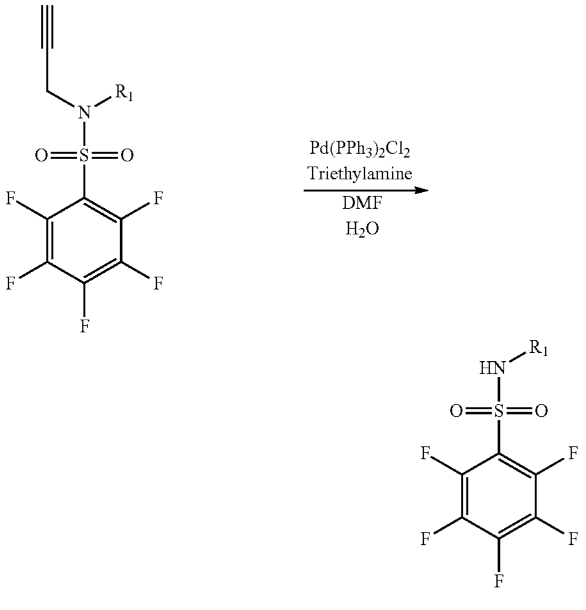

Sulfonamide (1 eq.) was dissolved in a mixture of dimethylformamide (0.33 M) and water (0.66 M). The resulting solution was stirred at room temperature. After 10 minutes, the solution was added with trans-dichlorobis(triphenylphosphine)palladium(II)(0.1 eq.) and triethylamine (8 eq.) and the resulting solution was stirred at 80° C. After 12 hours, the reaction was quenched with 0.1 M hydrochloric acid and the aqueous phase was extracted thrice with dichloromethane. The combined organic layer was washed thrice with saturated sodium chloride solution, dried with sodium sulfate, and concentrated in vacuo. The crude sample was absorbed onto silica gel and purified using flash chromatography using a Hexane:Ethyl acetate gradient.

General Procedure B-1 (Conversion of Pentafluorobenzenesulfonamide into Ortho-O-Substituted Tetrafluorobenzenesulfonamide)

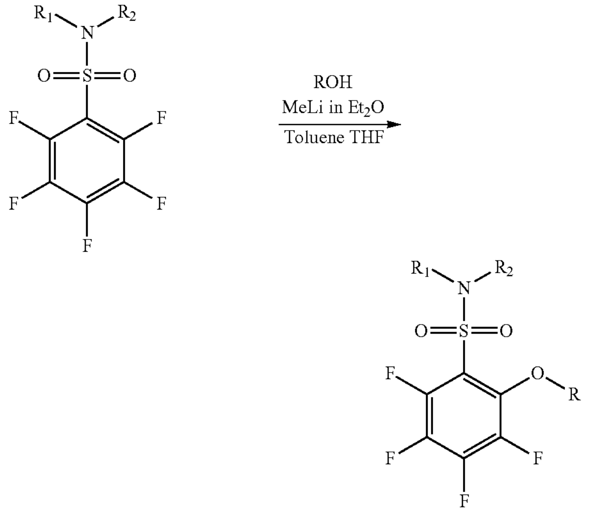

Appropriate alcohol (1-3 eq.) was added with toluene (0.1 M) and tetrahydrofuran (0.5 M-1 M). The resulting solution was stirred at 0° C., followed by dropwise addition of 1.6 M methyllithium in diethyl ether (1-3 eq.). The resulting solution was added with a solution of sulfonamide (1 eq.) in toluene (0.1 M) at 0° C. The resulting solution was then stirred at 80° C. for 12 hours. The reaction was quenched with 0.1 M HCl at 0° C. and the aqueous phase was extracted thrice with dichloromethane. The combined organic layer was washed once with saturated sodium chloride solution, dried with sodium sulfate, and concentrated in vacuo. The crude sample was absorbed onto silica gel and purified using flash chromatography using a Hexane:Ethyl acetate gradient.

General Procedure B-2 (Conversion of Pentafluorobenzenesulfonamide into Ortho-N-Substituted Tetrafluorobenzenesulfonamide)

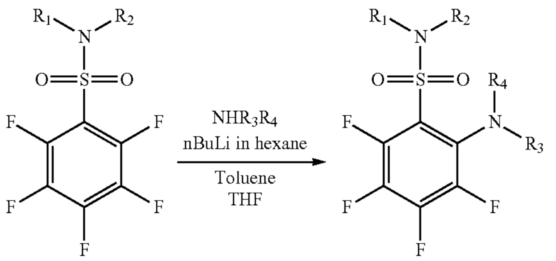

Appropriate amine (2 eq.) was added in toluene (0.1 M) and tetrahydrofuran (1 M) and stirred at −78° C. for 30 minutes. The resulting solution was added dropwise with n-butyllithium in hexane (2 eq.) and was stirred at room temperature. After 10 minutes, the solution was added to the solution of sulfonamide (1 eq.) in toluene (0.1 M) at −78° C. in a dropwise manner. The resulting solution was stirred at room temperature. The reaction was quenched with 0.1 M hydrochloric acid and extracted thrice with dichloromethane. The combined organic layer was washed with saturated sodium chloride solution, dried over sodium sulfate, filtered and concentrated in vacuo. The crude sample was absorbed onto silica gel and purified using flash chromatography using a Hexane:Ethyl acetate gradient.

General Procedure B-3 (Conversion of Pentafluorobenzenesulfonamide into Ortho-S-Substituted Tetrafluorobenzenesulfonamide)

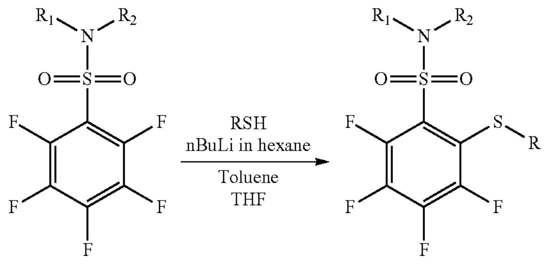

Appropriate thiol (1.1 eq.) was added with toluene (0.1 M) and resulting solution was stirred at 0° C. for 15 minutes. The resulting solution was added dropwise with n-butyllithium in hexane (0.9 eq.). After 1 hour, the resulting solution was added to a solution of sulfonamide (1 eq.) in toluene (0.1 M) at 0° C. The solution was quenched with 0.1 M HCl at 0° C. and the aqueous phase was extracted thrice with dichloromethane. The combined organic layer was washed once with saturated sodium chloride solution, dried with sodium sulfate, and concentrated in vacuo. The crude sample was absorbed onto silica gel and purified using flash chromatography using a Hexane:Ethyl acetate gradient.

General Procedure C (Alkylation and Acylation of ortho-OH)

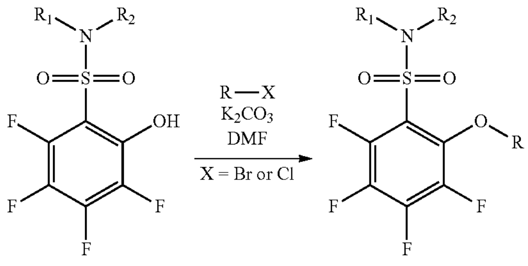

Sulfonamide (1 eq.) was added with dimethylformamide (0.2 M) and the resulting solution was stirred at 25° C. for 5 minutes. The solution was added with a base such as potassium carbonate (1.1 mmol) and then added with an appropriate chloride or bromide (1.1 eq.). The resulting solution was stirred at 25° C. After 12 hours, the reaction was quenched with water, and the aqueous phase was added with ethyl acetate. The organic layer was washed thrice with saturated sodium chloride solution, dried with sodium sulfate, and concentrated in vacuo. The crude sample was absorbed onto silica gel and purified using flash chromatography using a Hexane:Ethyl acetate gradient.

General Procedure D (Amide Coupling of Sulfonic Acid)

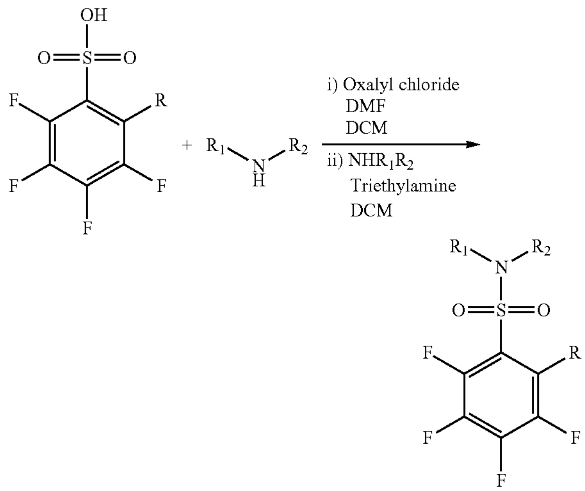

R = H, Br 2,3,4,5-tetrafluorobenzenesulfonic acid (1 eq.) was dissolved in dichloromethane (0.25 M) and the resulting solution was added with oxalyl chloride (2 eq.). The solution was then added with three drops of dimethylformamide. After 1 hour, the reaction solution was concentrated in vacuo. The mixture was dissolved in dichloromethane (0.25 M), and the resulting solution was stirred at 0° C. After 10 minutes, the solution was added with appropriate amine (1 eq.) and triethylamine (1.1 eq.). The reaction was quenched with water and the aqueous phase was extracted three times with dichloromethane. The collected organic layers were washed once with saturated sodium chloride solution, dried with sodium sulfate, and concentrated in vacuo. The crude sample was absorbed onto silica gel and purified using flash chromatography using a Hexane:Ethyl acetate gradient.

General Procedure E (Conversion of Tetrafluorobenzenesulfonamide into Ortho-C-Substituted Tetrafluorobenzenesulfonamide)

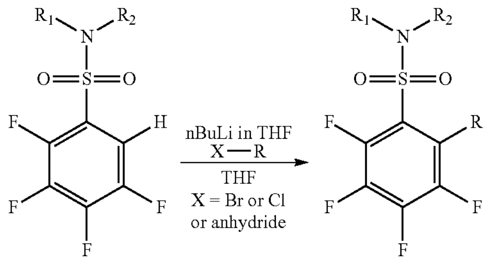

Sulfonamide (1 eq.) was dissolved in tetrahydrofuran (0.3 M), and the resulting solution was stirred at −78° C. The solution was added to a solution of n-butyllithium in tetrahydrofuran (1.5 eq, 0.2 M) cooled to −78° C., and allowed to stir for 30 minutes. An appropriate chloride or bromide or anhydride dissolved in tetrahydrofuran (5 eq, 0.3 M) was subsequently added dropwise and the resulting solution was allowed to stir at 25° C. After 12 hours, the reaction was quenched with saturated ammonium chloride solution and extracted thrice with ethyl acetate. The combined organic layer was washed with saturated sodium chloride solution, dried with sodium sulfate, and concentrated in vacuo. The crude sample was absorbed onto silica gel and purified using flash chromatography using a Hexane:Ethyl acetate gradient.

General Procedure F (Amide Coupling of Benzoic Acid)

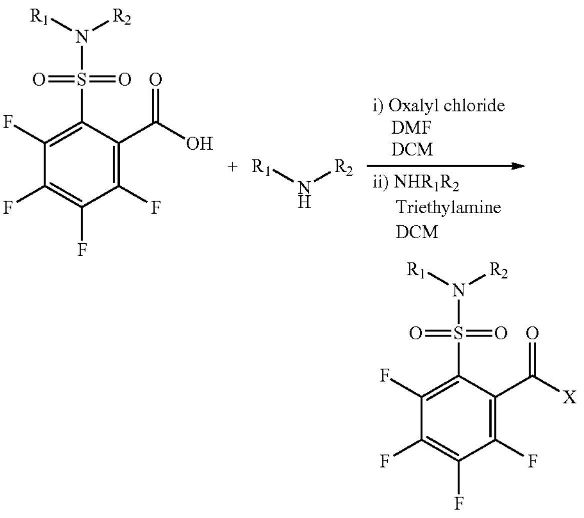

Benzoic acid (1 eq.) was dissolved in dichloromethane (0.3 M) was cooled to 0° C. and stirred for 15 minutes. The resulting solution was added with oxalyl chloride (1.5 eq) and catalytic amount of dimethylformamide in a dropwise manner. After 1 hour, the solution was concentrated in vacuo, purged with nitrogen and re-dissolved in dichloromethane (0.3 M). The resulting solution was cooled to 0° C. and stirred for 15 minutes. The solution was then added with an appropriate amine (1 eq.), followed by addition of triethylamine (3 eq.), and the resulting solution was stirred at 25° C. After 12 hours, the reaction was quenched with 1M hydrochloric acid and extracted thrice with dichloromethane. The combined organic layer was washed with saturated sodium chloride solution, dried with sodium sulfate, and concentrated in vacuo. The crude sample was absorbed onto silica gel and purified using flash chromatography using a Hexane:Ethyl acetate gradient.

General Procedure G (Suzuki Coupling of Arylbromide to Alkyl Boronic Acid)

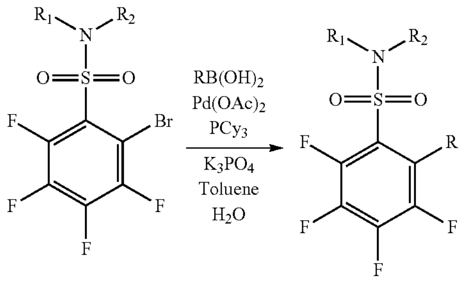

Sulfonamide (1 eq.) was dissolved in a mixture of toluene and water (20:1, 0.15 M) and the resulting solution was stirred at 25° C. The resulting solution was added with an appropriate boronic acid (1.2 eq.), palladium acetate (0.05 eq), tricyclohexylphosphine (0.12 eq.) and potassium phosphate (3 eq.). The resulting solution was stirred at 110° C.

After 10 hours, the solution was filtered through a pad of Celite. The collected solution was added with saturated sodium chloride solution, extracted thrice with ethyl acetate. The combined organic layer was dried over sodium sulfate, concentrated in vacuo. The crude sample was absorbed onto silica gel and purified using flash chromatography using a Hexane:Ethyl acetate gradient.

General Procedure H (Deprotection of bis-(PMB)-sulfonamide)

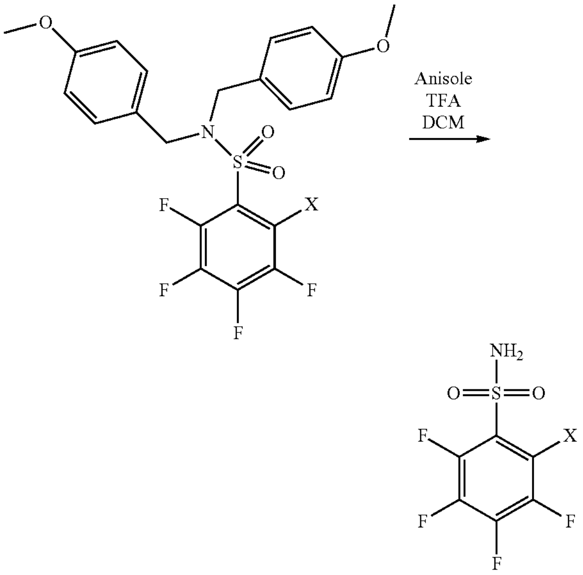

Sulfonamide (1 eq.) was dissolve in dichloromethane (0.11 M). The resulting solution was stirred at room temperature. After 10 minutes, the solution was added with anisole (3 eq.), and the resulting solution was stirred at room temperature. After 10 minutes, the solution was added with trifluoroacetic acid (0.11 M), and the resulting solution was stirred at 55° C. After 12 hours, the reaction mixture was concentrated in vacuo. The mixture was then re-dissolved in dichloromethane, washed thrice with saturated sodium bicarbonate solution. The collected organic layer was washed with saturated sodium chloride solution, dried over sodium sulfate, filtered and concentrated in vacuo. The crude sample was absorbed onto silica gel and purified using flash chromatography using a Hexane:Ethyl acetate gradient. The desired product was isolated as solid.

General Procedure I (Coupling of Primary Sulfonamide to Aryl Boronic Acid)

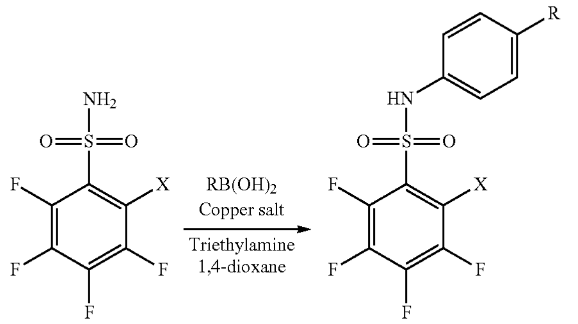

Sulfonamide (1 eq.) was dissolved in 1,4-dioxane (0.2 M) and the resulting solution was stirred at room temperature. After 10 minutes, the solution was added with an appropriate copper salt such as copper(I)$_2$-thiophenecarboxylate (0.4 eq.), triethylamine (1 eq.) and an appropriate boronic acid (1.5 eq.). The resulting mixture was stirred vigorously at room temperature. After 12 hours, the reaction mixture was filtered through a pad of Celite, and the collected organic layer was concentrated in vacuo. The crude sample was absorbed onto silica gel and purified using flash chromatography using a Hexane:Ethyl acetate gradient. The desired product was isolated as solid.

Example 1 Synthesis of 2,3,4,5,6-pentafluoro-N,N-dimethylbenzenesulfonamide (I-1)

I-1

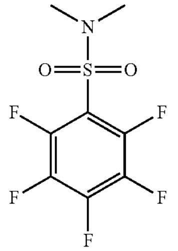

The title compound I-1, 2,3,4,5,6-pentafluoro-N,N-dimethylbenzenesulfonamide, was prepared via General Procedure A-1 using pentafluorobenzenesulfonyl chloride (1 g, 3.75 mmol), 2 M dimethylamine solution in tetrahydrofuran (1.71 mL, 2 M) and triethylamine (10.2 mmol, 1.43 mL). The title compound I-1 was isolated as a beige solid (920 mg, 92%) $^1$H NMR (400 MHz, $CDCl_3$) δ 2.97 (m, 6H). $^{19}$F NMR (376 MHz, $CDCl_3$) δ −158.25-−158.49 (m), −145.83 (tt, J=21.0, 6.1 Hz), −134.96 (dq, J=19.5, 7.6, 6.9 Hz).

Example 2 Synthesis of 2-(benzyloxy)-3,4,5,6-tetrafluoro-N,N-dimethylbenzenesulfonamide (I-2)

I-2

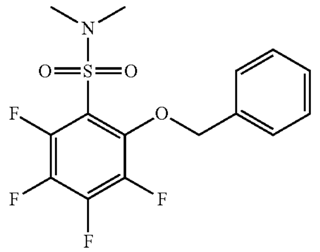

The title compound I-2, 2-(benzyloxy)-3,4,5,6-tetrafluoro-N,N dimethylbenzenesulfonamide, was prepared via General Procedure B-1 using 2,3,4,5,6-pentafluoro-N, N-dimethylbenzenesulfonamide (1 g, 3.63 mmol), benzyl alcohol (0.511 g, 4.72 mmol), 1.5 M methyllithium solution in ethyl ether (3.15 mL). The title compound I-2 was isolated as viscous oil (800 mg, 61%) $^1$H NMR (400 MHz, $CDCl_3$) δ 7.60-7.55 (m, 2H), 7.47-7.38 (m, 3H), 5.20 (s, 2H), 2.86-2.83 (m, 6H). $^{19}$F NMR (376 MHz, $CDCl_3$) −159.36 (dd, J=24.3, 20.8 Hz), −151.06 (dd, J=21.0, 9.4 Hz), −147.75 (td, J=20.9, 6.5 Hz), −135.22 (dt, J=24.2, 8.2 Hz)

Example 3 Synthesis of 2,3,4,5-tetrafluoro-6-hydroxy-N,N-dimethylbenzenesulfonamide (I-3)

I-3

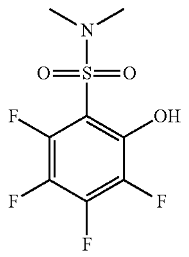

2-(benzyloxy)-3,4,5,6-tetrafluoro-N,N dimethylbenzenesulfonamide (133 mg, 0.366 mmol) was added with methanol (1 mL, 0.35 M) and tetrahydrofuran (2 mL, 0.17 M). The resulting solution was added with palladium 10% on carbon (13 mg) and stirred under hydrogen for 2 hours. The reaction mixture was filtered through a pad of Celite, and the collected organic layer was concentrated in vacuo. The title compound I-3 was isolated as beige solid and was lyophilized from water/acetonitrile to afford a white powder (100 mg, 100%). $^{1}H$ NMR (400 MHz, $CDCl_3$) δ 9.63 (s, 1H), 2.96 (m, 6H). $^{13}C$ NMR (101 MHz, $CDCl_3$) δ 37.33, 37.29. $^{19}F$ NMR (376 MHz, $CDCl_3$) δ −136.45--136.67 (m), −146.73 (td, J=21.0, 6.1 Hz), −158.40 (ddd, J=20.2, 8.9, 3.4 Hz), −166.98 (ddd, J=24.6, 21.3, 3.4 Hz).

Example 4 Synthesis of 2,3,4,5-tetrafluoro-6-methoxy-N,N-dimethylbenzenesulfonamide (I-4)

I-4

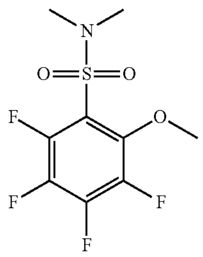

2,3,4,5-tetrafluoro-6-hydroxy-N,N-dimethylbenzenesulfonamide (40 mg, 0.146 mmol) was added with tetrahydrofuran (1.46 mL, 0.1 M) and the resulting solution was stirred at 0° C. for 5 minutes. The solution was added with sodium hydride 60% dispersion in paraffin (8.78 mg, 0.22 mmol) and then added with dimethyl sulfate (0.017 mL, 0.176 mmol). The resulting solution was stirred at 55° C. After 9 hours, the reaction was quenched with saturated solution of ammonium chloride, and the aqueous phase was extracted thrice with ethyl acetate. The combined organic layer was washed once with saturated sodium chloride solution, dried with sodium sulfate, and concentrated in vacuo. The crude sample was absorbed onto silica gel and purified using flash chromatography using a Hexane:Ethyl acetate gradient. The title compound I-4 was isolated as beige solid and was lyophilized from water/acetonitrile to afford a white powder (25 mg, 60%)

Example 5 Synthesis of 2-ethoxy-3,4,5,6-tetrafluoro-N,N-dimethylbenzenesulfonamide (I-5)

I-5

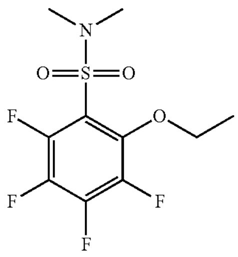

The title compound I-5, 2-ethoxy-3,4,5,6-tetrafluoro-N,N-dimethylbenzenesulfonamide, was prepared via General Procedure C using 2,3,4,5-tetrafluoro-6-hydroxy-N,N-dimethylbenzenesulfonamide (0.04 g, 0.146 mmol), bromoethane (0.015 mL, 0.201 mmol) and potassium carbonate (27.8 mg, 0.20 mmol). The title compound I-5 was isolated as beige solid and was lyophilized from water/acetonitrile to afford a white powder (35 mg, 63.5%)

Example 6 Synthesis of 2,3,4,5-tetrafluoro-6-isopropoxy-N,N-dimethylbenzenesulfonamide (I-6)

I-6

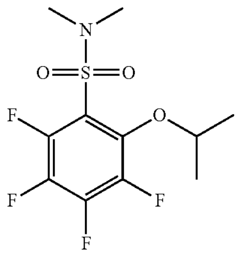

The title compound I-6, 2,3,4,5-tetrafluoro-6-isopropoxy-N,N-dimethylbenzenesulfonamide, was prepared via General Procedure B-1 using 2,3,4,5,6-pentafluoro-N,N-dimethylbenzenesulfonamide (0.069 g, 0.25 mmol), isopropanol (0.038 mL, 0.5 mmol), 1.5 M methyllithium solution in ethyl ether (0.35 mL). The title compound I-6 was isolated as viscous oil (35 mg, 44.4%)

Example 7 Synthesis of 2,3,4,5-tetrafluoro-6-(fluoromethoxy)-N,N-dimethylbenzenesulfonamide (I-7)

I-7

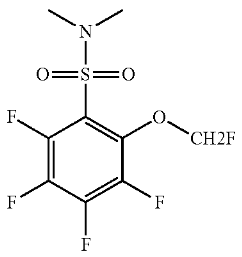

2,3,4,5-tetrafluoro-6-hydroxy-N,N-dimethylbenzenesulfonamide (40 mg, 0.146 mmol) was added with acetonitrile (0.725 mL, 0.2 M) and the resulting solution was stirred at 25° C. for 5 minutes. The solution was added with solution of S-monofluoromethyl-S-phenyl-2,3,4,5-tetramethylphenylsulfonium tetrafluoroborate in acetonitrile (0.75 mL, 0.2 M) and cesium carbonate (95 mg, 0.292 mmol). The reaction was stirred at room temperature for 48 hours. The reaction was quenched with water and extracted thrice with dichloromethane. The combined organic layer was washed once with saturated sodium chloride solution, dried with sodium sulfate, and concentrated in vacuo. The crude sample was absorbed onto silica gel and purified using flash chromatography using a Hexane:Ethyl acetate gradient. The title compound I-7 was isolated as beige solid and was lyophilized from water/acetonitrile to afford a white powder (15 mg, 34%)

Example 8 Synthesis of 2-(difluoromethoxy)-3,4,5,6-tetrafluoro-N,N-dimethylbenzenesulfonamide (I-8)

I-8

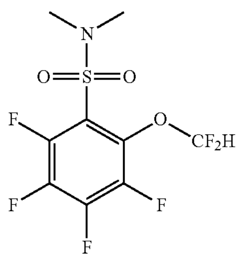

2,3,4,5-tetrafluoro-6-hydroxy-N,N-dimethylbenzenesulfonamide (120 mg, 0.439 mmol) was added with dimethylformamide (mL, 0.2 M) and the resulting solution was stirred at 25° C. for 5 minutes. The solution was added with potassium carbonate (67 mg, 0.483 mmol) and then added with ethyl bromodifluoroacetate (0.062 mL, 0.483 mmol). The reaction was stirred at room temperature for 12 hours. The reaction was quenched with water and diluted with ethyl acetate. The combined layer was washed thrice with saturated sodium chloride solution, dried with sodium sulfate, and concentrated in vacuo. The crude sample was absorbed onto silica gel and purified using flash chromatography using a Hexane:Ethyl acetate gradient. The title compound I-8 was isolated as beige solid and was lyophilized from water/acetonitrile to afford a white powder (30 mg, 21%)

Example 9 Synthesis of 2,3,4,5-tetrafluoro-N,N-dimethyl-6-(trifluoromethoxy)benzenesulfonamide (I-9)

I-9

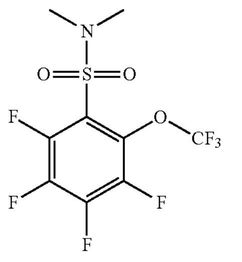

2,3,4,5-tetrafluoro-6-hydroxy-N,N-dimethylbenzenesulfonamide (100 mg, 0.366 mmol) was added with silver trifluoromethanesulfonate (47 mg, 1.83 mmol), Selectfluor (259 mg, 0.732 mmol), N-fluorobenzenesulfonimide (231 mg, 0.723 mmol), cesium fluoride (334 mg, 2.2 mmol). After two cycles of argon flush, the mixture was diluted in toluene (1.83 mL, 0.2 M), and the resulting solution was added with benzotrifluoride (0.045 mL, 0.366 mmol), 2-fluoropyridine (0.63 mL, 7.32 mmol), (trifluoromethyl) trimethylsilane (0.541 L, 3.66 mmol). After 12 hours, the reaction mixture was filtered through the Celite, washed with dichloromethane. The reaction was reduced under vacuo. The crude sample was absorbed onto silica gel and purified using flash chromatography using a Hexane:Ethyl acetate gradient. The title compound I-9 was isolated as beige solid and was lyophilized from water/acetonitrile to afford a beige powder.

Example 10 Synthesis of 2,3,4,5-tetrafluoro-N,N-dimethyl-6-(2,2,2-trifluoroethoxy)benzenesulfonamide (I-10)

I-10

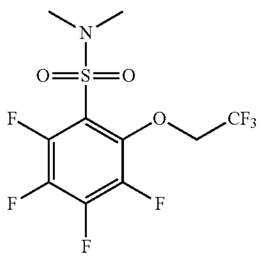

The title compound I-10, 2,3,4,5-tetrafluoro-N,N-dimethyl-6-(2,2,2-trifluoroethoxy)benzenesulfonamide, was prepared via General Procedure B-1 using 2,3,4,5,6-pentafluoro-N,N-dimethylbenzenesulfonamide (0.1 g, 0.363 mmol), 2,2,2-Trifluoroethanol (0.052 mL, 0.727 mmol), 1.5 M methyllithium solution in ethyl ether (0.51 mL). The title compound I-10 was isolated as viscous oil (70 mg, 54.2%)

Example 11 Synthesis of 2-cyclopropoxy-3,4,5,6-tetrafluoro-N,N-dimethylbenzenesulfonamide (I-11)

I-11

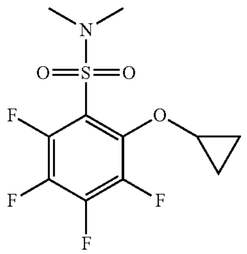

The title compound I-11, 2-cyclopropoxy-3,4,5,6-tetrafluoro-N,N-dimethylbenzenesulfonamide, was prepared via General Procedure B-1 using 2,3,4,5,6-pentafluoro-N,N-dimethylbenzenesulfonamide (0.05 g, 0.182 mmol), cyclopropanol (0.029 mL, 0.727 mmol), 1.5 M methyllithium solution in ethyl ether (0.30 mL). The title compound I-11 was isolated as viscous oil (19 mg, 33.4%)

Example 12 Synthesis of tert-butyl 3-(2-(N,N-dimethylsulfamoyl)-3,4,5,6-tetrafluorophenoxy)azetidine-1-carboxylate (I-12)

I-12

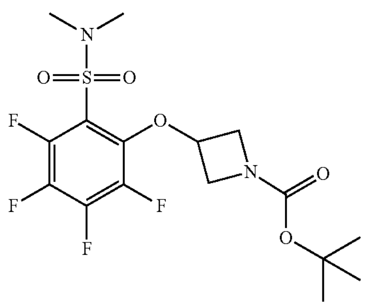

The title compound I-12, 3-(2-(N,N-dimethylsulfamoyl)-3,4,5,6-tetrafluorophenoxy)azetidine-1-carboxylate, was prepared via General Procedure B-1 using 2,3,4,5,6-pentafluoro-N,N-dimethylbenzenesulfonamide (0.1 g, 0.363 mmol), 1-(tert-butoxycarbonyl)-3-hydroxyazetidine (100 mg, 0.363 mmol), 1.5 M methyllithium solution in ethyl ether (0.36 mL). The title compound I-12 was isolated as viscous oil (31 mg, 20%)

Example 13 Synthesis of 2,3,4,5-tetrafluoro-N,N-dimethyl-6-(oxetan-3-ylmethoxy)benzenesulfonamide (I-13)

I-13

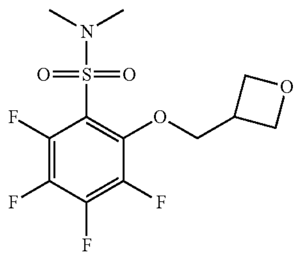

The title compound I-13, 2,3,4,5-tetrafluoro-N,N-dimethyl-6-(oxetan-3-ylmethoxy)benzenesulfonamide, was prepared via General Procedure B-1 using 2,3,4,5,6-pentafluoro-N,N-dimethylbenzenesulfonamide (0.07 g, 0.254 mmol), 3-Oxetanemethanol (0.027 mL, 0.331 mmol), 1.5 M methyllithium solution in ethyl ether (0.22 mL). The title compound I-13 was isolated as viscous oil (21 mg, 24%)

Example 14 Synthesis of 2-((4-cyanobenzyl)oxy)-3,4,5,6-tetrafluoro-N,N-dimethylbenzenesulfonamide (I-14)

I-14

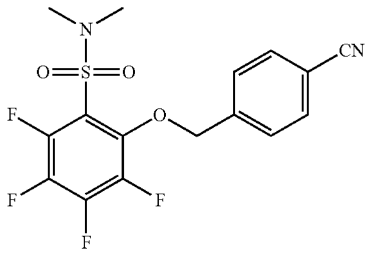

The title compound I-14, 2-((4-cyanobenzyl)oxy)-3,4,5,6-tetrafluoro-N,N-dimethylbenzenesulfonamide, was prepared via General Procedure C using 2,3,4,5-tetrafluoro-6-hydroxy-N,N-dimethylbenzenesulfonamide (0.05 g, 0.183 mmol), 4-cyanobenzyl bromide (40 mg, 0.201 mmol) and potassium carbonate (27.8 mg, 0.20 mmol). The title compound I-14 was isolated as beige solid and was lyophilized from water/acetonitrile to afford a white powder (60 mg, 84.4%)

Example 15 Synthesis of 2,3,4,5-tetrafluoro-N,N-dimethyl-6-((4-nitrobenzyl)oxy)benzenesulfonamide (I-15)

I-15

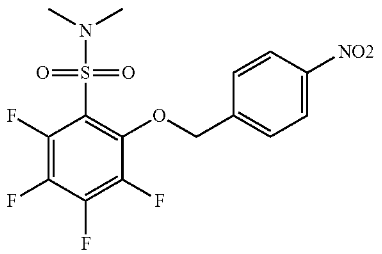

The title compound I-15, 2,3,4,5-tetrafluoro-N,N-dimethyl-6-((4-nitrobenzyl)oxy)benzenesulfonamide, was prepared via General Procedure C using 2,3,4,5-tetrafluoro-6-hydroxy-N,N-dimethylbenzenesulfonamide (0.03 g, 0.11 mmol), 4-nitrobenzyl bromide (26 mg, 0.121 mmol) and potassium carbonate (16.7 mg, 0.121 mmol). The title compound I-15 was isolated as beige solid and was lyophilized from water/acetonitrile to afford a white powder (40 mg, 89.2%)

Example 16 Synthesis of 2-((2,4-difluorobenzyl)oxy)-3,4,5,6-tetrafluoro-N,N-dimethylbenzenesulfonamide (I-16)

I-16

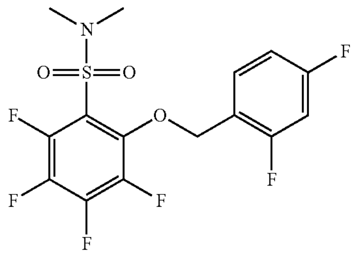

The title compound I-16, 2,3,4,5-tetrafluoro-N,N-dimethyl-6-((4-nitrobenzyl)oxy)benzenesulfonamide, was prepared via General Procedure C using 2,3,4,5-tetrafluoro-6-hydroxy-N,N-dimethylbenzenesulfonamide (0.04 g, 0.146 mmol), 2,4-Difluorobenzyl bromide (33 mg, 0.161 mmol) and potassium carbonate (22.3 mg, 0.161 mmol). The title compound I-16 was isolated as beige solid and was lyophilized from water/acetonitrile to afford a white powder (25 mg, 43%)

Example 17 Synthesis of 2,3,4,5-tetrafluoro-N,N-dimethyl-6-(pyridin-4-ylmethoxy)benzenesulfonamide (I-17)

I-17

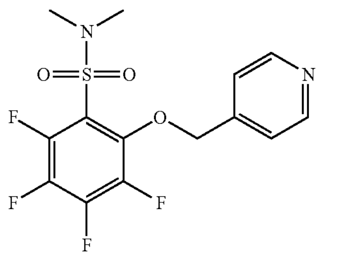

The title compound I-17, 2,3,4,5-tetrafluoro-N,N-dimethyl-6-((4-nitrobenzyl)oxy)benzenesulfonamide, was prepared via General Procedure C using 2,3,4,5-tetrafluoro-6-hydroxy-N,N-dimethylbenzenesulfonamide (0.05 g, 0.183 mmol), 4-(bromomethyl)pyridine hydrobromide (33 mg, 0.161 mmol) and potassium carbonate (53.1 mg, 0.161 mmol). The title compound I-17 was isolated as beige solid and was lyophilized from water/acetonitrile to afford a white powder (25 mg, 43%)

Example 18 Synthesis of 4-((2-(N,N-dimethylsulfamoyl)-3,4,5,6-tetrafluorophenoxy)methyl)benzamide (I-18)

I-18

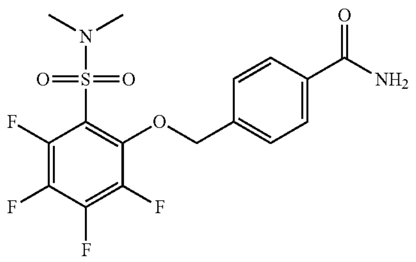

The title compound I-18, 4-((2-(N,N-dimethylsulfamoyl)-3,4,5,6-tetrafluorophenoxy)methyl)benzamide, was prepared via General Procedure C using 2,3,4,5-tetrafluoro-6-hydroxy-N,N-dimethylbenzenesulfonamide (0.03 g, 0.11 mmol), 4-bromomethylbenzamide (25 mg, 0.121 mmol) and potassium carbonate (53.1 mg, 0.161 mmol). The title compound I-18 was isolated as beige solid and was lyophilized from water/acetonitrile to afford a white powder (25 mg, 43%)

Example 19 Synthesis of 2,3,4,5-tetrafluoro-N,N-dimethyl-6-(pyridin-2-ylmethoxy)benzenesulfonamide (I-19)

I-19

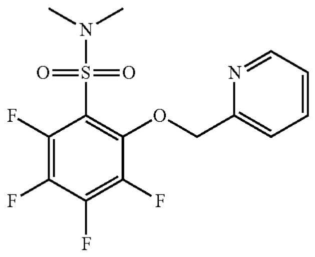

The title compound I-19, 2,3,4,5-tetrafluoro-N,N-dimethyl-6-(pyridin-2-ylmethoxy)benzenesulfonamide, was prepared via General Procedure C using 2,3,4,5-tetrafluoro-6-hydroxy-N,N-dimethylbenzenesulfonamide (0.04 g, 0.146 mmol), 2-(bromomethyl)pyridine hydrobromide (41 mg, 0.161 mmol) and potassium carbonate (42.5 mg, 0.307 mmol). The title compound I-19 was isolated as beige solid and was lyophilized from water/acetonitrile to afford a white powder (25 mg, 47%)

Example 20 Synthesis of 2-(N,N-dimethylsulfamoyl)-3,4,5,6-tetrafluorophenyl pivalate (I-20)

I-20

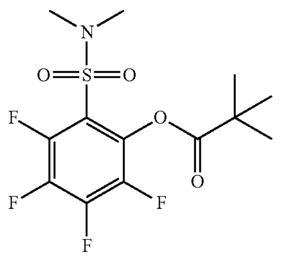

2,3,4,5-tetrafluoro-6-hydroxy-N,N-dimethylbenzenesulfonamide (30 mg, 0.11 mmol) was added with dichloromethane (0.329 mL, 0.33 M) and the resulting solution was stirred at 0° C. for 10 minutes. The solution was added with triethylamine (0.047 mL, 0.307 mmol) and then added with trimethylacetyl chloride (41 mg, 0.34 mmol). The resulting solution was stirred at 25° C. After 12 hours, the reaction was quenched with water, and the aqueous phase was added with ethyl acetate. The organic layer was washed thrice with saturated sodium chloride solution, dried with sodium sulfate, and concentrated in vacuo. The crude sample was absorbed onto silica gel and purified using flash chromatography using a Hexane:Ethyl acetate gradient. The title compound I-20 was isolated as beige solid and was lyophilized from water/acetonitrile to afford a white powder.

Example 21 Synthesis of tert-butyl (2-(N,N-dimethylsulfamoyl)-3,4,5,6-tetrafluorophenyl) carbonate (I-21)

I-21

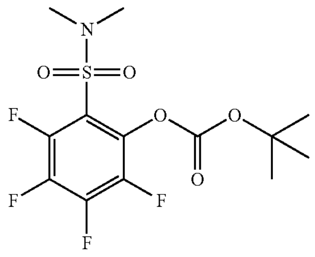

2,3,4,5-tetrafluoro-6-hydroxy-N,N-dimethylbenzenesulfonamide (100 mg, 0.366 mmol) was added with tetrahydrofuran (3.7 mL, 0.1 M) and the resulting solution was stirred at 0° C. for 10 minutes. The solution was added with potassium carbonate (55.6 mg, 0.403 mmol) and then added with di-tert-butyl decarbonate (88 mg, 0.1 mmol) and 18-crown-6-ether (16.5 mL, 0.0732 mmol). The resulting solution was stirred at 25° C. After 12 hours, the reaction was quenched with water, and the aqueous phase was added with ethyl acetate. The organic layer was washed thrice with saturated sodium chloride solution, dried with sodium sulfate, and concentrated in vacuo. The crude sample was absorbed onto silica gel and purified using flash chromatography using a Hexane:Ethyl acetate gradient. The title compound I-21 was isolated as beige solid and was lyophilized from water/acetonitrile to afford a white powder.

Example 22 Synthesis of 2-(N,N-dimethylsulfamoyl)-3,4,5,6-tetrafluorophenyl propane-2-sulfonate (I-22)

I-22

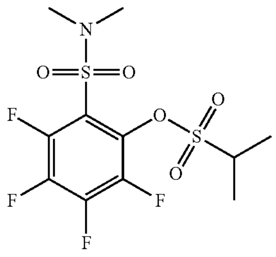

2,3,4,5-tetrafluoro-6-hydroxy-N,N-dimethylbenzenesulfonamide (88.8 mg, 0.33 mmol) was added with tetrahydrofuran (1.6 mL, 0.2 M) and the resulting solution was stirred at 0° C. for 10 minutes. The solution was added with potassium carbonate (49.4 mg, 0.358 mmol) and then added with isopropylsulfonyl chloride (51 mg, 0.358 mmol). The resulting solution was stirred at 25° C. After 12 hours, the reaction was quenched with water, and the aqueous phase was added with ethyl acetate. The organic layer was washed thrice with saturated sodium chloride solution, dried with sodium sulfate, and concentrated in vacuo. The crude sample was absorbed onto silica gel and purified using flash chromatography using a Hexane:Ethyl acetate gradient. The title compound I-22 was isolated as beige solid and was lyophilized from water/acetonitrile to afford a white powder.

Example 23 Synthesis of 2-allyl-3,4,5,6-tetrafluoro-N,N-dimethylbenzenesulfonamide (I-23)

I-23

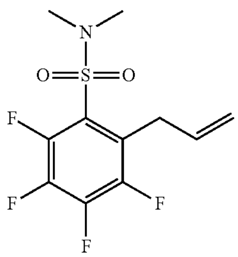

The title compound I-23, 2-allyl-3,4,5,6-tetrafluoro-N,N-dimethylbenzenesulfonamide, was prepared via General Procedure E using 2,3,4,5-tetrafluoro-N,N-dimethylbenzenesulfonamide (1 eq.), 2 M n-butyllithium in tetrahydrofuran (1.5 eq) and allyl bromide (5 eq.). The title compound I-23 was isolated as beige solid and was lyophilized from water/acetonitrile to afford a white powder. $^{1}$H NMR (400 MHz, $CDCl_3$) δ 2.96 (d, J=2.2 Hz, 5H), 3.90 (ddd, J=6.1, 3.7, 1.6 Hz, 2H), 4.95-5.25 (m, 2H), 5.98 (ddt, J=16.7, 10.0, 6.2 Hz, 1H). $^{19}$F NMR (376 MHz, $CDCl_3$) δ −155.58 (ddd, J=23.5, 20.2, 3.5 Hz), −148.43 (td, J=21.1, 8.1 Hz), −137.60-−137.20 (m), −135.80-−135.30 (m).

Example 24 Synthesis of 2-benzyl-3,4,5,6-tetrafluoro-N,N-dimethylbenzenesulfonamide (I-24)

I-24

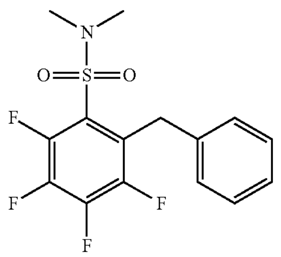

The title compound I-24, 2-benzyl-3,4,5,6-tetrafluoro-N,N-dimethylbenzenesulfonamide, was prepared via General Procedure E using 2,3,4,5-tetrafluoro-N,N-dimethylbenzenesulfonamide (1 eq.), 2 M n-butyllithium in tetrahydrofuran (1.5 eq) and benzyl bromide (5 eq.). The title compound I-24 was isolated as beige solid and was lyophilized from water/acetonitrile to afford a white powder. $^{1}H$ NMR (400 MHz, $CDCl_3$) δ 2.80 (d, J=2.2 Hz, 6H), 4.57 (d, J=3.5 Hz, 2H), 7.20 (dd, J=7.5, 1.5 Hz, 3H), 7.25-7.35 (m, 2H). $^{19}F$ NMR (376 MHz, $CDCl_3$) δ −155.12−−154.80 (m), −148.01 (td, J=21.0, 8.0 Hz), −135.90 (ddq, J=18.3, 11.2, 3.9 Hz), −134.00 (dtd, J=20.1, 10.4, 8.9, 5.0 Hz).

Example 25 Synthesis of 2,3,4,5-tetrafluoro-N,N,6-trimethylbenzenesulfonamide (I-25)

I-25

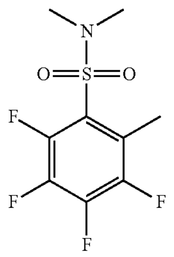

The title compound I-25, 2,3,4,5-tetrafluoro-N,N,6-trimethylbenzenesulfonamide, was prepared via General Procedure E using 2,3,4,5-tetrafluoro-N,N-dimethylbenzenesulfonamide (1 eq.), 2 M n-butyllithium in tetrahydrofuran (1.5 eq) and methyl iodide (5 eq.). The title compound I-25 was isolated as beige solid and was lyophilized from water/acetonitrile to afford a white powder. $^{1}H$ NMR (400 MHz, $CDCl_3$) δ 2.60 (dd, J=3.2, 1.4 Hz, 3H), 2.96 (d, J=2.0 Hz, 6H). $^{19}F$ NMR (376 MHz, $CDCl_3$) δ −156.73 (t, J=21.6 Hz), −148.89 (td, J=20.8, 7.7 Hz), −137.04−−136.88 (m), −136.87−−136.70 (m).

Example 26 Synthesis of 2-acetyl-3,4,5,6-tetrafluoro-N,N-dimethylbenzenesulfonamide (I-26)

I-26

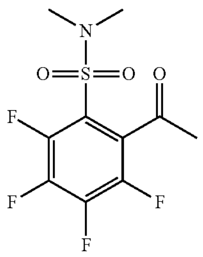

The title compound I-26, 2-acetyl-3,4,5,6-tetrafluoro-N,N-dimethylbenzenesulfonamide, was prepared via General Procedure E using 2,3,4,5-tetrafluoro-N,N-dimethylbenzenesulfonamide (1 eq.), 2 M n-butyllithium in tetrahydrofuran (1.5 eq) and acetic anhydride (5 eq.). The title compound I-26 was isolated as beige solid and was lyophilized from water/acetonitrile to afford a white powder. $^{1}H$ NMR (400 MHz, $CDCl_3$) δ 2.64 (d, J=0.8 Hz, 3H), 2.92 (d, J=2.0 Hz, 6H). $^{19}F$ NMR (376 MHz, $CDCl_3$) δ −150.95 (ddd, J=23.4, 19.9, 4.0 Hz), −144.98 (ddd, J=22.9, 19.8, 9.3 Hz), −141.16 (ddd, J=22.7, 12.1, 4.0 Hz), −130.54−−130.38 (m).

Example 27 Synthesis of 2-(cyclopropanecarbonyl)-3,4,5,6-tetrafluoro-N,N-dimethylbenzenesulfonamide (I-27)

I-27

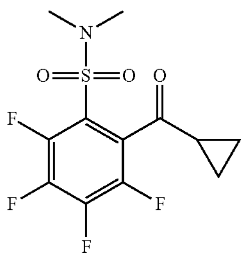

The title compound I-27, 2-(cyclopropanecarbonyl)-3,4,5,6-tetrafluoro-N,N-dimethylbenzenesulfonamide, was prepared via General Procedure E using 2,3,4,5-tetrafluoro-N,N-dimethylbenzenesulfonamide (1 eq.), 2 M n-butyllithium in tetrahydrofuran (1.5 eq.) and cyclopropanecarboxylic acid anhydride dissolved in tetrahydrofuran (5 eq.). The title compound I-27 was isolated as beige solid and was lyophilized from water/acetonitrile to afford a white powder. $^{1}H$ NMR (400 MHz, $CDCl_3$) δ 1.05 (dq, J=7.8, 4.6, 4.2 Hz, 2H), 1.19 (q, J=4.0 Hz, 2H), 1.72 (tt, J=8.3, 4.6 Hz, 1H). $^{19}F$ NMR (376 MHz, $CDCl_3$) δ −151.19 (dd, J=23.1, 19.6 Hz), −145.23 (t, J=18.8 Hz), −138.96 (dd, J=23.2, 12.4 Hz), −130.76 (d, J=12.4 Hz).

Example 28 Synthesis of 2,3,4,5-tetrafluoro-N,N-dimethyl-6-(2,2,2-trifluoroacetyl)benzenesulfonamide (I-28)

I-28

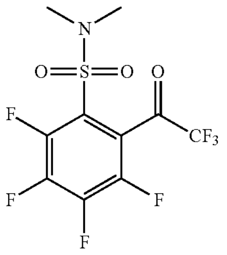

The title compound I-28, 2,3,4,5-tetrafluoro-N,N-dimethyl-6-(2,2,2-trifluoroacetyl)benzenesulfonamide, was prepared via General Procedure E using 2,3,4,5-tetrafluoro-N,N-dimethylbenzenesulfonamide (1 eq.), 2 M n-butyllithium in tetrahydrofuran (1.5 eq.) and trifluoroacetic anhydride dissolved in tetrahydrofuran (5 eq.). The title compound I-28 was isolated as beige solid and was lyophilized from water/acetonitrile to afford a white powder. $^1$H NMR (400 MHz, $CDCl_3$) δ 2.94 (d, J=2.2 Hz, 6H). $^{19}$F NMR (376 MHz, $CDCl_3$) δ −76.24 (d, J=6.8 Hz), −130.31--130.49 (m), −135.92 (ddt, J=20.9, 12.2, 6.1 Hz), −143.34 (ddd, J=21.7, 19.5, 9.8 Hz), −145.99 (ddd, J=22.6, 19.5, 6.0 Hz).

Example 29 Synthesis of 2,3,4,5-tetrafluoro-6-(4-methoxybenzoyl)-N,N-dimethylbenzenesulfonamide (I-29)

I-29

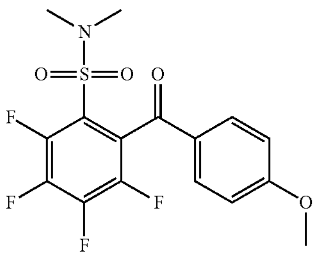

The title compound I-29, 2,3,4,5-tetrafluoro-6-(4-methoxybenzoyl)-N,N-dimethylbenzenesulfonamide, was prepared via General Procedure E using 2,3,4,5-tetrafluoro-N,N-dimethylbenzenesulfonamide (1 eq.), 2 M n-butyllithium in tetrahydrofuran (1.5 eq.) and 4-methoxybenzoyl chloride dissolved in tetrahydrofuran (5 eq.). The title compound I-29 was isolated as beige solid and was lyophilized from water/acetonitrile to afford a white powder. $^1$H NMR (400 MHz, $CDCl_3$) δ 7.80-7.75 (m, 2H), 6.88-6.84 (m, 2H), 3.88 (s, 3H), 2.92 (d, J=2.1 Hz, 6H). $^{19}$F NMR (376 MHz, $CDCl_3$) δ −130.59 (dt, J=22.8, 10.8 Hz), −137.96 (ddd, J=23.1, 12.1, 4.2 Hz), −145.53 (ddd, J=23.2, 19.9, 9.1 Hz), −150.82 (ddd, J=23.4, 19.9, 4.1 Hz).

Example 30 Synthesis of 2-benzoyl-3,4,5,6-tetrafluoro-N,N-dimethylbenzenesulfonamide (I-30)

I-30

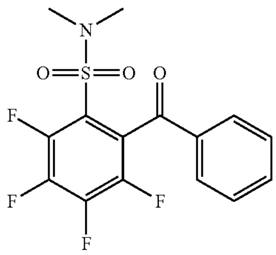

The title compound I-30, 2,3,4,5-tetrafluoro-6-(4-methoxybenzoyl)-N,N-dimethylbenzenesulfonamide, was prepared via General Procedure E using 2,3,4,5-tetrafluoro-N,N-dimethylbenzenesulfonamide (1 eq.), 2 M n-butyllithium in tetrahydrofuran (1.5 eq.) and benzoyl chloride dissolved in tetrahydrofuran (5 eq.). The title compound I-30 was isolated as beige solid and was lyophilized from water/acetonitrile to afford a white powder. $^1$H NMR (400 MHz, $CDCl_3$) δ 2.92 (d, J=2.1 Hz, 3H), 7.51 (t, J=7.8 Hz, 1H), 7.59-7.68 (m, OH), 7.70-8.27 (m, 1H). $^{19}$F NMR (376 MHz, $CDCl_3$) δ −150.97--149.64 (m), −145.31 (ddd, J=23.3, 19.8, 9.1 Hz), −137.92 (ddd, J=22.6, 11.9, 4.3 Hz), −131.49--129.74 (m).

Example 31 Synthesis of methyl 2-(N,N-dimethylsulfamoyl)-3,4,5,6-tetrafluorobenzoate (I-31)

I-31

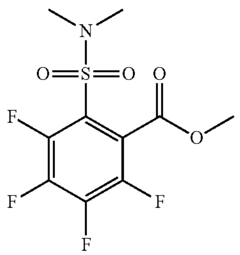

The title compound I-31, methyl 2-(N,N-dimethylsulfamoyl)-3,4,5,6-tetrafluorobenzoate, was prepared via General Procedure E using 2,3,4,5-tetrafluoro-N,N-dimethylbenzenesulfonamide (1 eq.), 2 M n-butyllithium in tetrahydrofuran (1.5 eq.) and methyl chloroformate dissolved in tetrahydrofuran (5 eq.). The title compound I-31 was isolated as beige solid and was lyophilized from water/acetonitrile to afford a white powder. $^1$H NMR (400 MHz, $CDCl_3$) δ 2.95 (t, J=1.6 Hz, 2H), 4.00 (d, J=1.2 Hz, 1H). $^{19}$F NMR (376 MHz, $CDCl_3$) δ −150.06 (ddd, J=23.4, 19.8, 4.6 Hz), −145.43 (td, J=20.8, 9.3 Hz), −138.43 (ddd, J=21.7, 11.4, 4.5 Hz), −130.71 (dt, J=22.0, 10.6 Hz).

Example 32 Synthesis of isobutyl 2-(N,N-dimethylsulfamoyl)-3,4,5,6-tetrafluorobenzoate (I-32)

I-32

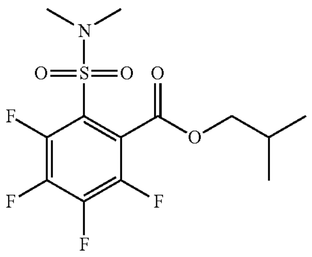

The title compound I-32, isobutyl 2-(N,N-dimethylsulfamoyl)-3,4,5,6-tetrafluorobenzoate, was prepared via General Procedure E using 2,3,4,5-tetrafluoro-N,N-dimethylbenzenesulfonamide (1 eq.), 2 M n-butyllithium in tetrahydrofuran (1.5 eq.) and isobutyl chloroformate dissolved in tetrahydrofuran (5 eq.). The title compound I-32 was isolated as beige solid and was lyophilized from water/acetonitrile to afford a white powder. $^1$H NMR (400 MHz, $CDCl_3$) δ 1.00 (d, J=6.7 Hz, 6H), 2.09 (dt, J=13.5, 6.7 Hz, 1H), 2.95 (d, J=2.2 Hz, 6H), 4.18 (d, J=6.7 Hz, 2H). $^{19}$F NMR (376 MHz, $CDCl_3$) δ −150.78--149.92 (m), −145.64--145.18 (m), −138.64 (ddd, J=21.7, 11.7, 4.6 Hz), −131.67--130.57 (m).

Example 33 Synthesis of benzyl 2-(N,N-dimethylsulfamoyl)-3,4,5,6-tetrafluorobenzoate (I-33)

I-33

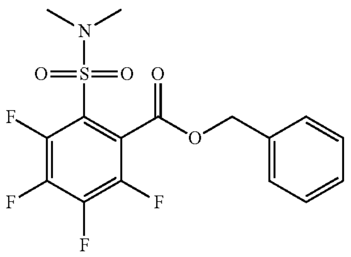

The title compound I-33, benzyl 2-(N,N-dimethylsulfamoyl)-3,4,5,6-tetrafluorobenzoate, was prepared via General Procedure E using 2,3,4,5-tetrafluoro-N,N-dimethylbenzenesulfonamide (1 eq.), 2 M n-butyllithium in tetrahydrofuran (1.5 eq.) and benzyl chloroformate dissolved in tetrahydrofuran (5 eq.). The title compound I-33 was isolated as beige solid and was lyophilized from water/acetonitrile to afford a white powder. $^1$H NMR (400 MHz, $CDCl_3$) δ 2.93 (d, J=2.1 Hz, 6H), 5.42 (s, 2H), 7.33-7.71 (m, 5H). $^{19}$F NMR (376 MHz, $CDCl_3$) δ −150.01 (ddd, J=23.6, 19.8, 4.7 Hz), −145.38 (td, J=20.9, 9.0 Hz), −138.35 (ddd, J=22.0, 11.5, 4.6 Hz), −131.35--129.49 (m).

Example 34 Synthesis of 2-(N,N-dimethylsulfamoyl)-3,4,5,6-tetrafluorobenzoic acid (I-34)

I-34

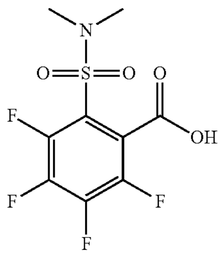

Benzyl 2-(N,N-dimethylsulfamoyl)-3,4,5,6-tetrafluorobenzoate was added with a mixture of methanol:tetrahydrofuran (2:1, 0.1 M). The resulting solution was added with palladium 10% on carbon (0.05 eq) and stirred under hydrogen for 2 hours. The reaction mixture was filtered through a pad of Celite, and the collected organic layer was concentrated in vacuo. The title compound I-34 was isolated as beige solid and was lyophilized from water/acetonitrile to afford a white powder. $^1$H NMR (400 MHz, $CDCl_3$) δ 2.96 (s, 4H), 7.88 (s, 1H). $^{19}$F NMR (376 MHz, $CDCl_3$) δ −150.39, −145.21, −138.13, −130.89.

Example 35 Synthesis of N-(2,4-dimethoxybenzyl)-2-(N,N-dimethylsulfamoyl)-3,4,5,6-tetrafluorobenzamide (I-35)

I-35

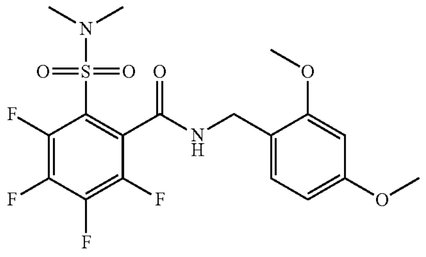

The title compound I-35, N-(2,4-dimethoxybenzyl)-2-(N,N-dimethylsulfamoyl)-3,4,5,6-tetrafluorobenzamide, was prepared via General Procedure F using 2-(N,N-dimethylsulfamoyl)-3,4,5,6-tetrafluorobenzoic acid (1 eq.), oxalyl chloride (1.5 eq.), bis(2,4-dimethoxybenzyl amine)(1 eq.) and triethylamine (3 eq.). The title compound I-35 was isolated as beige solid and was lyophilized from water/acetonitrile to afford a white powder. $^1$H NMR (400 MHz, $CDCl_3$) δ 2.96 (d, J=1.9 Hz, 6H), 3.84 (d, J=5.1 Hz, 6H), 4.59 (d, J=5.7 Hz, 2H), 6.18 (s, 1H), 6.42-6.69 (m, 2H), 7.18-7.38 (m, 2H). $^{19}$F NMR (376 MHz, $CDCl_3$) δ −151.54--150.17 (m), −145.65 (td, J=21.2, 8.9 Hz), −137.76 (ddd, J=22.6, 11.8, 4.6 Hz), −130.64 (dt, J=22.5, 10.3 Hz).

Example 36 Synthesis of 2-(N,N-dimethylsulfamoyl)-3,4,5,6-tetrafluoro-N-methylbenzamide (I-36)

I-36

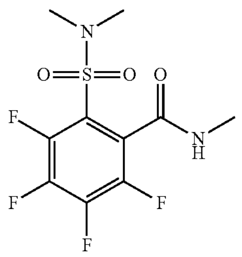

The title compound I-36, 2-(N,N-dimethylsulfamoyl)-3,4,5,6-tetrafluoro-N-methylbenzamide, was prepared via General Procedure F using 2-(N,N-dimethylsulfamoyl)-3,4,5,6-tetrafluorobenzoic acid (1 eq.), oxalyl chloride (1.5 eq.), methylamine (1 eq.) and triethylamine (3 eq.). The title compound I-36 was isolated as beige solid and was lyophilized from water/acetonitrile to afford a white powder. $^1$H NMR (400 MHz, $CDCl_3$) δ 2.95 (d, J=2.0 Hz, 7H), 3.03 (d, J=4.9 Hz, 3H), 6.04 (s, 1H). $^{19}$F NMR (376 MHz, $CDCl_3$ 6-150.77 (ddd, J=24.1, 19.9, 4.6 Hz), −145.39 (ddd, J=22.5, 19.9, 9.4 Hz), −137.92 (ddd, J=22.5, 11.7, 4.6 Hz), −131.51--130.20 (m).

Example 37 Synthesis of 2-(N,N-dimethylsulfamoyl)-3,4,5,6-tetrafluoro-N,N-dimethylbenzamide (I-37)

I-37

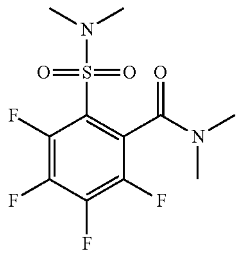

The title compound I-37, 2-(N,N-dimethylsulfamoyl)-3,4,5,6-tetrafluoro-N,N-dimethylbenzamide, was prepared via General Procedure F using 2-(N,N-dimethylsulfamoyl)-3,4,5,6-tetrafluorobenzoic acid (1 eq.), oxalyl chloride (1.5 eq.), dimethylamine (1 eq.) and triethylamine (3 eq.). The title compound I-37 was isolated as beige solid and was lyophilized from water/acetonitrile to afford a white powder. $^1$H NMR (400 MHz, $CDCl_3$) δ 2.91 (s, 3H), 2.97 (d, J=2.0 Hz, 6H), 3.14 (s, 3H). $^{19}$F NMR (376 MHz, $CDCl_3$) δ −151.37 (ddd, J=23.4, 19.9, 4.2 Hz), −145.40 (ddd, J=22.5, 20.0, 9.4 Hz), −138.73 (ddd, J=22.6, 11.8, 4.0 Hz), −130.22--129.33 (m).

Example 38 Synthesis of 2-(N,N-dimethylsulfamoyl)-3,4,5,6-tetrafluoro-N-phenylbenzamide (I-38)

I-38

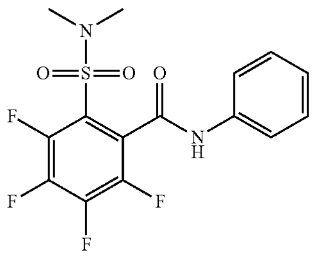

The title compound I-38, 2-(N,N-dimethylsulfamoyl)-3,4,5,6-tetrafluoro-N-phenylbenzamide, was prepared via General Procedure F using 2-(N,N-dimethylsulfamoyl)-3,4,5,6-tetrafluorobenzoic acid (1 eq.), oxalyl chloride (1.5 eq.), aniline (1 eq.) and triethylamine (3 eq.). The title compound I-38 was isolated as beige solid and was lyophilized from water/acetonitrile to afford a white powder. $^1$H NMR (400 MHz, $CDCl_3$) δ 1.59 (s, 3H), 2.97 (d, J=1.9 Hz, 7H), 7.17-7.27 (m, 1H), 7.38 (t, J=7.9 Hz, 2H), 7.54-7.59 (m, 2H), 7.61 (s, 1H). $^{19}$F NMR (376 MHz, $CDCl_3$) δ −149.98 (ddd, J=24.2, 19.8, 4.8 Hz), −144.87 (ddd, J=22.6, 19.9, 9.5 Hz), −137.50 (ddd, J=22.7, 11.8, 4.9 Hz), −130.43 (dt, J=22.8, 10.9 Hz).

Example 39 Synthesis of 2-cyclopropyl-3,4,5,6-tetrafluoro-N,N-dimethylbenzenesulfonamide (I-39)

I-39

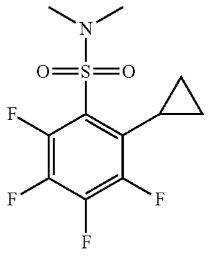

The title compound I-39, 2-cyclopropyl-3,4,5,6-tetrafluoro-N,N-dimethylbenzenesulfonamide, was prepared via General Procedure G using 2-bromo-3,4,5,6-tetrafluoro-N,N-dimethylbenzenesulfonamide (1 eq.), cyclopropyl boronic acid (1.2 eq.), palladium acetate (0.05 eq.), tricyclohexylphosphine (0.12 eq) and potassium phosphate (3 eq). The title compound I-39 was isolated as beige solid and was lyophilized from water/acetonitrile to afford a white powder. $^1$H NMR (400 MHz, $CDCl_3$) δ 0.92-0.99 (m, 2H), 1.16 (ddt, J=8.6, 5.1, 1.8 Hz, 2H), 2.18-2.27 (m, 1H), 3.00 (d, J=2.1 Hz, 6H). $^{19}$F NMR (376 MHz, $CDCl_3$) δ −156.46 (ddd, J=23.6, 19.9, 3.8 Hz), −149.25 (td, J=20.7, 7.8 Hz), −139.34--139.07 (m), −135.89--135.62 (m).

Example 40 Synthesis of 3,4,5,6-tetrafluoro-N,N,4'-trimethyl-[1,1'-biphenyl]-2-sulfonamide (I-40)

I-40

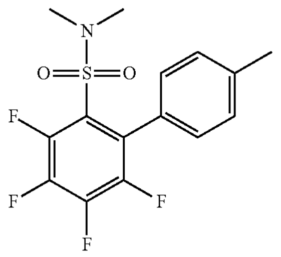

The title compound I-40, 2-cyclopropyl-3,4,5,6-tetrafluoro-N,N-dimethylbenzenesulfonamide, was prepared via General Procedure G using 2-bromo-3,4,5,6-tetrafluoro-N,N-dimethylbenzenesulfonamide (1 eq.), 4-methylphenyl boronic acid (1.2 eq.), palladium acetate (0.05 eq.), tricyclohexylphosphine (0.12 eq) and potassium phosphate (3 eq). The title compound I-40 was isolated as beige solid and was lyophilized from water/acetonitrile to afford a white powder. $^{1}$H NMR (400 MHz, $CDCl_3$) δ 2.44 (s, 2H), 2.78 (d, J=1.9 Hz, 4H), 7.17 (d, J=8.1 Hz, 1H), 7.25-7.31 (m, 2H). $^{19}$F NMR (376 MHz, $CDCl_3$) δ −154.19--153.28 (m), −148.29 (ddd, J=23.8, 20.2, 8.6 Hz), −134.84 (dt, J=21.7, 10.2 Hz), −134.49--133.96 (m).

Example 41 Synthesis of 2,3,4,5-tetrafluoro-N,N-dimethyl-6-((pyridin-2-ylmethyl)amino)benzenesulfonamide (I-41)

I-41

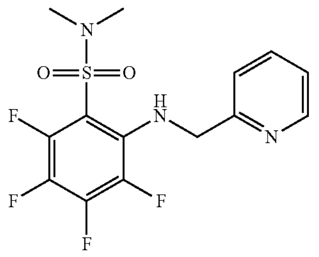

The title compound I-41, 2,3,4,5-tetrafluoro-N,N-dimethyl-6-((pyridin-2-ylmethyl)amino)benzenesulfonamide, was prepared via General Procedure B-2 using 2,3,4,5,6-pentafluoro-N,N-dimethylbenzenesulfonamide (0.1 g, 0.363 mmol), 2-picolylamine (0.086 g, 0.799 mmol) and 2.0 M n-butyllithium in hexane (0.29 mL), The title compound I-41 was isolated as solid and was lyophilized from water/acetonitrile to afford a white powder.

$^{1}$H NMR (400 MHz, $CDCl_3$) δ 8.61 (d, J=5, 1.5 Hz, 1H), 7.73 (td, J=7.5, 1.5 Hz, 1H), 7.33-7.23 (m, 2H), 6.16 (s, 1H), 4.81 (dt, J=4.5, 2.0 Hz, 2H), 2.87 (s, 6H). $^{19}$F NMR (376 MHz, $CDCl_3$) δ −134.34 (1F), −148.65 (1F), −154.58 (1F), −171.44 (1F)

Example 42 Synthesis of 2,3,4,5-tetrafluoro-6-((4-methoxybenzyl)amino)-N,N-dimethylbenzenesulfonamide (I-42)

I-42

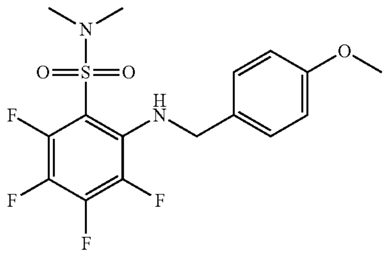

The title compound I-42, 2,3,4,5-tetrafluoro-6-((4-methoxybenzyl)amino)-N,N-dimethylbenzenesulfonamide, was prepared via General Procedure B-2 using 2,3,4,5,6-pentafluoro-N,N-dimethylbenzenesulfonamide (1.4 g, 5.09 mmol), 4-methoxybenzylamine (1.54 g, 11.2 mmol) and 2.0 M n-butyllithium in hexane (4.48 mL), The title compound I-42 was isolated as solid and was lyophilized from water/acetonitrile to afford a white powder. $^{1}$H NMR (400 MHz, $CDCl_3$) δ 7.26 (d, J=8.5 Hz, 2H), 6.88 (d, J=8.5 Hz, 2H), 4.49 (d, J=4.0 Hz, 2H), 3.80 (s, 3H), 2.83 (d, J=2 Hz, 6H). $^{19}$F NMR (376 MHz, $CDCl_3$) δ −134.35 (1F), −148.82 (1F), −152.79 (1F), −171.10 (1F).

Example 43 Synthesis of 2-amino-3,4,5,6-tetrafluoro-N,N-dimethylbenzenesulfonamide (I-43)

I-43

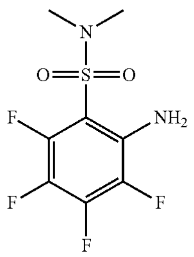

2,3,4,5-tetrafluoro-6-((4-methoxybenzyl)amino)-N,N-dimethylbenzenesulfonamide (730 mg, 1.86 mmol) was dissolved in dichloromethane (18.6 mL, 0.1 M) and the resulting solution was stirred at 25° C. for 5 minutes. The solution was added with trifluoroacetic acid (3.72 mL, 0.5 M) dropwise and was stirred at room temperature. After 12 hours, the reaction mixture was concentrated in vacuo. The mixture was then redissolved in dichloromethane, washed thrice with saturated sodium bicarbonate solution. The collected organic layer was washed with saturated sodium chloride solution, dried over sodium sulfate, filtered and concentrated in vacuo. The crude sample was absorbed onto silica gel and purified using flash chromatography using a Hexane:Ethyl acetate gradient. The title compound I-43 was isolated as solid and was lyophilized from water/acetonitrile to afford a white powder (452 mg, 1.66 mmol, 89.3% yield). $^{1}$H NMR (400 MHz, $CDCl_3$) δ 5.53 (s, 2H), 2.90 (s, 6H). $^{19}$F NMR (376 MHz, $CDCl_3$) δ −135.78 (1F), −149.72--149.95 (1F), −159.52--159.97 (1F), −172.74--172.98 (1F).

Example 44 Synthesis of 2-(dimethylamino)-3,4,5,6-tetrafluoro-N,N-dimethylbenzenesulfonamide (I-44)

I-44

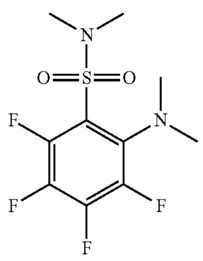

2-amino-3,4,5,6-tetrafluoro-N,N-dimethylbenzenesulfonamide (50 mg, 0.184 mmol) was dissolved in tetrahydrofuran (1.22 mL, 0.15 M) and the resulting solution was stirred at 25° C. for 5 minutes. The solution was added with iodomethane (57.2 μL, 0.918 mmol) and was stirred at 0° C. After 15 minutes, the resulting solution was added with potassium tert-butoxide (41.2 mg, 0367 mmol) slowly over 4 hours. The reaction was quenched with 0.1 M hydrochloric acid and extracted thrice with dichloromethane. The collected organic layer was washed with saturated sodium chloride solution, dried over sodium sulfate, filtered and concentrated in vacuo. The crude sample was absorbed onto silica gel and purified using flash chromatography using a Hexane:Ethyl acetate gradient. The title compound I-44 was isolated as solid and was lyophilized from water/acetonitrile to afford a white powder (452 mg, 1.66 mmol, 89.3% yield). $^1$H NMR (400 MHz, $CDCl_3$) δ 2.98 (d, J=1.5 Hz, 6H), 2.86 (d, J=1.5 Hz, 6H). $^{19}$F NMR (376 MHz, $CDCl_3$) δ −137.53 (1F), −143.25 (1F), −149.33 (1F), −157.14 (1F).

Example 45 Synthesis of 2,3,4,5-tetrafluoro-6-((3-fluoro-4-methoxybenzyl)amino)-N,N-dimethylbenzenesulfonamide (I-45)

I-45

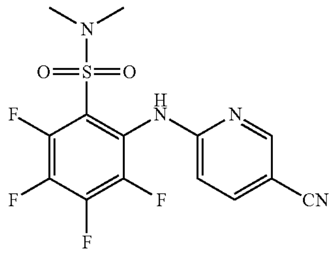

The title compound I-45, 2,3,4,5-tetrafluoro-6-((3-fluoro-4-methoxybenzyl)amino)-N,N-dimethylbenzenesulfonamide, was prepared via General Procedure B-2 using 2,3,4,5,6-pentafluoro-N,N-dimethylbenzenesulfonamide (0.1 g, 0.363 mmol), 6-amino-3-pyridinecarbonitrile (0.052 g, 0.436 mmol) and 2.0 M n-butyllithium in hexane (0.15 mL), The title compound I-45 was isolated as solid and was lyophilized from water/acetonitrile to afford a white powder. $^1$H NMR (400 MHz, $CDCl_3$) δ 8.45 (d, J=2.0, 1H), 8.07 (s, 1H), 7.81 (dd, J=8.5, 2.0 Hz, 1H), 6.85 (d, J=8.5 Hz, 1H), 2.81 (d, J=2.0 Hz, 6H). $^{19}$F NMR (376 MHz, $CDCl_3$) δ −133.63 (1F), −134.16 (1F), −146.72 (1F), −157.43 (1F).

Example 46 Synthesis of 2-((4-cyanophenyl)amino)-3,4,5,6-tetrafluoro-N,N-dimethylbenzenesulfonamide (I-46)

I-46

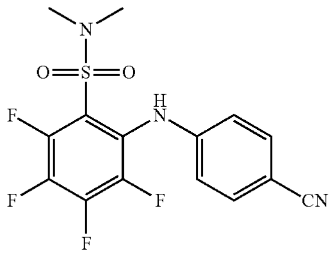

The title compound I-46, 2-((4-cyanophenyl)amino)-3,4,5,6-tetrafluoro-N,N-dimethylbenzenesulfonamide, was prepared via General Procedure B-2 using 2,3,4,5,6-pentafluoro-N,N-dimethylbenzenesulfonamide (0.074 g, 0.269 mmol), 4-aminobenzonitrile (38.1 mg, 0.323 mmol) and 2.0 M n-butyllithium in hexane (0.24 mL), The title compound I-46 was isolated as solid and was lyophilized from water/acetonitrile to afford a white powder. $^1$H NMR (400 MHz, $CDCl_3$) δ 7.91 (s, 1H), 7.62-7.54 (m, 2H), 6.85 (dd, J=8.5, 3.0 Hz, 2H), 2.85 (d, J=2.0 Hz, 6H). $^{19}$F NMR (376 MHz, $CDCl_3$) δ −133.06 (1F), −137.45 (1F), −146.12 (1F), −159.89 (1F).

Example 47 Synthesis of 2-((4-cyanobenzyl)amino)-3,4,5,6-tetrafluoro-N,N-dimethylbenzenesulfonamide (I-47)

I-47

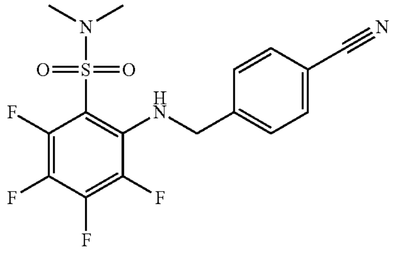

The title compound I-47, 2-((4-cyanobenzyl)amino)-3,4,5,6-tetrafluoro-N,N-dimethylbenzenesulfonamide, was prepared via General Procedure B-2 using 2,3,4,5,6-pentafluoro-N,N-dimethylbenzenesulfonamide (0.1 g, 0.363 mmol), 4-(aminomethyl)benzonitrile (72 mg, 0.545 mmol) and 2.0 M n-butyllithium in hexane (0.15 mL), The title compound I-47 was isolated as solid and was lyophilized from water/acetonitrile to afford a white powder. $^1$H NMR (400 MHz, $CDCl_3$) δ 7.66 (d, J=8 Hz, 2H), 7.46 (d, J=8 Hz, 2H), 7.23 (s, 1H), 4.62 (dd, J=7.0, 3.5 Hz, 2H), 2.91 (d, J=2 Hz, 6H). $^{19}$F NMR (376 MHz, $CDCl_3$) δ −134.20 (1F), −147.84 (1F), −153.44 (1F), −169.58 (1F).

Example 48 Synthesis of 2-(benzylamino)-3,4,5,6-tetrafluoro-N,N-dimethylbenzenesulfonamide (I-48)

I-48

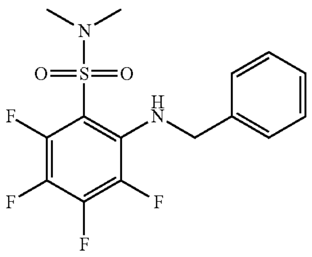

The title compound I-48, 2-(benzylamino)-3,4,5,6-tetrafluoro-N,N-dimethylbenzenesulfonamide, was prepared via General Procedure B-2 using 2,3,4,5,6-pentafluoro-N,N-dimethylbenzenesulfonamide (0.05 g, 0.182 mmol), Benzylamine (0.0437 mL, 0.4 mmol) and 2.0 M n-butyllithium in hexane (0.15 mL), The title compound I-48 was isolated as solid and was lyophilized from water/acetonitrile to afford a white powder. $^1$H NMR (400 MHz, CDC13) δ 7.38-7.27 (m, 5H), 7.14 (s, 1H), 4.56 (dd, J=6.3, 3.6 Hz, 2H), 2.84 (d, J=2.3 Hz, 6H). $^{13}$C NMR (101 MHz, CDC13) δ 138.60, 128.76, 127.58, 50.25, 37.13. $^{19}$F NMR (376 MHz, CDC13) δ −134.27 (1F), −148.50 (1F), −152.84 (1F), −170.81 (1F).

Example 49 Synthesis of 2,3,4,5-tetrafluoro-N,N-dimethyl-6-(methylamino)benzenesulfonamide (I-49)

I-49

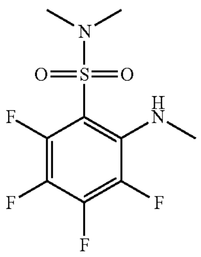

The title compound I-49, 2,3,4,5-tetrafluoro-N,N-dimethyl-6-(methylamino)benzenesulfonamide, was prepared via General Procedure B-2 using 2,3,4,5,6-pentafluoro-N,N-dimethylbenzenesulfonamide (0.05 g, 0.182 mmol), Methylamine in tetrahydrofuran (0.7273 mL, 0.545 mmol) and 2.0 M n-butyllithium in hexane (0.22 mL), The title compound I-49 was isolated as solid and was lyophilized from water/acetonitrile to afford a white powder. $^1$H NMR (400 MHz, CDC13) δ 6.70 (s, 1H), 3.09 (dd, J=6.6, 4.1 Hz, 3H), 2.89 (d, J=2.2 Hz, 6H). $^{13}$C NMR (101 MHz, CDC13) δ 37.18, 33.38. $^{19}$F NMR (376 MHz, CDC13) δ −134.83 (1F), −148.81 (1F), −155.94 (1F), −172.26 (1F).

Example 50 Synthesis of 2,3,4,5-tetrafluoro-N,N-dimethyl-6-(piperidin-1-yl)benzenesulfonamide (I-50)

I-50

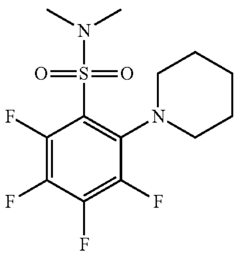

The title compound I-50, 2,3,4,5-tetrafluoro-N,N-dimethyl-6-(piperidin-1-yl)benzenesulfonamide, was prepared via General Procedure B-2 using 2,3,4,5,6-pentafluoro-N,N-dimethylbenzenesulfonamide (0.05 g, 0.182 mmol), Piperidine (0.038 mL, 0.382 mmol) and 2.0 M n-butyllithium in hexane (0.15 mL), The title compound I-50 was isolated as solid and was lyophilized from water/acetonitrile to afford a white powder. $^1$H NMR (400 MHz, $CDCl_3$) δ 3.08 (s, 4H), 2.98 (d, J=1.7 Hz, 6H), 1.79 and 1.66 overlap (s, s, total 6H). $^{13}$C NMR (101 MHz, $CDCl_3$) δ 52.46, 36.93, 25.86, 23.86. $^{19}$F NMR (376 MHz, $CDCl_3$) δ −140.56 (1F), −142.64 (1F), −149.79 (1F), −157.73 (1F).

Example 51 Synthesis of 2-((4-cyclohexylphenyl)amino)-3,4,5,6-tetrafluoro-N,N-dimethylbenzenesulfonamide (I-51)

I-51

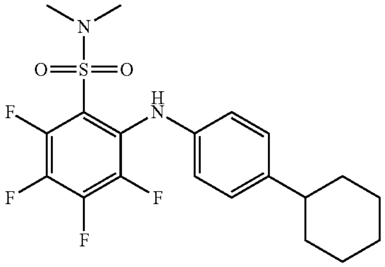

The title compound I-51, 2-((4-cyclohexylphenyl)amino)-3,4,5,6-tetrafluoro-N,N-dimethylbenzenesulfonamide, was prepared via General Procedure B-2 using 2,3,4,5,6-pentafluoro-N,N-dimethylbenzenesulfonamide (0.05 g, 0.182 mmol), 4-cyclohexylaniline (66.9, 0.382 mmol) and 2.0 M n-butyllithium in hexane (0.15 mL), The title compound I-51 was isolated as solid and was lyophilized from water/acetonitrile to afford a white powder. $^1$H NMR (400 MHz, $CDCl_3$) δ 7.94 (s, 1H), 7.14 (d, J=8.4 Hz, 2H), 6.83 (dd, J=8.5, 2.40 Hz, 2H), 2.87 (d, J=1.8 Hz, 6H), 2.51-2.46 (m, 1H), 1.90-1.85 (m, 4H), 1.41 (t, J=9.9 Hz, 4H), 1.31-1.22 (m, 2H). $^{13}$C NMR (101 MHz, $CDCl_3$) δ 143.09, 139.32, 127.36, 118.74, 43.84, 37.30, 34.53, 26.90, 26.15. $^{19}$F NMR (376 MHz, $CDCl_3$) δ −134.04 (1F), −140.10 (1F), −147.66 (1F), −165.78 (1F).

Example 52 Synthesis of 2,3,4,5-tetrafluoro-N,N-dimethyl-6-(pyridin-3-ylamino)benzenesulfonamide (I-52)

I-52

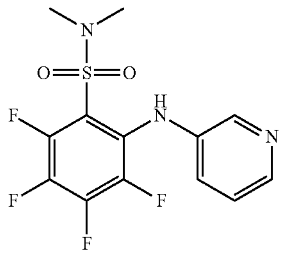

The title compound I-52, 2-((4-cyclohexylphenyl)amino)-3,4,5,6-tetrafluoro-N,N-dimethylbenzenesulfonamide, was prepared via General Procedure B-2 using 2,3,4,5,6-pentafluoro-N,N-dimethylbenzenesulfonamide (0.05 g, 0.182 mmol), 3-aminopyridine (51.3 mg, 0.545 mmol) and 2.0 M n-butyllithium in hexane (0.22 mL), The title compound I-52 was isolated as solid and was lyophilized from water/acetonitrile to afford a white powder. $^1H$ NMR (400 MHz, $CDCl_3$) δ 8.32 (s, 2H), 7.97 (s, 1H), 7.30-7.27 (m, 1H), 7.21 (d, J=8.1 Hz, 1H), 2.89 (d, J=1.9 Hz, 6H). $^{13}C$ NMR (101 MHz, $CDCl_3$) δ 37.14, 33.38. $^{19}F$ NMR (376 MHz, $CDCl_3$) δ −134.83 (1F), −148.81 (1F), −155.97 (1F), −172.28 (1F).

Example 53 Synthesis of 2,3,4,5-tetrafluoro-N,N-dimethyl-6-(pyridin-2-ylamino)benzenesulfonamide (I-53)

I-53

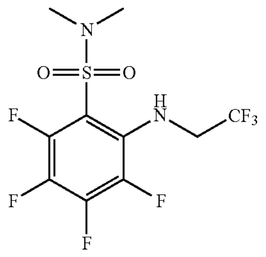

The title compound I-53, 2,3,4,5-tetrafluoro-N,N-dimethyl-6-(pyridin-2-ylamino)benzenesulfonamide, was prepared via General Procedure B-2 using 2,3,4,5,6-pentafluoro-N,N-dimethylbenzenesulfonamide (0.05 g, 0.182 mmol), 2,2,2-trifluoroethylamine (0.0438 mL, 0.545 mmol) and 2.0 M n-butyllithium in hexane (0.22 mL), The title compound I-53 was isolated as solid and was lyophilized from water/acetonitrile to afford a white powder. $^1H$ NMR (400 MHz, $CDCl_3$) δ 7.16 (s, 1H), 4.02 (quint, J=8.6 Hz, 2H), 2.93 (d, J=2.2 Hz, 6H). $^{13}C$ NMR (101 MHz, $CDCl_3$) δ 46.85, 46.65, 37.12. $^{19}F$ NMR (376 MHz, $CDCl_3$) δ −75.06 (3F), −135.87 (1F), −150.22 (1F), −154.68 (1F), −170.66 (1F).

Example 54 Synthesis of 2-((2,2-difluoroethyl)amino)-3,4,5,6-tetrafluoro-N,N-dimethylbenzenesulfonamide (I-54)

I-54

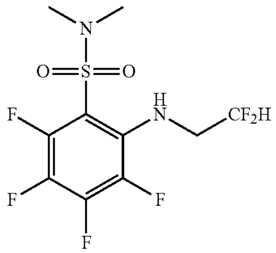

The title compound I-54, 2-((2,2-difluoroethyl)amino)-3,4,5,6-tetrafluoro-N,N-dimethylbenzenesulfonamide, was prepared via General Procedure B-2 using 2,3,4,5,6-pentafluoro-N,N-dimethylbenzenesulfonamide (0.07 g, 0.254 mmol), 2,2-difluoroethanamine hydrochloride salt (89 mg, 0.763 mmol) and 2.0 M n-butyllithium in hexane (0.41 mL), The title compound I-54 was isolated as solid and was lyophilized from water/acetonitrile to afford a white powder.

Example 55 Synthesis of 2,3,4,5-tetrafluoro-6-((4-fluorobenzyl)amino)-N,N-dimethylbenzenesulfonamide (I-55)

I-55

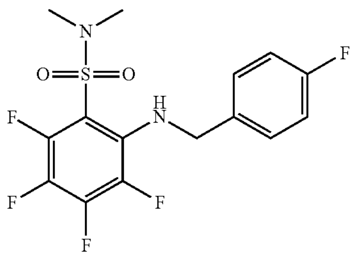

The title compound I-55, 2,3,4,5-tetrafluoro-6-((4-fluorobenzyl)amino)-N,N-dimethylbenzenesulfonamide, was prepared via General Procedure B-2 using 2,3,4,5,6-pentafluoro-N,N-dimethylbenzenesulfonamide (0.1 g, 0.363 mmol), 4-fluorobenzylamine (0.127 mL, 1.09 mmol) and 2.0 M n-butyllithium in hexane (0.44 mL), The title compound I-55 was isolated as solid and was lyophilized from water/acetonitrile to afford a white powder.

Example 56 Synthesis of 2,3,4,5-tetrafluoro-N,N-dimethyl-6-(pyridin-2-ylamino)benzenesulfonamide (I-56)

I-56

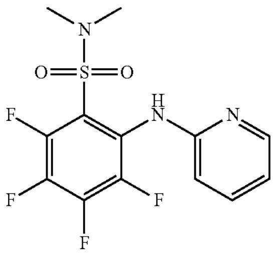

The title compound I-56, 2,3,4,5-tetrafluoro-N,N-dimethyl-6-(pyridin-2-ylamino)benzenesulfonamide, was prepared via General Procedure B-2 using 2,3,4,5,6-pentafluoro-N,N-dimethylbenzenesulfonamide (0.05 g, 0.182 mmol), 2-aminopyridine (52 mg, 0.545 mmol) and 2.0 M n-butyllithium in hexane (0.22 mL), The title compound I-56 was isolated as solid and was lyophilized from water/acetonitrile to afford a white powder.

Example 57 Synthesis of 2,3,4,5-tetrafluoro-6-((3-fluoro-4-methoxybenzyl)amino)-N,N-dimethylbenzenesulfonamide (I-57)

I-57

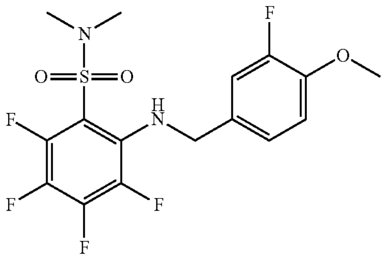

The title compound I-57, 2,3,4,5-tetrafluoro-6-((3-fluoro-4-methoxybenzyl)amino)-N,N-dimethylbenzenesulfonamide, was prepared via General Procedure B-2 using 2,3,4,5,6-pentafluoro-N,N-dimethylbenzenesulfonamide (0.1 g, 0.363 mmol), 3-fluoro-4-methoxybenzylamine (124 mg, 0.799 mmol) and 2.0 M n-butyllithium in hexane (0.32 mL). The title compound I-57 was isolated as solid and was lyophilized from water/acetonitrile to afford a white powder. $^1$H NMR (400 MHz, $CDCl_3$) δ 7.10-7.02 (m, 2H), 6.94 (t, J=8.5 Hz, 1H), 4.48 (d, J=4.0 Hz, 2H), 3.89 (s, 3H), 2.87 (d, J=2.0 Hz, 6H). $^{19}$F NMR (376 MHz, $CDCl_3$) δ −134.30 (1F), −134.52 (1F), −148.35 (1F), −152.91 (1F), −170.42 (1F).

Example 58 Synthesis of 2-(benzylthio)-3,4,5,6-tetrafluoro-N,N-dimethylbenzenesulfonamide (I-58)

I-58

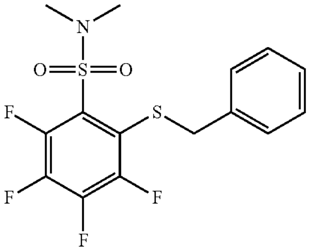

The title compound I-58, 2-(benzylthio)-3,4,5,6-tetrafluoro-N,N-dimethylbenzenesulfonamide, was prepared via General Procedure B-3 using 2,3,4,5,6-pentafluoro-N,N-dimethylbenzenesulfonamide (0.2 g, 0.727 mmol), benzyl mercaptan (76.8 μL, 0.654 mmol) and 1.5 M methyllithium in ethyl ether (0.68 mL). The title compound I-58 was isolated as solid and was lyophilized from water/acetonitrile to afford a white solid (66 mg, 27%)

Example 59 Synthesis of 2,3,4,5-tetrafluoro-6-((4-methoxybenzyl)thio)-N,N-dimethylbenzenesulfonamide (I-59)

I-59

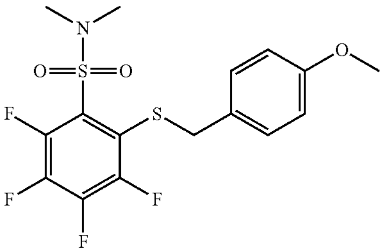

The title compound I-59, 2-(benzylthio)-3,4,5,6-tetrafluoro-N,N-dimethylbenzenesulfonamide, was prepared via General Procedure B-3 using 2,3,4,5,6-pentafluoro-N,N-dimethylbenzenesulfonamide (0.2 g, 0.727 mmol), 4-methoxybenzenethiol (124 μL, 0.799 mmol) and 2.0 M n-butyllithium in hexane (0.26 mL). The title compound I-59 was isolated as the white solid (90 mg, 30%) $^1$H NMR (400 MHz, $CDCl_3$) δ 7.24 (d, J=8.5 Hz, 2H), 6.82 (d, J=8.5 Hz, 2H), 4.17 (s, 2H), 3.81 (s, 3H), 2.96 (d, J=1.5 Hz, 6H). $^{19}$F NMR (376 MHz, $CDCl_3$) δ −123.28 (1F), −135.35 (1F), −147.78 (1F), −151.41 (1F).

Example 60 Synthesis of 2,3,4,5-tetrafluoro-6-((4-methoxybenzyl)thio)-N,N-dimethylbenzenesulfonamide (I-60)

I-60

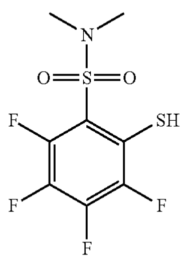

2,3,4,5-tetrafluoro-6-((4-methoxybenzyl)thio)-N,N-dimethylbenzenesulfonamide (50 mg, 0.122 mmol) was dissolved in dichloromethane (1.22 mL, 0.1 M) and the resulting solution was stirred at 25° C. for 5 minutes. The solution was added with trifluoroacetic acid (0.244 mL, 0.5 M) dropwise and was stirred at room temperature. After 12 hours, the reaction mixture was concentrated in vacuo. The mixture was then redissolved in dichloromethane, washed thrice with saturated sodium bicarbonate solution. The collected organic layer was washed with saturated sodium chloride solution, dried over sodium sulfate, filtered and concentrated in vacuo. The crude sample was absorbed onto silica gel and purified using flash chromatography using a Hexane:Ethyl acetate gradient. The title compound I-60 was isolated as solid and was lyophilized from water/acetonitrile to afford a white powder (20 mg, 0.069 mmol, 56.8%). $^{1}H$ NMR (400 MHz, $CDCl_3$) δ 4.61-4.54 (m, 1H), 2.96 (d, J=2.0 Hz, 6H). $^{19}F$ NMR (376 MHz, $CDCl_3$) δ −128.63 (1F), −131.54 (1F), −147.03 (1F), −157.67 (1F).

Example 61 Synthesis of 2,3,4,5-tetrafluoro-N-(3-fluoro-4-methoxyphenyl)-6-isopropoxybenzenesulfonamide (I-61)

I-61

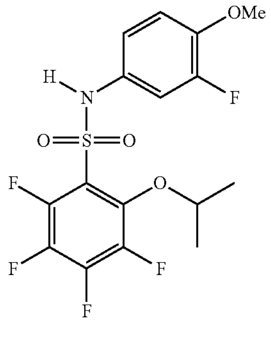

The title compound I-61, 2,3,4,5-tetrafluoro-N-(3-fluoro-4-methoxyphenyl)-6-isopropoxybenzenesulfonamide, was prepared via General Procedure B-1 using 2,3,4,5,6-pentafluoro-N-(3-fluoro-4-methoxyphenyl)benzenesulfonamide (80 mg, 0.215 mmol), 2-propanol (0.068 mL, 0.883 mmol), 1.5 M methyllithium solution in ethyl ether (0.58 mL). The title compound I-61 was isolated as solid and was lyophilized from water/acetonitrile to afford a white powder.

Example 62 Synthesis of 2-(benzyloxy)-3,4,5,6-tetrafluoro-N-(3-fluoro-4-methoxyphenyl)benzenesulfonamide (I-62)

I-62

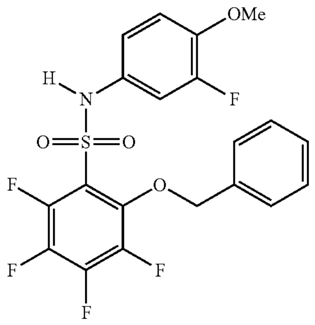

The title compound I-62, 2-(benzyloxy)-3,4,5,6-tetrafluoro-N-(3-fluoro-4-methoxyphenyl)benzenesulfonamide, was prepared via General Procedure B-1 using 2,3,4,5,6-pentafluoro-N-(3-fluoro-4-methoxyphenyl)benzenesulfonamide (100 mg, 0.269 mmol), benzyl alcohol (0.056 mL, 0.539 mmol), 1.5 M methyllithium solution in ethyl ether (0.36 mL). The title compound I-62 was isolated as solid and was lyophilized from water/acetonitrile to afford a white powder.

Example 63 Synthesis of 2,3,4,5-tetrafluoro-N-(3-fluoro-4-methoxyphenyl)-6-hydroxybenzenesulfonamide (I-63)

I-63

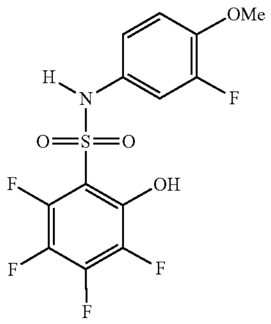

2-(benzyloxy)-3,4,5,6-tetrafluoro-N-(3-fluoro-4-methoxyphenyl)benzenesulfonamide (400 mg, 0.871 mmol) was added with methanol (3.73 mL, 0.23 M) and tetrahydrofuran (7.8 mL, 0.11 M). The resulting solution was added with palladium 10% on carbon (40 mg) and stirred under hydrogen for 2 hours. The reaction mixture was filtered through a pad of Celite, and the collected organic layer was concentrated in vacuo. The title compound I-63 was isolated as beige solid and was lyophilized from water/acetonitrile to afford a white powder (27.6 mg, 86%).

Example 64 Synthesis of 2,3,4,5-tetrafluoro-N-(3-fluoro-4-methoxyphenyl)-6-methoxybenzenesulfonamide (I-64)

I-64

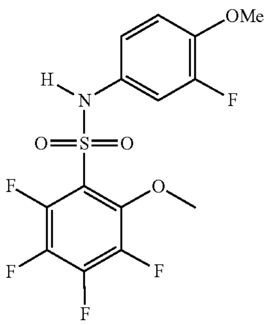

2,3,4,5-tetrafluoro-N-(3-fluoro-4-methoxyphenyl)-6-hydroxybenzenesulfonamide (50 mg, 0.135 mmol) was dissolved in tetrahydrofuran (1.35 mL) and stirred at 0° C. After 15 minutes, the resulting solution was sodium hydride 60% dispersion in paraffin (4.87 mg, 0.122 mmol) and then added with dimethyl sulfate (0.0115 mL, 0.122 mmol). The resulting solution was stirred at 55° C. After 9 hours, the reaction was quenched with saturated solution of ammonium chloride, and the aqueous phase was extracted thrice with dichloromethane. The combined organic layer was washed once with saturated sodium chloride solution, dried with sodium sulfate, and concentrated in vacuo. The crude sample was absorbed onto silica gel and purified using flash chromatography using a Hexane:Ethyl acetate gradient. The isolated product was further purified using preparative HPLC using a water (+0.1% v/v formic acid):acetonitrile (+0.1% v/v formic acid) gradient. The title compound I-64 was isolated as solid and was lyophilized from water/acetonitrile to afford a white powder.

Example 65 Synthesis of 2-(difluoromethoxy)-3,4,5,6-tetrafluoro-N-(3-fluoro-4-methoxyphenyl)benzenesulfonamide (I-65)

I-65

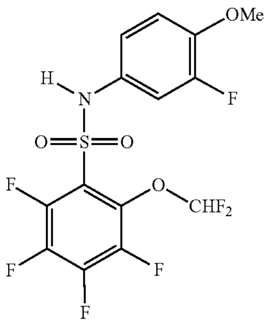

2,3,4,5-tetrafluoro-N-(3-fluoro-4-methoxyphenyl)-6-hydroxybenzenesulfonamide (276 mg, 0.746 mmol) was dissolved in dimethylformamide (2.5 mL) and stirred at 0° C. After 15 minutes, the resulting solution was sodium hydride 60% dispersion in paraffin (27 mg, 0.671 mmol) and the resulting solution was stirred at room temperature for 10 minutes. The solution was added with ethyl bromodifluoroacetate (0.0861 mL, 0.671 mmol). The resulting solution was stirred at room temperature. After 9 hours, the reaction was quenched with saturated solution of ammonium chloride, and the aqueous phase was extracted thrice with dichloromethane. The combined organic layer was washed thrice with saturated sodium chloride solution, dried with sodium sulfate, and concentrated in vacuo. The crude sample was absorbed onto silica gel and purified using flash chromatography using a Hexane:Ethyl acetate gradient. The isolated product was further purified using preparative HPLC using a water (+0.1% v/v formic acid):acetonitrile (+0.1% v/v formic acid) gradient. The title compound I-65 was isolated as solid and was lyophilized from water/acetonitrile to afford a white powder.

Example 66 Synthesis of 2,3,4,5-tetrafluoro-N-(3-fluoro-4-methoxyphenyl)-6-(2-fluoroethoxy)benzenesulfonamide (I-66)

I-66

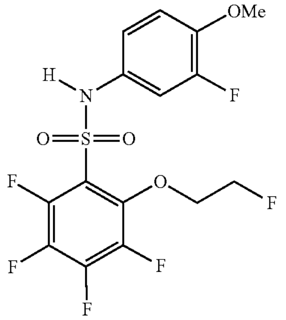

2,3,4,5,6-pentafluoro-N-(3-fluoro-4-methoxyphenyl)-N-(prop-2-yn-1-yl)benzenesulfonamide was prepared via General Procedure A-2 using 2,3,4,5,6-pentafluoro-N-(3-fluoro-4-methoxyphenyl)benzenesulfonamide (2 g 5.39 mmol), potassium carbonate (819 mg, 5.93 mmol) and propargyl bromide in toluene (0.78 mL, 7 mmol). The desired product, was isolated as the solid and used for subsequent reactions.

2,3,4,5-tetrafluoro-N-(3-fluoro-4-methoxyphenyl)-6-(2-fluoroethoxy)-N-(prop-2-yn-1-yl)benzenesulfonamide was prepared via General Procedure B-1, using 2,3,4,5,6-pentafluoro-N-(3-fluoro-4-methoxyphenyl)-N-(prop-2-yn-1-yl) benzenesulfonamide (200 mg), 2-Fluoroethanol (0.043 mL, 0.733 mmol) and of 1.5 M methyllithium in ethyl ether (0.458 mL, 0.733 mmol). The desired product was isolated as solid and used for subsequent reactions.

The title compound I-66, 2,3,4,5-tetrafluoro-N-(3-fluoro-4-methoxyphenyl)-6-(2-fluoroethoxy)benzenesulfonamide, was prepared via General Procedure A-3 using 2,3,4,5-tetrafluoro-N-(3-fluoro-4-methoxyphenyl)-6-(2-fluoroethoxy)-N-(prop-2-yn-1-yl)benzenesulfonamide (0.065 g, 0143 mmol), trans-dichlorobis(triphenylphosphine)palladium(II) (10 mg, 0.0143 mmol) and triethylamine (0.16 mL, 1.15 mmol). The title compound I-66 was isolated as solid and was lyophilized from water/acetonitrile to afford a white powder.

Example 67 Synthesis of 2-(2,2-difluoroethoxy)-3,4,5,6-tetrafluoro-N-(3-fluoro-4-methoxyphenyl)benzenesulfonamide (I-67)

I-67

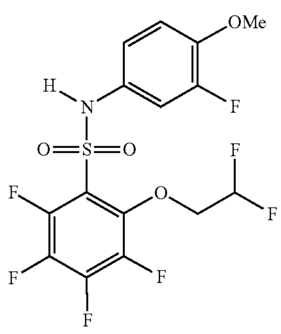

2-(2,2-difluoroethoxy)-3,4,5,6-tetrafluoro-N-(3-fluoro-4-methoxyphenyl)-N-(prop-2-yn-1-yl)benzenesulfonamide was prepared via General Procedure B-1, using 2,3,4,5,6-pentafluoro-N-(3-fluoro-4-methoxyphenyl)-N-(prop-2-yn-1-yl)benzenesulfonamide (200 mg), 2,2-Difluoroethanol (0.046 mL, 0.733 mmol) and of 1.5 M methyllithium in ethyl ether (0.489 mL, 0.733 mmol). The desired product was isolated as solid and used for subsequent reactions.

The title compound I-67, 2-(2,2-difluoroethoxy)-3,4,5,6-tetrafluoro-N-(3-fluoro-4-methoxyphenyl)benzenesulfonamide, was prepared via General Procedure A-3 using 2-(2,2-difluoroethoxy)-3,4,5,6-tetrafluoro-N-(3-fluoro-4-methoxyphenyl)-N-(prop-2-yn-1-yl)benzenesulfonamide (150 mg, 0.318 mmol), trans-dichlorobis(triphenylphosphine)palladium(II) (9 mg, 0.0127 mmol) and triethylamine (0.355 mL, 2.55 mmol). The title compound I-67 was isolated as solid and was lyophilized from water/acetonitrile to afford a white powder.

Example 68 Synthesis of 2,3,4,5-tetrafluoro-N-(3-fluoro-4-methoxyphenyl)-6-(2,2,2-trifluoroethoxy)benzenesulfonamide (I-68)

I-68

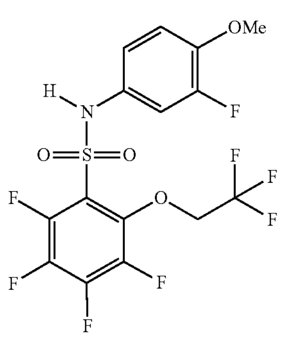

2,3,4,5-tetrafluoro-N-(3-fluoro-4-methoxyphenyl)-N-(prop-2-yn-1-yl)-6-(2,2,2-trifluoroethoxy)benzenesulfonamide was prepared via General Procedure B-1, using 2,3,4,5,6-pentafluoro-N-(3-fluoro-4-methoxyphenyl)-N-(prop-2-yn-1-yl)benzenesulfonamide (408 mg, 0.997 mmol), 2,2,2-Trifluoroethanol (0.109 mL, 1.5 mmol) and of 1.5 M methyllithium in ethyl ether (1.12 mL, 1.79 mmol). The desired product was isolated as solid and used for subsequent reactions.

The title compound I-68, 2,3,4,5-tetrafluoro-N-(3-fluoro-4-methoxyphenyl)-6-(2,2,2-trifluoroethoxy)benzenesulfonamide, was prepared via General Procedure A-3 using 2,3,4,5-tetrafluoro-N-(3-fluoro-4-methoxyphenyl)-N-(prop-2-yn-1-yl)-6-(2,2,2-trifluoroethoxy)benzenesulfonamide (340 mg, 0.695 mmol), trans-dichlorobis(triphenylphosphine)palladium(II) (48.8 mg, 0.0695 mmol) and triethylamine (0.78 mL, 5.56 mmol). The title compound I-68 was isolated as solid and was lyophilized from water/acetonitrile to afford a white powder. $^{1}H$ NMR (400 MHz, $CDCl_3$) δ 7.01-6.95 (m, 1H), 6.94-6.86 (m, 2H), 4.60 (q, J=8.0 Hz, 2H), 3.87 (s, 3H). $^{19}F$ NMR (376 MHz, $CDCl_3$) δ −74.16 (3F), −131.38 (1F), −134.61 (1F), −144.82 (1F), −151.54 (1F), −155.54 (1F). LRMS (ESI−) m/z calc'd for $C_{15}H_8F_8SO_4N^-$ $[M-H]^-$ 450.01, found 450.44.

Example 69 Synthesis of 2-cyclobutoxy-3,4,5,6-tetrafluoro-N-(3-fluoro-4-methoxyphenyl)benzenesulfonamide (I-69)

I-69

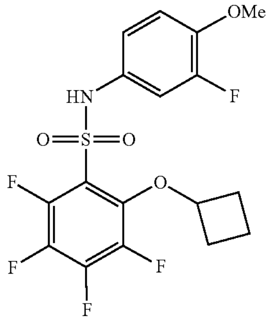

2-cyclobutoxy-3,4,5,6-tetrafluoro-N-(3-fluoro-4-methoxyphenyl)-N-(prop-2-yn-1-yl)benzenesulfonamide was prepared via general procedure B-1, using 2,3,4,5,6-pentafluoro-N-(3-fluoro-4-methoxyphenyl)-N-(prop-2-yn-1-yl)benzenesulfonamide (399 mg, 0.976 mmol), cyclobutanol (0.115 mL, 1.46 mmol), and 1.5 M methyllithium in ethyl ether (0.915 mL, 1.46 mmol). The desired product was isolated as solid and used for subsequent reactions.

The title compound I-69, 2-cyclobutoxy-3,4,5,6-tetrafluoro-N-(3-fluoro-4-methoxyphenyl)benzenesulfonamide, was prepared via general procedure A-3, using 2-cyclobutoxy-3,4,5,6-tetrafluoro-N-(3-fluoro-4-methoxyphenyl)-N-(prop-2-yn-1-yl)benzenesulfonamide (350 mg, 0.759 mmol), trans-dichlorobis(triphenylphosphine)palladium(II) (53.3 mg, 0.0759 mmol) and triethylamine (0.846 mL, 6.07 mmol). $^{1}H$ NMR (400 MHz, $CDCl_3$) δ 7.02-6.82 (m, 3H), 4.89 (pd, J=7.4, 2.4 Hz, 1H), 3.86 (s, 3H), 2.51-2.34 (m, 4H), 1.94-1.81 (m, 1H), 1.69-1.51 (m, 1H). $^{19}F$ NMR (376 MHz, $CDCl_3$) δ −131.88 (1F), −136.13 (1F), −146.56 (1F), −152.15 (1F), −159.77 (1F). LRMS (ESI−) m/z calc'd for $C_{17}H_{13}F_5SO_4N^-$ $[M-H]^-$ 422.06, found 422.47.

Example 70 Synthesis of 2-(cyclopentyloxy)-3,4,5,6-tetrafluoro-N-(3-fluoro-4-methoxyphenyl)benzenesulfonamide (I-70)

I-70

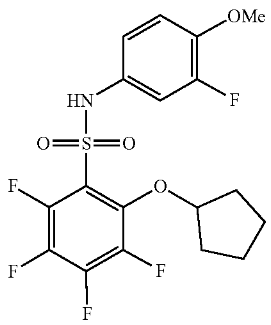

2-(cyclopentyloxy)-3,4,5,6-tetrafluoro-N-(3-fluoro-4-methoxyphenyl)-N-(prop-2-yn-1-yl)benzenesulfonamide was prepared via general procedure B-1, using 2,3,4,5,6-pentafluoro-N-(3-fluoro-4-methoxyphenyl)-N-(prop-2-yn-1-yl)benzenesulfonamide (408 mg, 0.997 mmol), cyclopentanol (0.136 mL, 1.5 mmol), and 1.5 M methyllithium in ethyl ether (0.935 mL, 1.5 mmol).

The title compound I-70, 2-(cyclopentyloxy)-3,4,5,6-tetrafluoro-N-(3-fluoro-4-methoxyphenyl)benzenesulfonamide, was prepared via general procedure A-3, using 2-(cyclopentyloxy)-3,4,5,6-tetrafluoro-N-(3-fluoro-4-methoxyphenyl)-N-(prop-2-yn-1-yl)benzenesulfonamide (280 mg, 0.589 mmol), trans-dichlorobis(triphenylphosphine)palladium(II) (41.3 mg, 0.0589 mmol) and triethylamine (0.657 mL, 4.71 mmol). $^{1}$H NMR (400 MHz, $CDCl_3$) δ 6.98-6.84 (m, 3H), 5.31-5.25 (m, 1H), 3.87 (s, 3H), 2.02 (m, 2H), 1.95 (m, 2H), 1.76-1.68 (m, 2H), 1.30 (m, 2H). $^{19}$F NMR (376 MHz, $CDCl_3$) δ −131.85 (1F), −135.75 (1F), −146.64 (1F), −151.17 (1F), −160.75 (1F). LRMS (ESI−) m/z calc'd for $C_{18}H_{15}F_5SO_4N^-$ $[M-H]^-$ 436.07, found 436.49.

Example 71 Synthesis of 2-(cyclopropylmethoxy)-3,4,5,6-tetrafluoro-N-(3-fluoro-4-methoxyphenyl)benzenesulfonamide (I-71)

I-71

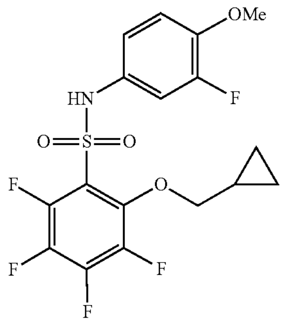

2-(cyclopropylmethoxy)-3,4,5,6-tetrafluoro-N-(3-fluoro-4-methoxyphenyl)-N-(prop-2-yn-1-yl)benzenesulfonamide was prepared via general procedure B-1, using 2,3,4,5,6-pentafluoro-N-(3-fluoro-4-methoxyphenyl)-N-(prop-2-yn-1-yl)benzenesulfonamide (150 mg, 0.366 mmol), cyclopropanemethanol (0.045 mL, 0.55 mmol), and 1.5 M methyllithium in ethyl ether (0.366 mL, 0.55 mmol).

The title compound I-71, 2-(cyclopropylmethoxy)-3,4,5,6-tetrafluoro-N-(3-fluoro-4-methoxyphenyl)benzenesulfonamide, was prepared via general procedure A-3, using 2-(cyclopropylmethoxy)-3,4,5,6-tetrafluoro-N-(3-fluoro-4-methoxyphenyl)-N-(prop-2-yn-1-yl)benzenesulfonamide (50 mg, 0.108 mmol), trans-dichlorobis(triphenylphosphine) palladium(II) (3 mg, 0.0043 mmol) and triethylamine (0.121 mL, 0.87 mmol).

Example 72 Synthesis of 2,3,4,5-tetrafluoro-N-(3-fluoro-4-methoxyphenyl)-6-(oxetan-3-yloxy)benzenesulfonamide (I-72)

I-72

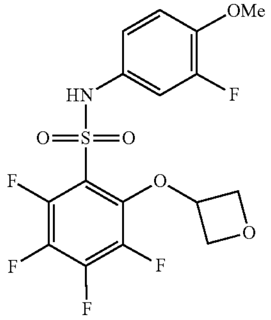

2,3,4,5-tetrafluoro-N-(3-fluoro-4-methoxyphenyl)-6-(oxetan-3-yloxy)-N-(prop-2-yn-1-yl)benzenesulfonamide was prepared via general procedure B-1, using 2,3,4,5,6-pentafluoro-N-(3-fluoro-4-methoxyphenyl)-N-(prop-2-yn-1-yl)benzenesulfonamide (200 mg, 0.489 mmol), oxetan-3-ol (0.064 mL, 0.977 mmol), and 1.5 M methyllithium in ethyl ether (0.611 mL, 0.977 mmol).

The title compound I-72, 2,3,4,5-tetrafluoro-N-(3-fluoro-4-methoxyphenyl)-6-(oxetan-3-yloxy)benzenesulfonamide, was prepared via general procedure A-3, using 2,3,4,5-tetrafluoro-N-(3-fluoro-4-methoxyphenyl)-6-(oxetan-3-yloxy)-N-(prop-2-yn-1-yl)benzenesulfonamide (51 mg, 0.11 mmol), trans-dichlorobis(triphenylphosphine)palladium (II)(8 mg, 0.011 mmol) and triethylamine (0.123 mL, 0.88 mmol).

Example 73 Synthesis of 2,3,4,5-tetrafluoro-N-(3-fluoro-4-methoxyphenyl)-6-(oxetan-3-ylmethoxy)benzenesulfonamide (I-73)

I-73

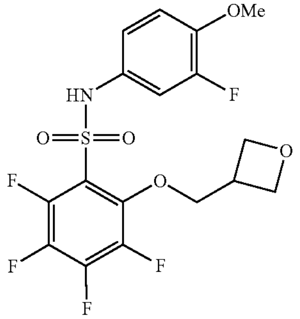

2,3,4,5-tetrafluoro-N-(3-fluoro-4-methoxyphenyl)-6-(oxetan-3-ylmethoxy)-N-(prop-2-yn-1-yl)benzenesulfonamide was prepared via general procedure B-1, using 2,3,4,5,6-pentafluoro-N-(3-fluoro-4-methoxyphenyl)-N-(prop-2-yn-1-yl)benzenesulfonamide (200 mg, 0.489 mmol), 3-oxetanemethanol (0.06 mL, 0.733 mmol), and 1.5 M methyllithium in ethyl ether (0.489 mL, 0.733 mmol).

The title compound I-73, 2,3,4,5-tetrafluoro-N-(3-fluoro-4-methoxyphenyl)-6-(oxetan-3-ylmethoxy)benzenesulfonamide, was prepared via general procedure A-3, using 2,3,4,5-tetrafluoro-N-(3-fluoro-4-methoxyphenyl)-6-(oxetan-3-ylmethoxy)-N-(prop-2-yn-1-yl)benzenesulfonamide (56 mg, 0.12 mmol), trans-dichlorobis(triphenylphosphine)palladium(II) (8 mg, 0.011 mmol) and triethylamine (0.131 mL, 0.94 mmol).

Example 74 Synthesis of 2,3,4,5-tetrafluoro-N-(3-fluoro-4-methoxyphenyl)-6-(neopentyloxy)benzenesulfonamide (I-74)

I-74

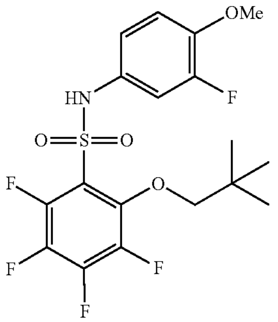

2,3,4,5-tetrafluoro-N-(3-fluoro-4-methoxyphenyl)-6-(neopentyloxy)-N-prop-2-yn-1-yl)benzenesulfonamide was prepared via general procedure B-1, using 2,3,4,5,6-pentafluoro-N-(3-fluoro-4-methoxyphenyl)-N-(prop-2-yn-1-yl)benzenesulfonamide (200 mg, 0.489 mmol), 2,2-dimethyl-1-propanol (0.079 mL, 0.733 mmol), and methyllithium in ethyl ether (0.489 mL, 0.733 mmol).

The title compound I-74, 2,3,4,5-tetrafluoro-N-(3-fluoro-4-methoxyphenyl)-6-(oxetan-3-ylmethoxy)benzenesulfonamide, was prepared via general procedure A-3, using 2,3,4,5-tetrafluoro-N-(3-fluoro-4-methoxyphenyl)-6-(neopentyloxy)-N-(prop-2-yn-1-yl)benzenesulfonamide (110 mg, 0.23 mmol), trans-dichlorobis(triphenylphosphine) palladium(II) (16 mg, 0.023 mmol) and triethylamine (0.257 mL, 1.84 mmol).

Example 75 Synthesis of 2-cyclopropoxy-3,4,5,6-tetrafluoro-N-(3-fluoro-4-methoxyphenyl)benzenesulfonamide (I-75)

I-75

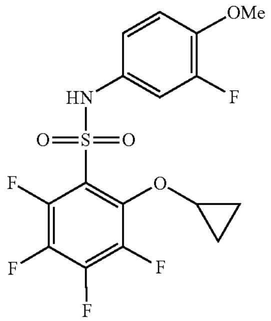

2-cyclopropoxy-3,4,5,6-tetrafluoro-N-(3-fluoro-4-methoxyphenyl)-N-(prop-2-yn-1-yl)benzenesulfonamide was prepared via general procedure B-1 using 2,3,4,5,6-pentafluoro-N-(3-fluoro-4-methoxyphenyl)-N-(prop-2-yn-1-yl)benzenesulfonamide (288 mg, 0.703 mmol), cyclopropanol (0.09 mL, 1.41 mmol) and methyllithium in ethyl ether (0.879 mL, 1.41 mmol). The isolated product was used for subsequent reactions.

The title compound I-75, 2-cyclopropoxy-3,4,5,6-tetrafluoro-N-(3-fluoro-4-methoxyphenyl)benzenesulfonamide, was prepared via general procedure A-3 using 2-cyclopropoxy-3,4,5,6-tetrafluoro-N-(3-fluoro-4-methoxyphenyl)-N-(prop-2-yn-1-yl)benzenesulfonamide (250 mg, 0.559 mmol), trans-dichlorobis(triphenylphosphine)palladium(II) (39.2 mg, 0.0559 mmol) and triethylamine (0.623 mL, 4.47 mmol).

Example 76 Synthesis of 2,3,4,5-tetrafluoro-N-(3-fluoro-4-methoxyphenyl)-6-phenoxybenzenesulfonamide (I-76)

I-76

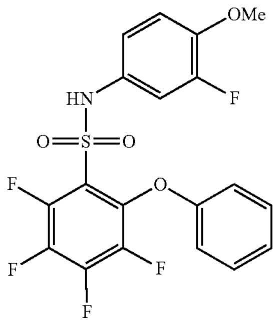

2,3,4,5-tetrafluoro-N-(3-fluoro-4-methoxyphenyl)-6-phenoxy-N-(prop-2-yn-1-yl)benzenesulfonamide was prepared via general procedure B-1 using 2,3,4,5,6-pentafluoro-N-(3-fluoro-4-methoxyphenyl)-N-(prop-2-yn-1-yl)benzenesulfonamide (200 mg, 0.489 mmol), phenol (0.215 mL, 2.44 mmol) and 1.5 M methyllithium in ethyl ether (1.53 mL, 2.44 mmol). The isolated product was used for subsequent reactions.

The title compound I-76, 2,3,4,5-tetrafluoro-N-(3-fluoro-4-methoxyphenyl)-6-phenoxybenzenesulfonamide, was prepared via general procedure A-3 using 2,3,4,5-tetrafluoro-N-(3-fluoro-4-methoxyphenyl)-6-phenoxy-N-(prop-2-yn-1-yl)benzenesulfonamide (75 mg, 0.0155 mmol), trans-dichlorobis(triphenylphosphine)palladium(II) (10.9 mg, 0.0559 mmol) and triethylamine (0.173 mL, 1.24 mmol). $^1$H NMR (400 MHz, Chloroform-d) δ 7.37 (dd, J=8.7, 7.3 Hz, 2H), 7.20 (d, J=7.4 Hz, 1H), 7.01-6.84 (m, 6H), 3.89 (s, 3H). $^{19}$F NMR (376 MHz, Chloroform-d) δ −131.45 (dd, J=11.9, 7.7 Hz), −134.98--135.31 (m), −145.02--145.33 (m), −147.59 (dd, J=20.5, 9.8 Hz), −156.61 (dd, J=23.6, 20.9 Hz).

Example 77 Synthesis of 2,3,4,5-tetrafluoro-N-(3-fluoro-4-methoxyphenyl)-6-(4-hydroxyphenoxy) benzenesulfonamide (I-77)

I-77

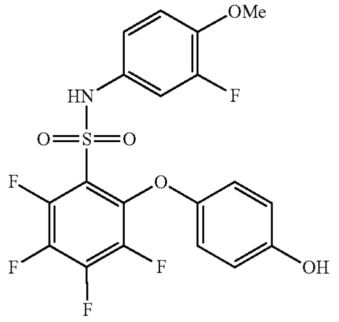

2-(4-(benzyloxy)phenoxy)-3,4,5,6-tetrafluoro-N-(3-fluoro-4-methoxyphenyl)-N-(prop-2-yn-1-yl)benzenesulfonamide was prepared via general procedure B-1 using 2,3,4,5,6-pentafluoro-N-(3-fluoro-4-methoxyphenyl)-N-(prop-2-yn-1-yl)benzenesulfonamide (200 mg, 0.489 mmol), 4-(phenylmethoxy)-phenol (245 mg, 1.22 mmol) and 1.5 M methyllithium in ethyl ether (0.76 mL, 1.22 mmol). The isolated product was used for subsequent reactions.

The title compound I-77, 2,3,4,5-tetrafluoro-N-(3-fluoro-4-methoxyphenyl)-6-(4-hydroxyphenoxy)benzenesulfonamide, was prepared via general procedure A-3 using 2-(4-(benzyloxy)phenoxy)-3,4,5,6-tetrafluoro-N-(3-fluoro-4-methoxyphenyl)-N-(prop-2-yn-1-yl)benzenesulfonamide (112 mg, 0.19 mmol), trans-dichlorobis(triphenylphosphine) palladium(II) (13.3 mg, 0.019 mmol) and triethylamine (0.212 mL, 1.52 mmol). $^1$H NMR (400 MHz, Chloroform-d) δ 7.50-7.32 (m, 5H), 7.05-6.81 (m, 8H), 3.88 (s, 3H). $^{19}$F NMR (376 MHz, Chloroform-d) δ −131.47 (dd, J=11.5, 8.0 Hz), −135.42 (d, J=25.0 Hz), −145.31 (d, J=7.3 Hz), −147.93 (dd, J=20.2, 9.8 Hz), −157.01--157.19 (m).

Example 78 Synthesis of 2,3,4,5-tetrafluoro-6-(3-fluoro-4-methoxyphenoxy)-N-(3-fluoro-4-methoxyphenyl)benzenesulfonamide (I-78)

I-78

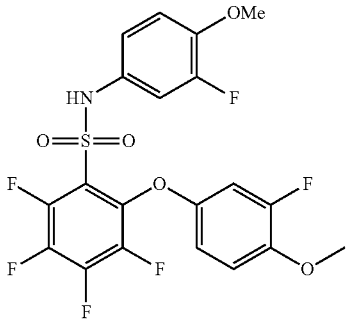

2,3,4,5-tetrafluoro-6-(3-fluoro-4-methoxyphenoxy)-N-(3-fluoro-4-methoxyphenyl)-N-(prop-2-yn-1-yl)benzenesulfonamide was prepared via general procedure B-1 using 2,3,4,5,6-pentafluoro-N-(3-fluoro-4-methoxyphenyl)-N-(prop-2-yn-1-yl)benzenesulfonamide (200 mg, 0.489 mmol), 3-fluoro-4-methoxyphenol (174 mg, 1.22 mmol) and 1.5 M methyllithium in ethyl ether (0.76 mL, 1.22 mmol). The isolated product was used for subsequent reactions.

The title compound I-78, 2,3,4,5-tetrafluoro-6-(3-fluoro-4-methoxyphenoxy)-N-(3-fluoro-4-methoxyphenyl)benzenesulfonamide, was prepared via general procedure A-3 using 2,3,4,5-tetrafluoro-6-(3-fluoro-4-methoxyphenoxy)-N-(3-fluoro-4-methoxyphenyl)-N-(prop-2-yn-1-yl)benzenesulfonamide (120 mg, 0.226 mmol), trans-dichlorobis(triphenylphosphine)palladium(II) (15.8 mg, 0.0226 mmol) and triethylamine (0.252 mL, 1.81 mmol). $^1$H NMR (400 MHz, Chloroform-d) δ 7.01-6.84 (m, 5H), 6.76 (dd, J=11.4, 3.0 Hz, 1H), 6.67 (dt, J=9.0, 2.3 Hz, 1H), 3.89 (d, J=3.4 Hz, 6H). $^{19}$F NMR (376 MHz, Chloroform-d) δ −130.25--130.84 (m), −131.38 (dd, J=11.6, 6.8 Hz), −134.68--135.34 (m), −144.71--145.00 (m), −147.88 (dd, J=20.6, 9.7 Hz), −156.22 (dd, J=23.8, 20.8 Hz).

Example 79 Synthesis of 2,3,4,5-tetrafluoro-N-(3-fluoro-4-methoxyphenyl)-6-(4-methoxyphenoxy) benzenesulfonamide (I-79)

I-79

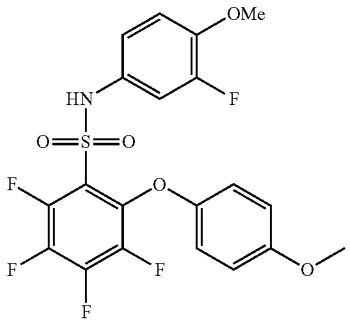

2,3,4,5-tetrafluoro-N-(3-fluoro-4-methoxyphenyl)-6-(4-methoxyphenoxy)-N-(prop-2-yn-1-yl)benzenesulfonamide was prepared via general procedure B-1 using 2,3,4,5,6- pentafluoro-N-(3-fluoro-4-methoxyphenyl)-N-(prop-2-yn-1-yl)benzenesulfonamide (200 mg, 0.489 mmol), 4-methoxyphenol (152 mg, 1.22 mmol) and methyllithium in ethyl ether (0.76 mL, 1.22 mmol). The isolated product was used for subsequent reactions.

The title compound I-79, 2,3,4,5-tetrafluoro-N-(3-fluoro-4-methoxyphenyl)-6-(4-methoxyphenoxy)benzenesulfonamide, was prepared via general procedure A-3 using 2,3,4,5-tetrafluoro-N-(3-fluoro-4-methoxyphenyl)-6-(4-methoxyphenoxy)-N-(prop-2-yn-1-yl)benzenesulfonamide (110 mg, 0.214 mmol), trans-dichlorobis(triphenylphosphine)palladium(II) (15 mg, 0.0214 mmol) and triethylamine (0.239 mL, 1.71 mmol). 1H NMR (400 MHz, Chloroform-d) δ 6.95 (ddd, J=26.5, 19.4, 8.3 Hz, 9H), 3.90 (s, 3H), 3.84 (s, 3H). $^{19}$F NMR (376 MHz, Chloroform-d) δ −131.49 (d, J=10.5 Hz), −135.44, −145.36, −148.01, −157.17 (t, J=22.5 Hz).

Example 80 Synthesis of 2,3,4,5-tetrafluoro-N-(3-fluoro-4-methoxyphenyl)-6-(4-fluorophenoxy)benzenesulfonamide (I-80)

I-80

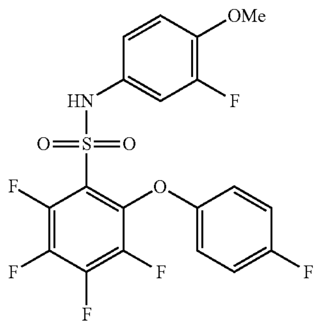

2,3,4,5-tetrafluoro-N-(3-fluoro-4-methoxyphenyl)-6-(4-fluorophenoxy)-N-(prop-2-yn-1-yl)benzenesulfonamide was prepared via general procedure B-1 using 2,3,4,5,6-pentafluoro-N-(3-fluoro-4-methoxyphenyl)-N-(prop-2-yn-1-yl)benzenesulfonamide (100 mg, 0.244 mmol), 4-fluorophenol (0.056 mL, 0.611 mmol) and methyllithium in ethyl ether (0.382 mL, 0.611 mmol) and 1,2-dichloroethane as the solvent. The isolated product was used for subsequent reactions.

The title compound I-80, 2,3,4,5-tetrafluoro-N-(3-fluoro-4-methoxyphenyl)-6-(4-fluorophenoxy)benzenesulfonamide, was prepared via general procedure A-3 using 2,3,4,5-tetrafluoro-N-(3-fluoro-4-methoxyphenyl)-6-(4-fluorophenoxy)-N-(prop-2-yn-1-yl)benzenesulfonamide (170 mg, 0.339 mmol), trans-dichlorobis(triphenylphosphine)palladium(II) (23.8 mg, 0.0339 mmol) and triethylamine (0.378 mL, 2.71 mmol). $^{1}$H NMR (400 MHz, Chloroform-d) δ 7.06-6.96 (m, 3H), 6.95-6.84 (m, 4H), 3.88 (s, 3H). $^{19}$F NMR (376 MHz, Chloroform-d) δ −118.60 (dt, J=7.8, 3.9 Hz), −131.53 (dd, J=11.7, 8.5 Hz), −135.05 (ddd, J=23.6, 9.6, 7.2 Hz), −144.82-−145.56 (m), −147.96 (dd, J=20.5, 9.8 Hz), −156.15-−156.72 (m).

Example 81 Synthesis of 2-(benzyloxy)-3,4,5,6-tetrafluoro-N,N-bis(4-methoxybenzyl)benzenesulfonamide (I-81)

I-81

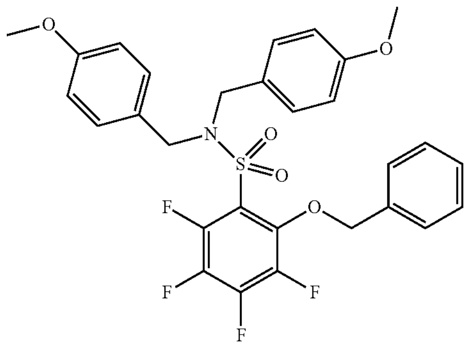

2,3,4,5,6-pentafluoro-N,N-bis(4-methoxybenzyl)benzenesulfonamide was prepared via General Procedure A-1 using pentafluorobenzenesulfonyl chloride (5 g, 18.8 mmol), Bis-(4-methoxybenzyl)amine (4.39 g, 17.1 mmol) and triethylamine (3.56 mL, 25.6 mmol). The title compound I-81 was isolated as a beige solid. The title compound I-81, 2-(benzyloxy)-3,4,5,6-tetrafluoro-N,N-bis(4-methoxybenzyl)benzenesulfonamide, was prepared via General Procedure B-1 using 2,3,4,5,6-pentafluoro-N,N-bis(4-methoxybenzyl)benzenesulfonamide (5 g, 10.3 mmol), benzyl alcohol (1.59 mL, 15.4 mmol), 1.5 M methyllithium solution in ethyl ether (10.3 mL). The title compound I-81 was isolated as viscous oil.

Example 82 Synthesis of 2,3,4,5-tetrafluoro-6-hydroxy-N,N-bis(4-methoxybenzyl)benzenesulfonamide (I-82)

I-82

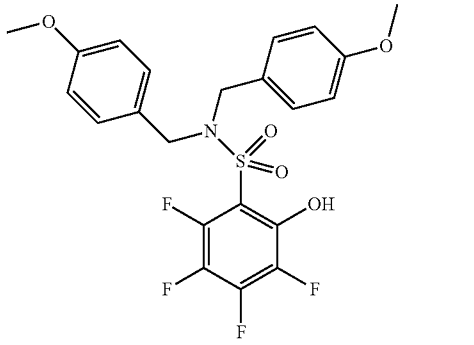

2-(benzyloxy)-3,4,5,6-tetrafluoro-N,N-bis(4-methoxybenzyl)benzenesulfonamide (3 g, 4.72 mmol) was added with methanol (20 mL) and tetrahydrofuran (40 mL). The resulting solution was added with palladium 10% on carbon (0.753 mg) and stirred under hydrogen for 2 hours. The reaction mixture was filtered through a pad of Celite, and the collected organic layer was concentrated in vacuo. The title compound I-82 was isolated as beige solid.

Example 83 Synthesis of 2,3,4,5-tetrafluoro-N-(3-fluoro-4-methoxyphenyl)-6-(fluoromethoxy)benzenesulfonamide (I-83)

I-83

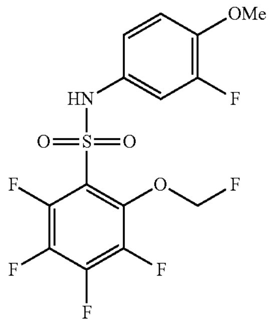

2,3,4,5-tetrafluoro-6-hydroxy-N,N-bis(4-methoxybenzyl) benzenesulfonamide was prepared as described in Example 82. 2,3,4,5-tetrafluoro-6-hydroxy-N,N-bis(4-methoxybenzyl)benzenesulfonamide (200 mg, 0.412 mmol) was dissolved in acetonitrile (4.1 mL). The resulting solution was stirred at room temperature. After 10 minutes, the solution was added with cesium carbonate (268 mg, 0.822 mmol), and the resulting solution was stirred at room temperature. After 10 minutes, the solution was added with S-monofluoromethyl-S-phenyl-2,3,4,5-tetramethylphenylsulfonium tetrafluoroborate (164 mg, 0.452 mmol). The reaction was stirred at room temperature for 3 hours. The reaction was quenched with water and extracted thrice with dichloromethane. The combined organic layer was washed once with saturated sodium chloride solution, dried with sodium sulfate, and concentrated in vacuo. The crude sample was absorbed onto silica gel and purified using flash chromatography using a Hexane:Ethyl acetate gradient. The desired product, 2,3,4,5-tetrafluoro-6-(fluoromethoxy)-N,N-bis(4-methoxybenzyl)benzenesulfonamide, was isolated as beige solid and used for subsequent reactions.

2,3,4,5-tetrafluoro-6-(fluoromethoxy)benzenesulfonamide was prepared via general procedure H using 2,3,4,5-tetrafluoro-6-(fluoromethoxy)-N,N-bis(4-methoxybenzyl) benzenesulfonamide (220 mg, 0.425 mmol) and anisole (0.139 mL, 1.28 mmol). The isolated product was used for subsequent reaction.

The title compound I-83, 2,3,4,5-tetrafluoro-N-(3-fluoro-4-methoxyphenyl)-6-(fluoromethoxy)benzenesulfonamide, was prepared via general procedure I using 2,3,4,5-tetrafluoro-6-(fluoromethoxy)benzenesulfonamide (81 mg, 0.292 mmol), 3-fluoro-4-methoxyphenylboronic acid (74.5 mg, 0.438 mmol), copper(I)$_2$-thiophenecarboxylate (23.5 mg, 0.117 mmol) and triethylamine (0.041 mL, 0.292 mmol).

Example 84 Synthesis of 2,3,4,5-tetrafluoro-N-(3-fluoro-4-methoxyphenyl)-6-(trifluoromethoxy)benzenesulfonamide (I-84)

I-84

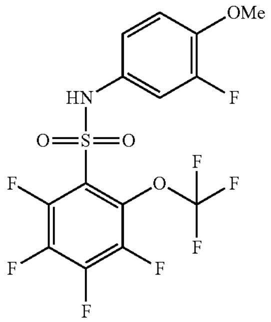

2,3,4,5-tetrafluoro-6-hydroxy-N,N-bis(4-methoxybenzyl) benzenesulfonamide was prepared as described in Example 82. 2,3,4,5-tetrafluoro-6-hydroxy-N,N-bis(4-methoxybenzyl)benzenesulfonamide (270 mg, 0.556 mmol) was added with silver trifluoromethanesulfonate (715 mg, 2.78 mmol), Selectfluor (394 mg, 1.11 mmol), N-fluorobenzenesulfonimide (351 mg, 1.11 mmol), cesium fluoride (507 mg, 3.34 mmol). After two cycles of argon flush, the mixture was diluted in toluene (2.78 mL), and the resulting solution was added with benzotrifluoride (0.068 mL, 0.556 mmol), 2-fluoropyridine (0.96 mL, 11.1 mmol), (trifluoromethyl) trimethylsilane (0.822 mL, 5.56 mmol). After 12 hours, the reaction mixture was filtered through the Celite, washed with dichloromethane. The solution was concentrated in vacuo. The crude sample was absorbed onto silica gel and purified using flash chromatography using a Hexane:Ethyl acetate gradient. The desired product, 2,3,4,5-tetrafluoro-N,N-bis(4-methoxybenzyl)-6-(trifluoromethoxy)benzenesulfonamide, was isolated as beige solid and was used for subsequent reactions.

2,3,4,5-tetrafluoro-6-(fluoromethoxy)benzenesulfonamide was prepared via general procedure H using 2,3,4,5-tetrafluoro-N,N-bis(4-methoxybenzyl)-6-(trifluoromethoxy)benzenesulfonamide (175 mg, 0.316 mmol) and anisole (0.103 mL, 0.949 mmol). The desired product was used for subsequent reactions.

The title compound I-84, 2,3,4,5-tetrafluoro-N-(3-fluoro-4-methoxyphenyl)-6-(trifluoromethoxy)benzenesulfonamide, was prepared via general procedure I using 2,3,4,5-tetrafluoro-6-(trifluoromethoxy)benzenesulfonamide (60 mg, 0.192 mmol), 3-fluoro-4-methoxyphenylboronic acid (48.8 mg, 0.287 mmol), copper(I)$_2$-thiophenecarboxylate (15.4 mg, 0.0766 mmol) and triethylamine (0.027 mL, 0.192 mmol).

Example 85 Synthesis of 2-ethoxy-3,4,5,6-tetrafluoro-N-(3-fluoro-4-methoxyphenyl)benzenesulfonamide (I-85)

I-85

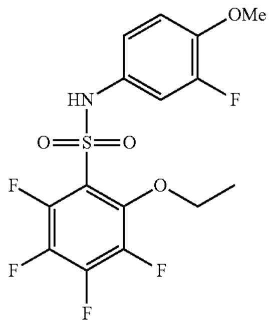

2,3,4,5-tetrafluoro-6-hydroxy-N,N-bis(4-methoxybenzyl) benzenesulfonamide was prepared as described in Example 82. 2-ethoxy-3,4,5,6-tetrafluoro-N,N-bis(4-methoxybenzyl) benzenesulfonamide was prepared via General Procedure C using 2,3,4,5-tetrafluoro-6-hydroxy-N,N-bis(4-methoxybenzyl)benzenesulfonamide (120 mg, 0.247 mmol), bromoethane (0.037 mL, 0.494 mmol) and potassium carbonate (37.6 mg, 0.27 mmol). The desired product, 2-ethoxy-3,4,5,6-tetrafluoro-N,N-bis(4-methoxybenzyl)benzenesulfonamide, was isolated as beige solid and used for subsequent reactions. 2-ethoxy-3,4,5,6-tetrafluorobenzenesulfonamide was prepared via general procedure H using 2-ethoxy-3,4,5,6-tetrafluoro-N,N-bis(4-methoxybenzyl)benzenesulfonamide (118 mg, 0.23 mmol) and anisole (0.075 mL, 0.69 mmol). The isolated product was used for subsequent reactions.

2-ethoxy-3,4,5,6-tetrafluorobenzenesulfonamide (21 mg, 0.077 mmol) was dissolved in acetonitrile (0.5 mL), and the resulting solution was stirred at room temperature. After 5 minutes, the solution was added with copper(I) iodide (1.5 mg, 0.0077 mmol), 4-bromo-2-fluoroanisole (32 mg, 0.154 mmol), potassium carbonate (32 mg, 0.231 mmol) and N,N'-dimethylethylenediamine (0.004 mL, 0.0384 mmol). The resulting solution was stirred at 90° C. After 12 hours, the reaction was quenched with saturated ammonium chloride solution and extracted thrice with ethyl acetate. The combined organic layer was dried over sodium sulfate, filtered and concentrated in vacuo. The crude sample was absorbed onto silica gel and purified using flash chromatography using a Hexane:Ethyl acetate gradient. The isolated product was further purified using preparative HPLC using a water (+0.1% v/v formic acid):acetonitrile (+0.1% v/v formic acid) gradient. The title compound I-85 was isolated as solid and was lyophilized from water/acetonitrile to afford a white powder.

Example 86 Synthesis of 2,3,4,5-tetrafluoro-N-(3-fluoro-4-methoxyphenyl)-6-(methylamino)benzenesulfonamide (I-86)

I-86

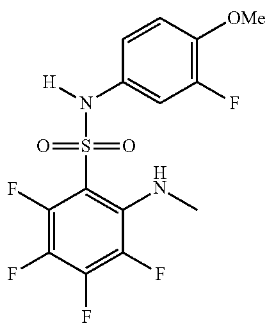

The title compound I-86, 2,3,4,5-tetrafluoro-N-(3-fluoro-4-methoxyphenyl)-6-(methylamino)benzenesulfonamide, was prepared via general procedure B-2 using 2,3,4,5,6-pentafluoro-N-(3-fluoro-4-methoxyphenyl)benzenesulfonamide (99.9 mg, 0.269 mmol), 2 M methylamine in tetrahydrofuran (0.336 mL, 0.673 mmol) and 1.6 M n-butyllithium in hexane (0.237 mL, 0.592 mmol). $^1H$ NMR (400 MHz, $CDCl_3$) δ 6.99 (dd, J=11.5, 2.5 Hz, 1H), 6.90 (t, J=9.0 Hz, 1H), 6.85-6.78 (m, 1H), 6.74 (s, 1H), 6.45 (s, 1H), 3.89 (s, 3H), 3.00 (dd, J=7.0, 5.0 Hz, 3H). $^{19}F$ NMR (376 MHz, $CDCl_3$) δ −131.47 (1F), −137.10 (1F), −147.39 (1F), −155.41 (1F), −172.20 (1F). LRMS (ESI−) m/z calc'd for $C_{14}H_{10}F_5SO_3N^-$ $[M-H]^-$ 381.04, found 381.40.

Example 87 Synthesis of 2,3,4,5-tetrafluoro-N-(3-fluoro-4-methoxyphenyl)-6-((4-methoxybenzyl)amino)benzenesulfonamide (I-87)

I-87

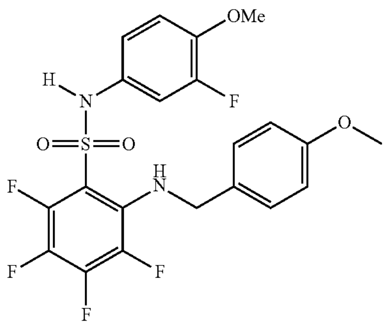

2,3,4,5-tetrafluoro-N-(3-fluoro-4-methoxyphenyl)-6-((4-methoxybenzyl)amino)-N-(prop-2-yn-1-yl)benzenesulfonamide was prepared via general procedure B-2, using 2,3,4,5,6-pentafluoro-N-(3-fluoro-4-methoxyphenyl)-N-(prop-2-yn-1-yl)benzenesulfonamide (200 mg, 0.489 mmol), 4-methoxybenzylamine (0.099 mL, 0.733 mmol), and 1.6 M n-butyllithium in hexane (0.274 mL, 0.685 mmol). The isolated product was used for subsequent reactions.

The title compound I-87, 2,3,4,5-tetrafluoro-N-(3-fluoro-4-methoxyphenyl)-6-((4-methoxybenzyl)amino)benzenesulfonamide, was prepared via general procedure A-3, using 2,3,4,5-tetrafluoro-N-(3-fluoro-4-methoxyphenyl)-6-((4- methoxybenzyl)amino)-N-(prop-2-yn-1-yl)benzenesulfonamide (140 mg, 0.265 mmol), trans-dichlorobis(triphenylphosphine)palladium(II) (18 mg, 0.027 mmol) and triethylamine (0.295 mL, 2.12 mmol). $^1$H NMR (400 MHz, $CDCl_3$) δ 7.14-7.07 (m, 2H), 6.97 (dd, J=11.5, 2.5 Hz, 1H), 6.91-6.81 (m, 4H), 6.81-6.72 (m, 2H), 4.42 (dd, J=6.0, 4.0 Hz, 2H), 3.90 (s, 3H), 3.82 (s, 3H). $^{19}$F NMR (376 MHz, $CDCl_3$) δ −131.38 (1F), −136.49 (1F), −147.13 (1F), −152.58 (1F), −170.95 (1F). LRMS (ESI−) m/z calc'd for $C_{21}H_{16}F_5SO_4N_2^-$ [M−H]$^-$ 487.08, found 487.36.

Example 88 Synthesis of 2-amino-3,4,5,6-tetrafluoro-N-(3-fluoro-4-methoxyphenyl)benzenesulfonamide (I-88)

I-88

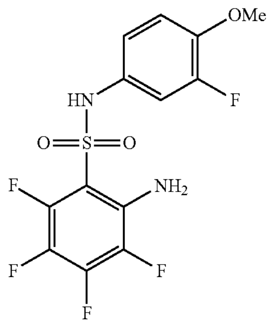

2,3,4,5-tetrafluoro-N-(3-fluoro-4-methoxyphenyl)-6-((4-methoxybenzyl)amino)benzenesulfonamide (6.98 mg, 0.0143 mmol) was dissolved in dichloromethane (0.029 mL) and the resulting solution was stirred at 25° C. for 5 minutes. The solution was added with trifluoroacetic acid (0.286 mL) dropwise and was stirred at room temperature. After 12 hours, the reaction mixture was concentrated in vacuo. The mixture was then re-dissolved in dichloromethane, washed thrice with saturated sodium bicarbonate solution. The collected organic layer was washed with saturated sodium chloride solution, dried over sodium sulfate, filtered and concentrated in vacuo. The crude sample was absorbed onto silica gel and purified using flash chromatography using a Hexane:Ethyl acetate gradient. The title compound I-88 was isolated as solid and was lyophilized from water/acetonitrile to afford a white powder. $^1$H NMR (400 MHz, $CDCl_3$) δ 7.00 (dd, J=11.5, 2.5 Hz, 1H), 6.92-6.82 (m, 2H), 6.77 (s, 1H), 5.40 (s, 2H), 3.88 (s, 3H). $^{19}$F NMR (376 MHz, $CDCl_3$) δ −131.49 (1F), −138.63 (1F), −148.34 (1F), −159.41 (1F), −172.59 (1F). LRMS (ESI−) m/z calc'd for $C_{13}H_8F_5SO_3N_2^-$ [M−H]$^-$ 367.03, found 367.38.

Example 89 Synthesis of 2-allyl-3,4,5,6-tetrafluoro-N-(3-fluoro-4-methoxyphenyl)benzenesulfonamide (I-89)

I-89

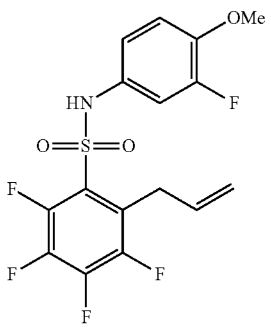

The title compound I-89, 2-allyl-3, 4,5,6-tetrafluoro-N-(3-fluoro-4-methoxyphenyl)benzenesulfonamide, was prepared via general procedure E, using 2,3,4,5-tetrafluoro-N-(3-fluoro-4-methoxyphenyl)benzenesulfonamide (50 mg, 0.142 mmol), allyl bromide (0.0612 mL, 0.708 mmol), and 1.6 M n-butyllithium in hexane (0.142 mL, 0.354 mmol). $^1$H NMR (400 MHz, $CDCl_3$) δ 3.81 (ddd, J=5.9, 3.5, 1.6 Hz, 2H), 3.87 (s, 3H), 4.86-5.04 (m, 2H), 5.72-5.84 (m, 1H), 6.83-6.91 (m, 3H), 6.97-7.02 (m, 1H). $^{19}$F NMR (376 MHz, $CDCl_3$) δ −154.94 (ddd, J=23.6, 20.5, 3.9 Hz), −146.27 (td, J=20.9, 8.7 Hz), −137.77−−136.80 (m), −133.89 (ddd, J=23.2, 11.0, 8.7 Hz), −131.64 (dd, J=11.7, 7.3 Hz).

Example 90 Synthesis of 2,3,4,5-tetrafluoro-N-(3-fluoro-4-methoxyphenyl)-6-(2,2,2-trifluoroacetyl) benzenesulfonamide (I-90)

I-90

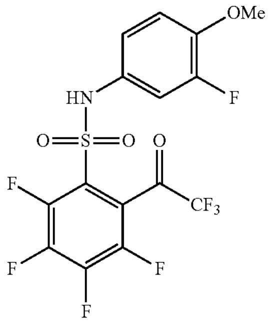

The title compound I-90, 2,3,4,5-tetrafluoro-N-(3-fluoro-4-methoxyphenyl)-6-(2,2,2-trifluoroacetyl)benzenesulfonamide, was prepared via general procedure E, using 2,3,4,5-tetrafluoro-N-(3-fluoro-4-methoxyphenyl) benzenesulfonamide (50 mg, 0.142 mmol), trifluoroacetic anhydride (0.098 mL, 0.708 mmol), and n-butyllithium in hexane (0.142 mL, 0.354 mmol). $^1$H NMR (400 MHz, $CDCl_3$) δ 3.97 (s, 2H), 4.90 (s, OH), 7.08 (t, J=8.8 Hz, 1H), 7.21-7.28 (m, 1H). $^{19}$F NMR (376 MHz, $CDCl_3$) δ −143.91 (ddd, J=21.7, 18.3, 9.0 Hz), −142.11 (td, J=19.2, 7.9 Hz), −137.23 (ddd, J=21.6, 15.9, 8.0 Hz), −132.41−−131.87 (m), −131.46 (t, J=10.0 Hz), −77.97 (d, J=21.7 Hz).

Example 91 Synthesis of benzyl 2,3,4,5-tetrafluoro-6-(N-(3-fluoro-4-methoxyphenyl)sulfamoyl)benzoate (I-91)

I-91

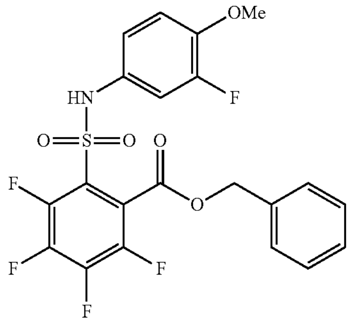

2,3,4,5-Tetrafluoro-N,N-bis(4-methoxybenzyl)benzenesulfonamide was prepared via general procedure D using 2,3,4,5-tetrafluorobenzenesulfonic acid (5 g, 21.7), oxalyl chloride (3.68 mL, 43.5 mmol), 2,3,4,5-tetrafluoro-N-(3-fluoro-4-methoxyphenyl)benzenesulfonamide (6.9 g, 26.8 mmol) and triethylamine (3.33 mL, 23.9 mmol). The isolated product was used for subsequent reactions.

Benzyl 2-(N,N-bis(4-methoxybenzyl)sulfamoyl)-3,4,5,6-tetrafluorobenzoate was prepared via general procedure E using 2,3,4,5-Tetrafluoro-N,N-bis(4-methoxybenzyl)benzenesulfonamide (0.1 g, 0.189 mmol), 2 M n-butyllithium in tetrahydrofuran (0.113 mL) and benzyl chloroformate (30-35% in toluene)(0.135 mL, 0.944 mmol). The desired compound was isolated as beige solid. The isolated product was used for subsequent reactions.

Benzyl 2,3,4,5-tetrafluoro-6-sulfamoylbenzoate was prepared via general procedure H, using benzyl 2-(N,N-bis(4-methoxybenzyl)sulfamoyl)-3,4,5,6-tetrafluorobenzoate (55 mg, 0.0829 mmol) and anisole (0.027 mL, 0.25 mmol). The isolated product was used for subsequent reactions.

The title compound I-91, benzyl 2,3,4,5-tetrafluoro-6-(N-(3-fluoro-4-methoxyphenyl)sulfamoyl)benzoate, was prepared via general procedure E using benzyl 2,3,4,5-tetrafluoro-6-sulfamoylbenzoate (30 mg, 0.0826 mmol), 3-fluoro-4-methoxyphenylboronic acid (21.1 mg, 0.124 mmol), copper(I)$_2$-thiophenecarboxylate (6.63 mg, 0.033 mmol) and triethylamine (0.0115 mL, 0.0826 mmol). $^1$H NMR (400 MHz, $CDCl_3$) δ 3.86 (s, 3H), 5.45 (s, 2H), 6.76-6.90 (m, 1H), 6.94 (dd, J=11.5, 2.5 Hz, 1H), 7.34-7.52 (m, 5H). $^{19}$F NMR (376 MHz, $CDCl_3$) δ −148.83−−148.23 (m), −143.97−−143.35 (m), −136.53 (ddd, J=21.7, 12.1, 5.7 Hz), −131.92 (dt, J=22.5, 11.2 Hz), −131.58 (dd, J=11.5, 8.8 Hz).

Example 92 Synthesis of 2,3,4,5-tetrafluoro-6-(N-(3-fluoro-4-methoxyphenyl)sulfamoyl)benzoic acid (I-92)

I-92

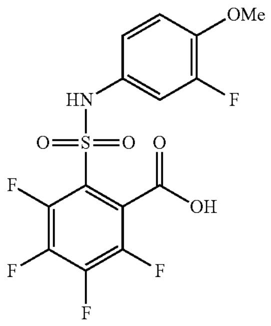

Benzyl 2-(N-((benzyloxy)carbonyl)-N-(3-fluoro-4-methoxyphenyl)sulfamoyl)-3,4,5,6-tetrafluorobenzoate was prepared via general procedure E, using 2,3,4,5-tetrafluoro-N-(3-fluoro-4-methoxyphenyl)benzenesulfonamide (50 mg, 0.142 mmol), benzyl chloroformate (0.101 mL, 0.708 mmol), and n-butyllithium in hexane (0.142 mL, 0.354 mmol). The isolated product was used for subsequent reactions.

Benzyl 2-(N-((benzyloxy)carbonyl)-N-(3-fluoro-4-methoxyphenyl)sulfamoyl)-3,4,5,6-tetrafluorobenzoate (30.5 mg, 0.0491 mmol) was added with methanol (0.2 mL) and tetrahydrofuran (0.4 mL). The resulting solution was added with palladium 10% on carbon (5.22 mg) and stirred under hydrogen for 2 hours. The reaction mixture was filtered through a pad of Celite, and the collected organic layer was concentrated in vacuo. The title compound I-92 was isolated as beige solid and was lyophilized from water/acetonitrile to afford a white powder. $^1$H NMR (400 MHz, Methanol-d$_4$) δ 3.83 (s, 2H), 6.92 (ddd, J=8.8, 2.6, 1.3 Hz, 1H), 6.98 (d, J=9.0 Hz, 1H), 7.01-7.07 (m, 1H). $^{19}$F NMR (376 MHz, Methanol-d$_4$) δ −155.00 (t, J=21.2 Hz), −148.28 (td, J=20.3, 9.7 Hz), −142.75−−141.86 (m), −135.49 (dt, J=21.4, 10.6 Hz), −134.77 (dd, J=12.4, 9.0 Hz).

Example 93 Synthesis of 2,3,4,5-tetrafluoro-N-(3-fluoro-4-methoxyphenyl)benzenesulfonamide (I-93)

I-93

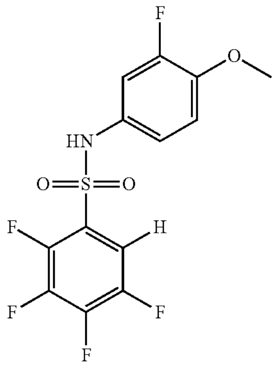

The title compound I-93, 2,3,4,5-tetrafluoro-N-(3-fluoro-4-methoxyphenyl)benzenesulfonamide, was prepared via General Procedure F using 2,3,4,5-tetrafluorobenzenesulfonic acid (1 eq.), oxalyl chloride (1.5 eq.), 3-fluoro-4-methoxyaniline (1 eq.) and triethylamine (3 eq.). The title compound I-93 was isolated as beige solid and was lyophilized from water/acetonitrile to afford a white powder.

Example 94 Synthesis of 2-cyclopropoxy-3,4,5,6-tetrafluoro-N-(3-fluoro-4-hydroxyphenyl)benzenesulfonamide (I-94)

I-94

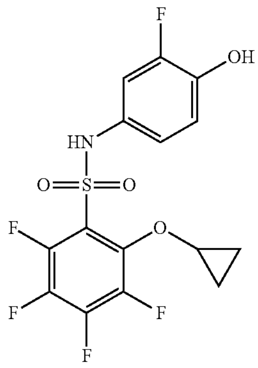

2-cyclopropoxy-3,4,5,6-tetrafluoro-N,N-bis(4-methoxybenzyl)benzenesulfonamide was prepared using general procedure B-1, using 2,3,4,5,6-pentafluoro-N,N-bis(4-methoxybenzyl)benzenesulfonamide (4 g, 8.21 mmol), cyclopropanol (1.04 mL, 16.4 mmol) and 1.5 M methyllithium in ethyl ether (10.3 mL, 16.4 mmol). The desired product was used for subsequent reactions.

2-cyclopropoxy-3,4,5,6-tetrafluorobenzenesulfonamide was prepared via general procedure H, using 2-cyclopropoxy-3,4,5,6-tetrafluoro-N,N-bis(4-methoxybenzyl)benzenesulfonamide (2.6 g, 4.95 mmol) and anisole (1.61 mL, 14.8 mmol). The desired product was used for subsequent reactions.

N-(4-(benzyloxy)-3-fluorophenyl)-2-cyclopropoxy-3,4,5,6-tetrafluorobenzenesulfonamide was prepared via general procedure I using 2-cyclopropoxy-3,4,5,6-tetrafluorobenzenesulfonamide (40 mg, 0.162 mmol), 4-benzyloxy-3-fluorophenylboronic acid (79.6 mg, 0.324 mmol), copper(I)$_2$-thiophenecarboxylate (13 mg, 0.064 mmol) and triethylamine (0.023 mL, 0.162 mmol). The desired product was used for subsequent reactions.

N-(4-(benzyloxy)-3-fluorophenyl)-2-cyclopropoxy-3,4,5,6-tetrafluorobenzenesulfonamide (57 mg, 0.117 mmol) was added with methanol (0.5 mL, 0.23 M) and tetrahydrofuran (1 mL, 0.11 M). The resulting solution was added with palladium 10% on carbon (19 mg) and stirred under hydrogen for 2 hours. The reaction mixture was filtered through a pad of Celite, and the collected organic layer was concentrated in vacuo. The title compound I-94 was isolated as beige solid and was lyophilized from water/acetonitrile to afford a white powder.

Example 95 Synthesis of 2-cyclopropoxy-3,4,5,6-tetrafluoro-N-phenylbenzenesulfonamide (I-95)

I-95

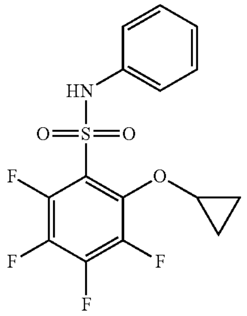

2-cyclopropoxy-3,4,5,6-tetrafluorobenzenesulfonamide was prepared via general procedure H, using 2-cyclopropoxy-3,4,5,6-tetrafluoro-N,N-bis(4-methoxybenzyl)benzenesulfonamide (2.6 g, 4.95 mmol) and anisole (1.61 mL, 14.8 mmol). The desired product was used for subsequent reactions.

2-cyclopropoxy-3,4,5,6-tetrafluoro-N-phenylbenzenesulfonamide was prepared via general procedure I using 2-cyclopropoxy-3,4,5,6-tetrafluorobenzenesulfonamide (30 mg, 0.105 mmol), phenylboronic acid (19.2 mg, 0.158 mmol), copper(I)$_2$-thiophenecarboxylate (8.5 mg, 0.0421 mmol) and triethylamine (0.015 mL, 0.105 mmol). The title compound I-95 was isolated as beige solid and was lyophilized from water/acetonitrile to afford a white powder.

$^1$H NMR (400 MHz, ACN-d$_3$) δ 8.08 (s, 1H), 7.38-7.10 (m, 5H), 4.52 (m, 1H), 1.08-0.98 (m, 2H), 0.80-0.63 (m, 2H). $^{19}$F NMR (376 MHz, ACN-d$_3$) δ −139.09 (1F), −149.60 (1F), −152.65 (1F), −163.60 (1F).

Example 96 Synthesis of 2-cyclopropoxy-3,4,5,6-tetrafluoro-N-(4-fluorophenyl)benzenesulfonamide (I-96)

I-96

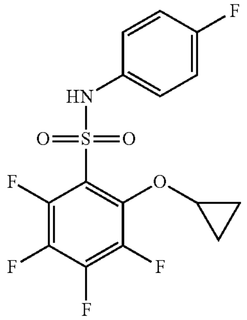

2-cyclopropoxy-3,4,5,6-tetrafluorobenzenesulfonamide was prepared via general procedure H, using 2-cyclopropoxy-3,4,5,6-tetrafluoro-N,N-bis(4-methoxybenzyl)benzenesulfonamide (2.6 g, 4.95 mmol) and anisole (1.61 mL, 14.8 mmol). The desired product was used for subsequent reactions.

2-cyclopropoxy-3,4,5,6-tetrafluoro-N-(4-fluorophenyl) benzenesulfonamide was prepared via general procedure I using 2-cyclopropoxy-3,4,5,6-tetrafluorobenzenesulfonamide, 4-fluoro-phenylboronic acid, copper(I)$_2$-thiophenecarboxylate and triethylamine. The title compound I-96 was isolated as beige solid and was lyophilized from water/acetonitrile to afford a white powder.

Example 97 Synthesis of 2-cyclopropoxy-N-(2,4-difluorophenyl)-3,4,5,6-tetrafluorobenzenesulfonamide (I-97)

I-97

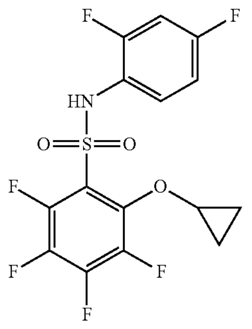

2-cyclopropoxy-3,4,5,6-tetrafluorobenzenesulfonamide was prepared via general procedure H, using 2-cyclopropoxy-3,4,5,6-tetrafluoro-N,N-bis(4-methoxybenzyl)benzenesulfonamide (2.6 g, 4.95 mmol) and anisole (1.61 mL, 14.8 mmol). The desired product was used for subsequent reactions.

2-cyclopropoxy-N-(2,4-difluorophenyl)-3,4,5,6-tetrafluorobenzenesulfonamide was prepared via general procedure I using 2-cyclopropoxy-3,4,5,6-tetrafluorobenzenesulfonamide (30 mg, 0.105 mmol), 2,4-difluorophenylboronic acid (33.2 mg, 0.21 mmol), tetrakis (acetonitrile)copper(I) hexafluorophosphate (19.6 mg, 0.0526 mmol) and triethylamine (0.058 mL, 0.421 mmol). The title compound I-97 was isolated as beige solid and was lyophilized from water/acetonitrile to afford a white powder. $^1$H NMR (400 MHz, ACN-d$_3$)$_\delta$ $_{8.01}$ (s, 1H), 7.37 (td, J=9.0, 6.0 Hz, 1H), 7.06-6.90 (m, 2H), 4.49 (m, 1H), 1.03-0.94 (m, 2H), 0.73-0.66 (m, 2H). $^{19}$F NMR (376 MHz, ACN-d$_3$) δ −112.03 (1F), −112.06 (1F), −139.09 (1F), −149.64 (1F), −152.95 (1F), −163.80 (1F).

Example 98 Synthesis of 2-cyclopropoxy-3,4,5,6-tetrafluoro-N-(2,4,5-trifluorophenyl)benzenesulfonamide (I-98)

I-98

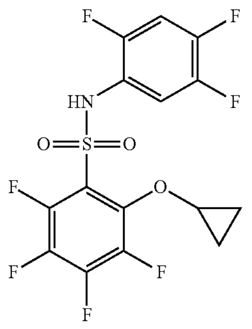

2-cyclopropoxy-3,4,5,6-tetrafluorobenzenesulfonamide was prepared via general procedure H, using 2-cyclopropoxy-3,4,5,6-tetrafluoro-N,N-bis(4-methoxybenzyl)benzenesulfonamide (2.6 g, 4.95 mmol) and anisole (1.61 mL, 14.8 mmol). The desired product was used for subsequent reactions.

2-cyclopropoxy-3,4,5,6-tetrafluoro-N-(2,4,5-trifluorophenyl)benzenesulfonamide was prepared via general procedure I using 2-cyclopropoxy-3,4,5,6-tetrafluorobenzenesulfonamide (30 mg, 0.105 mmol), 2,4,5-trifluorophenylboronic acid (37 mg, 0.21 mmol), tetrakis (acetonitrile)copper(I) hexafluorophosphate (19.6 mg, 0.0526 mmol) and triethylamine (0.058 mL, 0.421 mmol). The title compound I-98 was isolated as beige solid and was lyophilized from water/acetonitrile to afford a white powder. $^1$H NMR (400 MHz, ACN-d$_3$)$_\delta$ $_{8.16}$ (s, 1H), 7.36 (ddd, J=11.0, 8.5, 7.0 Hz, 1H), 7.18 (td, J=10.0, 7.0 Hz, 1H), 4.50 (m, 1H), 1.02-0.93 (m, 2H), 0.75-0.65 (m, 2H). $^{19}$F NMR (376 MHz, ACN-d$_3$) δ −126.27 (1F), −137.28 (1F), −138.91 (1F), −142.60 (1F), −149.52 (1F), −152.91 (1F), −163.71 (1F).

Example 99 Synthesis of N-(3-chlorophenyl)-2-cyclopropoxy-3,4,5,6-tetrafluorobenzenesulfonamide (I-99)

I-99

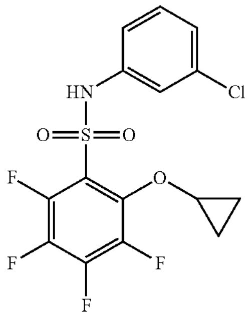

2-cyclopropoxy-3,4,5,6-tetrafluorobenzenesulfonamide was prepared via general procedure H, using 2-cyclopropoxy-3,4,5,6-tetrafluoro-N,N-bis(4-methoxybenzyl)benzenesulfonamide (2.6 g, 4.95 mmol) and anisole (1.61 mL, 14.8 mmol). The desired product was used for subsequent reactions.

N-(3-chlorophenyl)-2-cyclopropoxy-3,4,5,6-tetrafluorobenzenesulfonamide was prepared via general procedure I using 2-cyclopropoxy-3,4,5,6-tetrafluorobenzenesulfonamide (30 mg, 0.105 mmol), 3-chlorophenylboronic acid (24.7 mg, 0.158 mmol), copper(I)$_2$-thiophenecarboxylate (8.5 mg, 0.0421 mmol) and triethylamine (0.058 mL, 0.421 mmol). The title compound I-99 was isolated as beige solid and was lyophilized from water/acetonitrile to afford a white powder. $^1$H NMR (400 MHz, ACN-d$_3$) δ 7.30 (t, J=8.0 Hz, 1H), 7.24-7.17 (m, 2H), 7.11 (dd, J=8.0, 2.0 Hz, 1H), 4.52 (m, 1H), 1.07-0.98 (m, 2H), 0.76-0.68 (m, 2H). $^{19}$F NMR (376 MHz, ACN-d$_3$) δ −139.02 (1F), −149.23 (1F), −152.50 (1F), −163.49 (1F).

Example 100 Synthesis of N-(3-cyanophenyl)-2-cyclopropoxy-3,4,5,6-tetrafluorobenzenesulfonamide (I-100)

I-100

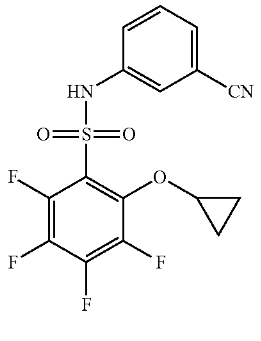

2-cyclopropoxy-3,4,5,6-tetrafluorobenzenesulfonamide was prepared via general procedure H, using 2-cyclopropoxy-3,4,5,6-tetrafluoro-N,N-bis(4-methoxybenzyl)benzenesulfonamide (2.6 g, 4.95 mmol) and anisole (1.61 mL, 14.8 mmol). The desired product was used for subsequent reactions.

N-(3-cyanophenyl)-2-cyclopropoxy-3,4,5,6-tetrafluorobenzenesulfonamide was prepared via general procedure I using 2-cyclopropoxy-3,4,5,6-tetrafluorobenzenesulfonamide (30 mg, 0.105 mmol), 3-chlorophenylboronic acid (24.7 mg, 0.158 mmol), copper$(I)_2$-thiophenecarboxylate (8.5 mg, 0.0421 mmol) and triethylamine (0.015 mL, 0.105 mmol). The title compound I-100 was isolated as beige solid and was lyophilized from water/acetonitrile to afford a white powder. $^1$H NMR (400 MHz, ACN-$d_3$) δ 7.57-7.41 (m, 4H), 4.57-4.47 (m, 1H), 1.01 (tdq, J=4.1, 2.7, 1.3 Hz, 2H), 0.81-0.65 (m, 2H). $^{19}$F NMR (376 MHz, ACN-$d_3$) δ −138.93 (1F), −149.20 (1F), −152.44 (1F), −163.42 (1F).

Example 101 Synthesis of N-(4-cyanophenyl)-2-cyclopropoxy-3,4,5,6-tetrafluorobenzenesulfonamide (I-101)

I-101

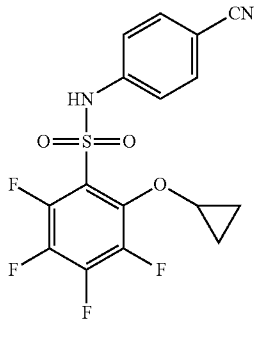

2-cyclopropoxy-3,4,5,6-tetrafluorobenzenesulfonamide was prepared via general procedure H, using 2-cyclopropoxy-3,4,5,6-tetrafluoro-N,N-bis(4-methoxybenzyl)benzenesulfonamide (2.6 g, 4.95 mmol) and anisole (1.61 mL, 14.8 mmol). The desired product was used for subsequent reactions.

N-(4-cyanophenyl)-2-cyclopropoxy-3,4,5,6-tetrafluorobenzenesulfonamide was prepared via general procedure I using 2-cyclopropoxy-3,4,5,6-tetrafluorobenzenesulfonamide (30 mg, 0.105 mmol), 4-cyanophenylboronic acid (30.9 mg, 0.21 mmol), copper$(I)_2$-thiophenecarboxylate (8.5 mg, 0.0421 mmol) and triethylamine (0.015 mL, 0.105 mmol). The title compound I-101 was isolated as beige solid and was lyophilized from water/acetonitrile to afford a white powder. $^1$H NMR (400 MHz, ACN-$d_3$) δ 7.57-7.41 (m, 4H), 4.57-4.47 (m, 1H), 1.01 (tdq, J=4.1, 2.7, 1.3 Hz, 2H), 0.81-0.65 (m, 2H). $^{19}$F NMR (376 MHz, ACN-$d_3$) δ −138.93 (1F), −149.20 (1F), −152.44 (1F), −163.42 (1F).

Example 102 Synthesis of methyl 4-((2-cyclopropoxy-3,4,5,6-tetrafluorophenyl)sulfonamido) benzoate (I-102)

I-102

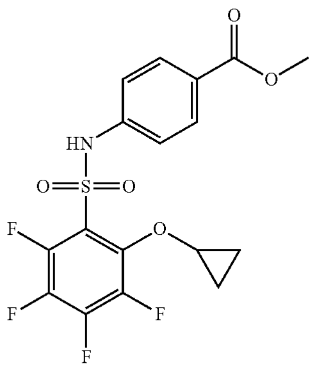

2-cyclopropoxy-3,4,5,6-tetrafluorobenzenesulfonamide was prepared via general procedure H, using 2-cyclopropoxy-3,4,5,6-tetrafluoro-N,N-bis(4-methoxybenzyl)benzenesulfonamide (2.6 g, 4.95 mmol) and anisole (1.61 mL, 14.8 mmol). The desired product was used for subsequent reactions.

methyl 4-((2-cyclopropoxy-3,4,5,6-tetrafluorophenyl) sulfonamido)benzoate was prepared via general procedure I using 2-cyclopropoxy-3,4,5,6-tetrafluorobenzenesulfonamide (30 mg, 0.105 mmol), 4-(Methoxycarbonyl)phenylboronic acid (28.4 mg, 0.158 mmol), copper$(I)_2$-thiophenecarboxylate (8.5 mg, 0.0421 mmol) and triethylamine (0.015 mL, 0.105 mmol). The title compound I-102 was isolated as beige solid and was lyophilized from water/acetonitrile to afford a white powder.

Example 103 Synthesis of 2-cyclopropoxy-3,4,5,6-tetrafluoro-N-(4-phenoxyphenyl)benzenesulfonamide (I-103)

I-103

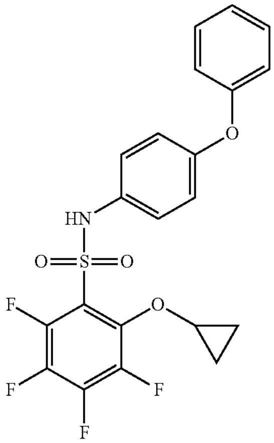

2-cyclopropoxy-3,4,5,6-tetrafluorobenzenesulfonamide was prepared via general procedure H, using 2-cyclopropoxy-3,4,5,6-tetrafluoro-N,N-bis(4-methoxybenzyl)benzenesulfonamide (2.6 g, 4.95 mmol) and anisole (1.61 mL, 14.8 mmol). The desired product was used for subsequent reactions.

2-cyclopropoxy-3,4,5,6-tetrafluoro-N-(4-phenoxyphenyl)benzenesulfonamide was prepared via general procedure I using 2-cyclopropoxy-3,4,5,6-tetrafluorobenzenesulfonamide (30 mg, 0.105 mmol), 4-phenoxyphenylboronic acid (33.8 mg, 0.158 mmol), copper(I)$_2$-thiophenecarboxylate (8.4 mg, 0.0421 mmol) and triethylamine (0.015 mL, 0.105 mmol). The title compound I-103 was isolated as beige solid and was lyophilized from water/acetonitrile to afford a white powder.

Example 104 Synthesis of 2-cyclopropoxy-3,4,5,6-tetrafluoro-N-(naphthalen-1-yl)benzenesulfonamide (I-104)

I-104

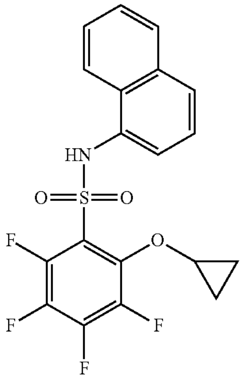

2-cyclopropoxy-3,4,5,6-tetrafluorobenzenesulfonamide was prepared via general procedure H, using 2-cyclopropoxy-3,4,5,6-tetrafluoro-N,N-bis(4-methoxybenzyl)benzenesulfonamide (2.6 g, 4.95 mmol) and anisole (1.61 mL, 14.8 mmol). The desired product was used for subsequent reactions.

2-cyclopropoxy-3,4,5,6-tetrafluoro-N-(4-phenoxyphenyl)benzenesulfonamide was prepared via general procedure I using 2-cyclopropoxy-3,4,5,6-tetrafluorobenzenesulfonamide (30 mg, 0.105 mmol), 1-napthaleneboronic acid (27.1 mg, 0.158 mmol), copper(I)$_2$-thiophenecarboxylate (8.4 mg, 0.0421 mmol) and triethylamine (0.015 mL, 0.105 mmol). The title compound I-104 was isolated as beige solid and was lyophilized from water/acetonitrile to afford a white powder.

Example 105 Synthesis of phenyl 2-(N,N-dimethylsulfamoyl)-3,4,5,6-tetrafluorobenzoate (I-105)

I-105

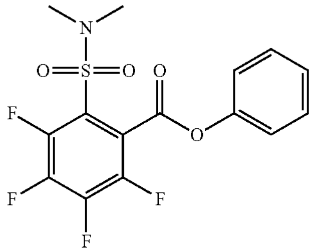

The title compound I-105, phenyl 2-(N,N-dimethylsulfamoyl)-3,4,5,6-tetrafluorobenzoate, was prepared via General Procedure E using 2,3,4,5-tetrafluoro-N,N-dimethylbenzenesulfonamide (1 eq.), 2 M n-butyllithium in tetrahydrofuran (1.5 eq.) and phenyl chloroformate dissolved in tetrahydrofuran (5 eq.). The title compound I-105 was isolated as beige solid and was lyophilized from water/acetonitrile to afford a white powder.

$^1$H NMR (400 MHz, Chloroform-d) δ 2.98 (d, J=2.1 Hz, 7H), 7.30-7.38 (m, 3H), 7.47 (dd, J=8.6, 7.1 Hz, 2H). $^{19}$F NMR (376 MHz, Chloroform-d) δ −149.23 (ddd, J=24.1, 19.8, 4.8 Hz), −145.32–−144.59 (m), −138.14 (ddd, J=21.7, 11.4, 4.8 Hz), −130.80–−130.12 (m).

Example 106 Synthesis of 2,3,4,5-tetrafluoro-6-(4-methoxybenzoyl)-N,N-dimethylbenzenesulfonamide (I-106)

I-106

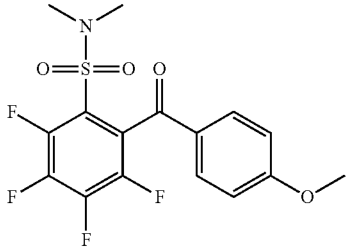

The title compound I-106, 2,3,4,5-tetrafluoro-6-(4-methoxybenzoyl)-N,N-dimethylbenzenesulfonamide, was prepared via General Procedure E using 2,3,4,5-tetrafluoro-N,N-dimethylbenzenesulfonamide (1 eq.), 2 M n-butyllithium in tetrahydrofuran (1.5 eq.) and 4-methoxybenzoyl chloride dissolved in tetrahydrofuran (5 eq.). The title compound I-106 was isolated as beige solid and was lyophilized from water/acetonitrile to afford a white powder. $^1$H NMR (400 MHz, Chloroform-d) δ 2.93 (d, J=2.0 Hz, 6H), 3.90 (s, 3H), 6.92-7.02 (m, 2H), 7.72-7.85 (m, 2H). $^{19}$F NMR (376 MHz, Chloroform-d) δ −150.80 (ddd, J=23.4, 19.9, 4.2 Hz), −145.46 (ddd, J=22.7, 19.9, 9.1 Hz), −137.85 (ddd, J=23.3, 12.1, 4.2 Hz), −131.07--130.10 (m).

Example 107 Synthesis of 2,3,4,5-tetrafluoro-N,N-dimethyl-6-(4-(trifluoromethyl)benzoyl)benzenesulfonamide (I-107)

I-107

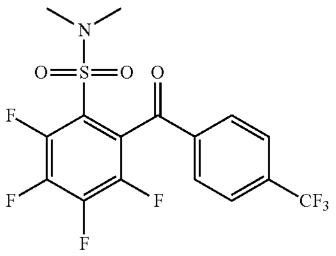

The title compound I-107, 2,3,4,5-tetrafluoro-N,N-dimethyl-6-(4-(trifluoromethyl)benzoyl)benzenesulfonamide, was prepared via General Procedure E using 2,3,4,5-tetrafluoro-N,N-dimethylbenzenesulfonamide (1 eq.), 2 M n-butyllithium in tetrahydrofuran (1.5 eq.) and 4-trifluoromethylbenzoyl chloride dissolved in tetrahydrofuran (5 eq.). The title compound I-107 was isolated as beige solid and was lyophilized from water/acetonitrile to afford a white powder. $^1$H NMR (400 MHz, Chloroform-d) δ 2.94 (d, J=2.0 Hz, 8H), 7.78 (dt, J=8.3, 0.7 Hz, 2H), 7.92-7.95 (m, 2H). $^{19}$F NMR (376 MHz, Chloroform-d) δ −149.42--149.15 (m), −144.63 (ddd, J=23.2, 19.9, 9.5 Hz), −137.93 (ddd, J=22.6, 11.9, 4.7 Hz), −130.16--129.98 (m), −63.27.

Example 108 Synthesis of 2,3,4,5-tetrafluoro-N,N-dimethyl-6-(4-nitrobenzoyl)benzenesulfonamide (I-108)

I-108

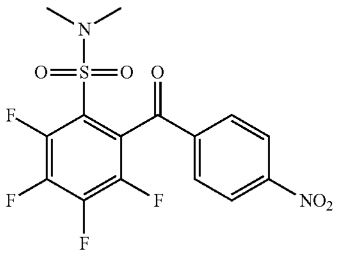

The title compound I-108, 2,3,4,5-tetrafluoro-N,N-dimethyl-6-(4-nitrobenzoyl)benzenesulfonamide, was prepared via General Procedure E using 2,3,4,5-tetrafluoro-N,N-dimethylbenzenesulfonamide (1 eq.), 2 M n-butyllithium in tetrahydrofuran (1.5 eq.) and 4-nitrobenzoyl chloride dissolved in tetrahydrofuran (5 eq.). The title compound I-108 was isolated as beige solid and was lyophilized from water/acetonitrile to afford a white powder. $^1$H NMR (400 MHz, Chloroform-d) δ 2.94 (d, J=1.9 Hz, 3H), 7.82-8.08 (m, 1H), 8.26-8.42 (m, 1H). $^{19}$F NMR (376 MHz, Chloroform-d) δ −148.68 (ddd, J=23.7, 19.3, 4.5 Hz), −144.25 (ddd, J=22.8, 19.6, 9.7 Hz), −137.94 (ddd, J=22.5, 12.0, 4.6 Hz), −129.86 (dt, J=21.8, 10.7 Hz).

Example 109 Synthesis of 2,3,4,5-tetrafluoro-N,N-dimethyl-6-(2,2,2-trifluoro-1-hydroxy-1-phenylethyl)benzenesulfonamide (I-109)

I-109

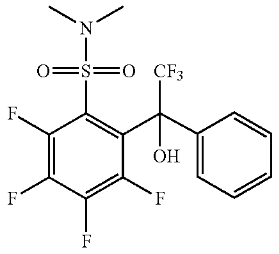

The title compound I-108, 2,3,4,5-tetrafluoro-N,N-dimethyl-6-(2,2,2-trifluoro-1-hydroxy-1-phenylethyl)benzenesulfonamide, was prepared via General Procedure E using 2,3,4,5-tetrafluoro-N,N-dimethylbenzenesulfonamide (1 eq.), 2 M n-butyllithium in tetrahydrofuran (1.5 eq.) and 2,2,2-Trifluoroacetophenone dissolved in tetrahydrofuran (5 eq.). The title compound I-109 was isolated as beige solid and was lyophilized from water/acetonitrile to afford a white powder. $^1$H NMR (400 MHz, Chloroform-d) δ 2.89 (d, J=2.6 Hz, 7H), 7.08 (s, 1H), 7.39 (s, 5H). $^{19}$F NMR (376 MHz, Chloroform-d) δ −150.19 (ddd, J=24.0, 20.7, 8.2 Hz), −145.36 (td, J=21.0, 9.9 Hz), −131.13--130.72 (m), −122.92--121.94 (m), −72.90 (d, J=43.4 Hz).

Example 110 Synthesis of 2,3,4,5-tetrafluoro-6-(furan-2-carbonyl)-N,N-dimethylbenzenesulfonamide (I-110)

I-110

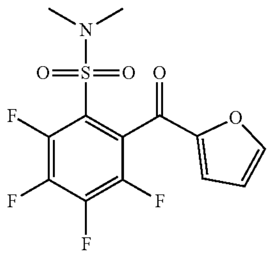

The title compound I-110, 2,3,4,5-tetrafluoro-6-(furan-2-carbonyl)-N,N-dimethylbenzenesulfonamide, was prepared via General Procedure E using 2,3,4,5-tetrafluoro-N,N-dimethylbenzenesulfonamide (1 eq.), 2 M n-butyllithium in tetrahydrofuran (1.5 eq.) and 2-furoyl chloride dissolved in tetrahydrofuran (5 eq.). The title compound I-110 was isolated as beige solid and was lyophilized from water/acetonitrile to afford a white powder. $^1$H NMR (400 MHz, Chloroform-d) δ 2.92 (d, J=2.0 Hz, 6H), 6.43-6.51 (m, 1H), 7.23 (dd, J=11.5, 3.7 Hz, 2H), 7.63-7.65 (m, 1H). $^{19}$F NMR (376 MHz, Chloroform-d) δ −149.86 (ddd, J=23.9, 19.6, 4.6 Hz), −145.44 (ddd, J=22.9, 19.5, 9.2 Hz), −138.26 (ddd, J=22.2, 11.3, 4.3 Hz), −130.62 (dt, J=22.1, 10.5 Hz).

Example 111 Synthesis of 2,3,4,5-tetrafluoro-6-(methoxymethyl)-N,N-dimethylbenzenesulfonamide (I-111)

I-111

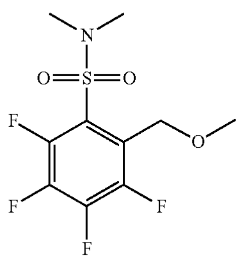

The title compound I-111, 2,3,4,5-tetrafluoro-6-(methoxymethyl)-N,N-dimethylbenzenesulfonamide, was prepared via General Procedure E using 2,3,4,5-tetrafluoro-N,N-dimethylbenzenesulfonamide (1 eq.), 2 M n-butyllithium in tetrahydrofuran (1.5 eq.) and methoxymethyl chloride dissolved in tetrahydrofuran (5 eq.). The title compound I-111 was isolated as beige solid and was lyophilized from water/acetonitrile to afford a white powder. $^{1}H$ NMR (400 MHz, Chloroform-d) δ 2.97 (d, J=2.2 Hz, 5H), 3.45 (s, 3H), 4.88 (d, J=3.6 Hz, 2H). $^{19}F$ NMR (376 MHz, Chloroform-d) δ −152.21 (ddd, J=23.4, 20.4, 5.1 Hz), −147.74 (td, J=21.1, 8.5 Hz), −137.84 (ddt, J=21.7, 11.3, 4.2 Hz), −132.62-−132.34 (m).

Example 112 Synthesis of 2,3,4,5-tetrafluoro-6-(methoxymethyl)-N,N-dimethylbenzenesulfonamide (I-112)

I-112

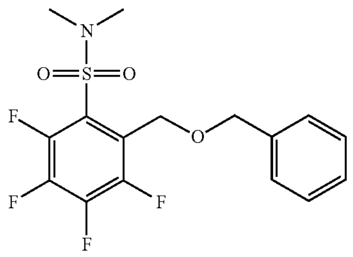

The title compound I-112, 2-((benzyloxy)methyl)-3,4,5,6-tetrafluoro-N,N-dimethylbenzenesulfonamide, was prepared via General Procedure E using 2,3,4,5-tetrafluoro-N,N-dimethylbenzenesulfonamide (1 eq.), 2 M n-butyllithium in tetrahydrofuran (1.5 eq.) and benzyl chloromethyl ether dissolved in tetrahydrofuran (5 eq.). The title compound I-112 was isolated as beige solid and was lyophilized from water/acetonitrile to afford a white powder. $^{1}H$ NMR (400 MHz, Chloroform-d) δ 2.95 (d, J=2.2 Hz, 6H), 4.67 (d, J=1.7 Hz, 3H), 5.01 (d, J=3.5 Hz, 2H), 7.34-7.42 (m, 5H). $^{19}F$ NMR (376 MHz, Chloroform-d) δ −152.47-−152.21 (m), −147.76 (td, J=21.3, 8.5 Hz), −137.52 (ddt, J=20.9, 7.7, 4.3 Hz), −132.69-−132.49 (m).

Example 113 Synthesis of 2,3,4,5-tetrafluoro-6-(hydroxymethyl)-N,N-dimethylbenzenesulfonamide (I-113)

I-113

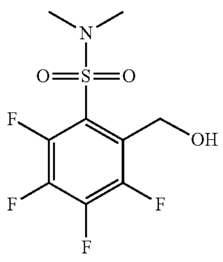

2-((benzyloxy)methyl)-3,4,5,6-tetrafluoro-N,N-dimethylbenzenesulfonamide was added with a mixture of methanol: tetrahydrofuran (2:1, 0.1 M). The resulting solution was added with palladium 10% on carbon (0.05 eq) and stirred under hydrogen for 2 hours. The reaction mixture was filtered through a pad of Celite, and the collected organic layer was concentrated in vacuo. The title compound I-113 was isolated as beige solid and was lyophilized from water/acetonitrile to afford a white powder. $^{1}H$ NMR (400 MHz, Chloroform-d) δ 3.01 (d, J=2.1 Hz, 6H), 4.97 (d, J=3.2 Hz, 2H). $^{19}F$ NMR (376 MHz, Chloroform-d) δ −152.85-−152.31 (m), −146.67-−146.37 (m), −137.85 (ddq, J=22.7, 11.6, 3.6 Hz), −136.01-−135.79 (m).

Example 114 Synthesis of N,N-bis(2,4-dimethoxybenzyl)-2,3,4,5-tetrafluorobenzenesulfonamide (I-114)

I-114

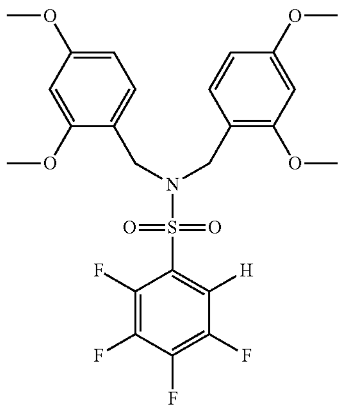

N,N-bis(2,4-dimethoxybenzyl)-2,3,4,5-tetrafluorobenzenesulfonamide was prepared via General Procedure D using 2,3,4,5-tetrafluorobenzenesulfonic acid (1.2 g, 5.21 mmol), Bis-(4-methoxybenzyl)amine (1.65 g, 5.21 mmol) and triethylamine (0.8 mL, 1.1 mmol). The title compound I-114 was isolated as a beige solid. $^{1}H$ NMR (400 MHz, Chloroform-d) δ 3.74 (s, 6H), 3.81 (s, 6H), 4.53 (s, 4H), 6.29 (d, J=2.4 Hz, 2H), 6.44 (dd, J=8.3, 2.4 Hz, 2H), 7.01-7.10 (m, 1H), 7.21 (d, J=8.3 Hz, 2H). $^{19}F$ NMR (376 MHz, Chloroform-d) δ −154.56-−153.75 (m), −149.45 (tt, J=20.2, 7.7 Hz), −139.16-−137.74 (m), −134.90 (ddt, J=20.0, 13.0, 6.6 Hz).

Example 115 Synthesis of benzyl 2-(N,N-bis(2,4-dimethoxybenzyl)sulfamoyl)-3,4,5,6-tetrafluorobenzoate (I-115)

I-115

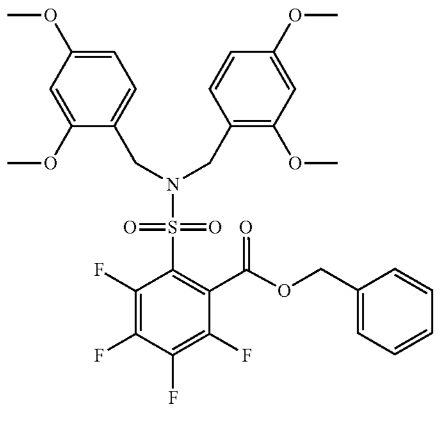

The title compound I-115, benzyl 2-(N,N-bis(2,4-dimethoxybenzyl)sulfamoyl)-3,4,5,6-tetrafluorobenzoate, was prepared via General Procedure E using N,N-bis(2,4-dimethoxybenzyl)-2,3,4,5-tetrafluorobenzenesulfonamide (1 eq.), 2 M n-butyllithium in tetrahydrofuran (1.5 eq.) and benzyl chloroformate dissolved in tetrahydrofuran (5 eq.). The title compound I-115 was isolated as beige solid and was lyophilized from water/acetonitrile to afford a white powder. $^1$H NMR (400 MHz, Chloroform-d) δ 3.73 (s, 6H), 3.79 (s, 6H), 4.55 (s, 4H), 5.43 (s, 2H), 7.07-7.14 (m, 2H), 7.34-7.42 (m, 3H), 7.45-7.49 (m, 2H). $^{19}$F NMR (376 MHz, Chloroform-d) δ −151.75 (ddd, J=23.4, 19.8, 4.2 Hz), −147.98 (td, J=20.6, 8.9 Hz), −139.91 (ddd, J=21.5, 11.0, 4.1 Hz), −132.56 (dt, J=21.5, 10.2 Hz).

Example 116 Synthesis of 2-(N,N-bis(2,4-dimethoxybenzyl)sulfamoyl)-3,4,5,6-tetrafluorobenzoic acid (I-116)

I-116

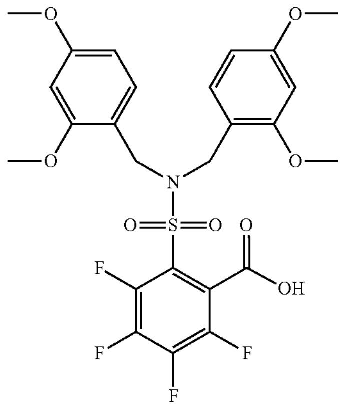

2-(N,N-bis(2,4-dimethoxybenzyl)sulfamoyl)-3,4,5,6-tetrafluorobenzoate was added with a mixture of methanol: tetrahydrofuran (2:1, 0.1 M). The resulting solution was added with palladium 10% on carbon (0.05 eq) and stirred under hydrogen for 2 hours. The reaction mixture was filtered through a pad of Celite, and the collected organic layer was concentrated in vacuo. The title compound I-116 was isolated as beige solid and was lyophilized from water/acetonitrile to afford a white powder. $^1$H NMR (400 MHz, Chloroform-d) δ 3.72 (s, 5H), 3.78 (s, 6H), 4.55 (s, 4H), 6.31-6.40 (m, 3H), 7.06-7.15 (m, 2H). $^{19}$F NMR (376 MHz, Chloroform-d) δ −153.18--151.61 (m), −147.91 (td, J=20.9, 8.8 Hz), −140.43--139.30 (m), −132.75 (dq, J=21.2, 9.9, 8.9 Hz).

Example 117 Synthesis of 2-(N,N-bis(2,4-dimethoxybenzyl)sulfamoyl)-3,4,5,6-tetrafluoro-N,N-dimethylbenzamide (I-117)

I-117

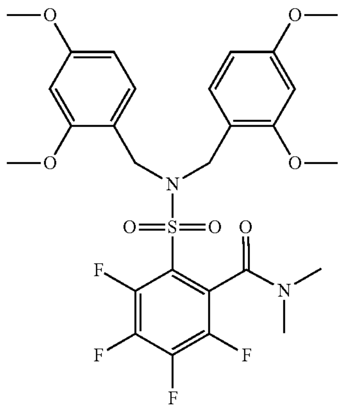

The title compound I-117, 2-(N,N-bis(2,4-dimethoxybenzyl)sulfamoyl)-3,4,5,6-tetrafluoro-N,N-dimethylbenzamide, was prepared via General Procedure F using 2-(N,N-bis(2,4-dimethoxybenzyl)sulfamoyl)-3,4,5,6-tetrafluorobenzoic acid (1 eq.), oxalyl chloride (1.5 eq.), dimethylamine (1 eq.) and triethylamine (3 eq.). The title compound I-117 was isolated as beige solid and was lyophilized from water/acetonitrile to afford a white powder. $^1$H NMR (400 MHz, Chloroform-d) δ 2.93 (s, 3H), 3.17 (s, 3H), 3.66 (s, 7H), 3.78 (s, 7H), 4.46 (d, J=15.8 Hz, 2H), 4.60 (d, J=15.7 Hz, 2H), 6.29-6.37 (m, 4H), 7.07 (d, J=9.0 Hz, 2H). $^{19}$F NMR (376 MHz, Chloroform-d) δ −152.82 (ddd, J=23.3, 20.0, 3.7 Hz), −147.56--146.93 (m), −139.65 (ddd, J=22.8, 11.7, 3.6 Hz), −131.33 (dt, J=21.6, 10.2 Hz).

Example 118 Synthesis of benzyl 2,3,4,5-tetrafluoro-6-sulfamoylbenzoate (I-118)

I-118

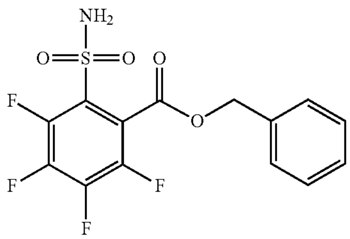

Benzyl 2,3,4,5-tetrafluoro-6-sulfamoylbenzoate was prepared via general procedure H using 2 benzyl 2-(N,N-bis (2,4-dimethoxybenzyl)sulfamoyl)-3,4,5,6-tetrafluorobenzoate (55 mg, 0.083 mmol) and anisole (0.027 mL, 0.249 mmol). $^1$H NMR (400 MHz, Chloroform-d) δ 5.40 (s, 2H), 5.54 (s, 2H), 7.36-7.48 (m, 5H). $^{19}$F NMR (376 MHz, Chloroform-d) δ −149.06 (ddd, J=22.4, 19.8, 5.4 Hz), −145.25 (ddd, J=22.3, 19.7, 9.9 Hz), −137.69 (ddd, J=21.8, 11.6, 5.4 Hz), −133.37 (dt, J=21.7, 10.5 Hz).

Example 119 Synthesis of 2,3,4,5-tetrafluoro-N,N-dimethyl-6-sulfamoylbenzamide (I-119)

I-119

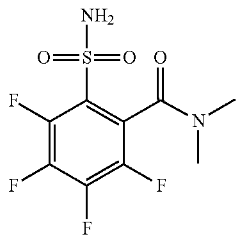

2,3,4,5-tetrafluoro-N,N-dimethyl-6-sulfamoylbenzamide was prepared via general procedure H using 2-(N,N-bis(2,4-dimethoxybenzyl)sulfamoyl)-3,4,5,6-tetrafluoro-N,N-dimethylbenzamide (65 mg, 0.108 mmol) and anisole (0.0353 mL, 0.325 mmol). The desired product was used for subsequent reactions. $^1$H NMR (400 MHz, Chloroform-d) δ 2.95 (s, 3H), 3.13 (s, 3H), 6.03 (s, 2H). $^{19}$F NMR (376 MHz, Chloroform-d) δ −150.40 (ddd, J=21.8, 19.4, 4.5 Hz), −145.89 (ddd, J=23.1, 19.7, 9.9 Hz), −138.91 (ddd, J=22.5, 12.1, 4.5 Hz), −132.97 (ddd, J=21.7, 12.1, 9.7 Hz).

Example 120 Synthesis of benzyl 2,3,4,5-tetrafluoro-6-(N-(3-fluoro-4-methoxyphenyl)sulfamoyl)benzoate (I-120)

I-120

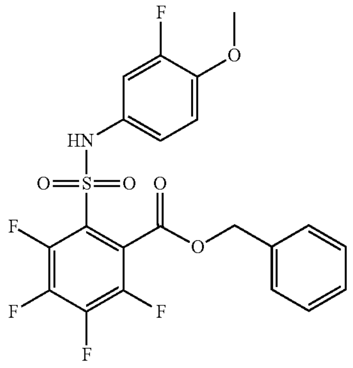

The title compound I-120, benzyl 2,3,4,5-tetrafluoro-6-(N-(3-fluoro-4-methoxyphenyl)sulfamoyl)benzoate, was prepared via general procedure E using benzyl 2,3,4,5-tetrafluoro-6-sulfamoylbenzoate (30 mg, 0.0826 mmol), 3-fluoro-4-methoxyphenylboronic acid (21.1 mg, 0.124 mmol), copper(I)$_2$-thiophenecarboxylate (6.63 mg, 0.033 mmol) and triethylamine (0.0115 mL, 0.0826 mmol). $^1$H NMR (400 MHz, $CDCl_3$) δ 3.86 (s, 3H), 5.45 (s, 2H), 6.76-6.90 (m, 1H), 6.94 (dd, J=11.5, 2.5 Hz, 1H), 7.34-7.52 (m, 5H). $^{19}$F NMR (376 MHz, $CDCl_3$) δ −148.83--148.23 (m), −143.97--143.35 (m), −136.53 (ddd, J=21.7, 12.1, 5.7 Hz), −131.92 (dt, J=22.5, 11.2 Hz), −131.58 (dd, J=11.5, 8.8 Hz).

Example 121 Synthesis of 2,3,4,5-tetrafluoro-6-(N-(3-fluoro-4-methoxyphenyl)sulfamoyl)-N,N-dimethylbenzamide (I-121)

I-121

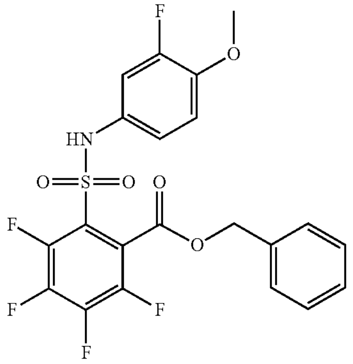

The title compound I-121, 2,3,4,5-tetrafluoro-6-(N-(3-fluoro-4-methoxyphenyl)sulfamoyl)-N,N-dimethylbenzamide, was prepared via general procedure E using 2,3,4,5-tetrafluoro-N,N-dimethyl-6-sulfamoylbenzamide (30 mg, 0.0826 mmol), 3-fluoro-4-methoxyphenylboronic acid (21.1 mg, 0.124 mmol), copper(I)$_2$-thiophenecarboxylate (6.63 mg, 0.033 mmol) and triethylamine (0.0115 mL, 0.0826 mmol). $^1$H NMR (400 MHz, Chloroform-d) δ 2.97 (d, J=0.7 Hz, 4H), 3.15 (s, 4H), 3.89 (s, 3H), 6.93 (t, J=9.0 Hz, 1H), 7.14-7.24 (m, 2H). $^{19}$F NMR (376 MHz, Chloroform-d) δ −151.66--150.56 (m), −143.99--143.00 (m), −138.52--138.00 (m), −131.79 (dd, J=11.0, 8.3 Hz), −129.33--128.81 (m).

Example 122 Synthesis of 2,3,4,5-tetrafluoro-N-(3-fluoro-4-methoxyphenyl)-6-(prop-2-yn-1-yloxy) benzenesulfonamide (I-122)

I-122

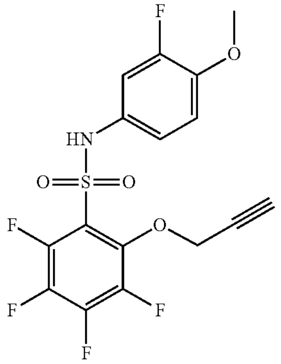

The title compound I-122, 2,3,4,5-tetrafluoro-N-(3-fluoro-4-methoxyphenyl)-6-(prop-2-yn-1-yloxy)benzenesulfonamide, was prepared via General Procedure B-1 using 2,3,4,5,6-pentafluoro-N-(3-fluoro-4-methoxyphenyl)benzenesulfonamide (1 eq.), 2-propyn-1-ol (3 eq.), 1.5 M methyllithium solution in ethyl ether (3 eq.). The title compound I-122 was isolated as solid and was lyophilized from water/acetonitrile to afford a white powder.

Example 123 Synthesis of 2-cyclopropoxy-3,4,5,6-tetrafluoro-N-(3-fluoro-4-(prop-2-yn-1-yloxy)phenyl)-N-(prop-2-yn-1-yl)benzenesulfonamide (I-123)

I-123

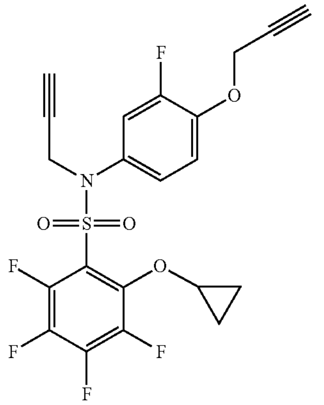

2-cyclopropoxy-3,4,5,6-tetrafluoro-N-(3-fluoro-4-hydroxyphenyl)benzenesulfonamide was prepared as described for the compound I-93. The title compound I-123, 2-cyclopropoxy-3,4,5,6-tetrafluoro-N-(3-fluoro-4-(prop-2-yn-1-yloxy)phenyl)-N-(prop-2-yn-1-yl)benzenesulfonamide, was prepared via general procedure A-2 using 2-cyclopropoxy-3,4,5,6-tetrafluoro-N-(3-fluoro-4-hydroxyphenyl)benzenesulfonamide (0.06 g, 0.152 mmol), 9.2 M propargyl bromide in toluene (0.0186 mL, 0.167 mmol) and sodium hydride 60% dispersion paraffin (0.0067 g, 0.167 mmol). The title compound I-123 was isolated as beige solid and was lyophilized from water/acetonitrile to afford a white powder Example 124 Synthesis of 2-cyclopropoxy-3,4,5,6-tetrafluoro-N-(3-fluoro-4-methoxyphenyl)-N-(prop-2-yn-1-yl)benzenesulfonamide (I-124)

I-124

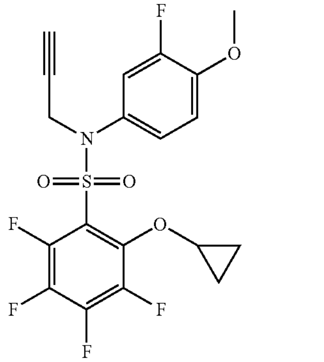

The title compound I-124, 2-cyclopropoxy-3,4,5,6-tetrafluoro-N-(3-fluoro-4-methoxyphenyl)-N-(prop-2-yn-1-yl)benzenesulfonamide, was prepared via general procedure B-1, using 2,3,4,5,6-pentafluoro-N-(3-fluoro-4-methoxyphenyl)-N-(prop-2-yn-1-yl)benzenesulfonamide (50 mg, 0.122 mmol), cyclopropanol (0.016 mL, 0.244 mmol), and 1.5 M methyllithium in ethyl ether (0.163 mL, 0.244 mmol).

Example 125 Synthesis of 2,3,4,5-tetrafluoro-6-(2-fluoroethoxy)-N,N-dimethylbenzenesulfonamide (I-125)

I-125

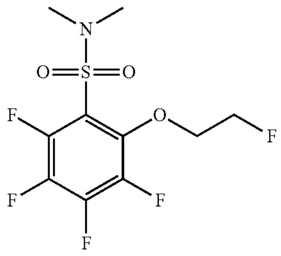

The title compound I-125, 2,3,4,5-tetrafluoro-6-(2-fluoroethoxy)-N,N-dimethylbenzenesulfonamide, was prepared via General Procedure C using 2,3,4,5-tetrafluoro-6-hydroxy-N,N-dimethylbenzenesulfonamide (0.057 g, 0.209 mmol), 1-Fluoro-2-iodoethane (0.02 mL, 0.229 mmol) and potassium carbonate (31.7 mg, 0.229 mmol). The title compound I-125 was isolated as beige solid and was lyophilized from water/acetonitrile to afford a white powder (35 mg, 52.5%).

Example 126 Synthesis of 2,3,4,5-tetrafluoro-6-(fluoromethyl)-N,N-dimethylbenzenesulfonamide (I-126)

I-126

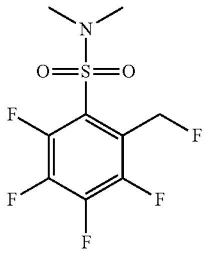

To a stirred solution of 2,3,4,5-tetrafluoro-6-(hydroxymethyl)-N,N-dimethylbenzenesulfonamide (0.12 g, 0.418 mmol, 1 eq.) in anhydrous DCM (0.2 M) at −40° C. was added diethylaminosulfur trifluoride (0.135 g, 0.836 mmol, 2 eq.) in a dropwise manner. The resulting solution was stirred for 12 hours while slowly warming up to room temperature. The reaction mixture was quenched with water and extracted thrice with DCM. The collected organic layers were washed with saturated sodium chloride solution, dried over sodium sulfate and concentrated under reduced pressure using rotatory evaporator. The resulting residue was separated on a pad of silica by eluting a gradient of 0-20% EtOAc in Hexanes and further purified by prep-HPLC by eluting a gradient of 0-100% acetonitrile (0.1% formic acid) in water (0.1% formic acid) to furnish the title compound (50%). $^{1}$H NMR (400 MHz, Chloroform-d) δ 5.90 (dd, J=46.4, 3.3 Hz, 2H), 2.97 (d, J=2.1 Hz, 6H). $^{19}$F NMR (376 MHz, Chloroform-d) δ −131.55 (dt, J=21.6, 10.0 Hz, 1F), −136.88 (ddd, J=16.1, 11.0, 5.4 Hz, 1F), −146.71 (td, J=21.2, 20.8, 8.7 Hz, 1F), −149.32-−149.55 (m, 1F), −205.38 (tt, J=47.1, 5.2 Hz, 1F).

Example 127 Synthesis of 2-(difluoromethyl)-3,4,5,6-tetrafluoro-N,N-dimethylbenzenesulfonamide (I-127)

I-127

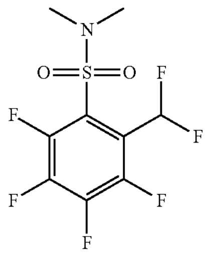

To a stirred solution of 2,3,4,5-tetrafluoro-6-(hydroxymethyl)-N,N-dimethylbenzenesulfonamide (1 eq.) in anhydrous DCE (0.1 M) at room temperature was added PCC (2.5 eq.) and refluxed for 4 hours. The reaction mixture was filtered through a pad of Celite and washed with DCM. The collected filtrate was concentrated under reduced pressure using rotatory evaporator. The resulting residue was separated on a pad of silica by eluting a gradient of 0-40% EtOAc in Hexanes to furnish the aldehyde, 2,3,4,5-tetrafluoro-6-formyl-N,N-dimethylbenzenesulfonamide, which was used in the next step for the synthesis of I-127 (60%). $^{1}$H NMR (400 MHz, $CDCl_3$) δ 10.31 (d, J=1.3 Hz, 1H), 2.93 (d, J=2.1 Hz, 6H). $^{19}$F NMR (376 MHz, $CDCl_3$) δ −132.02-−132.96 (m, 1F), −138.97 (ddd, J=21.5, 12.3, 6.2 Hz, 1F), −144.43 (td, J=20.4, 9.2 Hz, 1F), −147.75 (ddd, J=22.7, 19.7, 6.3 Hz, 1F).

To a stirred solution of 2,3,4,5-tetrafluoro-6-formyl-N,N-dimethylbenzenesulfonamide (0.05 g, 0.175 mmol, 1 eq.) in anhydrous DCM (0.2 M) at −40° C. was added diethylaminosulfur trifluoride (0.085 g, 0.526 mmol, 3 eq.) in a dropwise manner. The resulting solution was stirred for 12 hours while slowly warming up to room temperature. The reaction mixture was quenched with water and extracted thrice with DCM. The collected organic layers were washed with saturated sodium chloride solution, dried over sodium sulfate and concentrated under reduced pressure using rotatory evaporator. The resulting residue was separated on a pad of silica by eluting a gradient of 0-20% EtOAc in Hexanes and further purified by prep-HPLC by eluting a gradient of 0-100% acetonitrile (0.1% formic acid) in water (0.1% formic acid) to furnish the title compound (65%). $^{1}$H NMR (400 MHz, Chloroform-d) δ 7.79 (tt, J=52.3, 1.4 Hz, 1H), 2.99 (d, J=2.1 Hz, 6H). $^{19}$F NMR (376 MHz, Chloroform-d) δ −112.67 (dd, J=52.1, 26.6 Hz), −133.43 (dtt, J=37.1, 19.6, 9.3 Hz), −134.40 (dt, J=21.4, 10.1 Hz), −145.44 (td, J=20.2, 9.3 Hz), −147.48 (td, J=21.4, 7.8 Hz).

Example 128 Synthesis of 2-(difluoromethyl)-3,4,5,6-tetrafluoro-N,N-dimethylbenzenesulfonamide (I-128)

I-128

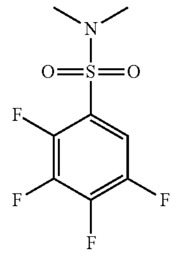

The title compound I-128, 2,3,4,5-tetrafluoro-N,N-dimethylbenzenesulfonamide, was prepared via General Procedure A using 2,3,4,5-tetrafluorobenzenesulfonyl chloride (0.1 g, 0.402 mmol), 2 M dimethylamine solution in tetrahydrofuran (0.2 mL, 2 M) and triethylamine (0.442 mmol, 0.06 mL). The title compound I-128 was isolated as a white solid (74%) $^{1}$H NMR (400 MHz, $CDCl_3$) δ 7.57 (dd, J=9.4, 6.5 Hz, 1H), 3.20-2.84 (m, 6H). $^{19}$F NMR (376 MHz, $CDCl_3$) δ −132.89 (tq, J=12.6, 6.4 Hz, 1F), −135.34-−135.88 (m, 1F), −146.39 (tt, J=20.0, 8.0 Hz, 1F), −151.03 (t, J=20.6 Hz, 1F).

Example 129 Synthesis of 3,4,5,6-tetrafluoro-4'-methoxy-N,N-dimethyl-[1,1'-biphenyl]-2-sulfonamide (I-129)

I-129

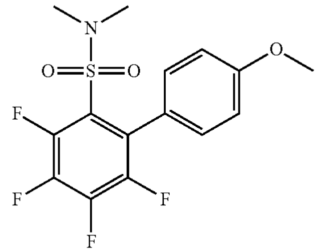

The title compound I-129, 3,4,5,6-tetrafluoro-4'-methoxy-N,N-dimethyl-[1,1'-biphenyl]-2-sulfonamide, was prepared via General Procedure G using 2-bromo-3,4,5,6-tetrafluoro-N,N-dimethylbenzenesulfonamide (0.1 g, 0.298 mmol) and 4-methoxyphenylboronic acid (0.054 g, 0.357 mmol). The title compound I-129 was isolated as a white solid (40%) $^{1}$H NMR (400 MHz, $CDCl_3$) δ 7.24-7.19 (m, 2H), 7.04-6.98 (m, 2H), 3.88 (s, 3H), 2.79 (d, J=1.8 Hz, 6H). $^{13}$C NMR (101 MHz, $CDCl_3$) δ 160.0, 131.0, 121.7, 113.6, 55.2, 36.8 (d, J=4.1 Hz). $^{19}$F NMR (376 MHz, $CDCl_3$) δ −134.21 (ddd, J=23.7, 11.4, 3.5 Hz, 1F), −135.16 (ddd, J=22.7, 11.9, 6.0 Hz, 1F), −148.31 (ddd, J=24.2, 20.3, 8.6 Hz, 1F), −153.88 (ddd, J=24.0, 20.7, 3.8 Hz, 1F).

Example 130 Synthesis of 3,4,5,6-tetrafluoro-4'-methoxy-N,N-dimethyl-[1,1'-biphenyl]-2-sulfonamide (I-130)

I-130

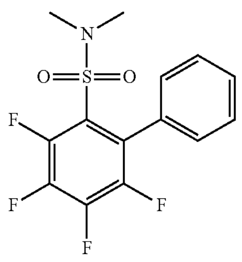

The title compound I-130, 3,4,5,6-tetrafluoro-N,N-dimethyl-[1,1'-biphenyl]-2-sulfonamide, was prepared via General Procedure G using 2-bromo-3,4,5,6-tetrafluoro-N,N-dimethylbenzenesulfonamide (0.1 g, 0.298 mmol) and phenylboronic acid (0.044 g, 0.357 mmol) The title compound I-130 was isolated as a white solid (45%) $^1$H NMR (400 MHz, $CDCl_3$) δ 7.68-7.38 (m, 3H), 7.30 (dd, J=6.7, 2.9 Hz, 2H), 2.78 (d, J=1.9 Hz, 6H). $^{13}$C NMR (101 MHz, $CDCl_3$) δ 129.9, 129.7, 128.9, 128.1, 36.7 (d, J=3.9 Hz). $^{19}$F NMR (376 MHz, $CDCl_3$) δ −134.17 (ddd, J=23.4, 11.3, 3.6 Hz, 1F), −134.54 (dt, J=21.5, 10.0 Hz, 1F), −147.81-−148.43 (m, 1F), −152.88-−153.91 (m, 1F).

Example 131 Synthesis of 3,4,5,6-tetrafluoro-N,N-dimethyl-4'-(trifluoromethyl)-[1,1'-biphenyl]-2-sulfonamide (I-131)

I-131

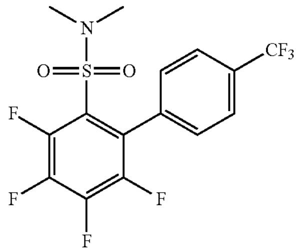

The title compound I-131, 3,4,5,6-tetrafluoro-N,N-dimethyl-4'-(trifluromethyl)-[1,1'-biphenyl]-2-sulfonamide, was prepared via General Procedure G using 2-bromo-3,4,5,6-tetrafluoro-N,N-dimethylbenzenesulfonamide (0.1 g, 0.298 mmol) and 4-(trifluoromethyl)phenylboronic acid (0.067 g, 0.357 mmol) The title compound I-131 was isolated as a white solid. $^1$H NMR (400 MHz, Chloroform-d) δ 7.77-7.72 (m, 2H), 7.45-7.41 (m, 2H), 2.84 (d, J=2.0 Hz, 6H). $^{19}$F NMR (376 MHz, Chloroform-d) δ −62.76, −133.85 (ddd, J=23.1, 11.3, 4.3 Hz), −134.66-−134.87 (m), −147.43 (ddd, J=22.7, 20.0, 8.7 Hz), −152.26 (ddd, J=23.8, 20.3, 4.0 Hz).

Example 132 Synthesis of 2-(N,N-dimethylsulfamoyl)-3,4,5,6-tetrafluorobenzamide (I-132)

I-132

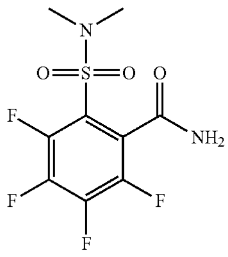

The title compound I-132, 2-(N,N-dimethylsulfamoyl)-3,4,5,6-tetrafluorobenzamide, was prepared via General Procedure H using N-(2,4-dimethoxybenzyl)-2-(N,N-dimethylsulfamoyl)-3,4,5,6-tetrafluorobenzamide (I-35)(0.08 g, 0.133 mmol) and anisole (0.043 ml, 0.4 mmol). The title compound I-132 was isolated as a white solid (40%). $^1$H NMR (400 MHz, Chloroform-d) δ 7.77-7.72 (m, 2H), 7.45-7.41 (m, 2H), 2.84 (d, J=2.0 Hz, 6H). $^1$H NMR (400 MHz, $CDCl_3$) δ 6.17 (d, J=41.1 Hz, 2H), 2.95 (d, J=2.0 Hz, 6H). $^{13}$C NMR (101 MHz, $CDCl_3$) δ 162.3, 37.2 (d, J=2.7 Hz). $^{19}$F NMR (376 MHz, $CDCl_3$) δ −130.52 (dt, J=22.4, 10.9 Hz, 1F), −137.74 (ddd, J=22.2, 11.7, 4.6 Hz, 1F), −145.17-−145.42 (m, 1F), −150.49 (ddd, J=24.2, 19.9, 4.8 Hz, 1F).

Example 133 Synthesis of methyl 2,3,4,5-tetrafluoro-6-(N-(3-fluoro-4-methoxyphenyl)sulfamoyl)benzoate (I-133)

I-133

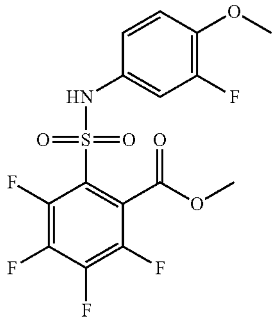

The intermediate, methyl 2-(N-allyl-N-(3-fluoro-4-methoxyphenyl)sulfamoyl)-3,4,5,6-tetrafluorobenzoate, was prepared via General Procedure E using N-allyl-2,3,4,5-tetrafluoro-N-(3-fluoro-4-methoxyphenyl)benzenesulfonamide (0.3 g, 0.763 mmol) and chloroformic acid (0.295 ml, 3.81 mmol). The intermediate was isolated (0.1 g, 0.222 mmol) and used or the next step. To a stirred solution of methyl 2-(N-allyl-N-(3-fluoro-4-methoxyphenyl)sulfamoyl)-3,4,5,6-tetrafluorobenzoate (0.1 g, 0.222 mmol, 1 eq.) in acetic acid (0.15 M) was added $Pd(PPh_3)_4$ (0.077 g, 0.067 mmol, 0.3 eq.) and stirred at 80° C. for 3 hours. The reaction mixture was separated on a pad of silica to furnish the title compound I-133. $^1$H NMR (400 MHz, Chloroform-d) δ 7.09 (s, 1H), 7.04-6.99 (m, 1H), 6.94-6.85 (m, 2H), 4.03 (s, 3H), 3.88 (s, 3H). $^{19}$F NMR (376 MHz, Chloroform-d) δ −131.61-−131.80 (m, 1F), −132.13 (dt, J=22.2, 10.9 Hz, 1F), −136.87 (ddd, J=21.8, 11.7, 5.3 Hz, 1F), −143.68 (ddd, J=21.8, 19.7, 10.4 Hz, 1F), −148.76 (ddd, J=22.6, 19.7, 5.3 Hz, 1F).

Example 134 Synthesis of 2,3,4,5-tetrafluoro-6-(N-(3-fluoro-4-methoxyphenyl)sulfamoyl)-N,N-dimethylbenzamide (I-134)

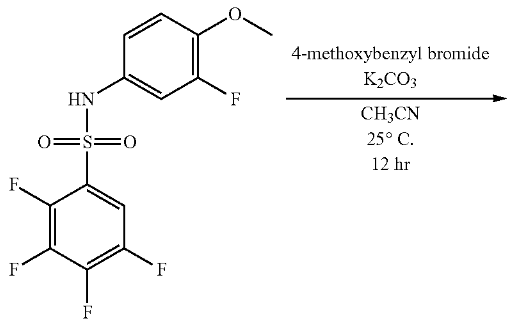

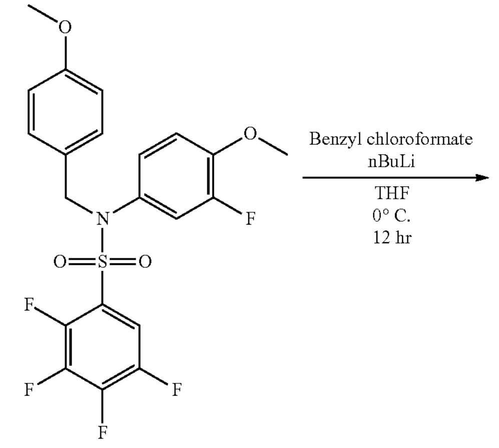

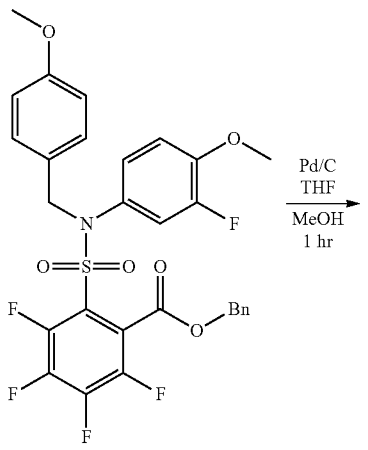

-continued

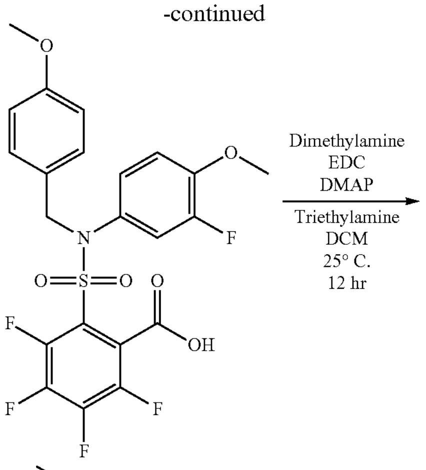

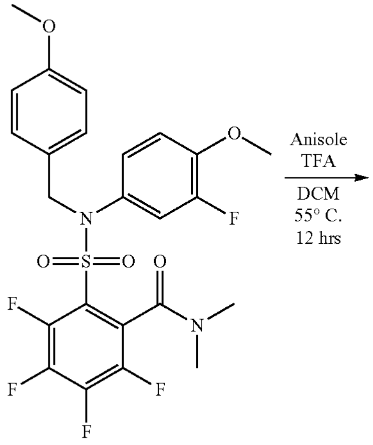

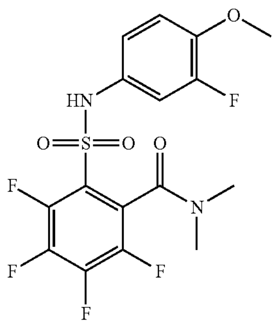

I-134

To a stirred solution of 2,3,4,5-tetrafluoro-N-(3-fluoro-4-methoxyphenyl)benzenesulfonamide (2 g, 5.66 mmol, 1 eq.) in anhydrous $CH_3CN$ (0.3 M) was added 4-methoxybenzyl bromide (0.975 ml, 6.79 mmol, 1.2 eq.). The solution was then added with potassium carbonate (2.35 g, 17 mmol, 3 eq.) and the resulting solution was stirred at room temperature for 12 hours. The mixture was quenched with water and extracted three times with EtOAc. The collected organic layers were washed with saturated sodium chloride solution, dried over sodium sulfate, filtered and evaporated under reduced pressure to yield the intermediate, 2,3,4,5-tetrafluoro-N-(3-fluoro-4-methoxyphenyl)-N-(4-methoxybenzyl)benzenesulfonamide.

The intermediate, benzyl 2,3,4,5-tetrafluoro-6-(N-(3-fluoro-4-methoxyphenyl)-N-(4-methoxybenzyl)sulfamoyl)benzoate, was prepared via General Procedure E using 2,3,4,5-tetrafluoro-N-(3-fluoro-4-methoxyphenyl)-N-(4-methoxybenzyl)benzenesulfonamide (0.1 g, 0.211 mmol)

and benzyl chloroformate (0.178 ml, 1.06 mmol, 5 eq.) to furnish the intermediate, benzyl 2,3,4,5-tetrafluoro-6-(N-(3-fluoro-4-methoxyphenyl)-N-(4-methoxybenzyl)sulfamoyl)benzoate.

benzyl 2,3,4,5-tetrafluoro-6-(N-(3-fluoro-4-methoxyphenyl)-N-(4-methoxybenzyl)sulfamoyl)benzoate (100 mg, 0.165 mmol) was added with methanol (0.2 M) and tetrahydrofuran (0.1 M). The resulting solution was added with palladium 10% on carbon (17.g mg) and stirred under hydrogen for 2 hours. The reaction mixture was filtered through a pad of Celite, and the collected organic layer was concentrated in vacuo to furnish 2,3,4,5-tetrafluoro-6-(N-(3-fluoro-4-methoxyphenyl)-N-(4-methoxybenzyl)sulfamoyl)benzoic acid.

To a stirred solution of 2,3,4,5-tetrafluoro-6-(N-(3-fluoro-4-methoxyphenyl)-N-(4-methoxybenzyl)sulfamoyl)benzoic acid (0.070 g, 0.135 mmol, 1 eq.), EDC-HCl (0.052 g, 0.271 mmol, 2 eq.), DMAP (8.26 mg, 0.068 mmol, 0.5 eq.), triethylamine (0.04 ml, 0.284 mmol, 2.1 eq.) in DCM (0.25 M) was added a solution of dimethylamine (0.068 ml, 0.135 mmol, 1 eq.) in DCM (0.25 M) at room temperature. The resulting solution was stirred for 12 hours and the mixture was further separate on a pad of silica using a gradient of 0-15% EtOAc in Hexanes to furnish the intermediate, 2,3,4,5-tetrafluoro-6-(N-(3-fluoro-4-methoxyphenyl)-N-(4-methoxybenzyl)sulfamoyl)-N,N-dimethylbenzamide.

The title compound I-134, 2,3,4,5-tetrafluoro-6-(N-(3-fluoro-4-methoxyphenyl)sulfamoyl)-N,N-dimethylbenzamide, was prepared via general procedure H using 2,3,4,5-tetrafluoro-6-(N-(3-fluoro-4-methoxyphenyl)-N-(4-methoxybenzyl)sulfamoyl)-N,N-dimethylbenzamide (90 mg, 0.165 mmol) and anisole (0.054 mL, 0.496 mmol). $^{1}H$ NMR (400 MHz, Chloroform-d) δ 7.55 (s, 1H), 7.07 (dd, J=11.7, 2.6 Hz, 1H), 6.97 (ddd, J=8.8, 2.6, 1.4 Hz, 1H), 6.87 (t, J=8.8 Hz, 1H), 3.88 (s, 3H), 3.20 (s, 3H), 2.99 (s, 3H). $^{19}F$ NMR (376 MHz, Chloroform-d) δ −130.97−−131.33 (m, 1F), −132.17 (dd, J=11.8, 8.8 Hz, 1F), −138.09 (ddd, J=23.1, 12.5, 4.7 Hz, 1F), −144.38 (ddd, J=22.6, 19.6, 10.4 Hz, 1F), −149.82 (ddd, J=23.7, 19.3, 4.5 Hz, 1F).

Example 135 Synthesis of 2,3,4,5-tetrafluoro-N-(3-fluoro-4-methoxyphenyl)-6-methylbenzenesulfonamide (I-135)

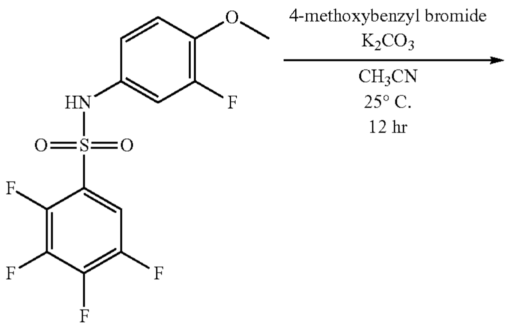

-continued

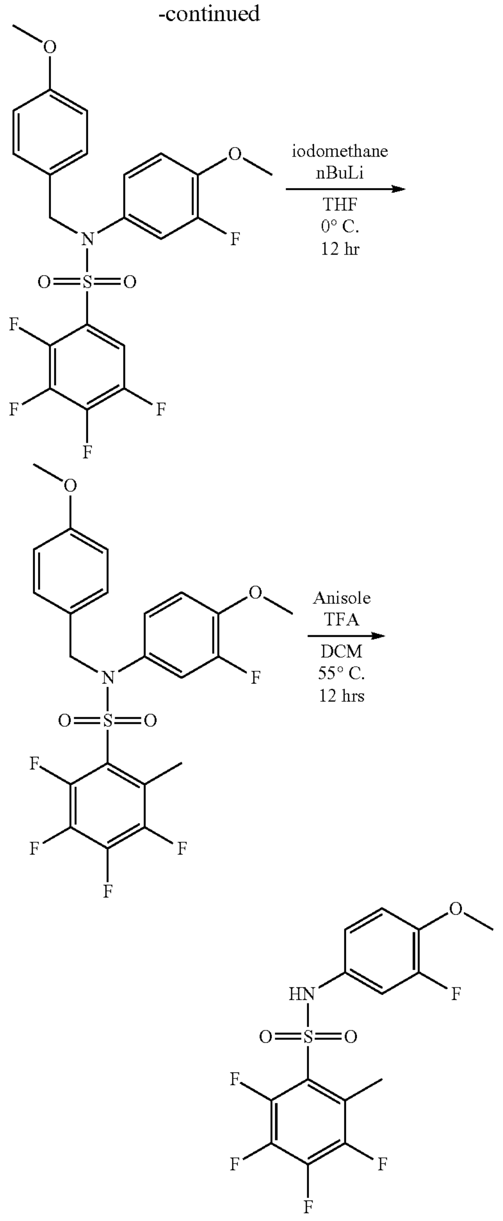

I-135

To a stirred solution of 2,3,4,5-tetrafluoro-N-(3-fluoro-4-methoxyphenyl)benzenesulfonamide (2 g, 5.66 mmol, 1 eq.) in anhydrous $CH_3CN$ (0.3 M) was added 4-methoxybenzyl bromide (0.975 ml, 6.79 mmol, 1.2 eq.). The solution was then added with potassium carbonate (2.35 g, 17 mmol, 3 eq.) and the resulting solution was stirred at room temperature for 12 hours. The mixture was quenched with water and extracted three times with EtOAc. The collected organic layers were washed with saturated sodium chloride solution, dried over sodium sulfate, filtered and evaporated under reduced pressure to yield the intermediate, 2,3,4,5-tetrafluoro-N-(3-fluoro-4-methoxyphenyl)-N-(4-methoxybenzyl)benzenesulfonamide.

The intermediate, 2,3,4,5-tetrafluoro-N-(3-fluoro-4-methoxyphenyl)-N-(4-methoxybenzyl)-6-methylbenzenesulfonamide, was prepared via General Procedure E using 2,3,4,5-tetrafluoro-N-(3-fluoro-4-methoxyphenyl)-N-(4-methoxybenzyl)benzenesulfonamide (0.3 g, 0.634 mmol)

and iodomethane (0.06 ml, 0.951 mmol, 1.5 eq.) to furnish the intermediate, 2,3,4,5-tetrafluoro-N-(3-fluoro-4-methoxyphenyl)-N-(4-methoxybenzyl)-6-methylbenzene-sulfonamide.

The title compound I-135, 2,3,4,5-tetrafluoro-N-(3-fluoro-4-methoxyphenyl)-6-methylbenzenesulfonamide, was prepared via general procedure H using 2,3,4,5-tetrafluoro-N-(3-fluoro-4-methoxyphenyl)-N-(4-methoxybenzyl)-6-methylbenzenesulfonamide (200 mg, 0.165 mmol) and anisole (0.134 mL, 1.23 mmol). $^1$H NMR (400 MHz, $CDCl_3$) δ 7.33 (s, 1H), 7.06-6.97 (m, 1H), 6.87 (d, J=4.9 Hz, 2H), 3.87 (d, J=1.3 Hz, 3H), 2.62-2.29 (m, 3H). $^{13}$C NMR (101 MHz, $CDCl_3$) δ 153.4, 150.9, 146.7, 146.6, 127.8, 127.7, 124.2 (d, J=4.4 Hz), 124.0, 118.7 (d, J=3.7 Hz), 113.8 (d, J=2.7 Hz), 111.8, 111.6, 56.4, 11.4 (d, J=5.6 Hz). $^{19}$F NMR (376 MHz, $CDCl_3$) δ −131.66 (dd, J=11.3, 5.6 Hz, 1F), −134.55 (dt, J=23.4, 9.9 Hz, 1F), −136.76 (ddd, J=21.6, 8.8, 3.5 Hz, 1F), −146.94 (td, J=20.9, 8.7 Hz, 1F), −156.20 (t, J=21.7 Hz, 1F). HR-MS (TOF ES−) m/z calcd for $[C_{14}H_{10}F_5NO_3S]^-$: 366.03, found: 366.10.

Example 136 Synthesis of 2,3,4,5-tetrafluoro-N-(3-fluoro-4-methoxyphenyl)-6-(fluoromethyl)benzene-sulfonamide (I-136)

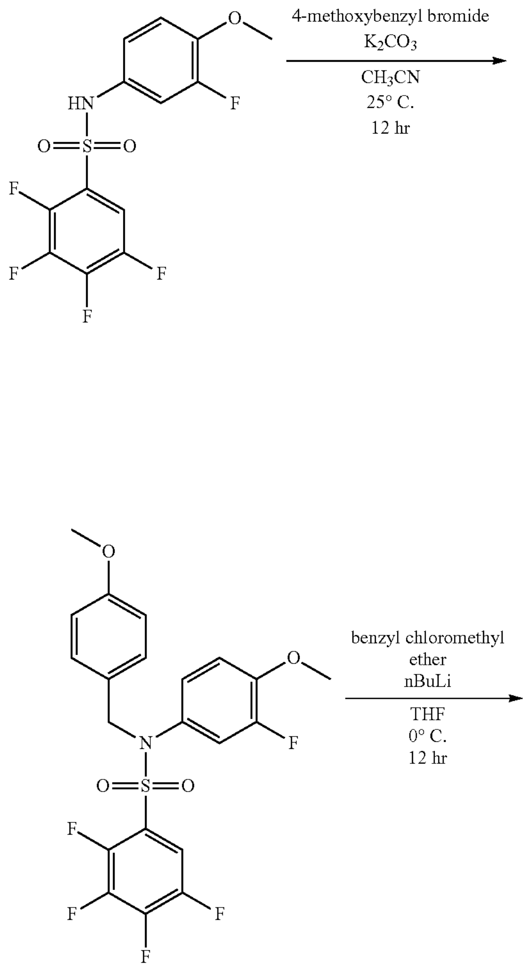

-continued

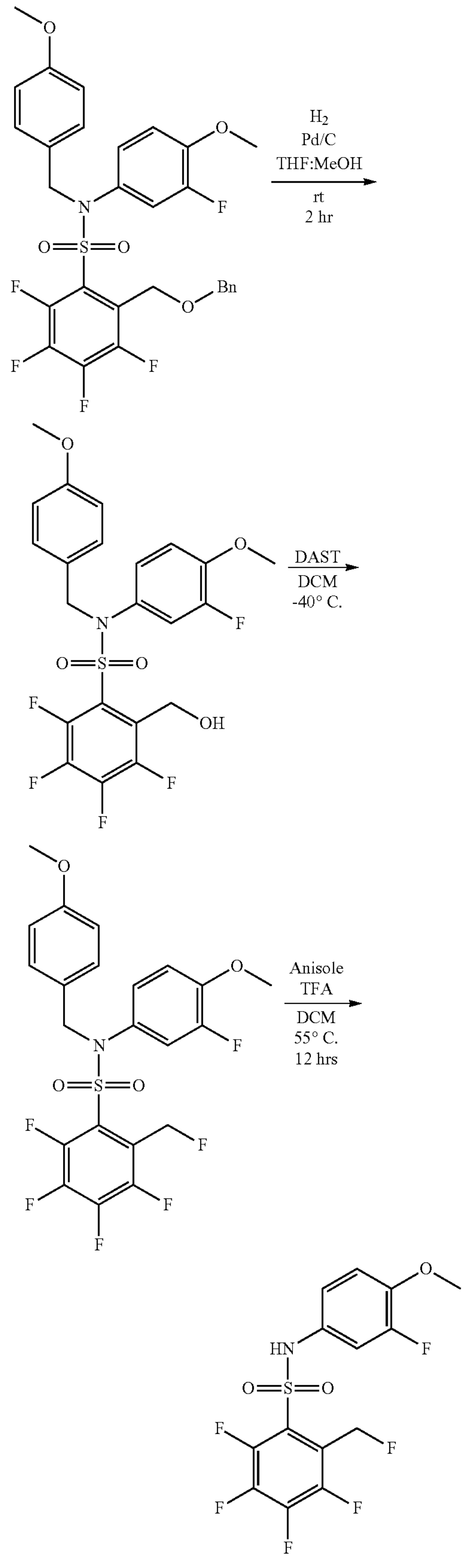

I-136

To a stirred solution of 2,3,4,5-tetrafluoro-N-(3-fluoro-4-methoxyphenyl)benzenesulfonamide (2 g, 5.66 mmol, 1 eq.) in anhydrous $CH_3CN$ (0.3 M) was added 4-methoxybenzyl bromide (0.975 ml, 6.79 mmol, 1.2 eq.). The solution was then added with potassium carbonate (2.35 g, 17 mmol, 3 eq.) and the resulting solution was stirred at room temperature for 12 hours. The mixture was quenched with water and extracted three times with EtOAc. The collected organic layers were washed with saturated sodium chloride solution, dried over sodium sulfate, filtered and evaporated under reduced pressure to yield the intermediate, 2,3,4,5-tetrafluoro-N-(3-fluoro-4-methoxyphenyl)-N-(4-methoxybenzyl)benzenesulfonamide.

The intermediate, 2-((benzyloxy)methyl)-3,4,5,6-tetrafluoro-N-(3-fluoro-4-methoxyphenyl)-N-(4-methoxybenzyl)benzenesulfonamide, was prepared via General Procedure E using 2,3,4,5-tetrafluoro-N-(3-fluoro-4-methoxyphenyl)-N-(4-methoxybenzyl)benzenesulfonamide (0.5 g, 0.634 mmol) and benzyl chloromethyl ether (0.441 ml, 3.17 mmol, 3 eq.) to furnish the intermediate, 2-((benzyloxy)methyl)-3,4,5,6-tetrafluoro-N-(3-fluoro-4-methoxyphenyl)-N-(4-methoxybenzyl)benzenesulfonamide (55%). $^1$H NMR (400 MHz, $CDCl_3$) δ 7.38 (d, J=3.7 Hz, 5H), 7.20-7.10 (m, 2H), 6.95-6.71 (m, 5H), 4.85 (d, J=4.4 Hz, 2H), 4.84-4.77 (m, 2H), 4.66 (s, 3H), 4.53 (s, 2H), 3.78 (d, J=1.5 Hz, 3H). $^{19}$F NMR (376 MHz, $CDCl_3$) δ −130.37 (dt, J=23.3, 9.9 Hz, 1F), −132.30 (dd, J=11.5, 9.0 Hz, 1F), −136.83-−137.39 (m, 1F), −146.66 (td, J=21.1, 8.8 Hz, 1F), −151.98 (ddd, J=24.1, 20.3, 4.7 Hz, 1F).

2-((benzyloxy)methyl)-3,4,5,6-tetrafluoro-N-(3-fluoro-4-methoxyphenyl)-N-(4-methoxybenzyl)benzenesulfonamide was added with a mixture of methanol:tetrahydrofuran (2:1, 0.1 M). The resulting solution was added with palladium 10% on carbon (0.05 eq) and stirred under hydrogen for 2 hours. The reaction mixture was filtered through a pad of Celite, and the collected organic layer was concentrated in vacuo to furnish the intermediate 2,3,4,5-tetrafluoro-N-(3-fluoro-4-methoxyphenyl)-6-(hydroxymethyl)-N-(4-methoxybenzyl)benzenesulfonamide (quantitative). $^1$H NMR (400 MHz, $CDCl_3$) δ 7.12 (dd, J=8.8, 2.4 Hz, 2H), 6.84-6.70 (m, 5H), 4.87 (dd, J=3.9, 1.5 Hz, 2H), 4.51 (dd, J=15.5, 3.1 Hz, 2H), 3.82 (d, J=2.1 Hz, 3H), 3.77 (d, J=1.8 Hz, 3H). $^{19}$F NMR (376 MHz, $CDCl_3$) δ −131.27 (dt, J=21.5, 10.4 Hz, 1F), −131.59 (dd, J=11.6, 8.5 Hz, 1F), −138.02 (ddq, J=19.1, 11.4, 3.7 Hz, 1F), −145.43 (td, J=21.0, 8.9 Hz, 1F), −152.24 (ddd, J=24.2, 20.2, 4.5 Hz, 1F).

To a stirred solution of 2,3,4,5-tetrafluoro-N-(3-fluoro-4-methoxyphenyl)-6-(hydroxymethyl)-N-(4-methoxybenzyl)benzenesulfonamide (0.2 g, 0.397 mmol, 1 eq.) in anhydrous DCM (0.2 M) at −40° C. was added diethylaminosulfur trifluoride (0.128 g, 0.795 mmol, 2 eq.) in a dropwise manner. The resulting solution was stirred for 12 hours while slowly warming up to room temperature. The reaction mixture was quenched with water and extracted thrice with DCM. The collected organic layers were washed with saturated sodium chloride solution, dried over sodium sulfate and concentrated under reduced pressure using rotatory evaporator. The resulting residue was separated on a pad of silica by eluting a gradient of 0-20% EtOAc in Hexanes to furnish 2,3,4,5-tetrafluoro-N-(3-fluoro-4-methoxyphenyl)-6-(fluoromethyl)-N-(4-methoxybenzyl)benzenesulfonamide (60%). $^1$H NMR (400 MHz, $CDCl_3$) δ 7.13 (dd, J=8.7, 2.3 Hz, 2H), 6.80 (dd, J=8.6, 3.0 Hz, 5H), 5.61 (ddd, J=46.5, 12.6, 3.2 Hz, 2H), 4.84 (d, J=4.2 Hz, 2H), 3.84 (d, J=2.1 Hz, 3H), 3.78 (d, J=2.0 Hz, 3H). $^{19}$F NMR (376 MHz, $CDCl_3$) δ −129.67 (dt, J=21.5, 10.4 Hz, 1F), −132.07-−132.20 (m, 1F), −136.68 (ddt, J=19.7, 15.1, 7.0 Hz, 1F), −145.79 (td, J=20.7, 9.1 Hz, 1F), −148.95-−149.62 (m, 1F), −205.82-−207.05 (m, 1F).

The title compound I-136, 2,3,4,5-tetrafluoro-N-(3-fluoro-4-methoxyphenyl)-6-(fluoromethyl)benzenesulfonamide, was prepared via general procedure H using 2,3,4,5-tetrafluoro-N-(3-fluoro-4-methoxyphenyl)-6-(fluoromethyl)-N-(4-methoxybenzyl)benzenesulfonamide (140 mg, 0.277 mmol) and anisole (0.09 mL, 0.83 mmol, 3 eq.). (65%) $^1$H NMR (400 MHz, $CDCl_3$) δ 7.06-6.81 (m, 4H), 5.89 (dd, J=46.2, 3.0 Hz, 3H), 3.87 (s, 5H). $^{13}$C NMR (101 MHz, $CDCl_3$) δ 153.4, 150.9, 147.0, 146.9, 127.1, 127.0, 119.3, 119.3, 113.7, 113.7, 112.2, 112.0, 73.7, 72.0 (d, J=6.7 Hz), 56.4. $^{19}$F NMR (376 MHz, $CDCl_3$) δ −131.00 (dt, J=22.3, 10.8 Hz, 1F), −131.59 (dd, J=10.9, 6.5 Hz, 1F), −136.61 (ddt, J=19.7, 12.4, 3.3 Hz, 1F), −144.71 (td, J=20.8, 9.9 Hz, 1F), −148.36-−149.12 (m, 1F), −206.92 (ddd, J=47.4, 42.5, 5.2 Hz, 1F). HR-MS (TOF ES−) m/z calcd for $[C_{14}H_9F_6NO_3S]^-$: 384.02, found: 384.08.

Example 137 Synthesis of 2-(difluoromethyl)-3,4,5,6-tetrafluoro-N-(3-fluoro-4-methoxyphenyl)benzenesulfonamide (I-137)

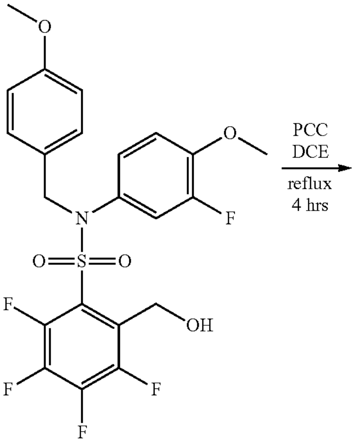

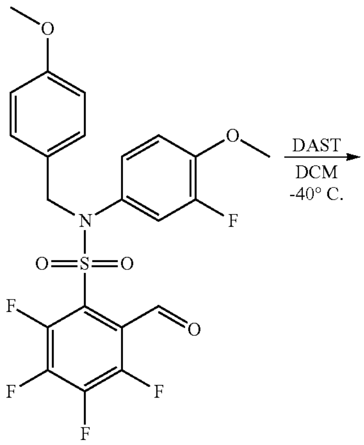

-continued

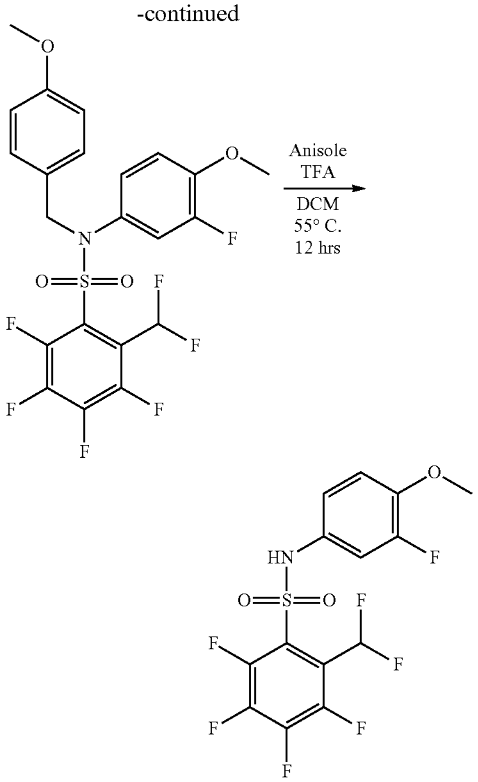

I-137

To a stirred solution of 2,3,4,5-tetrafluoro-N-(3-fluoro-4-methoxyphenyl)-6-(hydroxymethyl)-N-(4-methoxybenzyl) benzenesulfonamide (1 eq.) in anhydrous DCE (0.1 M) at room temperature was added PCC (2.5 eq.) and refluxed for 4 hours. The reaction mixture was filtered through a pad of Celite and washed with DCM. The collected filtrate was concentrated under reduced pressure using rotatory evaporator. The resulting residue was separated on a pad of silica by eluting a gradient of 0-40% EtOAc in Hexanes to furnish the aldehyde, 2,3,4,5-tetrafluoro-N-(3-fluoro-4-methoxyphenyl)-6-formyl-N-(4-methoxybenzyl)benzenesulfonamide, which was used in the next step (60%). $^{1}H$ NMR (400 MHz, $CDCl_3$) δ 9.87-9.59 (m, 1H), 7.11 (dd, J=8.7, 2.6 Hz, 2H), 6.79 (tt, J=10.2, 6.7 Hz, 5H), 4.84 (d, J=4.1 Hz, 2H), 3.84 (d, J=2.1 Hz, 3H), 3.77 (d, J=1.8 Hz, 3H). $^{19}F$ NMR (376 MHz, $CDCl_3$) δ −131.94 (dd, J=11.3, 7.9 Hz, 1F), −138.92 (ddd, J=19.7, 12.1, 6.5 Hz, 1F), −143.61 (td, J=20.5, 9.5 Hz, 1F), −144.29--144.66 (m, 1F), −147.32 (ddd, J=22.7, 19.5, 6.3 Hz, 1F).

To a stirred solution of 2,3,4,5-tetrafluoro-N-(3-fluoro-4-methoxyphenyl)-6-formyl-N-(4-methoxybenzyl)benzenesulfonamide (0.280 g, 0.558 mmol, 1 eq.) in anhydrous DCM (0.2 M) at −40° C. was added diethylaminosulfur trifluoride (0.204 ml, 1.67 mmol, 3 eq.) in a dropwise manner. The resulting solution was stirred for 12 hours while slowly warming up to room temperature. The reaction mixture was quenched with water and extracted thrice with DCM. The collected organic layers were washed with saturated sodium chloride solution, dried over sodium sulfate and concentrated under reduced pressure using rotatory evaporator. The resulting residue was separated on a pad of silica by eluting a gradient of 0-20% EtOAc in Hexanes to furnish 2-(difluoromethyl)-3,4,5,6-tetrafluoro-N-(3-fluoro-4-methoxyphenyl)-N-(4-methoxybenzyl)benzenesulfonamide (55%). $^{1}H$ NMR (400 MHz, $CDCl_3$) δ 7.16-7.07 (m, 2H), 6.90-6.71 (m, 5H), 4.85 (dd, J=4.9, 1.3 Hz, 2H), 4.36 (tt, J=6.5, 1.3 Hz, 1H), 3.85 (d, J=2.4 Hz, 3H), 3.78 (d, J=1.9 Hz, 3H). $^{19}F$ NMR (376 MHz, $CDCl_3$) δ −113.03 (ddd, J=131.2, 52.5, 26.9 Hz, 2F), −128.45 (tt, J=26.9, 10.7 Hz, 1F), −130.37 (dt, J=21.5, 10.1 Hz, 1F), −132.68 (dd, J=21.9, 10.1 Hz, 1F), −144.31 (dddd, J=42.8, 32.0, 22.0, 11.6 Hz, 1F), −147.16 (td, J=21.6, 7.8 Hz, 1F).

The title compound I-137, 2-(difluoromethyl)-3,4,5,6-tetrafluoro-N-(3-fluoro-4-methoxyphenyl)benzenesulfonamide, was prepared via general procedure H using 2-(difluoromethyl)-3,4,5,6-tetrafluoro-N-(3-fluoro-4-methoxyphenyl)-N-(4-methoxybenzyl)benzenesulfonamide (200 mg, 0.382 mmol) and anisole (0.125 mL, 1.15 mmol, 3 eq.). (87%) $^{1}H$ NMR (400 MHz, $CDCl_3$) δ 7.67 (tt, J=52.3, 1.3 Hz, 1H), 7.20-7.06 (m, 1H), 7.02-6.84 (m, 3H), 3.88 (s, 3H). $^{13}C$ NMR (101 MHz, $CDCl_3$) δ 153.5, 150.9, 147.4, 147.3, 126.4, 126.3, 119.5, 119.4, 113.9, 113.9, 112.4, 112.2, 108.8 (t, J=241.6 Hz), 56.4. $^{19}F$ NMR (376 MHz, $CDCl_3$) δ −112.96 (dd, J=52.4, 28.0 Hz, 2F), −130.54--131.16 (m, 1F), −132.56 (dt, J=21.8, 10.2 Hz, 1F), −132.90 (dtt, J=38.0, 19.3, 9.2 Hz, 1F), −143.24 (td, J=20.5, 10.2 Hz, 1F), −146.98 (td, J=21.7, 8.2 Hz, 1F). HR-MS (TOF ES−) m/z calcd for $[C_{14}H_8F_7NO_3S]^-$: 402.01, found: 402.07.

II. Biological Evaluation

Examples C1 In Vitro Cell Viability Studies

Representative selected kinase inhibition for exemplary compounds is presented in the following Table 6.

TABLE 6

| COMPOUND # | BTK | RL[a] |
|---|---|---|
| Ibrutinib | A | E |
| I-A1 | B | D |
| I-A2 | C | D |
| I-A3 | C | D |
| I-A4 | B | N/A |
| I-A5 | C | N/A |
| I-A6 | C | N/A |

[a]RL is a human non-Hodgkin's lymphoma B cell line

Note:

Biochemical assay $IC_{50}$ data are designated within the following ranges:

A: ≤0.01 μM

B: >0.01 μM to ≤0.1 μM

C: >0.1 μM to ≤1.0 μM

D: >1.0 μM to ≤10 μM

E: >10 μM to ≤30 μM

Examples C2: Toxicity Studies

Anti-cancer efficacy of exemplary compounds of this application was assessed in vitro in different cancer cell lines. Cell viability was examined following treatment at various concentration of inhibitor (0.097656-50 μM) using a cell Titer-Blue cell viability assay. 1×104 cells (NHF cells)/well were plated in 96-well assay plates in culture medium. All cells were grown in DMEM, IMDM and RPMI-1640 supplemented with 10% FBS. After 24 hrs, test compounds and vehicle controls were added to appropriate wells so the final volume was 100p in each well. The cells were cultured for the desired test exposure period (72 hrs) at 37° C. and 5% CO2. The assay plates were removed from 37° C. incubator and 20 μl/well of CellTiter-Blue® Reagent was added. The plates were incubated using standard cell culture conditions for 1-4 hours and the plates were shaken for 10 seconds and record fluorescence at 560/590 nm.

Representative data for exemplary compounds against select normal primary human fibroblast (NHF) cell lines are presented in the following Table 7.

TABLE 7

| COMPOUND # | IC50 (uM) |
| --- | --- |
| Ibrutinib | D |
| I-A1 | C |
| I-A2 | C |
| I-A4 | E |
| I-A5 | E |
| I-A6 | E |
| I-A7 | E |

Note:
Biochemical assay $IC_{50}$ data are designated within the following ranges:
A: ≤0.1 μM
B: >0.1 μM to ≤1.0 μM
C: >1.0 μM to ≤10 μM
D: >10 μM to ≤25 μM
E: >25 μM, e.g. 50 μM or 100 μM

Examples C3 Reactivity Profiling with Glutathione

The experiment was started by placing 1 μL of 1 mM stocking solution of the test compound in DMSO in 199 μL of PBS buffer at pH 7.4 with 5 mM GSH to reach a final concentration of 5 μM. The final DMSO concentration was 0.5%. The solution was then incubated at 25° C. at 600 rpm, and was quenched with 600 μL solution of acetonitrile at 0, 30, 60 and 120 minutes. The quenched solution was vortexed for 10 minutes and centrifuged for 40 minutes at 3,220 g. An aliquot of 100 μL of the supernatant was diluted by 100 μL ultra-pure water, and the mixture was used for LC/MS/MS analysis. The data was processed and analyzed using Microsoft Excel.

Representative reactivity profile of exemplary compounds disclosed in Table 1 with GSH as assessed by MS is presented in the following Table 8.

TABLE 8

| COMPOUND # | $T_{1/2}$ (min) |
| --- | --- |
| Ibrutinib | D |
| I-A1 | Not reactive |
| I-A4 | Not reactive |
| I-A5 | E |
| I-A6 | Not reactive |
| I-A7 | Not reactive |

Note:
Reactivity profile is designated within the following ranges:
A: ≤10 min
B: >10 min to ≤100 min
C: >100 min to ≤1,000 min
D: >1,000 min to ≤10,000 min
E: >10,000 min to ≤30,000 min

Examples C4 Parallel Artificial Membrane Permeability Assay (PAMPA)

The stock solutions of positive controls were prepared in DMSO at the concentration of 10 mM. Testosterone and methotrexate were used as control compounds in this assay. Prepare a stock solution of compounds in DMSO at the concentration of 10 mM, and further dilute with PBS (pH 7.4). The final concentration of the test compound is 10 μM.

Assay Procedures. 1) Prepare a 1.8% solution (w/v) of lecithin in dodecane, and sonicate the mixture to ensure a complete dissolution. 2)Carefully pipette 5 μL of the lecithin/dodecane mixture into each acceptor plate well (top compartment), avoiding pipette tip contact with the membrane. 3) Immediately after the application of the artificial membrane (within 10 minutes), add 300 μL of PBS (pH 7.4) solution to each well of the acceptor plate. Add 300 μL of drug-containing solutions to each well of the donor plate (bottom compartment) in triplicate. 4) Slowly and carefully place the acceptor plate into the donor plate, making sure the underside of the membrane is in contact with the drug-containing solutions in all wells. 5) Replace the plate lid and incubate at 25° C., 60 rpm for 16 hours. 6) After incubation, aliquots of 50 μL from each well of acceptor and donor plate are transferred into a 96-well plate. Add 200 μL of methanol (containing IS: 100 nM Alprazolam, 200 nM Labetalol and 2 μM Ketoprofen) into each well. 7) Cover with plate lid. Vortex at 750 rpm for 100 seconds. Samples were centrifuged at 3,220 g for 20 minutes. Determine the compound concentrations by LC/MS/MS.

Representative permeability profile of exemplary compounds disclosed in Table 1 is presented in the following Table 9.

TABLE 9

| COMPOUND # | −Log Pe |
| --- | --- |
| Ibrutinib | A |
| I-A1 | B |
| I-A4 | B |
| I-A5 | B |
| I-A6 | C |
| I-A7 | C |

Note:
Concentration is designated within the following ranges:
A: <5
B: >5 to ≤6
C: >6 to ≤7
D: >7 to ≤8

Examples D1 In Vitro Cell Viability Studies

Anti-cancer efficacy of exemplary compounds of this application was assessed in vitro in different cancer cell lines. Cell viability was examined following treatment at various concentration of inhibitor (0.097656-50 μM) using a cell Titer-Blue cell viability assay. $1\times10^4$ cells (NHF, MV4-11, K562 and MOLM-13 cells)/well were plated in 96-well assay plates in culture medium. All cells were grown in DMEM, IMDM and RPMI-1640 supplemented with 10% FBS. After 24 hrs, test compounds and vehicle controls were added to appropriate wells so the final volume was 100 μl in each well. The cells were cultured for the desired test exposure period (72 hrs) at 37° C. and 5% $CO_2$. The assay plates were removed from 37° C. incubator and 20 μl/well of CellTiter-Blue® Reagent was added. The plates were incubated using standard cell culture conditions for 1-4 hours and the plates were shaken for 10 seconds and record fluorescence at 560/590 nm.

Representative data for exemplary compounds disclosed in Table 4 are presented in the following Table 10.

TABLE 10

| COMPOUND # | MV-4-11 | MOLM-13 | K562 |
|---|---|---|---|
| I-1 | C | C | D |
| I-2 | B | C | D |
| I-3 | D | N/A | D |
| I-4 | C | N/A | N/A |
| I-5 | N/A | D | D |
| I-6 | C | C | D |
| I-8 | C | D | D |
| I-10 | C | N/A | D |
| I-16 | B | C | D |
| I-17 | N/A | C | D |
| I-18 | C | C | D |
| I-19 | C | C | D |
| I-20 | N/A | C | D |
| I-21 | D | D | D |
| I-22 | N/A | C | D |
| I-24 | C | C | D |
| I-25 | N/A | C | D |
| I-26 | C | C | D |
| I-31 | B | C | D |
| I-32 | B | C | D |
| I-37 | C | C | D |
| I-39 | C | C | D |
| I-48 | C | C | D |
| I-49 | C | C | D |
| I-52 | C | D | C |
| I-54 | C | C | D |
| I-61 | B | B | B |
| I-62 | D | D | D |
| I-63 | D | N/A | D |
| I-64 | A | B | B |
| I-65 | A | B | N/A |
| I-66 | B | C | N/A |
| I-67 | B | B | B |
| I-68 | B | C | B |
| I-69 | B | N/A | N/A |
| I-70 | D | N/A | N/A |
| I-71 | C | D | C |
| I-72 | B | D | D |
| I-73 | B | C | C |
| I-74 | D | D | D |
| I-75 | A | B | B |
| I-76 | N/A | C | B |
| I-77 | C | D | D |
| I-78 | C | C | C |
| I-79 | C | C | D |
| I-80 | B | N/A | N/A |
| I-83 | A | A | A |
| I-84 | A | A | N/A |
| I-85 | N/A | A | N/A |
| I-86 | B | N/A | N/A |
| I-90 | C | C | D |
| I-92 | B | C | D |
| I-93 | A | B | A |
| I-95 | C | N/A | N/A |
| I-96 | B | N/A | N/A |
| I-97 | D | N/A | N/A |
| I-98 | D | N/A | N/A |
| I-99 | D | N/A | D |
| I-100 | D | N/A | D |
| I-101 | D | N/A | N/A |
| I-102 | B | N/A | D |
| I-103 | D | N/A | N/A |
| I-104 | D | N/A | N/A |
| I-124 | C | N/A | C |
| I-125 | C | N/A | D |

Note:
Biochemical assay $IC_{50}$ data are designated within the following ranges:
A: ≤0.10 μM
B: >0.10 μM to ≤1.0 μM
C: >1.0 μM to ≤10 μM
D: >10 e.g. 15 μM, 50 μM, or 300 μM Examples D2 Reactivity Profiling with Glutathione 1) $^{19}$F NMR Method Compounds were prepared at a final concentration of 100 μM in 50 mM HEPES, pH 7.4, 100 M 5-fluorotryptophan, 10 mM L-glutathione, 10% $D_2O$ (in blank samples, an equivalent volume of HEPES solution was added) and 5% DMSO. 1D $^{19}$F NMR experiments were recorded at 25° C. on a 600 MHz spectrometer with an H(F)CN room temperature probe (number of transients=800)(scan width, 150 ppm). 5-Fluorotryptophan served as an internal reference to normalize peak intensity and was innocuous in the reaction. The data was processed and analyzed using MestreNova 10.0 and GraphPad.

Representative reactivity profile of exemplary compounds disclosed in Table 4 with GSH as assessed by $^{19}$F NMR is presented in the following Table 11.

TABLE 11

| COMPOUND | $T_{1/2}$ (min) |
|---|---|
| Batabulin | B |
| I-1 | B |
| I-5 | C |
| I-6 | C |
| I-8 | B |
| I-10 | B, B[1] |
| I-19 | B |
| I-24 | C |
| I-33 | B |
| I-34 | B, C[2] |
| I-39 | C |
| I-45 | B |
| I-58 | B |
| I-64 | B |
| I-65 | B |
| I-68 | C |
| I-83 | B |
| I-84 | B |
| I-86 | C |
| I-90 | C |
| I-92 | C |
| I-125 | A |

[1]Longer experiment
[2]Normalized $F^-$ peak
A: >10 min;
B: >50 min;
C >300 min 2) HPLC Method Compounds were prepared at a final concentration of 25 μM in IMDM buffer supplemented with 10% FBS, and 5 mM GSH. The rate of compound degradation is determined by the integrated area of the analytical peak corresponding to the intact compound (t=0) after each sampling time. The elution time was 13 minutes with the flow rate of 1.2 ml/min. The mobile phase was consisted of phase A and B. Mobile phase A was analytical grade acetonitrile (+0.1% formic acid) and mobile phase B was Milli-Q water (+0.1% formic acid). Each compound was tested in duplicate. The data was processed and analyzed using GraphPad.

Representative reactivity profile of exemplary compounds disclosed in Table 4 with GSH as assessed by HPLC is presented in the following Table 12.

TABLE 12

| COMPOUND # | $T_{1/2}$ (min) |
|---|---|
| Batabulin | C |
| I-64 | C |
| I-65 | C |
| I-75 | C |

TABLE 12-continued

| COMPOUND # | $T_{1/2}$ (min) |
|---|---|
| I-83 | C |
| I-84 | C |

Note:
Reactivity profile is designated within the following ranges:
A: <10 min
B: >10 min to ≤100 min
C: >100 min to ≤1,000 min
D: >1,000 min to ≤10.000 min

Examples D3 Intrinsic Clearance of Exemplary Compounds in Mouse Hepatocyte

A stock of 100 μM test compound was prepared by diluting the 10 mM test compound in DMSO with a solution of 50% acetonitrile and 50% water. In a 96-well non-coated plate, 198 μL of hepatocytes was pipetted, and the plate was placed in the incubator on an orbital shaker to allow the hepatocytes to warm for 10 minutes. To this solution was added 2 μL of the 100 μM test compound to start the reaction, and the plate was placed on an orbital shaker. At time points of 0, 15, 30, 60, 90 and 120 minutes, the aliquots were mixed with a solution of acetonitrile and internal standard (100 nM alprazolam, 200 nM labetalol, and 2 μM ketoprofen) to terminate the reaction. The reaction solution was then vortexed for 10 minutes and centrifuged at 4,000 rpm for 30 minutes at 4° C. 400 μL of the supernatant was transferred to one new 96-well plate. Centrifuged at 4,000 rpm for 30 minutes at 4° C. Transfer 100 μL of the supernatant to a new 96-well plate ensuring the pellet was not disturbed. Add 100 μL of ultrapure water to all samples for analysis by LC-MS/MS. Bioanalytical method: Column—Phenomenex Synergi 4μ Hydro-PR 80A (2.0×30 mm). Mobile phase—0.1% formic acid in water (solvent A) and 0.1% formic acid in acetonitrile (solvent B). Column temperature—room temperature. Injection volume—10 μL. MS analysis—API 4000 instrument from AB Inc (Canada) with an ESI interface.

Representative clearance of exemplary compounds disclosed in Table 4 in mouse hepatocyte is presented in the following Table 13.

TABLE 13

| COMPOUND # | $T_{1/2}$ (min) |
|---|---|
| Batabulin | A |
| I-64 | C |
| I-65 | C |
| I-75 | C |
| I-83 | C |
| I-84 | C |

Note:
Clearance is designated within the following ranges:
A: ≤10 min
B: >10 min to ≤100 min
C: >100 min to ≤1,000 min
D: >1,000 min to ≤10.000 min

Examples D4 Parallel Artificial Membrane Permeability Assay (PAMPA)

1) The stock solutions of positive controls were prepared in DMSO at the concentration of 10 mM. Testosterone and methotrexate were used as control compounds in this assay. 2) Prepare a stock solution of compounds in DMSO at the concentration of 10 mM, and further dilute with PBS (pH 7.4). The final concentration of the test compound is 10 μM.

Assay Procedures. 1) Prepare a 1.8% solution (w/v) of lecithin in dodecane, and sonicate the mixture to ensure a complete dissolution. 2)Carefully pipette 5 μL of the lecithin/dodecane mixture into each acceptor plate well (top compartment), avoiding pipette tip contact with the membrane. 3) Immediately after the application of the artificial membrane (within 10 minutes), add 300 μL of PBS (pH 7.4) solution to each well of the acceptor plate. Add 300 μL of drug-containing solutions to each well of the donor plate (bottom compartment) in triplicate. 4) Slowly and carefully place the acceptor plate into the donor plate, making sure the underside of the membrane is in contact with the drug-containing solutions in all wells. 5) Replace the plate lid and incubate at 25° C., 60 rpm for 16 hours. 6) After incubation, aliquots of 50 μL from each well of acceptor and donor plate are transferred into a 96-well plate. Add 200 μL of methanol (containing IS: 100 nM Alprazolam, 200 nM Labetalol and 2 μM Ketoprofen) into each well. 7) Cover with plate lid. Vortex at 750 rpm for 100 seconds. Samples were centrifuged at 3,220 g for 20 minutes. Determine the compound concentrations by LC/MS/MS.

Representative concentration of compounds disclosed in Table 4 is presented in the following Table 14.

TABLE 14

| COMPOUND # | −Log Pe | Recovery % |
|---|---|---|
| Batabulin | 5.00 | 67.41 |
| I-64 | 4.99 | 98.87 |
| I-65 | 4.98 | 64.19 |
| I-75 | 5.02 | 94.92 |
| I-83 | 5.00 | 77.50 |
| I-84 | 4.99 | 34.74 |

Examples D5 Plasma Concentration of Exemplary Compounds in Balb C Nude Mice

IP administration at 40 mg/kg

Formulation: 10% DMA/65% PEG400/25% Saline

Bioanalytical assay: Mobile phase: Solvent A=Water (0.1% Formic acid, 5% Acetonitrile), Solvent B=Acetonitrile (0.1% Formic acid, 5% Water), Column: Agilent ZORBAX XDB-Phenyl 5 μm (50×2.10 mm), MS: AB API 5500 LC/MS/MS instrument, HPLC: Shimadzu (DGU-20A5R)

Sampling time: 5 min, 15 min, 30 min, 1 hour, 2 hour, 4 hour, 6 hour, 8 hour, 12 hours post dose Number of mice: 3

Mouse species: Balb/C nude mice

Representative plasma concentration of exemplary compounds disclosed in Table 4 is presented in the following Table 15.

TABLE 15

| COMPOUND # | K ($h^{-1}$) | $C_{max}$ (ng/mL) | $C_{max}$ (μM) |
|---|---|---|---|
| Batabulin | C | BB | BBB |
| I-64 | A | CC | CCC |
| I-65 | B | CC | CCC |
| I-75 | A | AA | AAA |

TABLE 15-continued

| COMPOUND # | K ($h^{-1}$) | $C_{max}$ (ng/mL) | $C_{max}$ (μM) |
|---|---|---|---|
| I-83 | A | CC | CCC |
| I-84 | B | BB | BBB |

Note:
K values are designated within the following ranges:
A: ≤5 $h^{-1}$
B: >5 $h^{-1}$ to ≤10 $h^{-1}$
C: >10 $h^{-1}$ to ≤15 $h^{-1}$
D: >15 $h^{-1}$;
Average concentration values $C_{max}$ (ng/mL) are are designated within the following ranges:
AA: ≤20.000 ng/mL
BB: >20,000 ng/mL to ≤40,000 ng/mL
CC: >40,000 ng/mL to ≤65,000 ng/mL
DD: >65,000 ng/mL; and
Average concentration values $C_{max}$ (μM) are are designated within the following ranges:
AAA: ≤50 μM
BBB: >50 μM to ≤100 μM
CCC: >100 μM to ≤150 μM
DDD: >150 μM

Examples D6 Tubulin Polymerization Assay

A96-well half-area clear flat-bottom microplate (Corning® #3697) was pre-heated in a plate reader (Cytation 3, BioTek) at 37° C. for 15 minutes prior to the start of each assay. Tubulin polymerization buffer (80 mM PIPES pH 6.9, 2 mM $MgCl_2$, 0.5 mM EGTA, 15% glycerol, 1 mM GTP) was prepared from stock solutions and placed on ice. Inhibitors were prepared to M concentrations in buffer (80 mM PIPES pH 6.9, 2 mM $MgCl_2$, 0.5 mM EGTA, 5% DMSO) from DMSO stock solutions. After the assay plate was pre-warmed, 10 μL of inhibitor or buffer control was added to selected wells. Every assay contained a tubulin only negative control for normalization of data, and a batabulin positive control. The assay plate was incubated at 37° C. for 3 minutes. During this time, a frozen aliquot of tubulin (10 mg/mL) in buffer (80 mM PIPES pH 6.9, 2 mM $MgCl_2$, 0.5 mM EGTA) was defrosted by placing in a room temperature water bath. Once thawed, 200 μL of tubulin was mixed with 420 μL ice cold tubulin polymerization buffer (3 mg/mL tubulin in 80 mM PIPES, pH 6.9, 2 mM $MgCl_2$, 0.5 mM EGTA, 1 mM GTP, 10.2% glycerol). To a 96-well plate on ice, aliquots of 100 μL tubulin was added to each well. From this plate, 90 μL of tubulin was immediately pipetted into all sample wells of the warmed assay plate using a multichannel pipette. The assay plate was immediately put in the reader at 37° C. and shook for 5 s with orbital shaking at medium speed. The reader recorded the absorbance at 340 nm every 15 s for 30 min.

The resulting absorbance curves were normalized by subtracting each data point by the absorbance at time 0. The slope of the initial linear portion ("$V_{max}$") was determined in mOD/min, and normalized to the $V_{max}$ value of the tubulin only control, using the following equation, resulting in comparable % inhibition values:

$$\%\ \text{inhibition} = \left(1 - \frac{V_{max(tubulin+inhibitor)}}{V_{max(tubulin)}}\right) \times 100$$

The largest change in absorbance over the assay time course was also recorded and related to the tubulin control as the % degree of polymerization (% D.O.P.).

Representative tubulin polymerization of exemplary compounds disclosed in Table 4 is presented in the following Table 16.

TABLE 16

| COMPOUND # | % Inhibition | % D.O.P. |
|---|---|---|
| Batabulin | C | B |
| I-1 | A | A |
| I-61 | A | A |
| I-62 | A | A7 |
| I-63 | A | A |
| I-64 | A | A |
| I-65 | C | B |
| I-66 | B | B |
| I-67 | C | B |
| I-68 | B | B |
| I-69 | A | A |
| I-70 | A | A |
| I-71 | A | A |
| I-72 | A | A |
| I-73 | A | A |
| I-74 | A | A |
| I-75 | B | B |
| I-76 | C | B |
| I-77 | A | A |
| I-78 | B | B |
| I-79 | A | A |
| I-82 | B | A |
| I-83 | C | B |
| I-84 | C | B |
| I-85 | A | A |
| I-86 | A | A |
| I-87 | A | A |
| I-88 | A | A |
| I-90 | A | A |
| I-93 | C | B |
| I-96 | A | A |

Inhibition: A: <10%, B: 10-20%, C >20%
DOP: A: >85%, B: < 85%

Examples D7 Electrophoretic Mobility Shift Assay

Compounds were prepared to 2 μM in general tubulin buffer (80 mM PIPES pH 6.9, 2 mM $MgCl_2$, 0.5 mM EGTA, 5% DMSO). Compounds were serially diluted in a 96-well half-area plate to the desired concentration range for the assay. Tubulin glycerol buffer (80 mM PIPES pH 6.9, 2 mM $MgCl_2$, 0.5 mM EGTA, 15% glycerol) was prepared and placed on ice. A frozen aliquot of porcine brain tubulin (10 mg/mL, Cytoskeleton, Inc., Cat. #T240-DX) in buffer (80 mM PIPES pH 6.9, 2 mM $MgCl_2$, 0.5 mM EGTA, 1 mM GTP) was defrosted by placing in a room temperature water bath. Once thawed, 13 μL of tubulin was mixed with 1000 μL ice cold tubulin glycerol buffer (2 μM tubulin). Diluted tubulin was added to all compound wells using a multichannel pipette, followed by incubation at 37° C. for 2 hours. EBI (200 μM) in general tubulin buffer was added to specified wells and incubated for 2 hours at 37° C.

Afterwards, 30 μL of sample was added to 10 μL 4× Laemmli buffer and boiled for 5 min at 95° C. The gels were loaded with 8 μL sample (~0.5 ng protein per well) and were ran in 1×Tris/Glycine/SDS Buffer (Bio-Rad cat. #161-0732) at 120V-180V until the bromophenol blue band ran off the gel. The gel was soaked in transfer buffer for 5 minutes and then transferred to a midi 0.2 μM PVDF blotting membrane (Bio-Rad cat. #170-4157) using the Bio-Rad Trans-Blot Turbo transfer system. The blot was blocked in 3% BSA in TBS-T at rt for 1 hour. The primary antibody Rabbit Polyclonal beta-tubulin (Abbexa, Cat. #ab6406) was diluted 1:500 in 3% BSA and 0.02% $NaN_3$ and incubated with the blot overnight at 4° C. The blot was washed with TBS-T 3×5 minutes at rt. The secondary antibody Goat Anti-rabbit HRP conjugate (Bio-Rad, Cat. #170-5046) was diluted to 1:5000 with 3% BSA and incubated with the blot for 1 hr at rt. The blot was rinsed 3×5 min with TBS-T. Clarity Western ECL substrate (Bio-Rad) was added to the blot before imaging with ChemiDoc MP on high resolution.

Porcine brain tubulin (1 μM, Cytoskeleton) was incubated in vitro with or without compounds (various concentrations) for 2 hours at 37° C. Following this, the cross-linking agent N,N'-ethylene-bis(iodoacetamide), or EBI, was incubated with protein (200 μM) for 2 hours at 37° C. with covalently links Cys-239 and Cys-354 of beta-tubulin. The EBI adduct migrates faster than native beta-tubulin band on SDS-PAGE, but can be blocked by pre-incubated compound. Western blot is probing beta-tubulin (Rabbit Anti-beta Tubulin antibody (ab6046), Amgen).

Examples E1 Target Engagement and Mechanism of Action Studies

Target Engagement

IC50 values (nM) for the inhibition of BTK activity

In vitro BTK and JAK3 inhibition studies are shown in Table 17 and Table 18 (no preincubation).

TABLE 17

| Compound | BTK ($IC_{50}$, nM) |
|---|---|
| Ibrutinib | B |
| I-A1 | C |
| 3A-10 | B |
| 3A-11 | B |
| 3A-24 | B |
| 3A-1 | D |
| I-A5 | D |
| I-A6 | D |
| 3A-2 | D |
| 3A-6 | D |

Note:

Biochemical assay $IC_{50}$ data are designated within the following ranges:

A: ≤0.1 nM

B: >0.1 nM to ≤10 nM

C: >10 nM to ≤100 nM

D: >100 nM to ≤1000 nM

TABLE 18

| Compound | BTK ($IC_{50}$, nM) | JAK3 ($IC_{50}$, nM) |
|---|---|---|
| Spebrutinib | C | — |
| 3A-9 | B | — |
| 3A-39 | D | — |
| 3A-25 | — | E |
| 3A-27 | B | E |
| 3A-28 | D | E |

Note:
Biochemical assay $IC_{50}$ data are designated within the following ranges:
A: ≤0.1 nM
B: >0.1 nM to ≤10 nM
C: >10 nM to ≤100 nM
D: >100 nM to ≤1000 nM
E: >1000 nM to ≤10,000 nM In vitro kinase inhibition studies are shown in Table 19.

TABLE 19

| Kinase ($IC_{50}$, nM) | I-A1 | 3A-1 |
|---|---|---|
| BMX | B | C |

Note:
Biochemical assay $IC_{50}$ data are designated within the following ranges:
A: ≤0.1 nM
B: >0.1 nM to ≤10 nM
C: >10 nM to ≤100 nM In vitro irreversible inhibition studies are shown in Table 20.

TABLE 20

| Inhibitor | $k_{inact}$/Ki* |
|---|---|
| 3A-10 | B |
| 3A-11 | B |
| 3A-24 | B |
| 3A-1 | B |
| I-A1 | B |
| I-A6 | A |
| 3A-2 | A |

*Based on the following two-step kinetic scheme:

$$E + I \underset{K_I}{\rightleftharpoons} E{\bullet}I \xrightarrow{k_{inact}} E\text{-}I$$

A: <50 $mM^{-1}s^{-1}$, B: ≥50 $mM^{-1}s^{-1}$

Examples F1 Covalent Modification Experiments

General Definitions

Any suitable method for determining an irreversible (e.g., covalently irreversible) is used. In some instances, methods for identifying if a compound is acting as an irreversible inhibitor are known to one of ordinary skill in the art. Such methods include, but are not limited to, the use of mass spectrometry of the protein drug target modified in the presence of the inhibitor compound, enzyme kinetic analysis of the inhibition profile of the compound with the target protein, and discontinuous exposure, also known as "wash-out," experiments, as well as other methods known to one of skill in the art.

One of ordinary skill in the art will recognize that certain reactive functional groups can act as "warheads." As used herein, the term "warhead" or "warhead group" refers to a functional group present on a compound of the present invention wherein that functional group is capable of covalently binding to an amino acid residue (such as cysteine, lysine, histidine, or other residues capable of being covalently modified), present in or near the binding pocket of a target protein, thereby irreversibly inhibiting the protein. It will be appreciated that in some embodiments the Linker-Warhead group (L-WH), as defined and described herein, provides such warhead groups for covalently, and irreversibly, inhibiting the protein.

Figure 7:
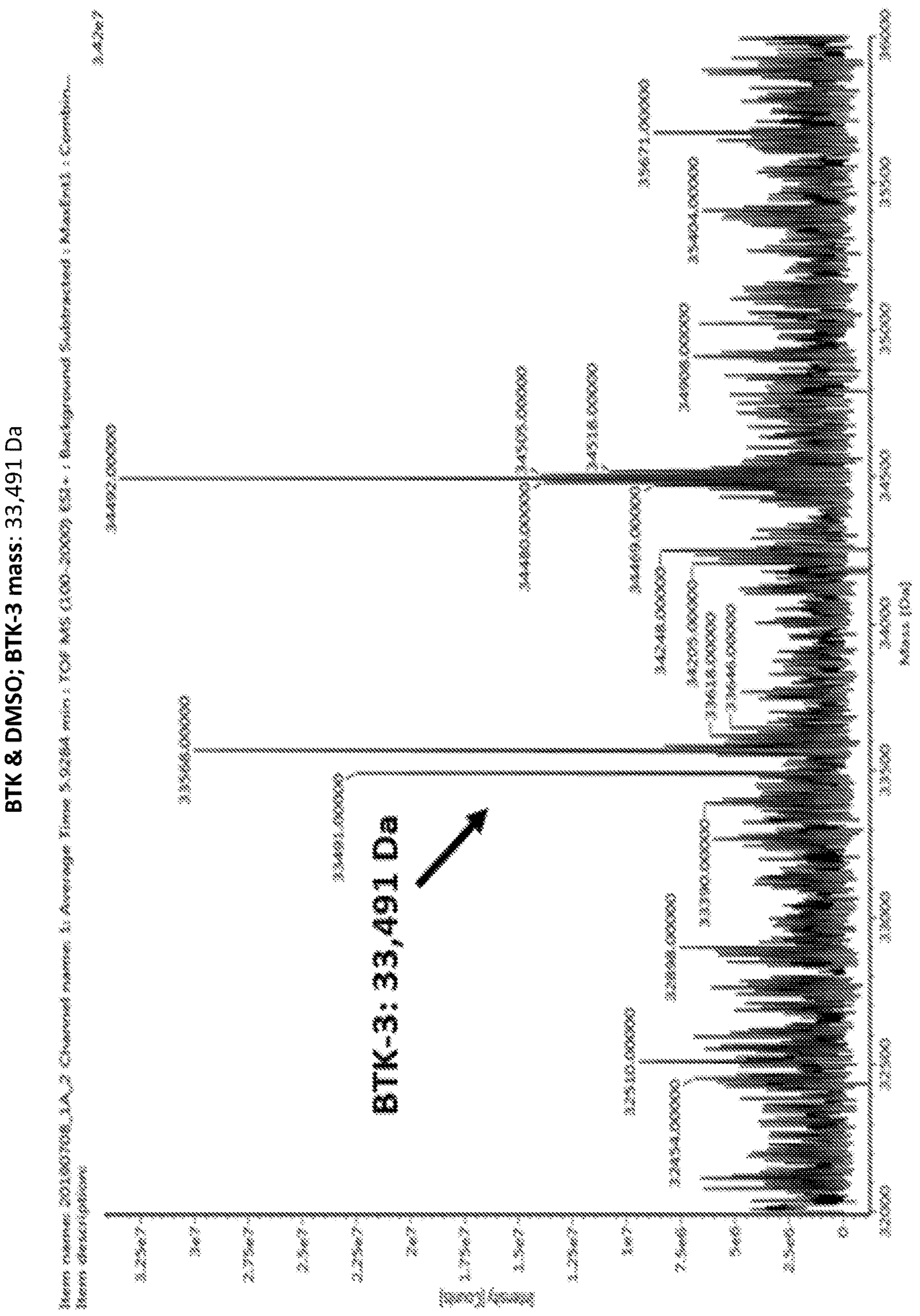
FIG. 7 illustrates representative covalent modification of the BTK enzyme with compound I-A1 demonstrated by mass spectrometry.

Description:

In one example, covalent modification of the enzyme BTK with compound I-A1 has been demonstrated by mass spectrometry. After incubation of 10 μM BTK in the presence of 50 μM of compound I-A1 for 2 hours at 30° C., the mass of the modified protein was determined by mass spectrometry. As shown in FIG. 7, the mass of the parent ion of the His-tagged protein prior to incubation was the third most intense peak, in this experiment corresponding to 33491 Da. After incubation with inhibitor I-A1, the intensity of this had decreased by an order of magnitude, and the most intense peak is consistent with the protein whose mass was increased by 595 Da, corresponding closely to the expected mass of the inhibitor I-A1 (less one fluoride from inhibitor, and one proton from protein, 596 Da). One of ordinary skill in the art will recognize that this is consistent with the covalent modification of BTK after irreversible inhibition by compound I-A1.

Figure 8:
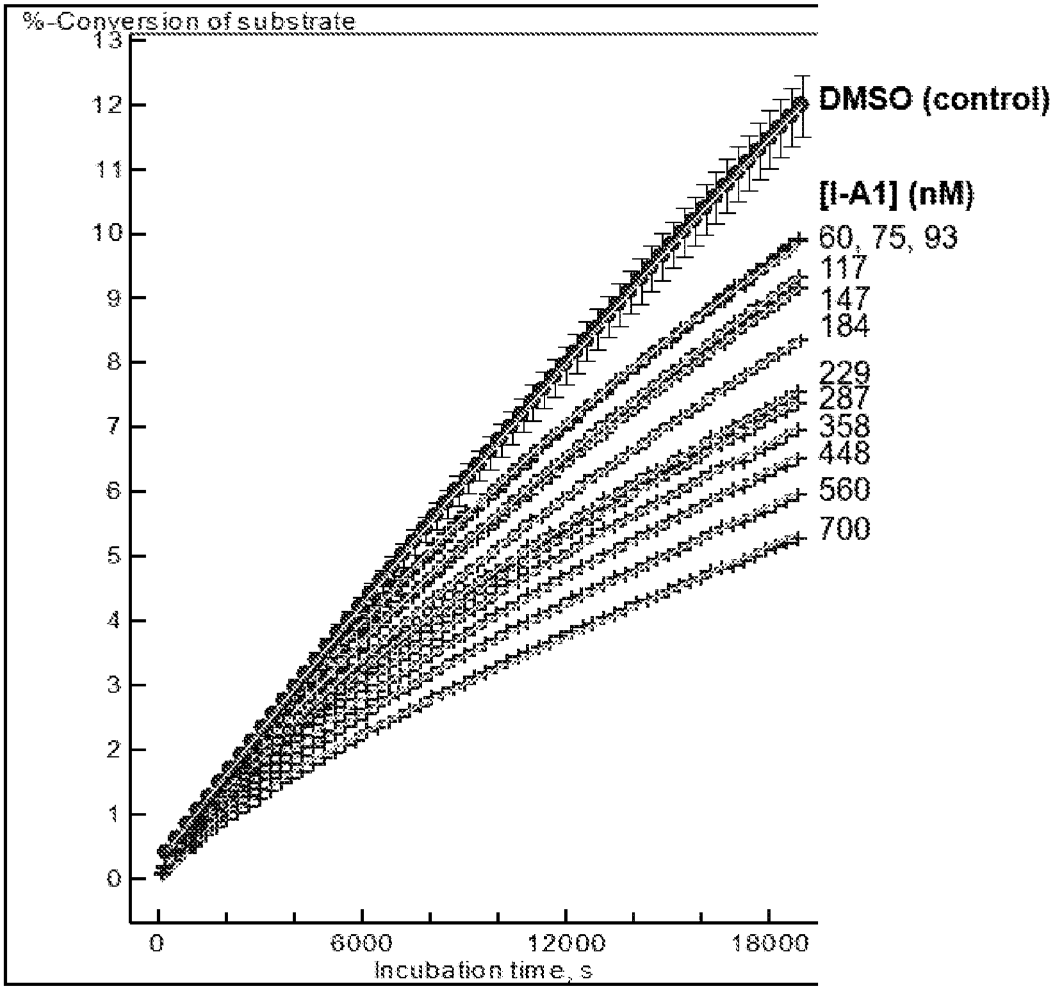
FIG. 8 illustrates representative covalent modification of the BTK enzyme with compound I-A1 demonstrated by enzyme kinetic analysis (time-dependent inhibition).

In another example, covalent modification of the enzyme BTK with compound I-A1 has been demonstrated by enzyme kinetic analysis of the inhibition profile of compound I-A1. The reaction of 0.1 nM BTK with 500 μM of its substrate ATP in the presence of 60-700 nM of compound I-A1 was shown to exhibit time-dependent inhibition corresponding to mono-exponential time courses (FIG. 8). Further, the rate constant of this time-dependent inhibition was shown to increase in a dose-dependent manner on the concentration of compound I-A1. One of ordinary skill in the art will recognize that this is consistent with the irreversible inhibition of BTK by compound I-A1.

Figure 9:
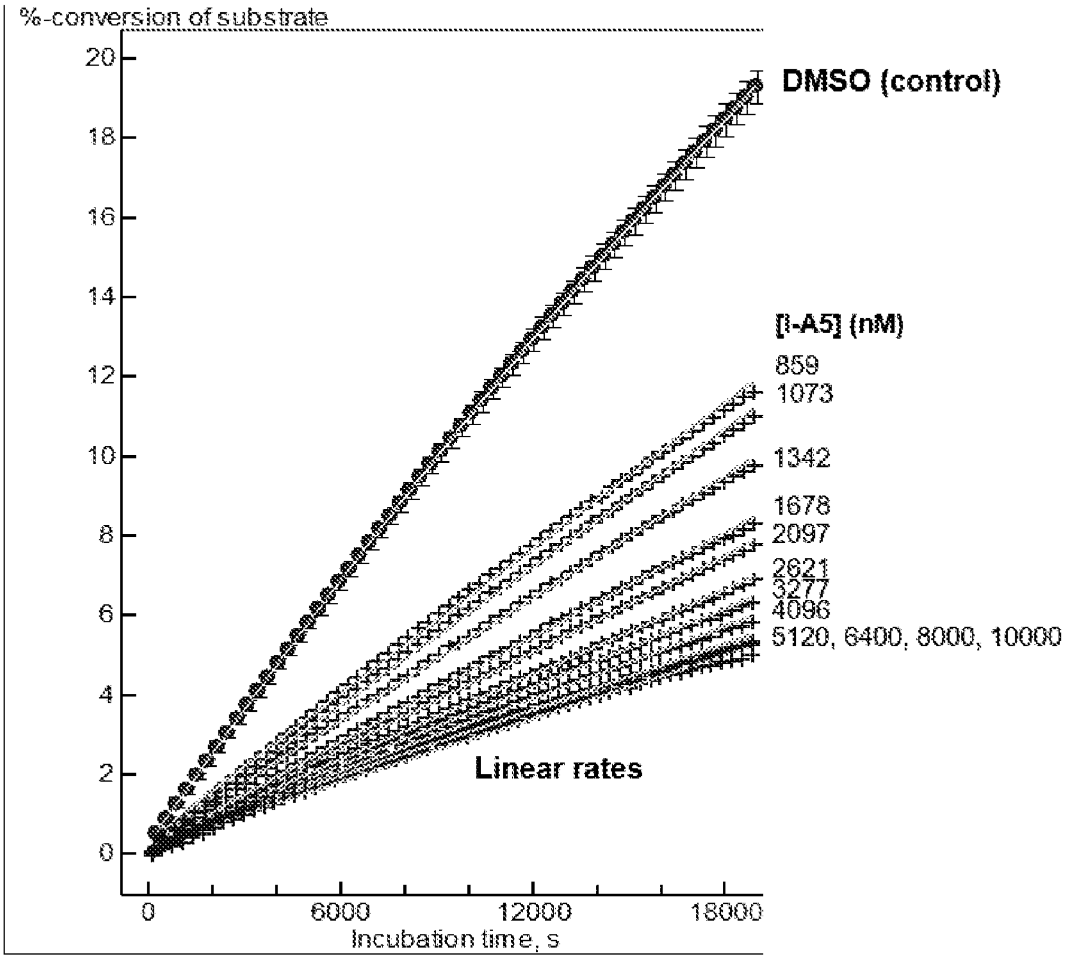
FIG. 9 illustrates comparative non-covalent modification of the BTK enzyme with compound I-A5 demonstrated by enzyme kinetic analysis (linear inhibition).

By way of contrast, the inhibition of BTK with I-A5 shows a very different inhibition profile, because the structure of this compound is identical to that of I-A1 except that it lacks a para-fluoro substituent and is unable to inhibit BTK irreversibly. As shown in FIG. 9, linear enzyme reaction rates are observed, as opposed to the time-dependent inhibition shown in FIG. 8. Fitting of the reaction rates of FIG. 9 to a reversible binding model gave an $IC_{50}$ value of 334 nM.

Figure 10:
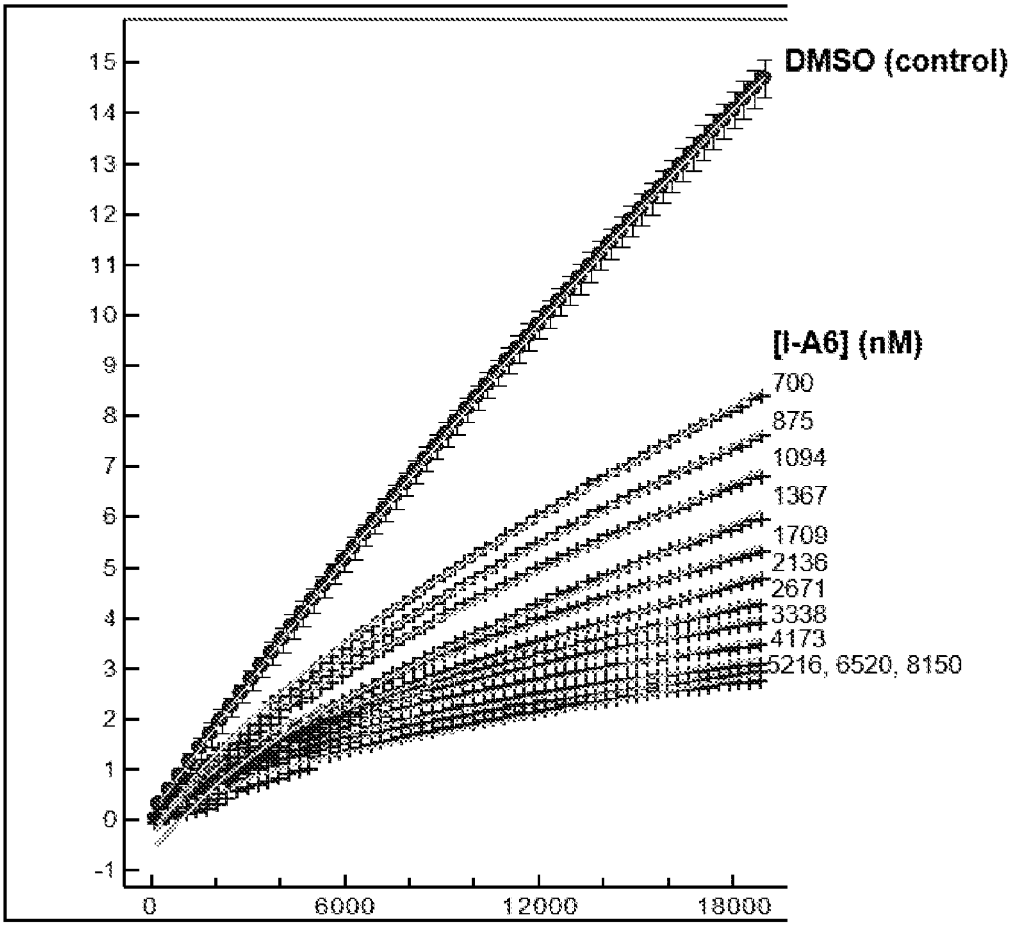
FIG. 10 illustrates representative covalent modification of the BTK enzyme with compound I-A6 demonstrated by enzyme kinetic analysis (time-dependent inhibition).
Figure 11:
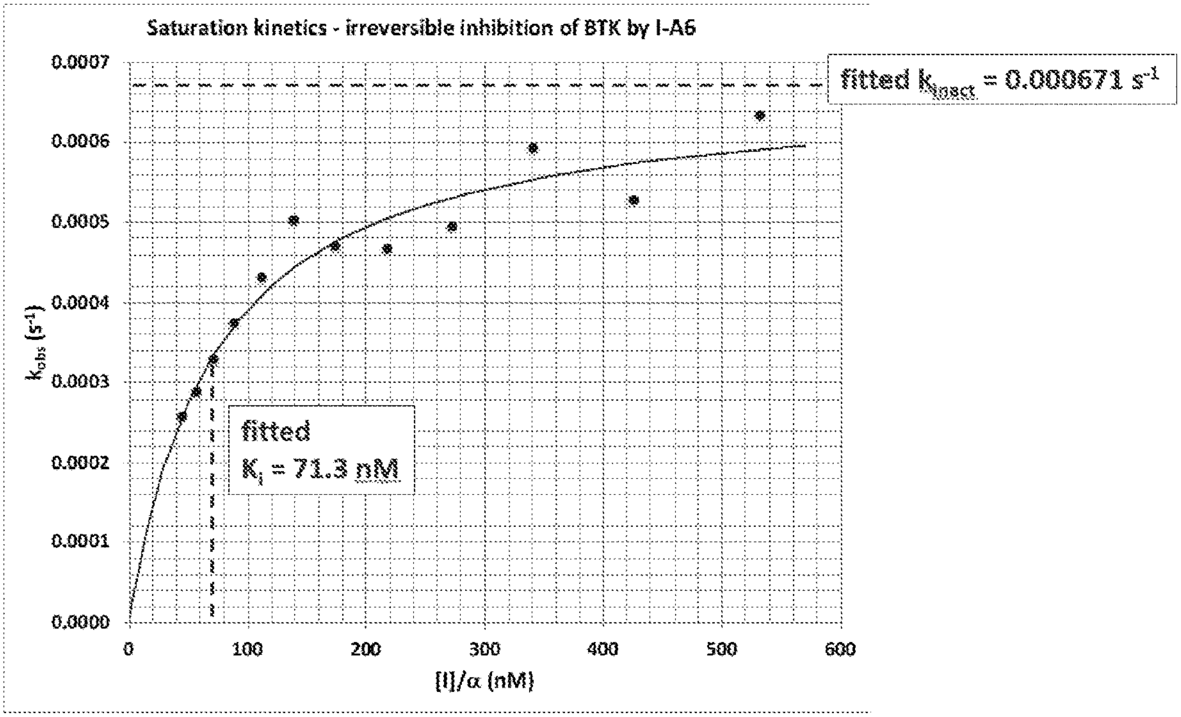
FIG. 11 illustrates representative saturation kinetics of irreversible inhibition of the BTK enzyme by compound I-A6.

In another example, covalent modification of the enzyme BTK with compound I-A6 has been demonstrated by enzyme kinetic analysis of the inhibition profile of compound I-A6. The reaction of 0.1 nM BTK with 500 μM of its substrate ATP in the presence of 700-8150 nM compound I-A6 was shown to exhibit time-dependent inhibition corresponding to mono-exponential time courses (FIG. 10). Further, the rate constant of this time-dependent inhibition was shown to increase in a dose-dependent manner on the concentration of compound I-A6. Still further, this dose-dependence was shown to exhibit saturation kinetics, which can be fitted to determine the irreversible inhibition parameters of $k_{inact}=0.671\times10^{-3}\ s^{-1}$ and $K_i=71.3$ nM (FIG. 11). One of ordinary skill in the art will recognize that this is consistent with the irreversible inhibition of BTK by compound I-A6.

Figure 12:
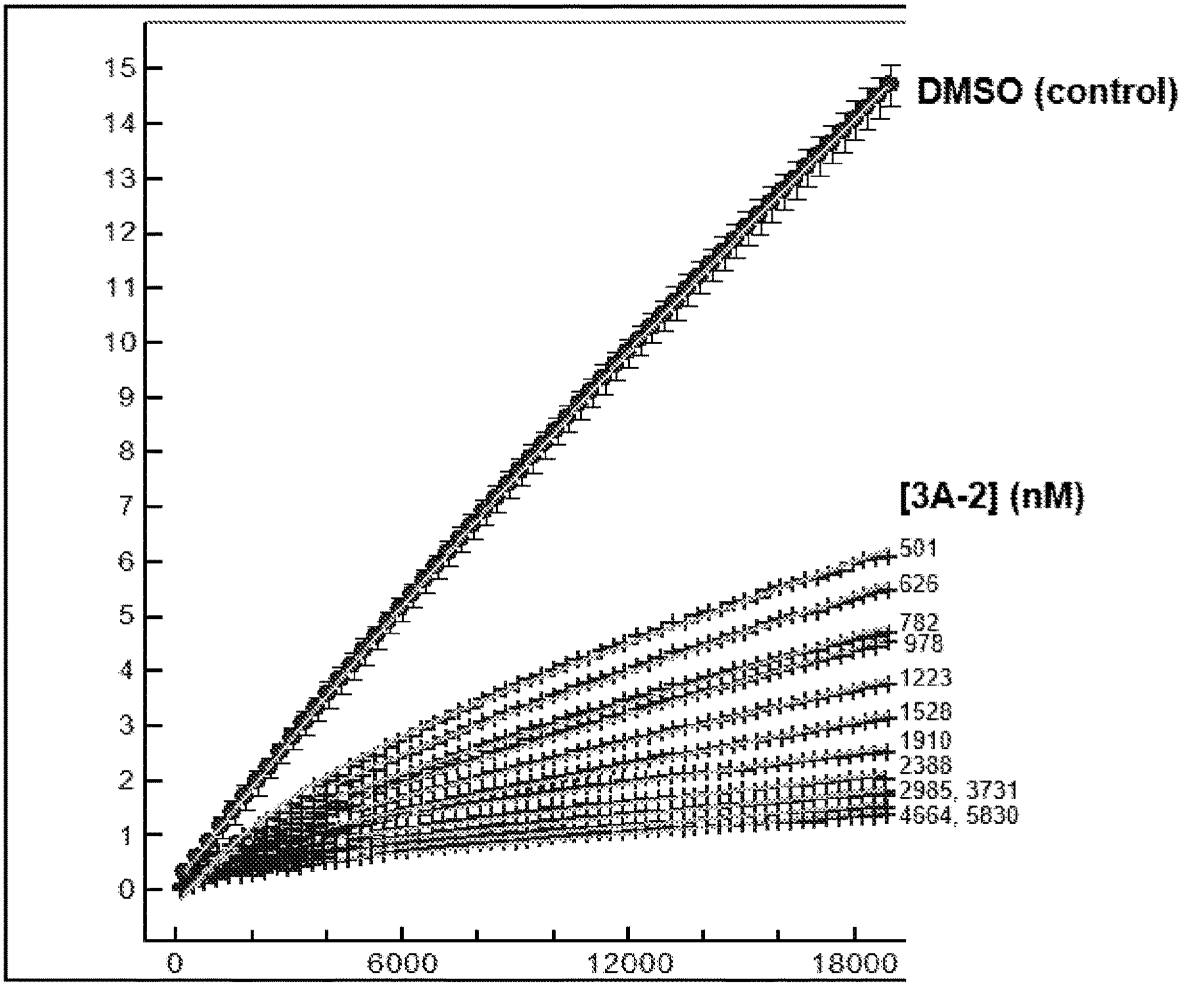
FIG. 12 illustrates representative covalent modification of the BTK enzyme with compound 3A-2 demonstrated by enzyme kinetic analysis (time-dependent inhibition).
Figure 13:
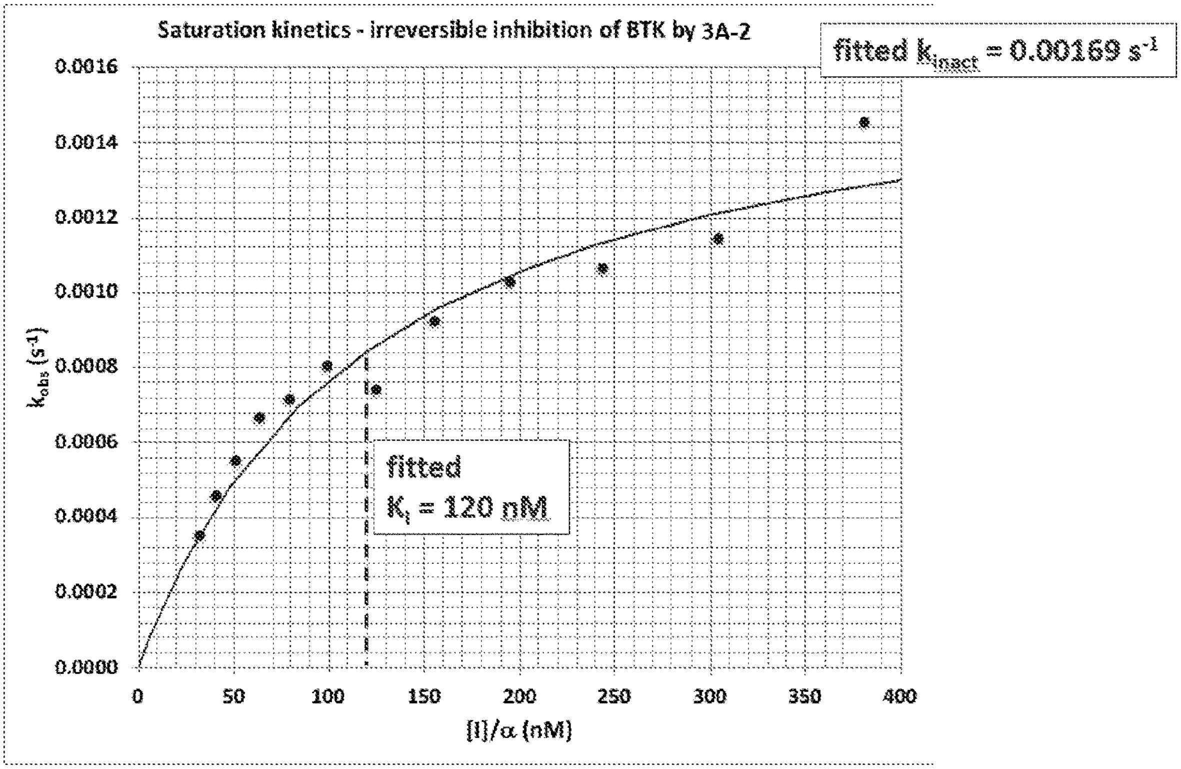
FIG. 13 illustrates representative saturation kinetics of irreversible inhibition of the BTK enzyme by compound 3A-2.

In another example, covalent modification of the enzyme BTK with compound 3A-2 has been demonstrated by enzyme kinetic analysis of the inhibition profile of compound 3A-2. The reaction of 0.1 nM BTK with 500 μM of its substrate ATP in the presence of 501-5830 nM of compound 3A-2 was shown to exhibit time-dependent inhibition corresponding to mono-exponential time courses (FIG. 12). Further, the rate constant of this time-dependent inhibition was shown to increase in a dose-dependent manner on the concentration of compound 3A-2. Still further, this dose-dependence was shown to exhibit saturation kinetics, which can be fitted to determine the irreversible inhibition parameters of $k_{inact}=1.69\times10^{-3}\ s^{-1}$ and $K_i=120$ nM (FIG. 13). One of ordinary skill in the art will recognize that this is consistent with the irreversible inhibition of BTK by compound 3A-2.

Figure 14:
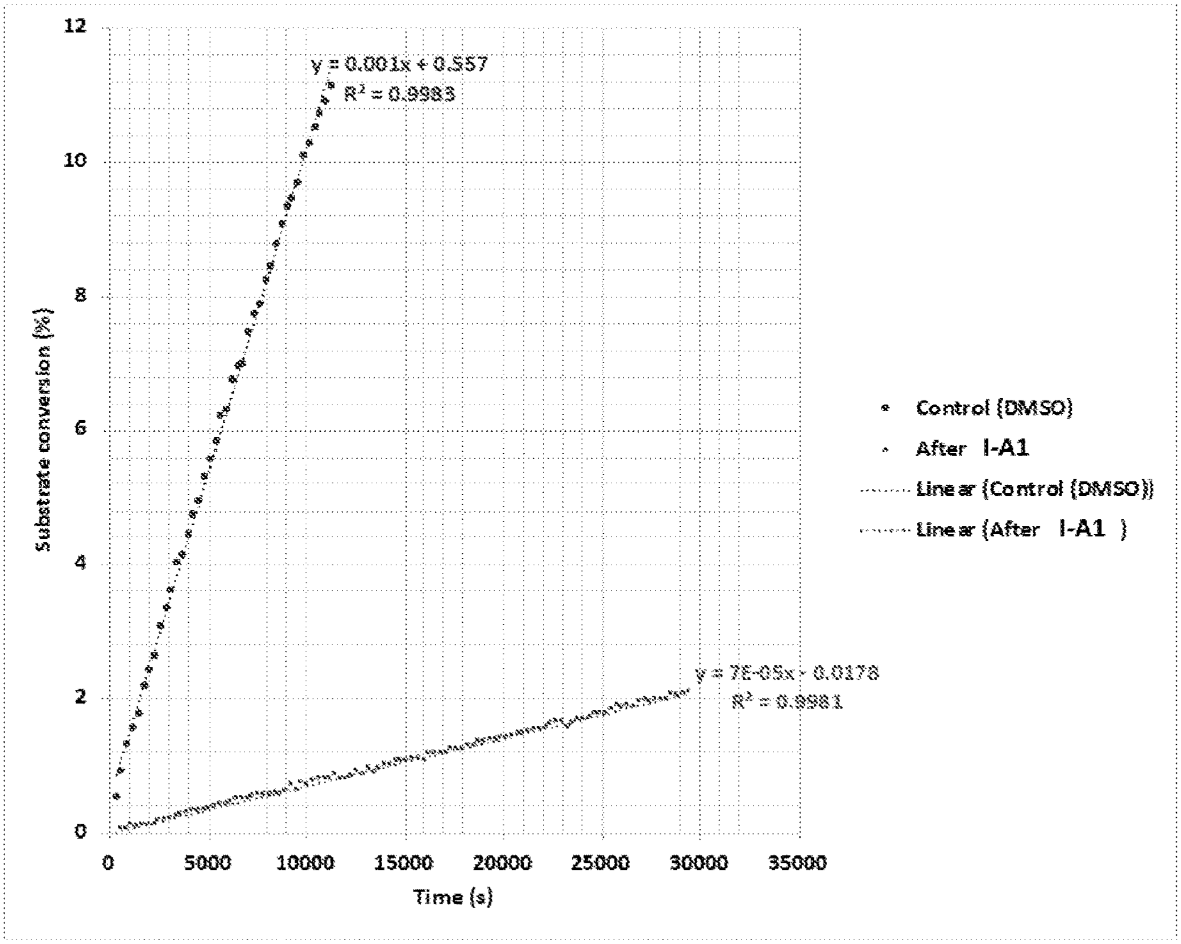
FIG. 14 illustrates representative residual activity of the BTK enzyme in the presence of compound I-A1.

In another example, covalent modification of the enzyme BTK with compound I-A1 has been demonstrated by a "washout" experiment. After a 3-h incubation of 40 nM BTK in the presence of 296 nM of compound I-A1, a 400-fold dilution was performed to remove excess inhibitor. As shown in FIG. 14, the residual activity of the enzyme was observed to be 7% of that of the enzyme incubated with DMSO alone (positive control), indicating to one of ordinary skill in the art that >90% of the enzyme was inhibited irreversibly during the incubation period.

Figure 15:
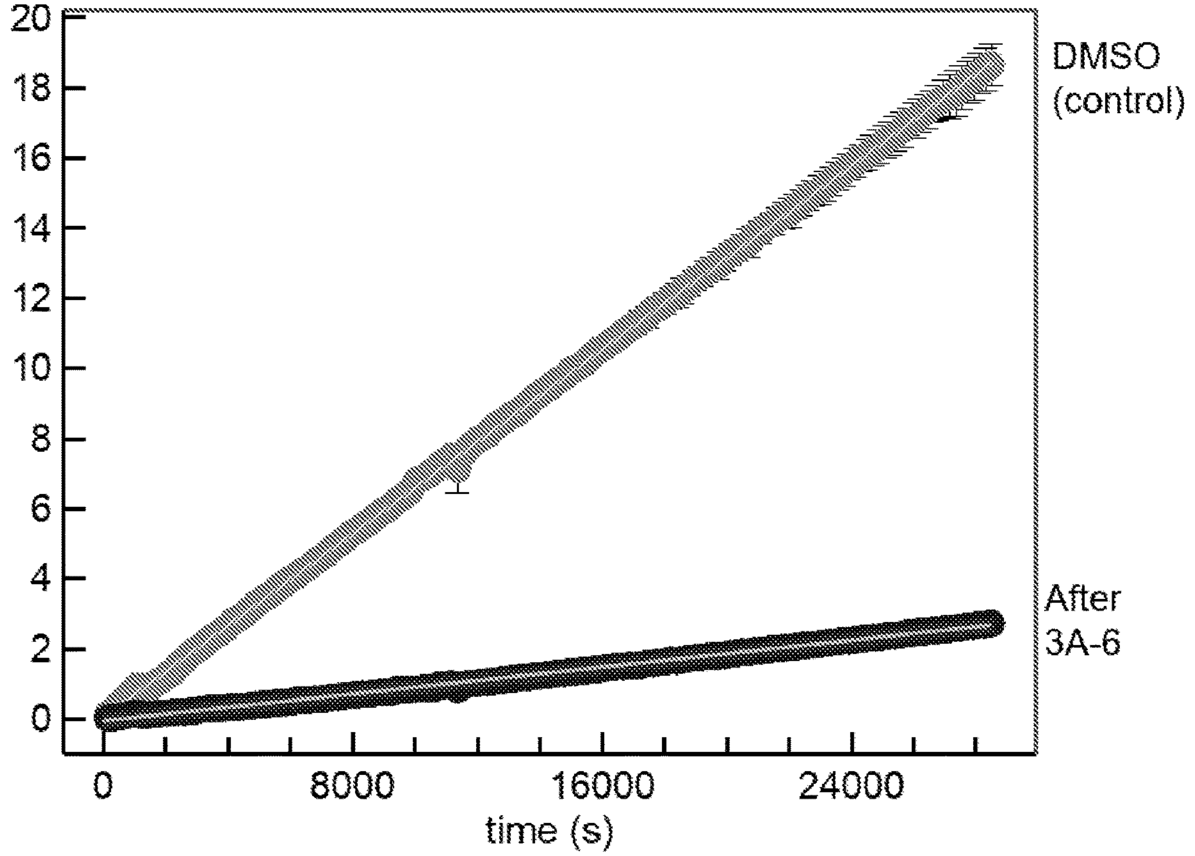
FIG. 15 illustrates representative residual activity of the BTK enzyme in the presence of compound 3A-6.

In another example, covalent modification of the enzyme BTK with compound 3A-6 has been demonstrated by a "washout" experiment. After a 6-h incubation of 50 nM BTK in the presence of 280 nM of compound 3A-6, a 400-fold dilution was performed to remove excess inhibitor. As shown in FIG. 15, the residual activity of the enzyme was observed to be 13% of that of the enzyme incubated with DMSO alone (positive control), indicating to one of ordinary skill in the art that 87% of the enzyme was inhibited irreversibly during the incubation period.

Figure 16:
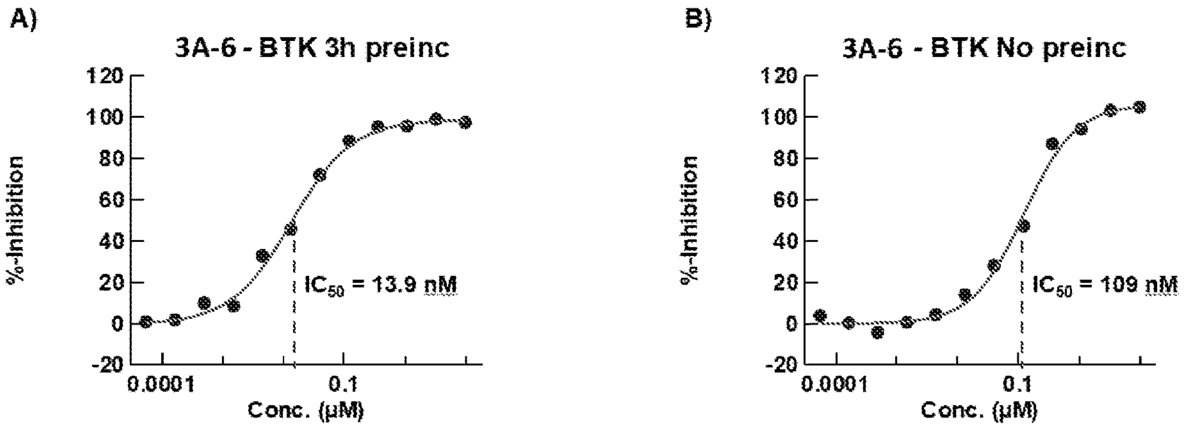
FIG. 16A illustrates representative $IC_{50}$ value of compound 3A-6 against pre-incubated BTK enzyme measured in the presence of ATP.
FIG. 16B illustrates representative $IC_{50}$ value of compound 3A-6 in the presence of ATP against BTK enzyme that had not been pre-incubated.

Further, after a 3-h incubation of 50 nM BTK in the presence of 280 nM of compound 3A-6, the $IC_{50}$ value of 3A-6 against this pre-treated enzyme was measured in the presence of 500 μM ATP and found to be 13.9 nM (FIG. 16A). When the $IC_{50}$ of 3A-6 was measured at 500 μM ATP against enzyme that had not been pre-incubated, the value was found to be 109 nM (FIG. 16B). The shift of $IC_{50}$ to a lower value after pre-incubation of the enzyme indicates to one of ordinary skill in the art that a significant portion of the enzyme was inhibited irreversibly during the incubation period.

Figure 17:
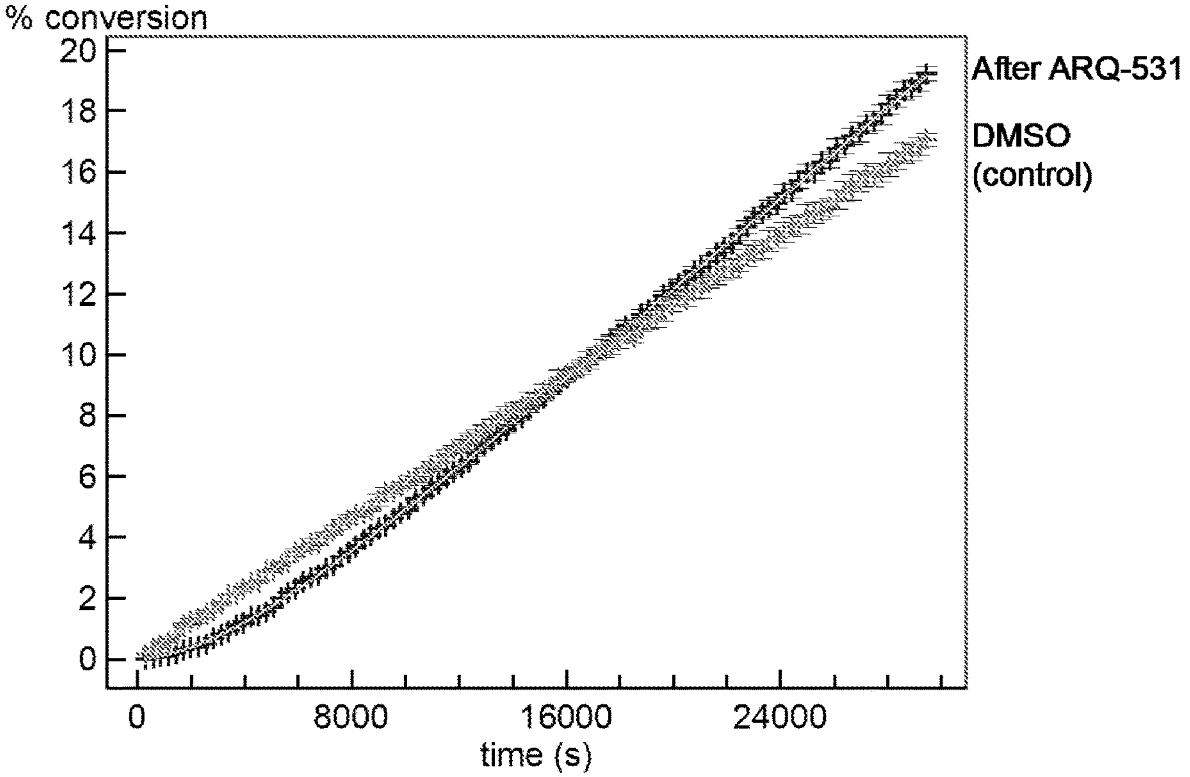
FIG. 17 illustrates representative residual activity of the enzyme BTK after incubation in the presence of ARQ-531.

By way of contrast, a "washout" experiment performed with ARQ-531 gives a very different result, because this compound lacks a warhead and is known to inhibit BTK reversibly. After a 6-h incubation of 50 nM BTK in the presence of 177 nM of ARQ-531, a 400-fold dilution was performed to remove excess inhibitor. As shown in FIG. 17, after a brief period during which reversibly bound inhibitor was released into solution, the enzyme recovered all of its activity relative to that of the enzyme incubated with DMSO alone (positive control). This indicates to one of ordinary skill in the art that the enzyme was not inhibited irreversibly during the incubation with ARQ-531. The comparison of this result, obtained with the known reversible inhibitor ARQ-531 (FIG. 17) to the results of the "washout" experiments performed with either compound I-A1 (FIG. 14) or compound 3A-6 (FIG. 15) indicates to one of ordinary skill in the art that the enzyme was inhibited irreversibly during incubation with compound I-A1 and compound 3A-6.

Examples G1 In Vitro Efficacy Studies

As a specific comparative example of the biological utility of the technology relative to Ibrutinib in RL cells, compound I-A6, possessing a representative warhead, exhibits greater potency (compound I-A6 $IC_{50}=1.0$ μM vs 10.26 μM for ibrutinib). Compound I-A6 (TI=>25) also exhibits a higher therapeutic index (TI) than ibrutinib (TI=2.6) or a PFBS analogue I-A1 (TI=2.5 uM) as assessed in normal pooled human fibroblasts vs RL cells as shown in Table 22.

Therapeutic index=($IC_{50}$ human fibroblasts/$IC_{50}$ RLcells)

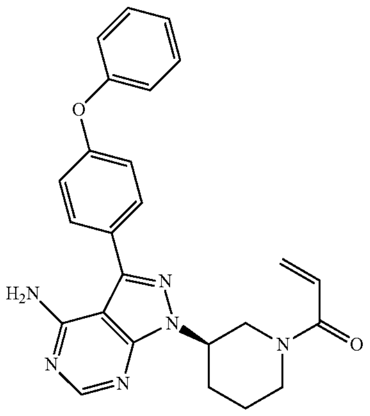

ibrutinib

I-A1

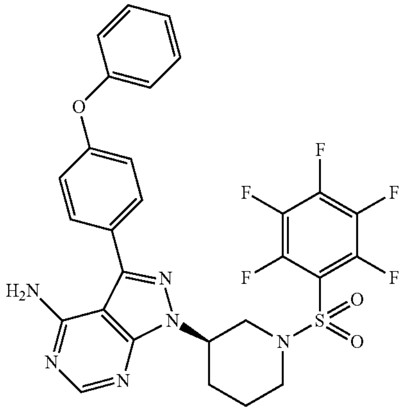

I-A6

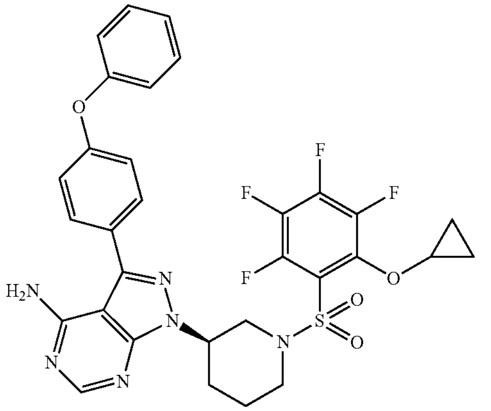

TABLE 22

| Reference | RL ($IC_{50}$, μM)[a] | Human Fibroblast ($IC_{50}$, μM)[b] |
|---|---|---|
| Ibrutinib | 10.26 | 26.8 |
| I-A1 | 1.61 | 3.98 |
| I-A6 | 1 | >25 |

[a]RL is a human non-Hodgkin's lymphoma B cell line
[b]Human fibroblast is a normal human cell line Warhead compound I-A6 shows better cell-based efficacy and therapeutic window than Ibrutinib (acrylamide) and pentafluorbenzenesulfonamide analog (1) in RL cells vs human fibroblasts.

Examples H1 Total BTK Degradation Assay (Compound 3A-39)

A Total BTK-HTRF assay (Cisbio Total BTK cat #63ADK064PEG) was performed to quantitate the ability of test compounds to degrade BTK protein levels in RAMOS cells. This total protein assay monitors the steady state protein level in a sandwich assay format using two different specific antibodies after lysis of the cell-membrane. The antibodies recognise two different epitopes on BTK and are labelled with Eu3+-cryptate (donor) and d2 (acceptor). When the dyes are in close proximity, the excitation of the donor with a light source triggers a Fluorescence Resonance Energy Transfer (FRET) towards the acceptor, which in turn fluoresces at a specific wavelength (665 nm). The specific signal modulates positively in proportion to the total concentration of BTK.

In order to evaluate the degradation of BTK by test compounds, a total BTK degradation assay was performed (Cisbio Total BTK cat #63ADK064PEG). The frozen stock solutions of the two different BTK antibodies were diluted 20-fold with the detection buffer and pre-mixed before use in the assay. Supplemented lysis buffer (4×) was prepared by diluting the blocking reagent solution 25-fold with lysis buffer (4×) and mixing gently. RAMOS B lymphocyte cell line (ATCC CRL-1596) were plated at a density of 50K cells/well (8 μL) in RPMI medium with 10% FBS into 384-well white detection plates. Test compound (4 μL, 5 μM), diluted with assay buffer was dispensed and the plate was incubated at 37° C. for 24 hours before addition of supplemented lysis buffer (5 μL). and incubation for 30 min at RT with shaking. The premixed antibody solution (1:1, 4 μL) was added before covering the plate and incubation for 24 hours at RT. The plate was read on a Biotek Synergy Neo2 plate reader using 330 nm excitation, 620 nm-donor emission and 670 nm-acceptor emission. An emission ratio was calculated (670/620) and converted to POC relative to control and blank wells. Percentage of residual BTK was calculated as follows:—100−(HTRF ratio without test compound−HTRF ratio with test compound)*100.

Compound 3A-39 was tested in the BTK total degradation assay described above and was found to reduce total BTK levels as shown in the table below:

| Compound | Percent residual BTK after 24 hours with test compound (5 μM) |
|---|---|
| Ibrutinib | 121% |
| compound 3A-39 | 63% |

Examples H2 NanoBRET Assay (Compound 3A-6)

Bioluminescence Resonance Energy Transfer (BRET) is used to quantitatively measure the interaction between proteins in live cells. The NanoBRET Target Engagement (TE) Assay ((Promega, Cat #N2500)) measures the apparent binding affinity of test compounds at select kinase proteins by competitive displacement of a fluorescent NanoBRET kinase-ligand tracer (K-5), from a target kinase fused to a NanoLuc luciferase protein within intact cells. To determine whether test compounds can bind BTK, a fixed concentration of NanoBRET tracer is added to cells expressing the NanoLuc-BTK fusion protein, thereby generating a BRET reporter complex. Application of competitive test compounds results in a dose-dependent decrease in Nano- BRET™ energy transfer, which allows quantitation of apparent intracellular affinity of the BTK target protein for the test compound.

In order to evaluate the binding between BTK and test compounds, an intracellular drug displacement assay was performed. HEK 293 cells were transfected with plasmids expressing NanoLuc-BTK (Promega, Cat #N2441) fusion protein in assay medium, seeded into 96-well plates and treated with NanoBRET Tracer K-5 (20 μM). Cells were then treated with increasing doses (from 5.6 μM to 1 μM) of the unlabelled test compound 3A-6 as a competitive inhibitor for 2 hours, before adding 3× Complete Substrate plus Inhibitor Solution. The plates were then analyzed with a Biotek Synergy Neo2 plate reader equipped with NanoBRET 618 filters (donor 450 nm/8 nm BP and acceptor 600 nm LP). A corrected BRET ratio was calculated and is defined as the ratio of the emission at 618 nm/460 nm for experimental samples (i.e. those treated with NanoBRET fluorescent ligand) subtracted by the emission at 610 nm/450 nm for control samples (not treated with NanoBRET fluorescent ligand). BRET ratios are expressed as milliBRET units (mBU), where 1 mBU corresponds to the corrected BRET ratio multiplied by 1000.

Compound 3A-6 was tested in the BTK assay described above and was found to have a IC50 as shown in the table below:

| Compound | BTK IC50 (μM) |
|---|---|
| 3A-6 | 0.094 |

Examples H3 Mass Spectral Analysis

A protein kinase that is inhibited by compound and/or pharmaceutically acceptable salt of the present disclosure may be subjected to mass spectral analysis to assess the formation of permanent, irreversible covalent adducts. Suitable analytical methods to examine peptide fragments generated upon tryptic cleavage of a protein are generally known in the art. Such methods identify permanent, irreversible covalent protein adducts by observing a mass peak that corresponds to the mass of a control sample plus the mass of an irreversible adduct.

Method: Intact His-tagged BTK kinase domain (SOURCE)(10 μM) was incubated for 45 min in 20 mM HEPES (pH 8.0) containing 10 μM compound with final DMSO concentration of 1%. After the incubation time, the reactions were quenched by acetone precipitation and the pellet was re-dissolved in 8 M Urea. Following the reaction, 4 g of control and test compound treated BTK were separated electrophoretically on a 4-12% BT gel and then stained with Coomassie blue protein stain. The BTK protein band was then excised and subjected to an in-gel trypsin digest by reducing the protein (5 mM DTT), alkylating the thiols with iodoacetamide (15 mM), and then incubating the protein gel band with trypsin in a 37 C water bath (4 hours). The tryptic digestion was then quenched by the addition of trifluoroacetic acid, and peptides were removed from the gel band by sonicating with increasing amounts of acetonitrile (0%, 30%, & 60%). Peptides were then purified using C18 ziptips, spotted on the MALDI target plate with α-cyano-4-hydroxycinnamic acid as the desorption matrix (10 mg/mL in 0.10% TFA:Acetonitrile 50:50), and analyzed in reflectron mode.

The peptide fragment coverage of His-BTK KD after trypsin digestion showed coverage of 92%-93% of the sequence and confirming covalent modification of peptide 467QRPIFIITEYMANGCLLNYLR487 at C481 by several compounds of the present disclosure, including 3A-39, 3A-9, 3A-4, 3A-6, 3A-37, and 3A-38. Compound 3A-9 also showed covalent modification of 526NCLVNDQGVVK536 at C527. Accordingly, two cysteines present in tryptic digest peptides were labelled by test compounds, cysteine 481 (C481) and cysteine 527 (C527) confirming irreversible covalent modification of BTK according to the table below.

| Compound ID | C481 | C527 |
|---|---|---|
| Ibrutinib | ✓ | |
| 3A-39 | ✓ | |
| 3A-9 | ✓ | ✓ |
| 3A-4 | ✓ | |
| 3A-6 | ✓ | |
| 3A-37 | ✓ | |
| 3A-38 | ✓ | |

III. Preparation of Pharmaceutical Dosage Forms

Example P1: Oral Capsule

The active ingredient is a compound of Table 1, Table 2, Table 3, Table 3A, Table 4, or Table 5, or a pharmaceutically acceptable salt thereof. A capsule for oral administration is prepared by mixing 1-1000 mg of active ingredient with starch or other suitable powder blend. The mixture is incorporated into an oral dosage unit such as a hard gelatin capsule, which is suitable for oral administration.

Example P2: Solution for Injection

The active ingredient is a compound of Table 1, Table 2, Table 3, Table 3A, Table 4, or Table 5, or a pharmaceutically acceptable salt thereof, and is formulated as a solution in sesame oil at a concentration of 50 mg-eq/mL.

The examples and embodiments described herein are for illustrative purposes only and various modifications or changes suggested to persons skilled in the art are to be included within the spirit and purview of this application and scope of the appended claims.

What is claimed is:

1. A compound represented by the structure:

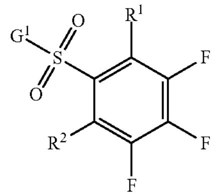

wherein:

$G^1$ is a protein binder;

$R^1$ is —CN, —$OR^3$, —$SR^3$, —$S(=O)R^3$, —$S(=O)_2R^3$, —$S(=O)(=NR^3)R^3$, —$S(=O)_2N(R^3)_2$, —$OS(=O)_2R^3$, —$N(R^3)_2$, —$NR^3C(=O)R^3$, —$NR^3C(=O)N(R^3)_2$, —$NR^3C(=NR^3)N(R^3)_2$, —$C(=O)R^3$, —$OC(=O)R^3$, —$C(=O)OR^3$, —$OC(=O)OR^3$, —$OC(=O)N(R^3)_2$, —$NR^3C(=O)OR^3$, —$C(=O)N(R^3)_2$, $NO_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

$R^2$ is hydrogen, halogen, —CN, —$OR^3$, —$SR^3$, —S(═O)$R^3$, —S(═O)$_2R^3$, —S(═O)$_2N(R^3)_2$, —$N(R^3)_2$, —C(═O)$R^3$, —OC(═O)$R^3$, —C(═O)O$R^3$, —OC(═O)N$(R^3)_2$, —N$R^3$C(═O)O$R^3$, or —C(═O)N$(R^3)_2$;

each $R^3$ is independently hydrogen, —C(═O)($C_2$-$C_6$ alkenyl), —C(═O)($C_2$-$C_6$ alkynyl), substituted or unsubstituted $C_1$-$C_4$ alkyl, —($C_1$-$C_4$ alkylene)-$R^4$, substituted or unsubstituted $C_1$-$C_4$ haloalkyl, substituted or unsubstituted $C_1$-$C_4$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

or two $R^3$ on the same nitrogen atom are joined together to form substituted or unsubstituted $C_2$-$C_7$ heterocycloalkyl; and $R^4$ is substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl, or a salt or solvate thereof.

2. The compound of claim 1, wherein $G^1$ is one or more cyclic group, each cyclic group being independently selected from optionally substituted carbocycle and optionally substituted heterocycle, wherein any two or more cyclic groups are independently connected by bond or linker (L').

3. The compound of claim 1, wherein $G^1$ is -L-G, L is a nitrogen containing linker, and G is one or more cyclic group, each cyclic group being independently selected from optionally substituted carbocycle and optionally substituted heterocycle, wherein any two or more cyclic groups are independently connected by bond or linker (L').

4. The compound of claim 3, wherein L is —N$R^5$—, —N$R^5$-(substituted or unsubstituted alkyl), —N$R^5$-(substituted or unsubstituted heteroalkyl), —N$R^5$-(substituted or unsubstituted cycloalkyl), —N$R^5$-(substituted or unsubstituted heterocycloalkyl), —N$R^5$-(substituted or unsubstituted aryl), or —N$R^5$-(substituted or unsubstituted heteroaryl); wherein $R^5$ is hydrogen, —CN, —C(═O)$R^6$, —C(═O)O$R^6$, substituted or unsubstituted $C_1$-$C_4$ alkyl, substituted or unsubstituted $C_1$-$C_4$ haloalkyl, substituted or unsubstituted $C_1$-$C_4$ heteroalkyl, —$C_1$-$C_4$ alkylene-O$R^6$, substituted or unsubstituted $C_3$-$C_5$ cycloalkyl, or substituted or unsubstituted $C_2$-$C_4$ heterocycloalkyl; and $R^6$ is hydrogen, substituted or unsubstituted $C_1$-$C_4$ alkyl, substituted or unsubstituted $C_1$-$C_4$ fluoroalkyl, or substituted or unsubstituted $C_1$-$C_4$ heteroalkyl.

5. The compound of claim 1, wherein the compound is represented by the structure of Formula (I):

Formula (I)

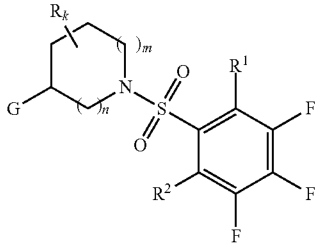

wherein:

$R^1$ is —CN, —$OR^3$, —$SR^3$, —S(═O)$R^3$, —S(═O)$_2R^3$, —S(═O)(═N$R^3$)$R^3$, —S(═O)$_2N(R^3)_2$, —OS(═O)$_2R^3$, —$N(R^3)_2$, —N$R^3$C(═O)$R^3$, —N$R^3$C(═O)N$(R^3)_2$, —N$R^3$C(═N$R^3$)N$(R^3)_2$, —C(═O)$R^3$, —OC(═O)$R^3$, —C(═O)O$R^3$, —OC(═O)O$R^3$, —OC(═O)N$(R^3)_2$, —C(═O)N$(R^3)_2$, —$NO_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

$R^2$ is hydrogen, halogen, —CN, —$OR^3$, —$SR^3$, —S(═O)$R^3$, —S(═O)$_2R^3$, —S(═O)$_2N(R^3)_2$, —$N(R^3)_2$, —C(═O)$R^3$, —OC(═O)$R^3$, —C(═O)O$R^3$, —OC(═O)N$(R^3)_2$, —N$R^3$C(═O)O$R^3$, or —C(═O)N$(R^3)_2$;

R is fluorine, substituted or unsubstituted $C_1$-$C_4$ alkyl, substituted or unsubstituted $C_1$-$C_4$ haloalkyl, or substituted or unsubstituted $C_1$-$C_4$ heteroalkyl;

G is one or more cyclic group, each cyclic group being independently selected from optionally substituted carbocycle and optionally substituted heterocycle, wherein any two or more cyclic groups are independently connected by bond or linker (L');

each $R^3$ is independently hydrogen, —C(═O)($C_2$-$C_6$ alkenyl), —C(═O)($C_2$-$C_6$ alkynyl), substituted or unsubstituted $C_1$-$C_4$ alkyl, —($C_1$-$C_4$ alkylene)-$R^4$, substituted or unsubstituted $C_1$-$C_4$ haloalkyl, substituted or unsubstituted $C_1$-$C_4$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

or two $R^3$ on the same nitrogen atom are joined together to form substituted or unsubstituted $C_2$-$C_7$ heterocycloalkyl;

$R^4$ is substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

k is 0, 1, 2, 3, 4, 5, 6, 7, or 8;

n is 0, 1, or 2; and m is 0, 1, or 2;

or a salt or solvate thereof.

6. The compound of claim 1, wherein the compound is represented by the structure of Formula (II):

Formula (II)

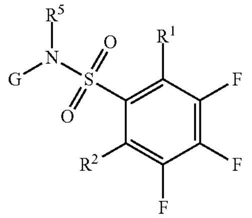

wherein:

$R^1$ is —CN, —$OR^3$, —$SR^3$, —S(=O)$R^3$, —S(=O)$_2R^3$, —S(=O)(=$NR^3$)$R^3$, —S(=O)$_2$N($R^3$)$_2$, —OS(=O)$_2$ $R^3$, —N($R^3$)$_2$, —$NR^3$C(=O)$R^3$, —$NR^3$C(=O)N($R^3$)$_2$, —$NR^3$C(=$NR^3$)N($R^3$)$_2$, —C(=O)$R^3$, —OC(=O)$R^3$, —C(=O)$OR^3$, —OC(=O)$OR^3$, —OC(=O)N($R^3$)$_2$, —$NR^3$C(=O)$OR^3$, —C(=O)N($R^3$)$_2$, —$NO_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

$R^2$ is hydrogen, halogen, —CN, —$OR^3$, —$SR^3$, —S(=O)$R^3$, —S(=O)$_2R^3$, —S(=O)$_2$N($R^3$)$_2$, —N($R^3$)$_2$, —C(=O)$R^3$, —OC(=O)$R^3$, —C(=O)$OR^3$, —OC(=O)N($R^3$)$_2$, —$NR^3$C(=O)$OR^3$, or —C(=O)N($R^3$)$_2$;

each $R^3$ is independently hydrogen, —C(=O)($C_2$-$C_6$ alkenyl), —C(=O)($C_2$-$C_6$ alkynyl), substituted or unsubstituted $C_1$-$C_4$ alkyl, —($C_1$-$C_4$ alkylene)-$R^4$, substituted or unsubstituted $C_1$-$C_4$ haloalkyl, substituted or unsubstituted $C_1$-$C_4$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

or two $R^3$ on the same nitrogen atom are joined together to form substituted or unsubstituted $C_2$-$C_7$ heterocycloalkyl;

$R^4$ is substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

G is one or more cyclic group, each cyclic group being independently selected from optionally substituted carbocycles and optionally substituted heterocycles, wherein any two or more ring systems are independently connected by bond or linker;

$R^5$ is hydrogen, —CN, —C(=O)$R^6$, —C(=O)$OR^6$, substituted or unsubstituted $C_1$-$C_4$ alkyl, substituted or unsubstituted $C_1$-$C_4$ haloalkyl, substituted or unsubstituted $C_1$-$C_4$ heteroalkyl, —$C_1$-$C_4$ alkylene-$OR^6$, substituted or unsubstituted $C_3$-$C_5$ cycloalkyl, or substituted or unsubstituted $C_2$-$C_4$ heterocycloalkyl; and $R^6$ is hydrogen, substituted or unsubstituted $C_1$-$C_4$ alkyl, substituted or unsubstituted $C_1$-$C_4$ fluoroalkyl, or substituted or unsubstituted $C_1$-$C_4$ heteroalkyl;

or a salt or solvate thereof.

7. The compound of claim 1, wherein $R^1$ is —$OR^3$, —$SR^3$, —OS(=O)$_2R^3$, —N($R^3$)$_2$, —$NR^3$C(=O)$R^3$, —$NR^3$C(=O)N($R^3$)$_2$, —OC(=O)$R^3$, —OC(=O)$OR^3$, —OC(=O)N($R^3$)$_2$, —$NR^3$C(=O)$OR^3$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, or substituted or unsubstituted $C_2$-$C_7$ heterocycloalkyl.

8. The compound of claim 1, wherein $R^2$ is halogen, —CN, —S(=O)$R^3$, —S(=O)$_2R^3$, —S(=O)$_2$N($R^3$)$_2$, —C(=O)$R^3$, —OC(=O)$R^3$, —C(=O)$OR^3$, —OC(=O)N($R^3$)$_2$, —$NR^3$C(=O)$OR^3$, or —C(=O)N($R^3$)$_2$.

9. The compound of claim 1, wherein $R^2$ is hydrogen.

10. The compound of claim 5, wherein k is 0, 1, 2, or 3; n is 0, 1, or 2; and m is 0, 1, or 2.

11. The compound of claim 6, wherein $R^5$ is hydrogen, —CN, substituted or unsubstituted $C_1$-$C_4$ alkyl, substituted or unsubstituted $C_1$-$C_4$ haloalkyl, or substituted or unsubstituted $C_3$-$C_5$ cycloalkyl.

12. The compound of claim 1, wherein $G^1$ comprises monocyclic aryl, monocyclic heteroaryl, monocyclic heteroaryl, bicyclic aryl, or bicyclic heteroaryl.

13. A protein modified with a compound of claim 1, wherein the compound forms a covalent bond with a sulfur atom of a cysteine residue of the protein.

14. A method of modifying a polypeptide with a compound of claim 1, comprising contacting the polypeptide with the compound, to form a covalent bond with a sulfur atom of a cysteine residue of the polypeptide.

15. A method of binding a compound of claim 1 to a polypeptide, comprising contacting the polypeptide with the compound, or a salt or solvate thereof.

16. A method of disrupting a polypeptide, comprising contacting the polypeptide with a compound of claim 1, or a salt or solvate thereof.

17. A compound of claim 6 having the formula:

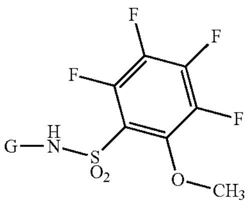

wherein G is one or more cyclic group, each cyclic group being independently selected from optionally substituted carbocycles and optionally substituted heterocycles, wherein any two or more ring systems are independently connected by bond or linker.

18. A compound of claim 1 having the formula:
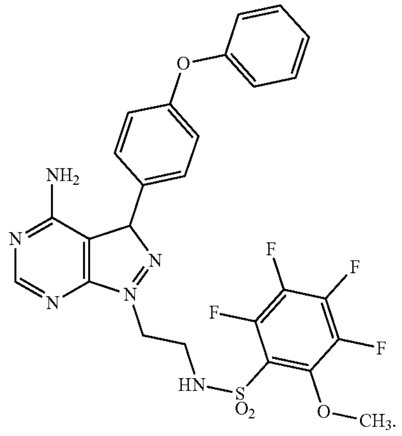
* * * * *